(12) United States Patent
Uno

(10) Patent No.: US 11,264,573 B2
(45) Date of Patent: Mar. 1, 2022

(54) ORGANIC ELECTROLUMINESCENCE DEVICE AND AMINE COMPOUND FOR ORGANIC ELECTROLUMINESCENCE DEVICE

(71) Applicant: SAMSUNG DISPLAY CO., LTD., Yongin-si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 428 days.

(21) Appl. No.: 16/454,465

(22) Filed: Jun. 27, 2019

(65) Prior Publication Data
US 2020/0119283 A1    Apr. 16, 2020

(30) Foreign Application Priority Data

Oct. 11, 2018  (KR) .................. 10-2018-0121336

(51) Int. Cl.
*H01L 51/00*    (2006.01)
*C07D 513/04*   (2006.01)
(Continued)

(52) U.S. Cl.
CPC ........ *H01L 51/0061* (2013.01); *C07D 498/04* (2013.01); *C07D 513/04* (2013.01); *H01L 51/001* (2013.01); *H01L 51/0071* (2013.01); *H01L 51/0072* (2013.01); *H01L 51/0073* (2013.01); *H01L 51/0074* (2013.01); *H01L 51/5012* (2013.01); *H01L 51/5056* (2013.01); *H01L 51/5072* (2013.01); *H01L 51/5088* (2013.01); *H01L 51/5092* (2013.01);
(Continued)

(58) Field of Classification Search
None
See application file for complete search history.

(56) References Cited

U.S. PATENT DOCUMENTS 9,997,724 B2    6/2018  Kim et al.
2014/0027755 A1 1/2014  Mujica-Fernaud et al.
(Continued)

FOREIGN PATENT DOCUMENTS

CN    103476774 A    12/2013
JP    2016-219490 A  12/2016
(Continued)

*Primary Examiner* — Robert S Loewe
(74) *Attorney, Agent, or Firm* — Lewis Roca Rothgerber Christie LLP

(57) ABSTRACT

An organic electroluminescence device includes an amine compound represented by Formula 1 below in at least one organic layer among a plurality of organic layers, and an amine compound represented by Formula 1:

[Formula 1]

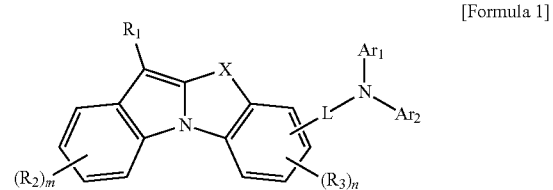

where $R_1$ to $R_3$, $Ar_1$, $Ar_2$, n, m, L and X are as defined in the specification.

20 Claims, 2 Drawing Sheets

(51) Int. Cl.
    *C07D 498/04*      (2006.01)
    *H01L 51/56*       (2006.01)
    *H01L 51/52*       (2006.01)
    *H01L 51/50*       (2006.01)

(52) U.S. Cl.
    CPC ...... *H01L 51/5206* (2013.01); *H01L 51/5221* (2013.01); *H01L 51/56* (2013.01); *H01L 2251/301* (2013.01); *H01L 2251/308* (2013.01); *H01L 2251/558* (2013.01)

(56) References Cited

U.S. PATENT DOCUMENTS

| | | | |
|---|---|---|---|
| 2016/0043334 A1 | 2/2016 | Sekine et al. | |
| 2019/0074449 A1* | 3/2019 | Chen | C07D 401/14 |
| 2019/0252623 A1* | 8/2019 | Layek | C07D 487/04 |

FOREIGN PATENT DOCUMENTS

| | | |
|---|---|---|
| JP | 6269655 B2 | 1/2018 |
| KR | 10-2016-0028979 A | 3/2016 |
| KR | 10-2016-0037788 A | 4/2016 |
| KR | 10-1622828 B1 | 5/2016 |
| KR | 10-1798307 B1 | 11/2017 |
| WO | WO 2016/036171 A1 | 3/2016 |

\* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

Korean Patent Application No. 10-2018-0121336, filed on Oct. 11, 2018, in the Korean Intellectual Property Office, and entitled: "Organic Electroluminescence Device and Amine Compound for Organic Electroluminescence Device," is incorporated by reference herein in its entirety.

BACKGROUND

1. Field

The development of an organic electroluminescence display device as an image display device is being actively conducted.

2. Description of the Related Art

As an organic electroluminescence device, for example, an organic device may be made up of a first electrode, a hole transport layer disposed on the first electrode, an emission layer disposed on the hole transport layer, an electron transport layer disposed on the emission layer and a second electrode disposed on the electron transport layer.

SUMMARY

Embodiments are directed to an organic electroluminescence device including a first electrode, a second electrode disposed on the first electrode, and a plurality of organic layers disposed between the first electrode and the second electrode. At least one organic layer among the organic layers includes an amine compound represented by the following Formula 1:

[Formula 1]

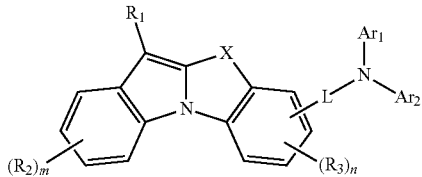

In Formula 1, X may be O or S. $R_1$ are a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms. $R_2$ and $R_3$ are each independently a hydrogen atom, a deuterium atom, a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms, or combined with an adjacent group to form a ring. "m" is an integer of 0 to 4, and "n" is an integer of 0 to 3. L is a direct linkage, a substituted or unsubstituted arylene group of 6 to 40 ring carbon atoms, or a substituted or unsubstituted heteroarylene group of 5 to 40 ring carbon atoms. $Ar_1$ and $Ar_2$ may be each independently a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms.

$R_2$ and $R_3$ may be each independently any one selected among a substituted or unsubstituted cyclohexyl group, a substituted or unsubstituted phenyl group, a substituted or unsubstituted biphenyl group, a substituted or unsubstituted dibenzofuran group, a substituted or unsubstituted dibenzothiophene group and a substituted or unsubstituted carbazole group, or combined with an adjacent group to form a benzene ring.

"m" and "n" may be 0.

$Ar_1$ and $Ar_2$ may be each independently a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted triphenylene group, a substituted or unsubstituted dibenzothiophene group, a substituted or unsubstituted dibenzofuran group, or a substituted or unsubstituted carbazole group.

In an embodiment, $Ar_1$ and $Ar_2$ may be each independently unsubstituted or substituted with at least one substituent selected from a hydrogen atom, a deuterium atom, a fluorine atom, an adamantyl group, a triphenylsilyl group, a phenoxy group, an aryl group of 6 to 30 ring carbon atoms, and a heteroaryl group of 5 to 30 ring carbon atoms, or adjacent substituents may be combined with each other to form a ring.

In an embodiment, L may be a direct linkage, a substituted or unsubstituted phenylene group, a substituted or unsubstituted divalent biphenyl group, a substituted or unsubstituted naphthylene group, a substituted or unsubstituted phenanthrylene group, or a substituted or unsubstituted fluorenylene group.

In an embodiment, a ring. Formula 1 may be represented by the following Formula 2-1 or 2-2:

[Formula 2-1]

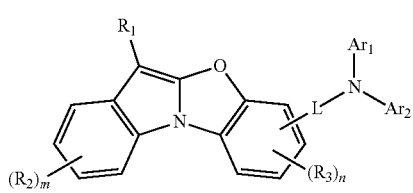

[Formula 2-2]

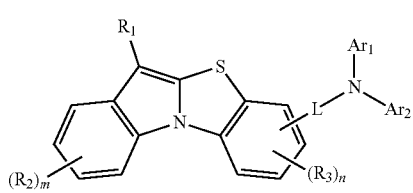

In Formulae 2-1 and 2-2, $R_1$, $R_2$, $R_3$, $Ar_1$, $Ar_2$ "m", "n" and L may be the same as defined in Formula 1.

In an embodiment, Formula 1 may be represented by any one among the following Formulae 3-1 to 3-4:

[Formula 3-1]

[Formula 3-2]

[Formula 3-3]

[Formula 3-4]

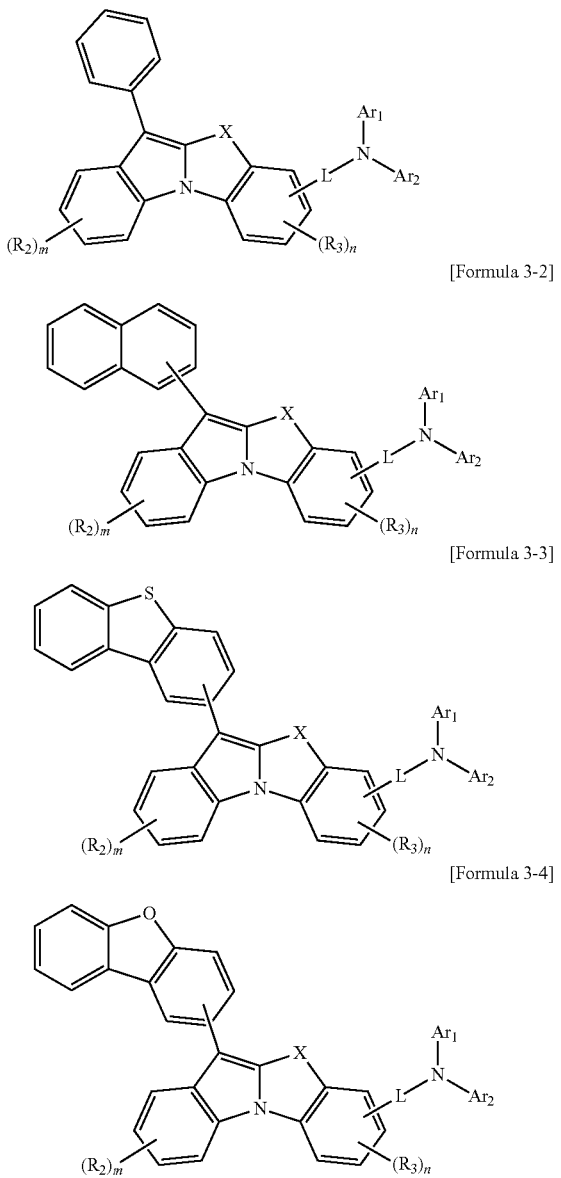

In Formulae 3-1 to 3-4, X, $R_2$, $R_3$, $Ar_1$, $Ar_2$ "m", "n" and L may be the same as defined in Formula 1.

In an embodiment, the organic layers may include a hole transport region disposed on the first electrode, an emission layer disposed on the hole transport region, and an electron transport region disposed on the emission layer, and the hole transport region may include the amine compound. The emission layer may emit any one among blue light and green light.

Embodiments are also directed to an amine compound represented by Formula 1 as described above.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
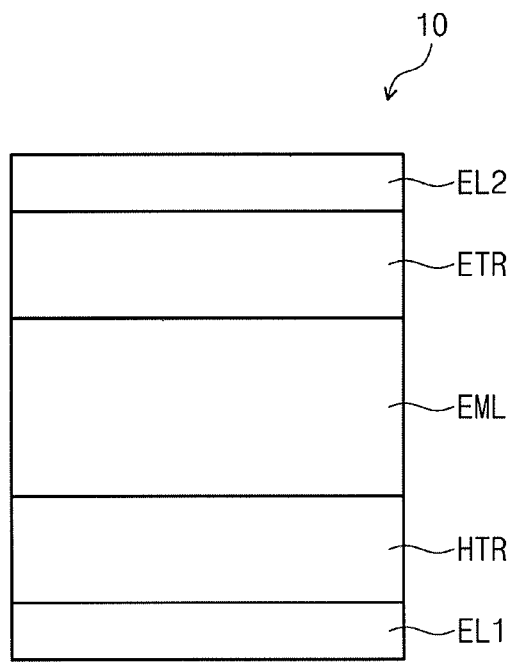
FIG. 1 illustrates a cross-sectional view schematically depicting an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

It will be understood that, although the terms first, second, etc. may be used herein to describe various elements, these elements should not be limited by these terms. These terms are only used to distinguish one element from another element. Thus, a first element could be termed a second element without departing from the teachings thereof. Similarly, a second element could be termed a first element. As used herein, the singular forms are intended to include the plural forms as well, unless the context clearly indicates otherwise.

In the description, the term "substituted or unsubstituted" corresponds to unsubstituted or substituted with at least one substituent selected from a deuterium atom, a halogen atom, a cyano group, a nitro group, an amino group, a silyl group, an oxy group, a thiol group, a sulfinyl group, a sulfonyl group, a carbonyl group, a boron group, a phosphine oxide group, a phosphine sulfide group, an alkyl group, an alkenyl group, an alkoxy group, a hydrocarbon ring, an aryl group, and a heterocyclic group. In addition, each of the substituents may be substituted or unsubstituted. For example, a biphenyl group may be interpreted as an aryl group or a phenyl group substituted with a phenyl group. The heterocyclic group may include an aliphatic heterocycle and an aromatic heterocycle (heteroaryl group).

In the description, the expression "forming a ring via the combination with an adjacent group" may refer to forming a substituted or unsubstituted hydrocarbon ring, or a substituted or unsubstituted heterocycle via the combination with an adjacent group. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may be a monocyclic ring or a polycyclic ring.

In addition, the ring formed via the combination with each other may be combined with another ring to form a spiro structure.

In the description, the term "adjacent group" may refer to a substituent substituted for an atom that is directly combined with an atom substituted with a corresponding substituent, another substituent substituted for an atom that is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen atom may include a fluorine atom, a chlorine atom, a bromine atom and an iodine atom.

In the description, the alkyl group may be a linear, branched or cyclic type. The carbon number of the alkyl group may be from 1 to 50, from 1 to 30, from 1 to 20, from 1 to 10, or from 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., groups.

In the description, the term "hydrocarbon ring" refers to an optional functional group or substituent derived from an aliphatic hydrocarbon. The hydrocarbon ring may be a saturated hydrocarbon ring of 5 to 20 ring carbon atoms.

In the description, the term "aryl group" refers to an optional functional group or substituent derived from an aromatic hydrocarbon ring. The aryl group may be a monocyclic aryl group or a polycyclic aryl group. The number of ring carbon atoms in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., groups.

In the description, the fluorenyl group may be substituted, and two substituents may be combined with each other to form a spiro structure. Examples of the substituted fluorenyl group include the following.

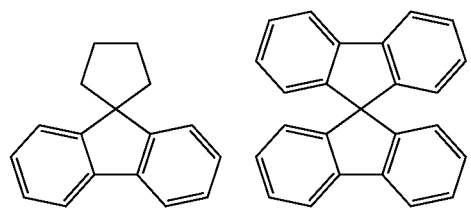

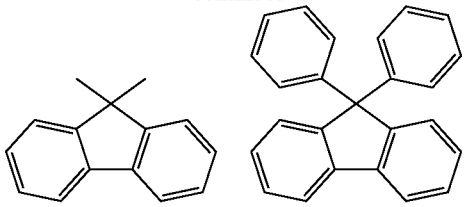

In the description, the heteroaryl group may include one or more among B, O, N, P, Si and S as a heteroatom. If the heteroaryl group includes two or more heteroatoms, two heteroatoms may be the same or different from each other. The heteroaryl group may be a monocyclic heteroaryl group or apolycyclic heteroaryl group. The ring carbon number of the heteroaryl may be 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., groups.

In the description, the explanation on the aryl group may be applied to the arylene group, except that the arylene group is a divalent group. The explanation on the heteroaryl group may be applied to the heteroarylene group, except that the heteroarylene group is a divalent group.

In the description, the silyl group includes an alkylsilyl group and an arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., groups.

In the description, a direct linkage may indicate a single bond.

FIG. 1 illustrates a cross-sectional view schematically depicting an organic electroluminescence device according to an embodiment. The organic electroluminescence device 10 according to an embodiment may include a first electrode EL1, a plurality of organic layers (HTR, EML and ETR) and a second electrode EL2, laminated one by one. The plurality of organic layers may include a hole transport region HTR, an emission layer EML and an electron transport region ETR, laminated one by one.

Figure 2:
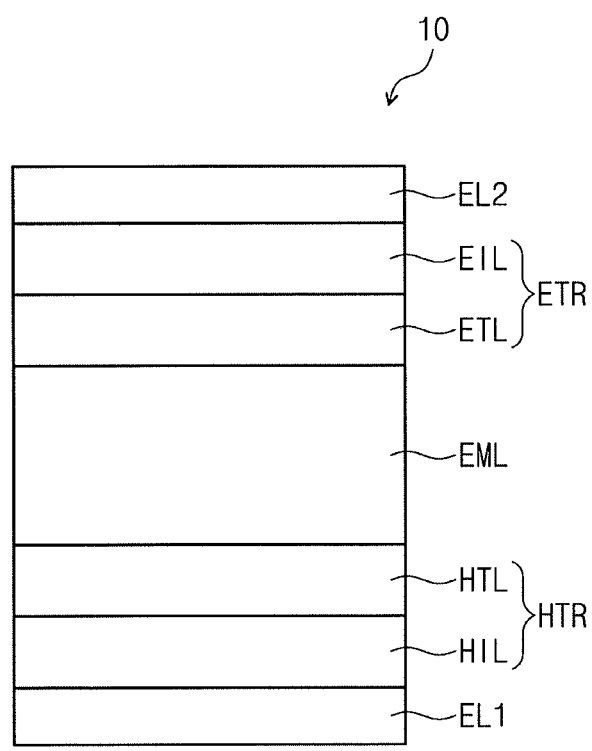
FIG. 2 illustrates a cross-sectional view schematically depicting an organic electroluminescence device according to an embodiment.
Figure 3:
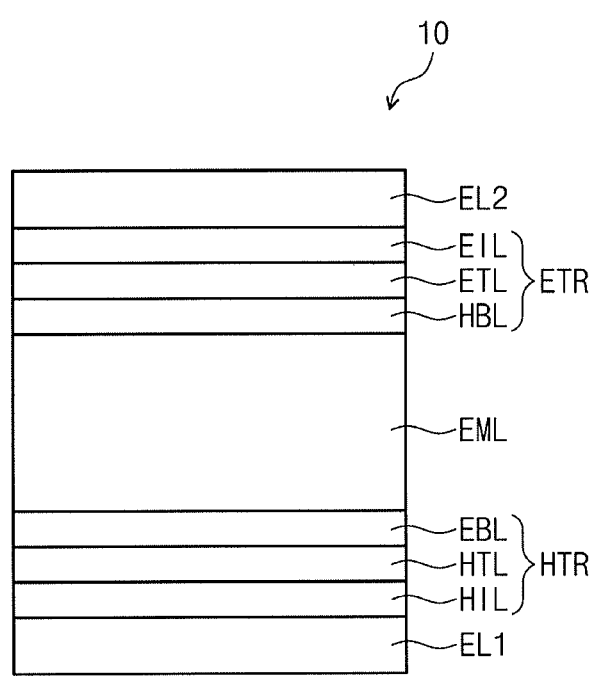
FIG. 3 illustrates a cross-sectional view schematically illustrating an organic electroluminescence device according to an embodiment.

As compared with FIG. 1, FIG. 2 shows a cross-sectional view of an organic electroluminescence device 10 of an embodiment wherein a hole transport region HTR includes a hole injection layer HIL and a hole transport layer HTL, and an electron transport region ETR includes an electron injection layer EIL and an electron transport layer ETL. FIG. 3 shows a cross-sectional view of an organic electroluminescence device 10 of an embodiment wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL.

The first electrode EL1 has conductivity. The first electrode EL1 may be formed using a metal alloy or a conductive compound. The first electrode EL1 may be an anode.

The first electrode may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The first electrode EL1 may have a structure including a plurality of layers including a reflective layer or a transflective layer formed using the above materials, and a transmissive conductive layer formed using ITO, IZO, ZnO, or ITZO. For example, the first electrode EL1 may have a three-layer structure of ITO/Ag/ITO. The thickness of the first electrode EL1 may be from about 1,000 Å to about 10,000 Å, or, for example, from about 1,000 Å to about 3,000 Å.

At least one organic layer among the hole transport region HTR, the emission layer EML and the electron transport region ETR may include an amine compound represented by the following Formula 1:

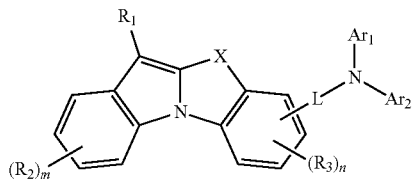

[Formula 1]

In Formula 1, X may be O or S.

$R_1$ may be an aryl group, a heteroaryl group, or an alkyl group. The aryl group may be a substituted or unsubstituted aryl group of 6 to 40 ring carbon atoms, the heteroaryl group may be a substituted or unsubstituted heteroaryl group of 5 to 40 ring carbon atoms, and the alkyl group may be a substituted or unsubstituted alkyl group of 1 to 20 carbon atoms. For example, $R_1$ may be a substituted or unsubstituted aryl group of 6 to 20 ring carbon atoms, or a substituted or unsubstituted heteroaryl group of 5 to 20 ring carbon atoms. The substituted or unsubstituted aryl group may be a substituted or unsubstituted phenyl group, or a substituted or unsubstituted naphthyl group. The substituted or unsubstituted heteroaryl group may be a substituted or unsubstituted dibenzothiophene group, or a substituted or unsubstituted dibenzofuran group. When $R_1$ is the phenyl group, $R_1$ may be an unsubstituted phenyl group. When $R_1$ is the naphthyl group, $R_1$ may be an unsubstituted naphthyl group, and carbon at position 1 of the naphthyl group may be combined with a core structure. When $R_1$ is an unsubstituted dibenzothiophene group or an unsubstituted dibenzofuran group, one of the carbon atoms at positions 2 to 9 may be combined with a core structure. In the description, the term "core structure" may refer to the structure shown in the following Formula 1-1:

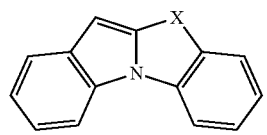

[Formula 1-1]

In Formula 1-1, X may be the same as defined in Formula 1.

$R_2$ and $R_3$ may be each independently a hydrogen atom, a deuterium atom, an aryl group, a heteroaryl group, or an alkyl group, or may be combined with an adjacent group to form a ring. The aryl group may be a substituted or unsubstituted aryl group of 6 to 40 ring carbon atoms, the heteroaryl group may be a substituted or unsubstituted heteroaryl group of 5 to 40 ring carbon atoms, and the alkyl group may be a substituted or unsubstituted alkyl group of 1 to 20 carbon atoms. For example, $R_2$ and $R_3$ may be each independently any one of a substituted or unsubstituted cyclohexyl group, a substituted or unsubstituted phenyl group, a substituted or unsubstituted biphenyl group, a substituted or unsubstituted dibenzofuran group, a substituted or unsubstituted dibenzothiophene group, and a substituted or unsubstituted carbazole group, or may be combined with an adjacent group to form a benzene ring. For example, $R_2$ and $R_3$ may be each independently selected from an unsubstituted cyclohexyl group, an unsubstituted phenyl group, an unsubstituted biphenyl group, an unsubstituted dibenzofuran group, an unsubstituted dibenzothiophene group, an unsubstituted carbazole group, and an unsubstituted 9-phenyl-9H-carbazole group, or may be combined with an adjacent group to form one or two benzene rings.

"m" may be an integer of 0 to 4, and "n" may be an integer of 0 to 3. For example, both "m" and "n" may be 0, or "m" may be 2 and "n" may be 0. If each of "m" and "n" is 2 or more, $R_2$ and $R_3$ may be the same or different from each other.

L may be a direct linkage, a substituted or unsubstituted arylene group of 6 to 40 ring carbon atoms, or a substituted or unsubstituted heteroarylene group of 5 to 40 ring carbon atoms. For example, L may be a direct linkage, or a substituted or unsubstituted arylene group of 6 to 20 ring carbon atoms. The arylene group may be unsubstituted, and the unsubstituted arylene group may be a phenylene group, a naphthylene group, a phenanthryl group, a divalent biphenyl group, or a fluorenylene group.

$Ar_1$ and $Ar_2$ may be each independently a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms. For example, $Ar_1$ and $Ar_2$ may be a substituted or unsubstituted aryl group of 6 to 30 ring carbon atoms, or a substituted or unsubstituted heteroaryl group of 5 to 30 ring carbon atoms. The substituted or unsubstituted aryl group may be a phenyl group, a biphenyl group, a naphthyl group, a phenanthryl group, a terphenyl group, or a triphenylene group. The substituted or unsubstituted heteroaryl group may be a dibenzothiophene group or a dibenzofuran group.

$Ar_1$ and $Ar_2$ may be each independently substituted with at least one of a hydrogen atom, a deuterium atom, a fluorine atom, an adamantyl group, a triphenylsilyl group, a phenoxy group, an aryl group of 6 to 30 ring carbon atoms, and a heteroaryl group of 5 to 30 ring carbon atoms. The aryl group may be a phenyl group, a biphenyl group, or a naphthyl group. If $Ar_1$ and $Ar_2$ have two or more substituents, the substituents may be the same or different from each other, and the substituents may be combined with each other to form a ring. For example, $Ar_1$ and $Ar_2$ may be a phenyl group substituted with five deuterium atoms, or adjacent two substituents may be combined with each other to form a benzene ring.

Formula 1 may be represented by the following Formula 2-1 or 2-2:

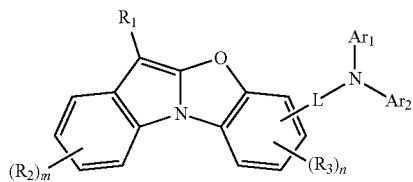
[Formula 2-1]

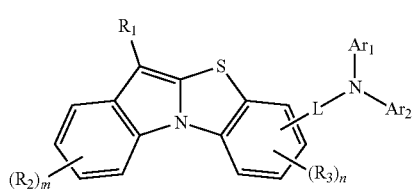
[Formula 2-2]

Formula 2-1 and Formula 2-2 are formulae in which X is concretely defined. Formula 2-1 corresponds to a case where X is O, and Formula 2-2 corresponds to a case where X is S. In Formulae 2-1 and 2-2, $R_1$, $R_2$, $R_3$, $Ar_1$, $Ar_2$ "m", "n" and L may be the same as defined in Formula 1.

Formula 1 may be represented by any one among the following Formulae 3-1 to 3-4:

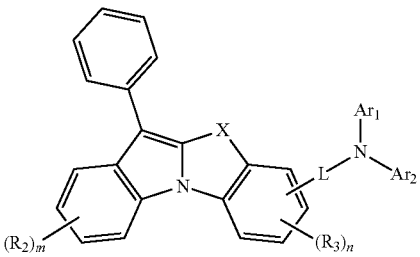
[Formula 3-1]

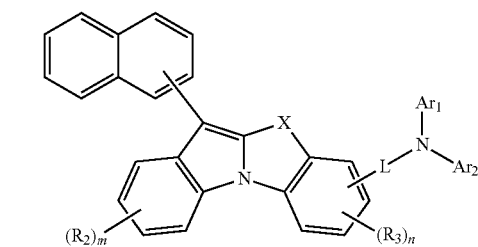
[Formula 3-2]

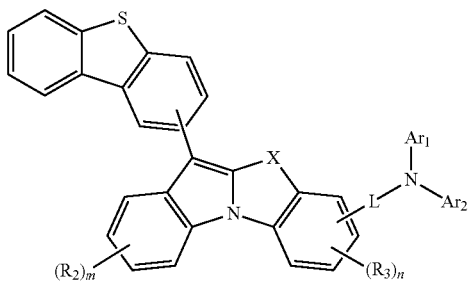
[Formula 3-3]

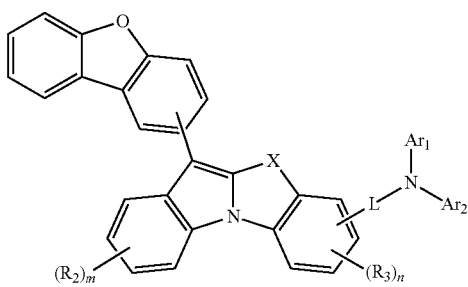
[Formula 3-4]

Formula 3-1 to Formula 3-4 are formulae in which $R_1$ is concretely defined. Formula 3-1 corresponds to a case where $R_1$ is an unsubstituted phenyl group, Formula 3-2 corresponds to a case where $R_1$ is an unsubstituted naphthyl group, Formula 3-3 corresponds to a case where $R_1$ is an unsubstituted dibenzothiophene group, and Formula 3-4 corresponds to a case where $R_1$ is an unsubstituted dibenzofuran group. Formula 3-2 may be represented by Formula 3-2-1.

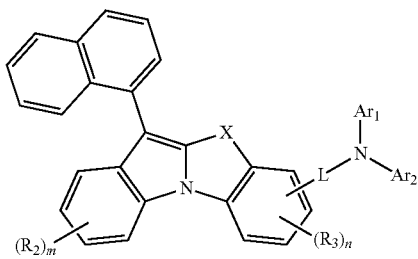
[Formula 3-2-1]

Formula 3-2-1 corresponds to a case where $R_1$ is an unsubstituted naphthyl group and position 1 of the naphthyl group is combined with a core structure.

In Formulae 3-1 to 3-4, and 3-2-1, X, $R_2$, $R_3$, $Ar_1$, $Ar_2$ "m", "n" and L may be the same as defined in Formula 1.

As examples, the amine compound of an embodiment may be any one of compounds represented in Compound Group A and Compound Group B.

[Compound Group A]
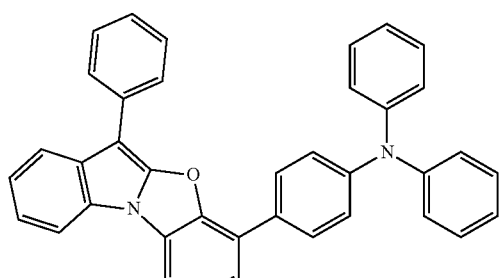 A1
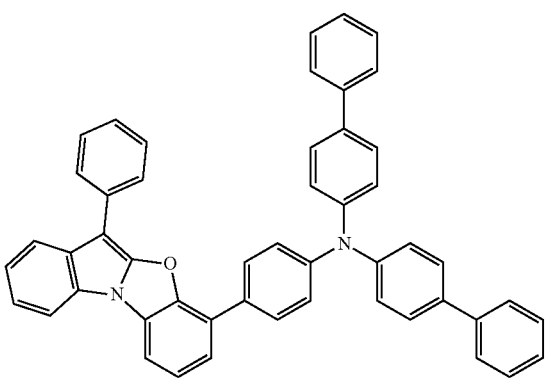 A2
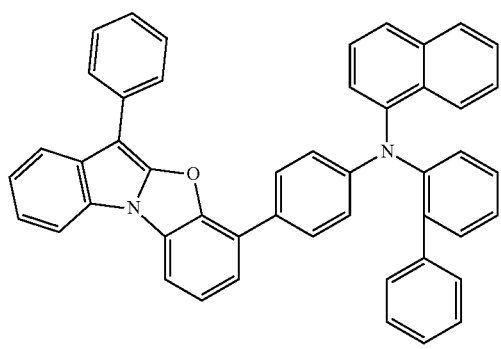 A3
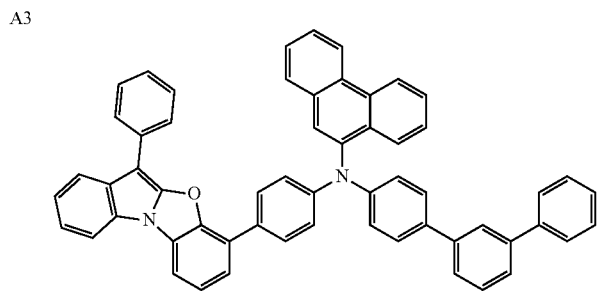 A4
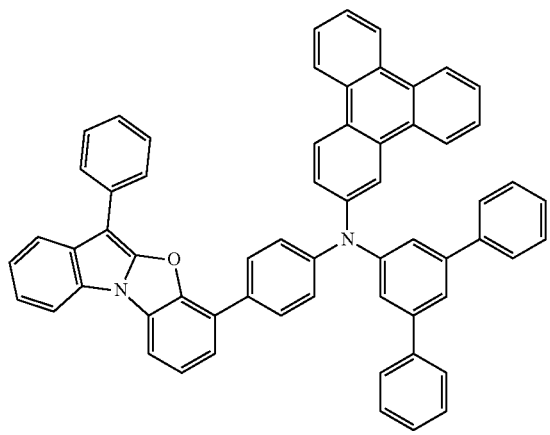 A5
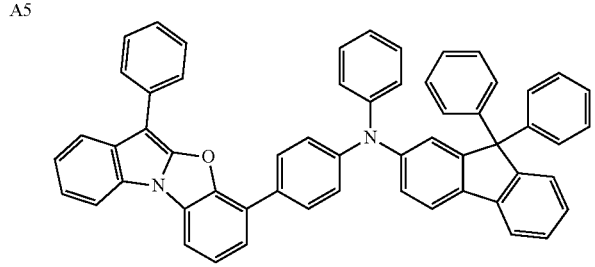 A6
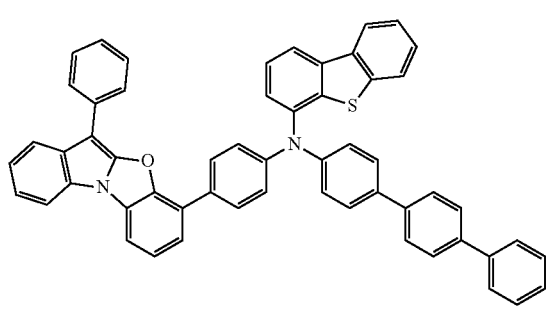 A7
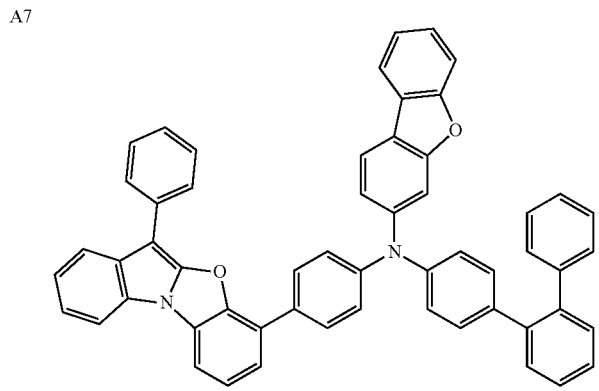 A8

-continued
A9
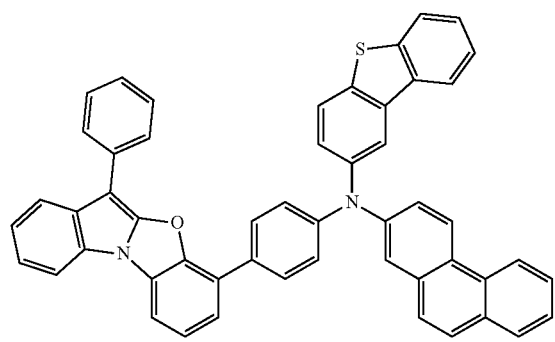
A10
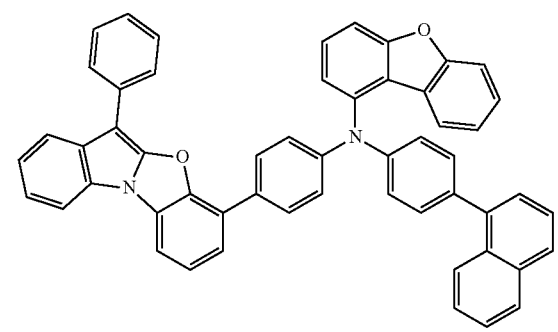
A11
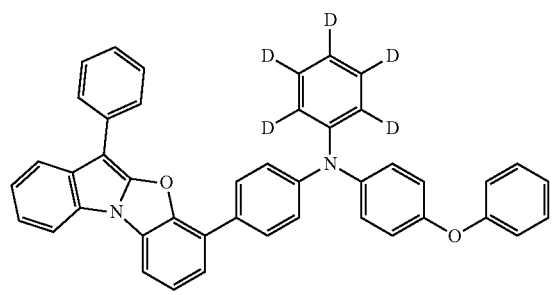
A12
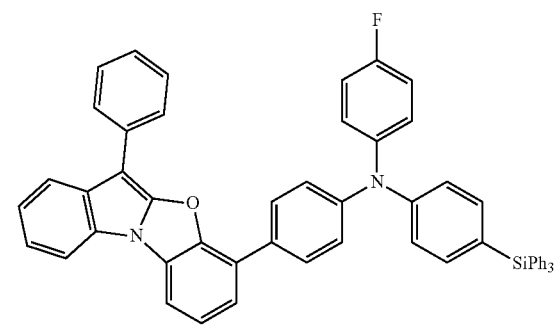
A13
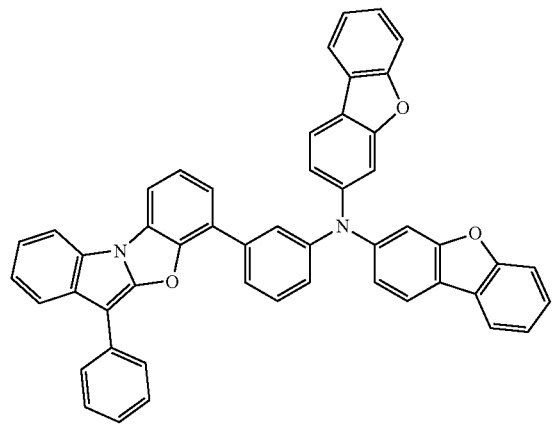
A14
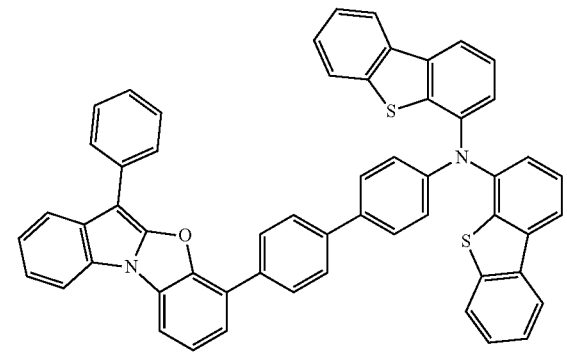
A15
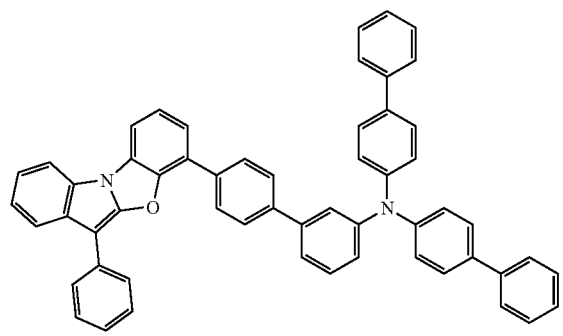
A16
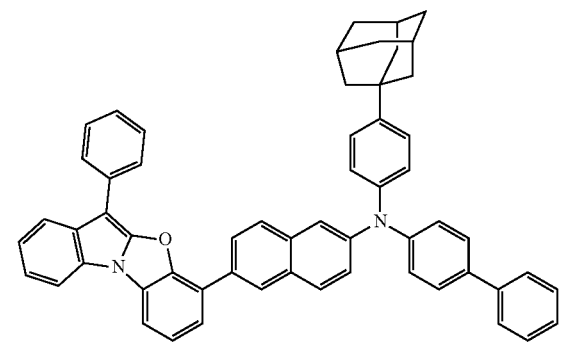

-continued
A17
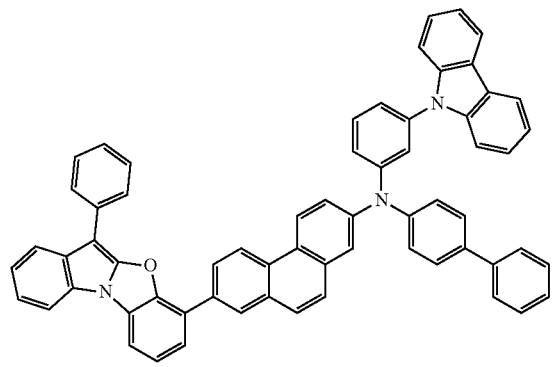
A18
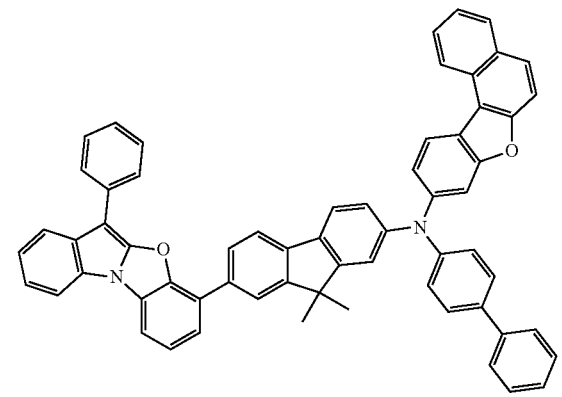
A19
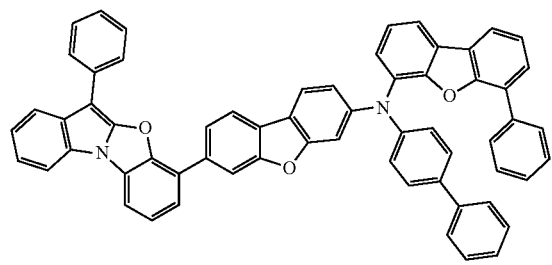
A20
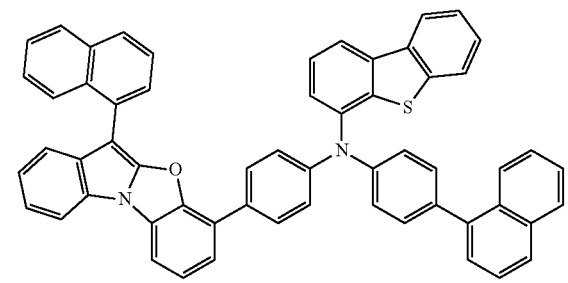
A21
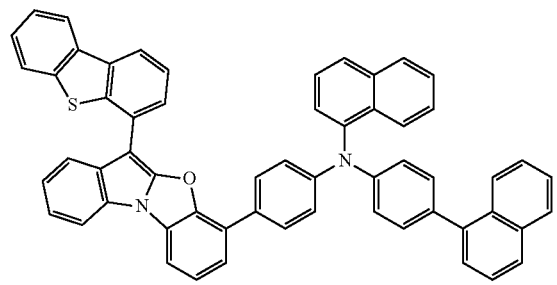
A22
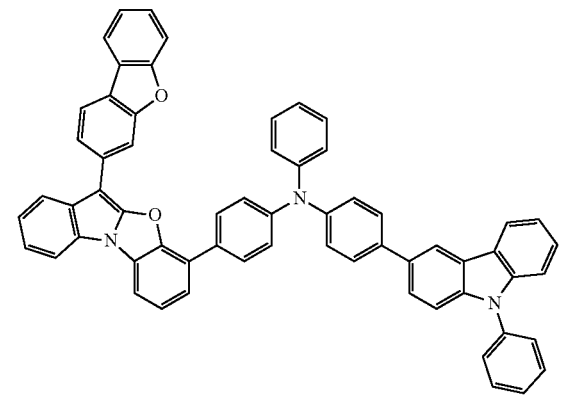
A23
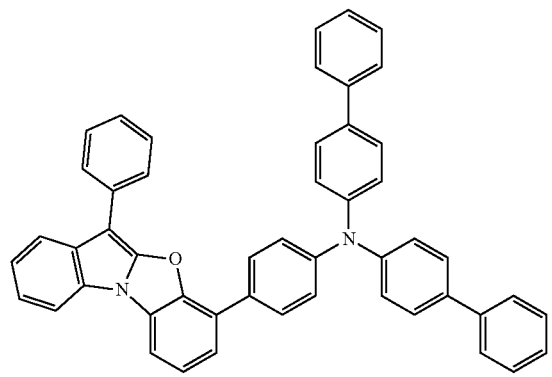
A24
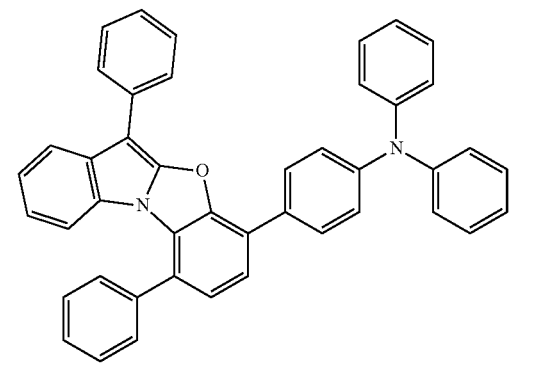

-continued
A25
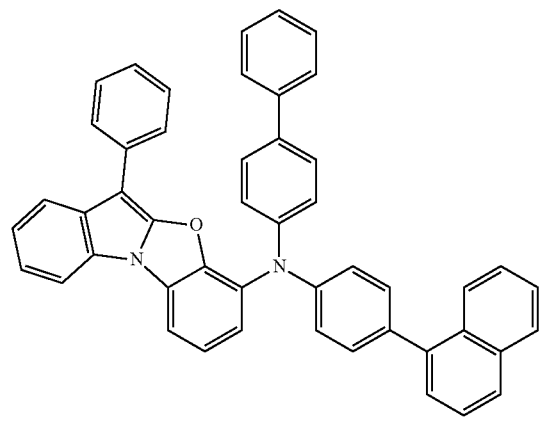
A26
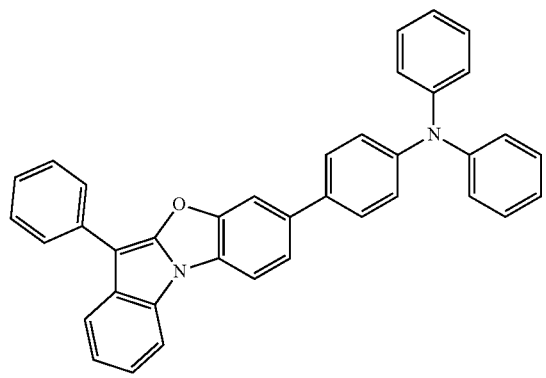
A27
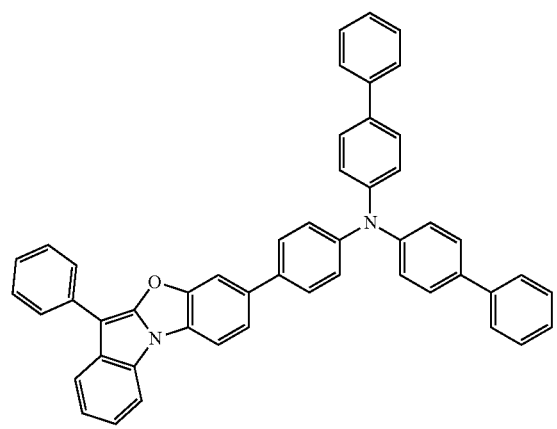
A28
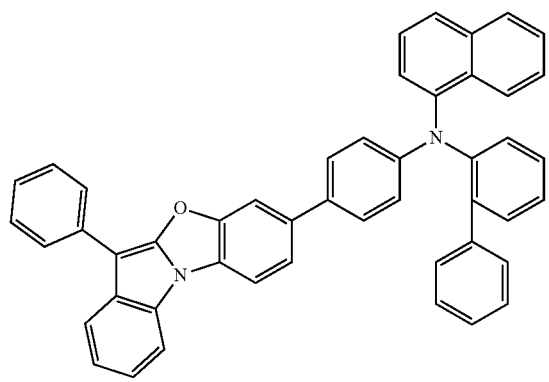
A29
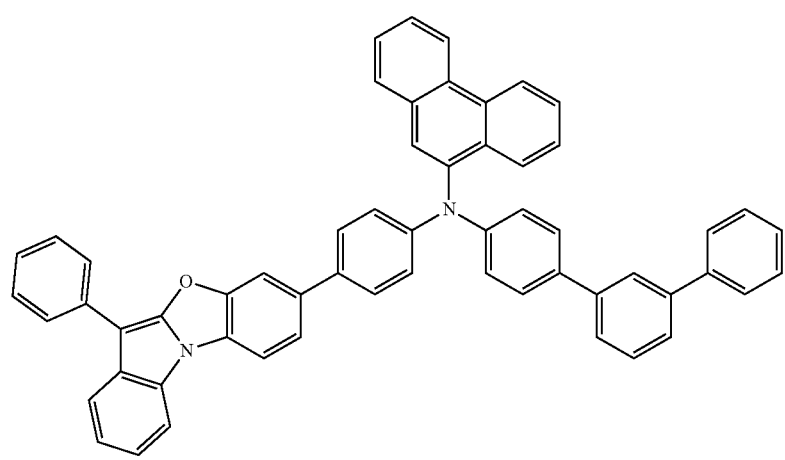

-continued
A30
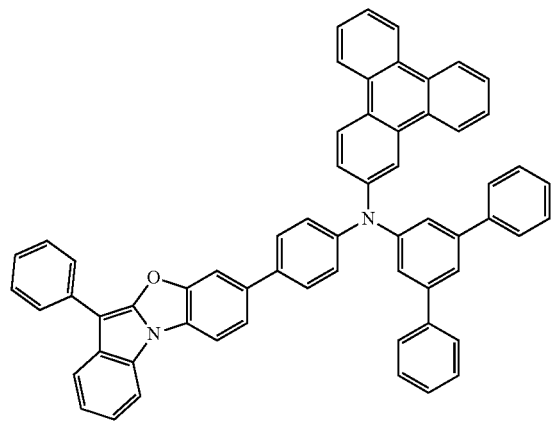
A31
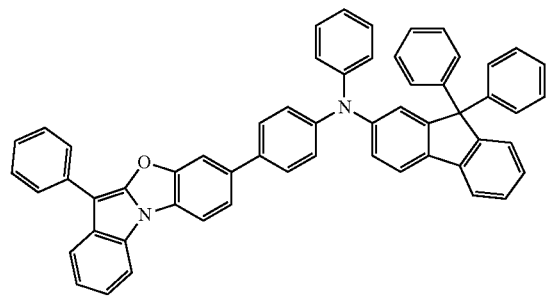
A32
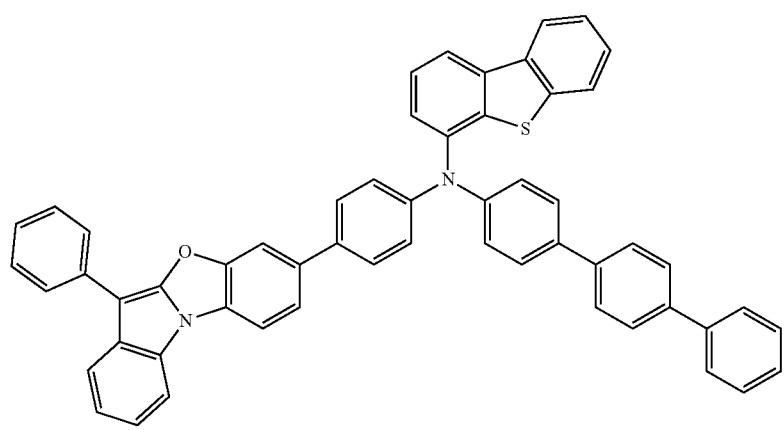
A33
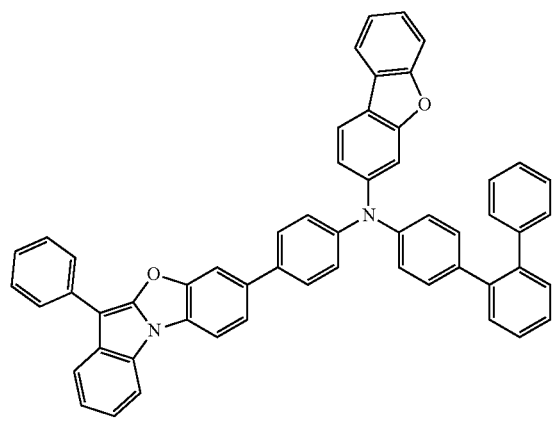
A34
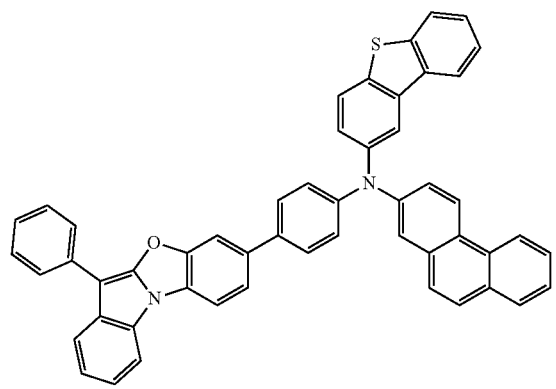

-continued
A35
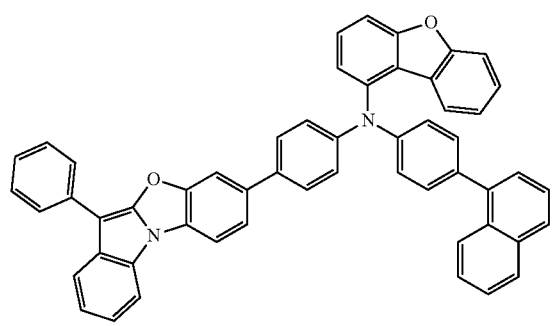
A36
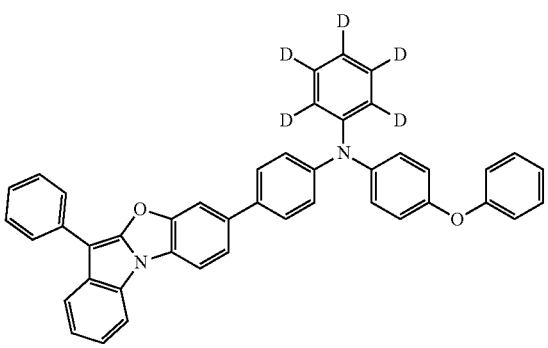
A37
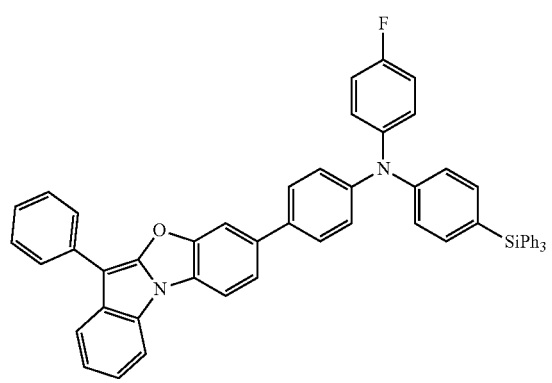
A38
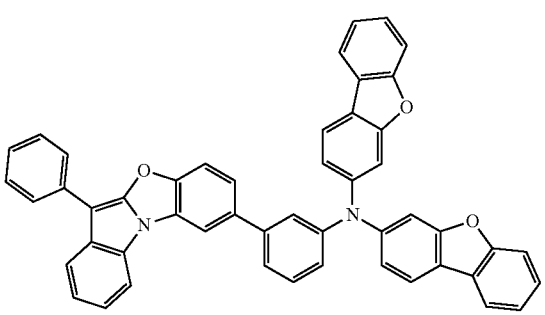
A39
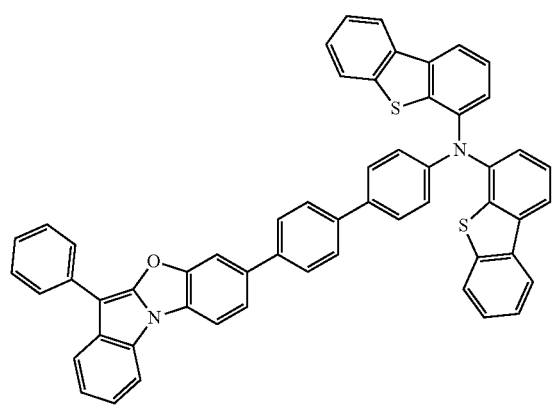
A40
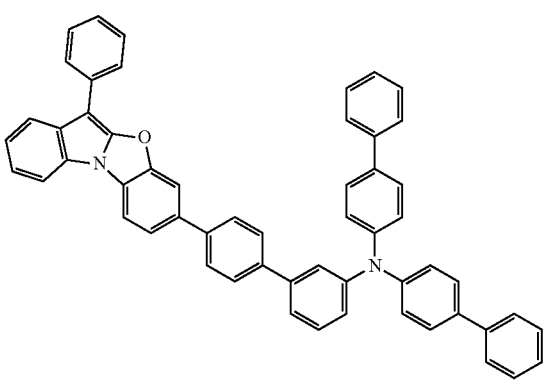

-continued
A41
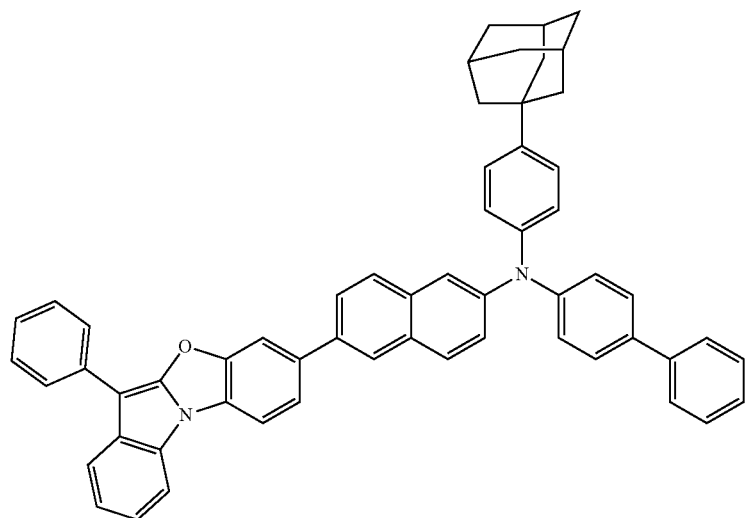
A42
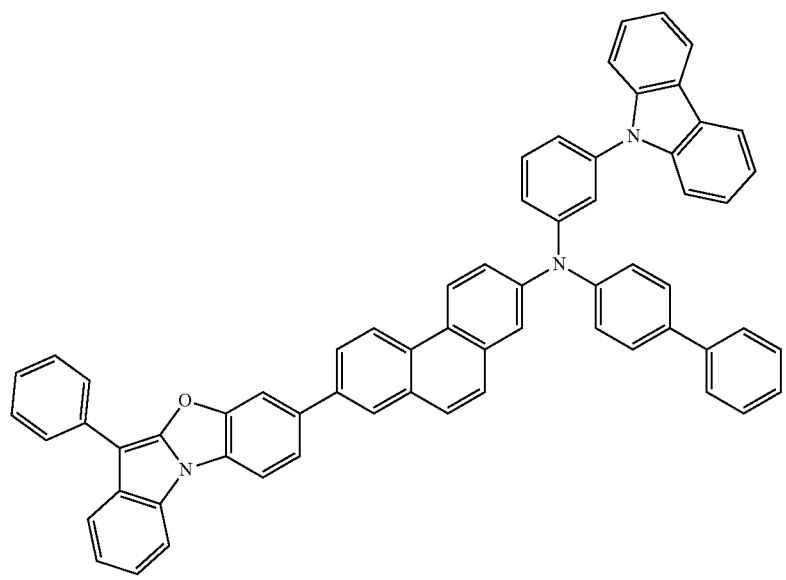
A43
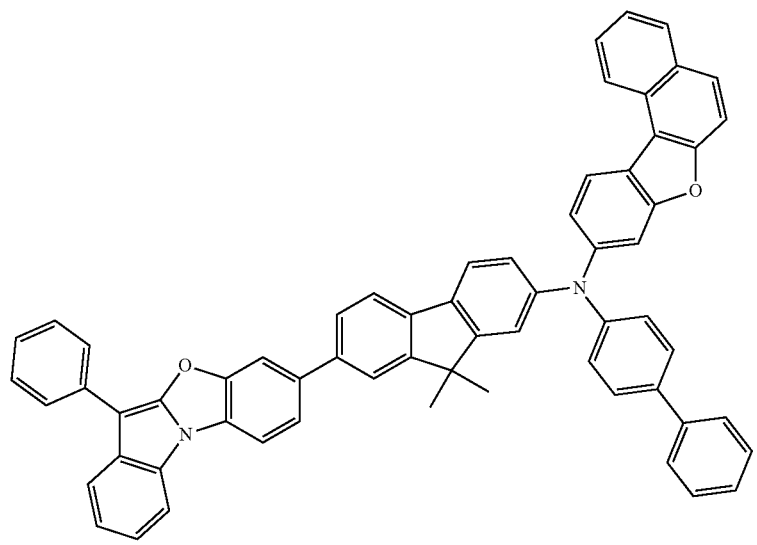

-continued
A44
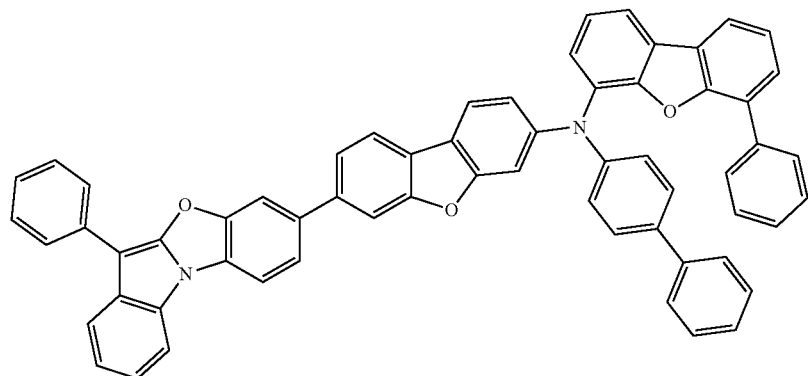
A45
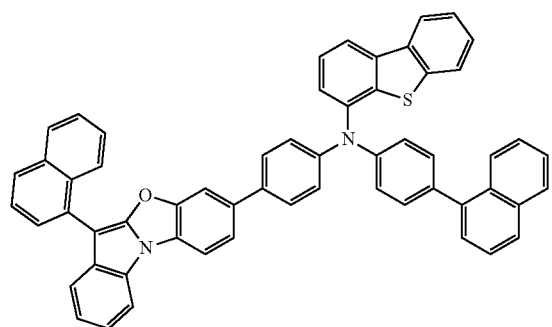
A46
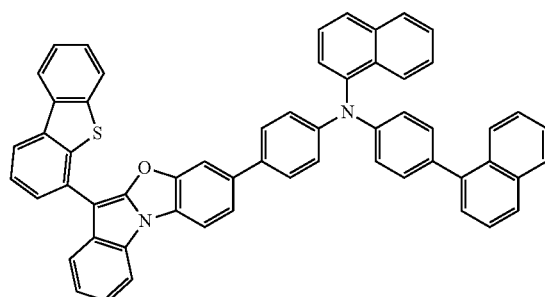
A47
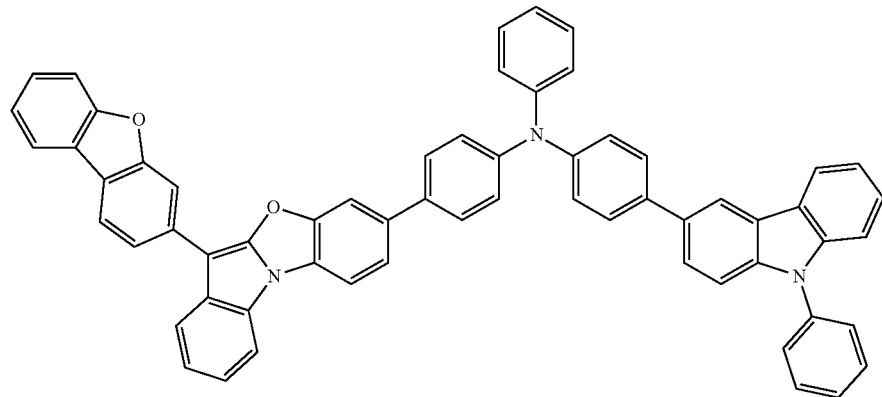
A48
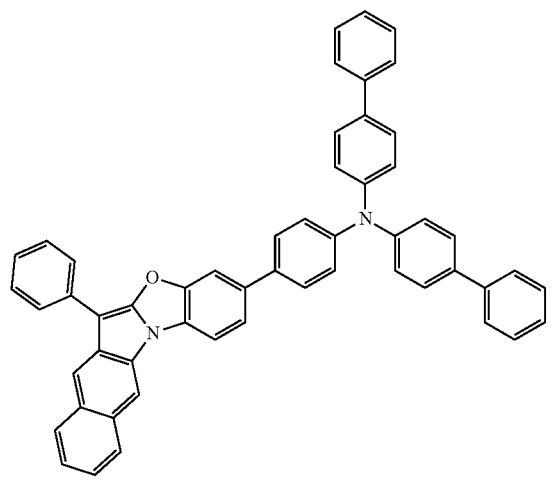
A49
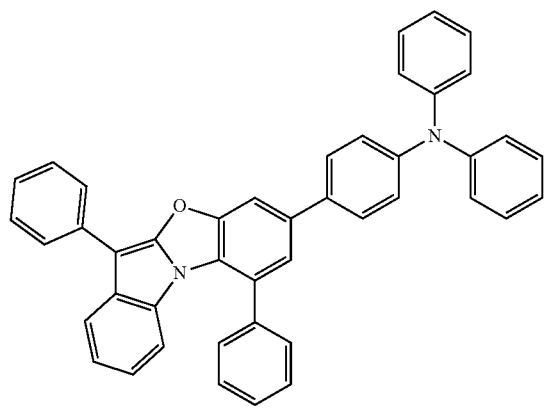

-continued
A50
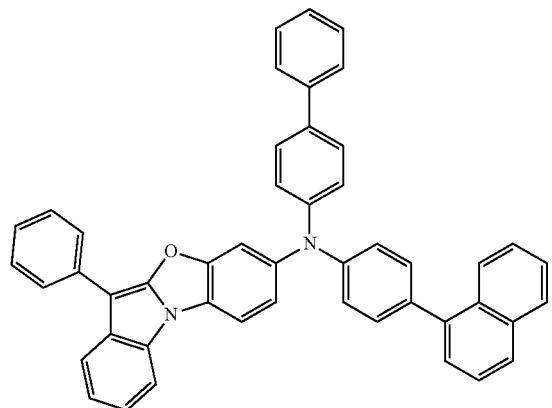
A51
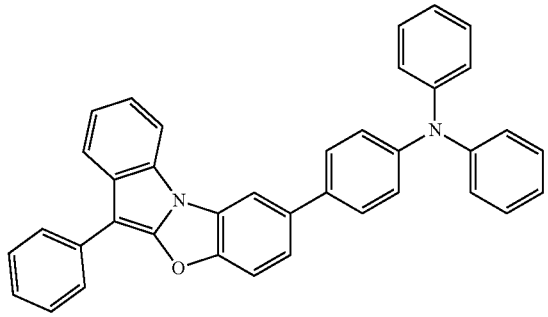
A52
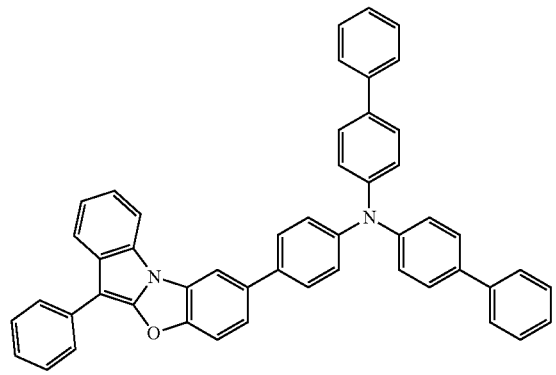
A53
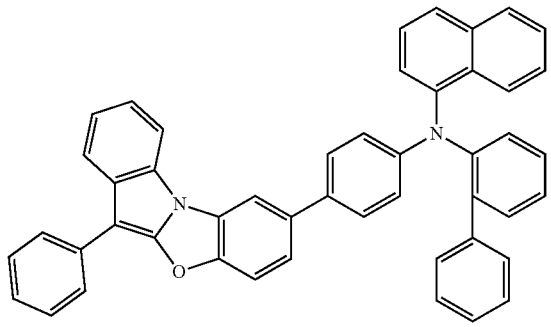
A54
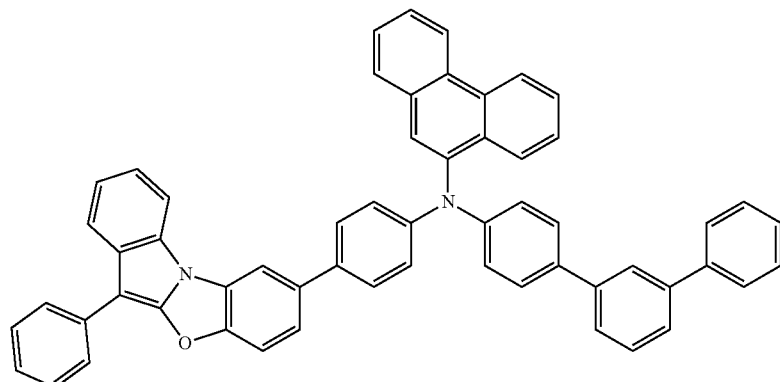
A55
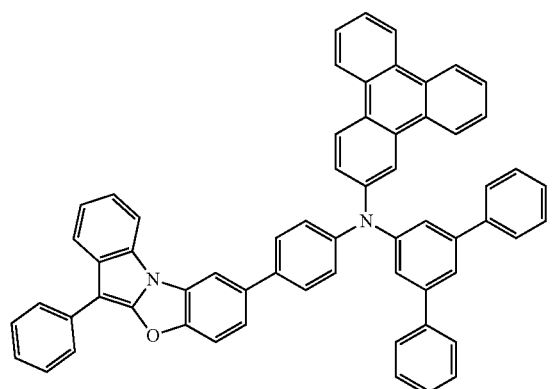
A56
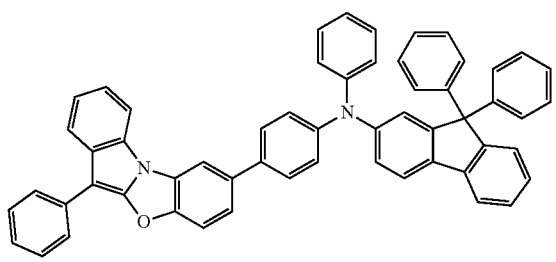

-continued
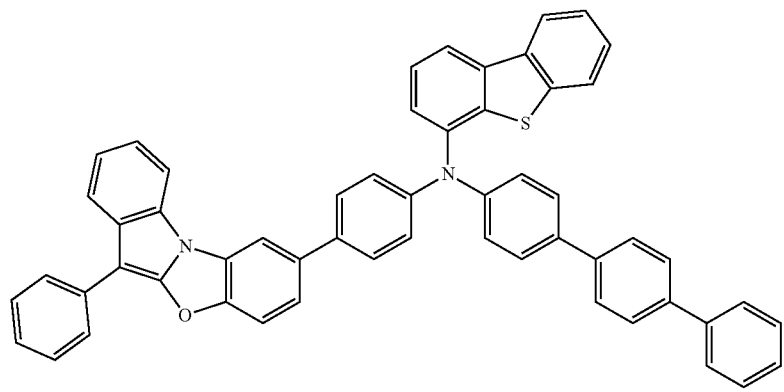
A57
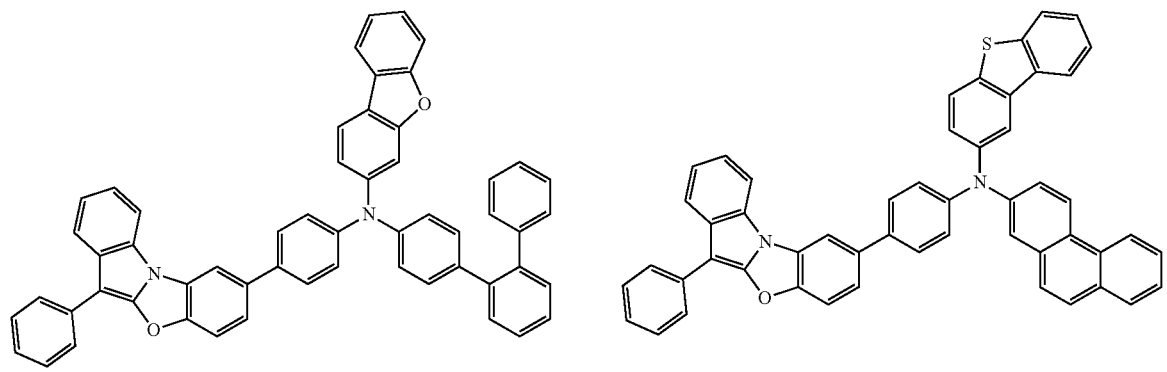
A58  A59
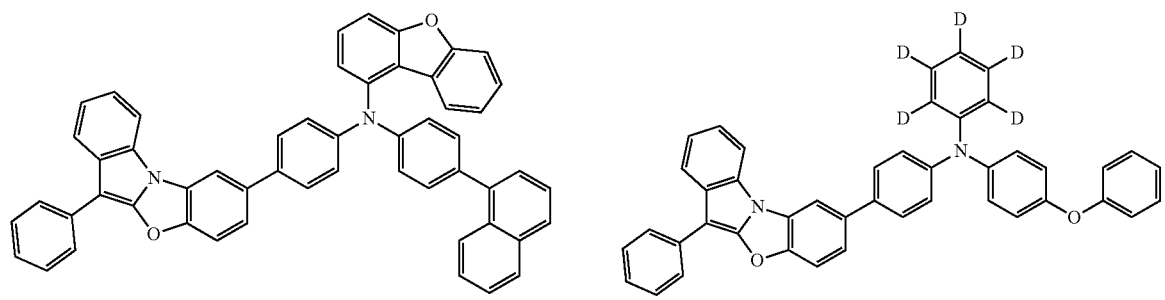
A61  A60
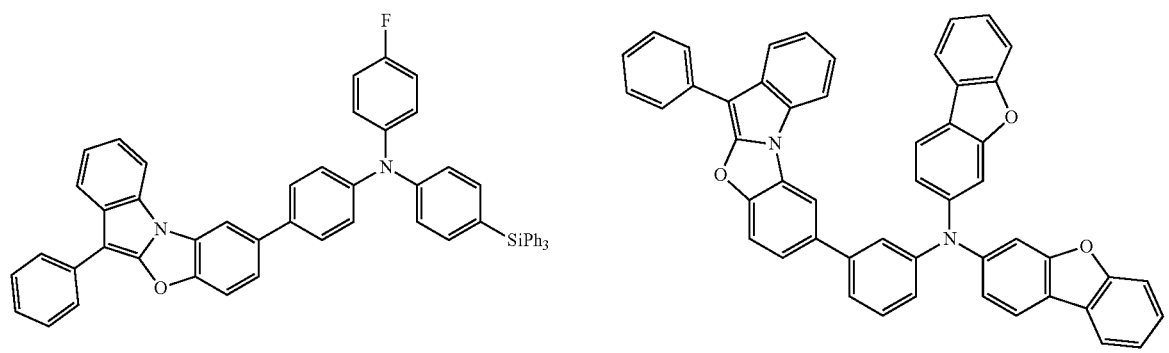
A62  A63

-continued
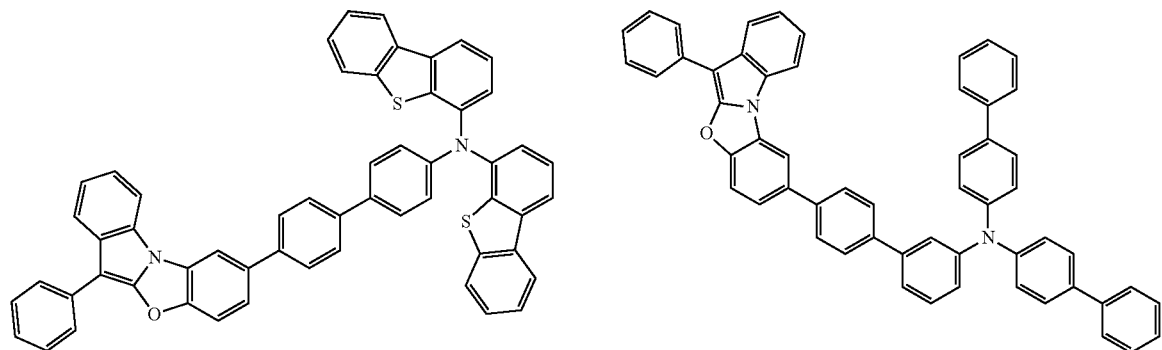
A64
A65
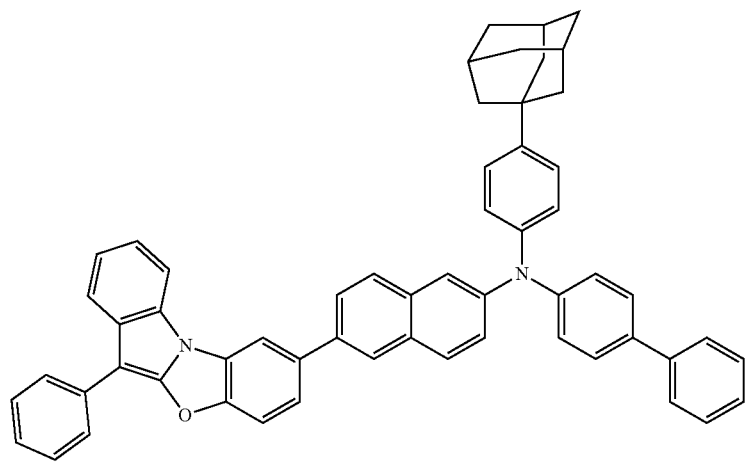
A66
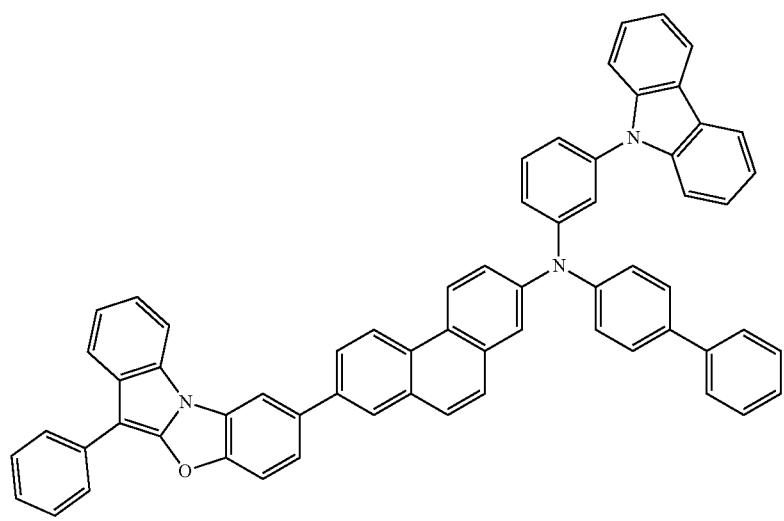
A67

-continued
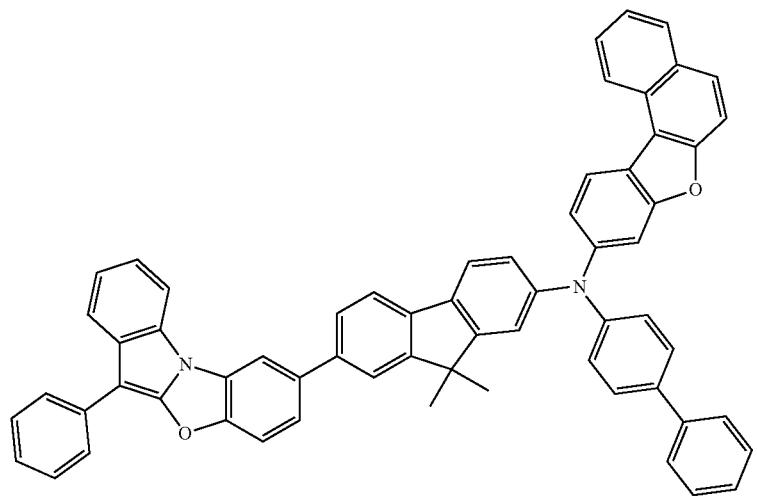
A68
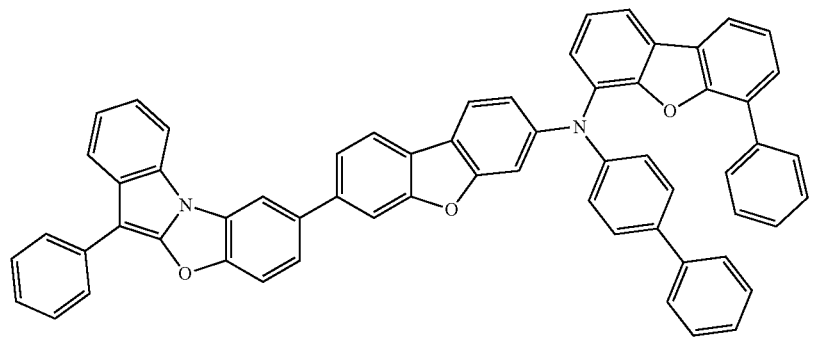
A69
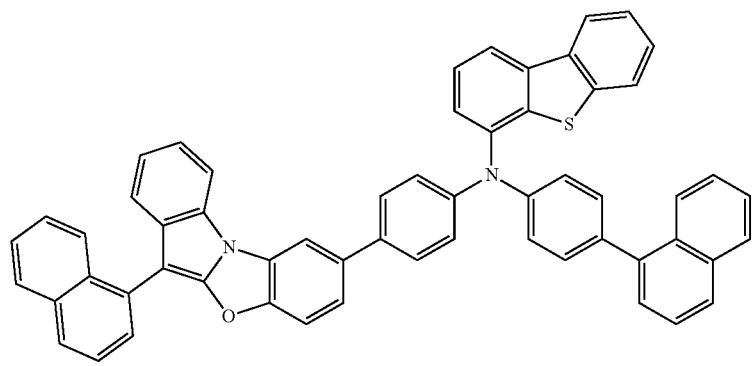
A70
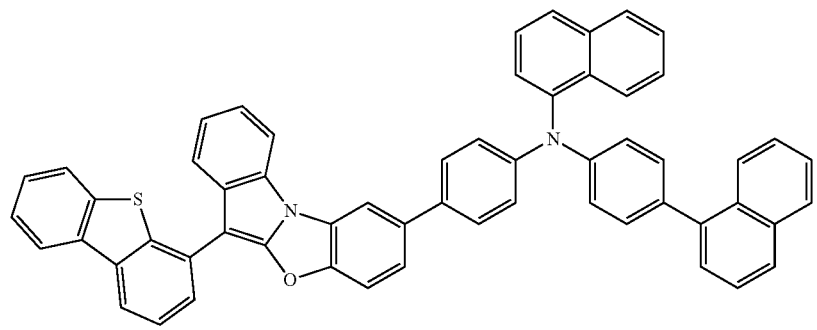
A71

-continued
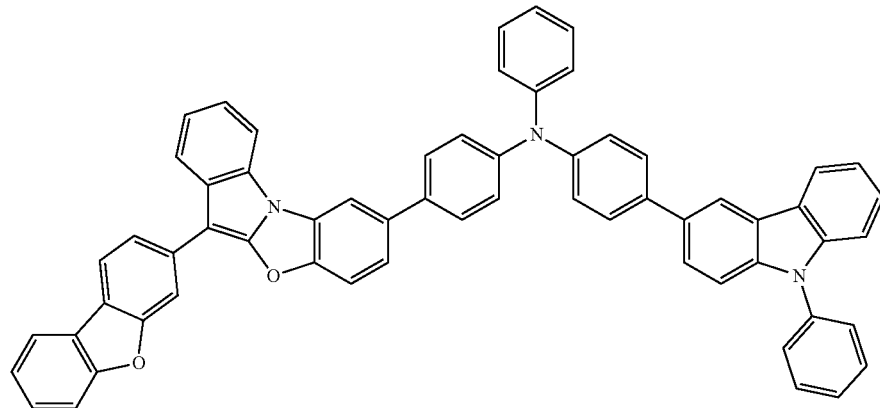
A72
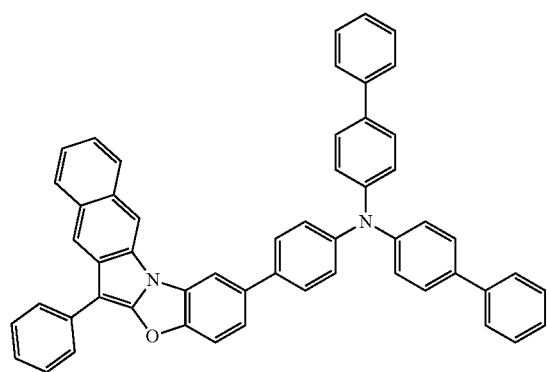
A73
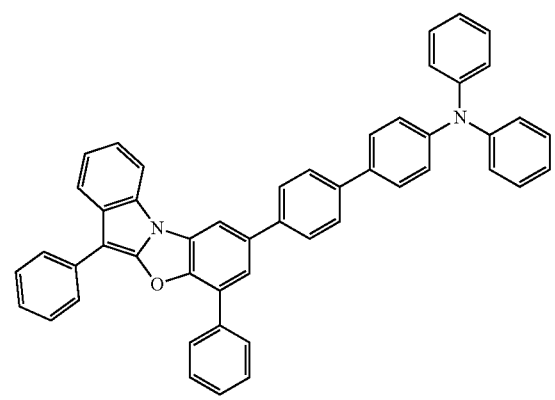
A74
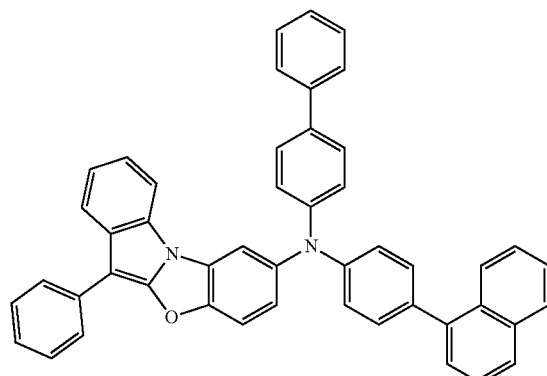
A75
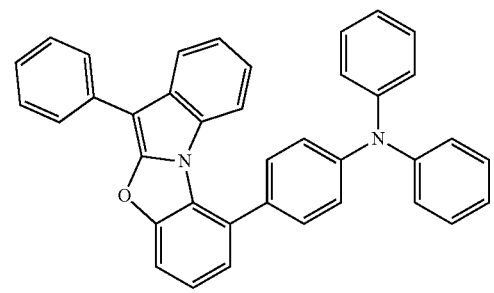
A76
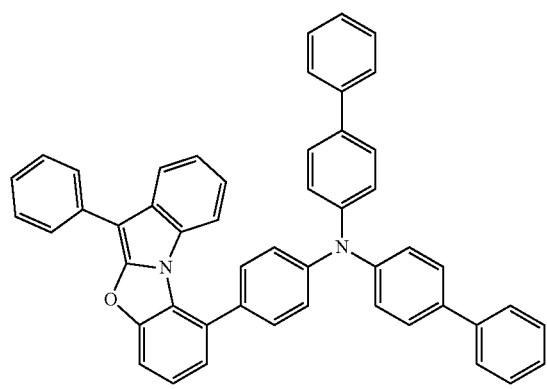
A77
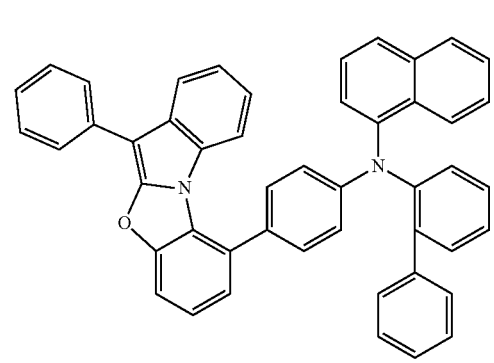
A78

-continued
A79
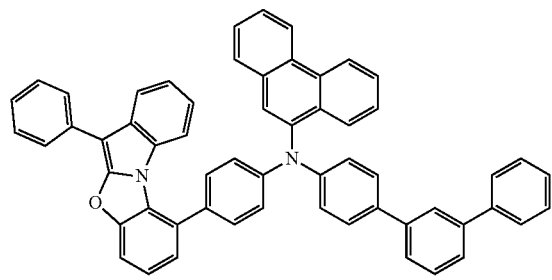
A80
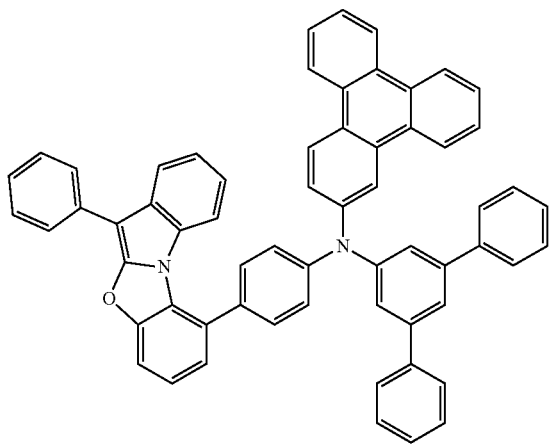
A81
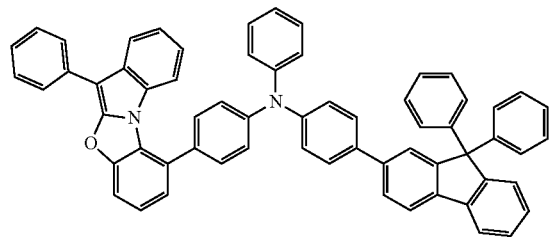
A82
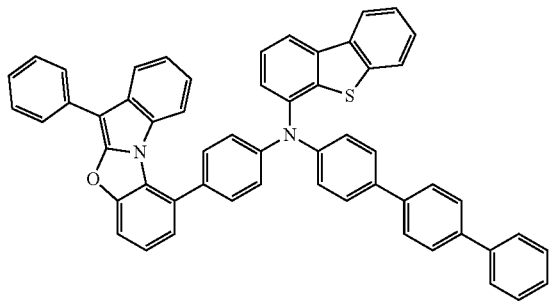
A83
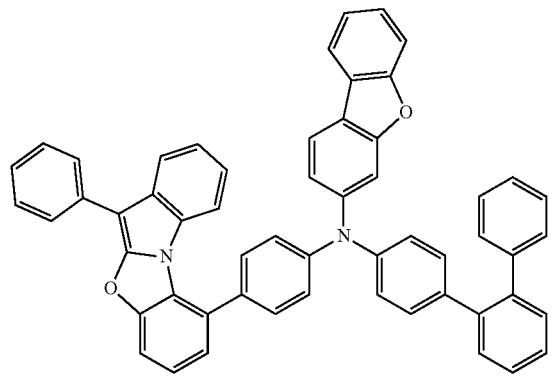
A84
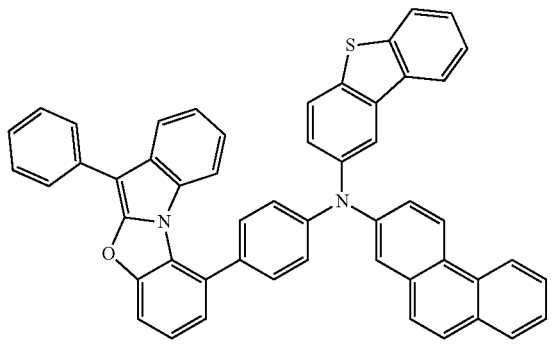
A85
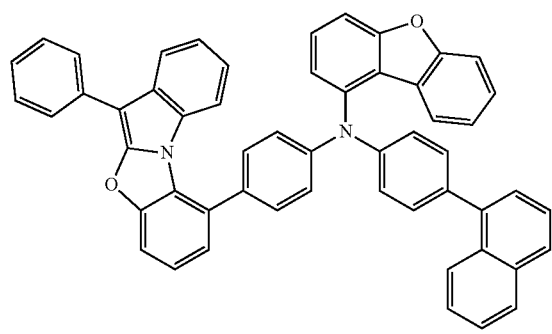
A86
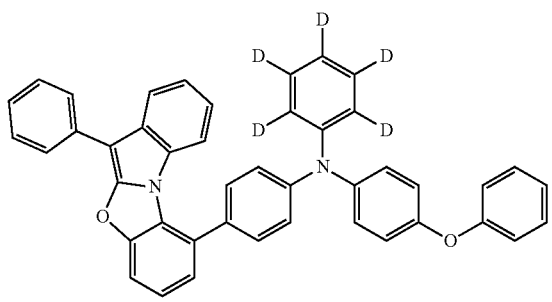

-continued
A87
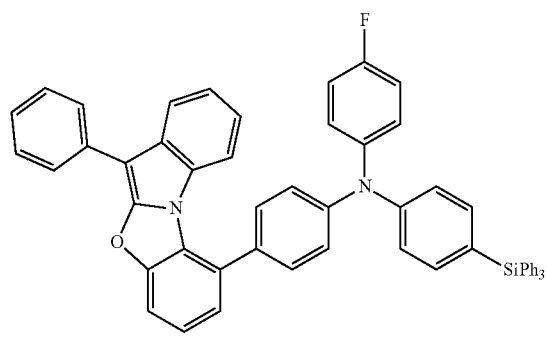
A88
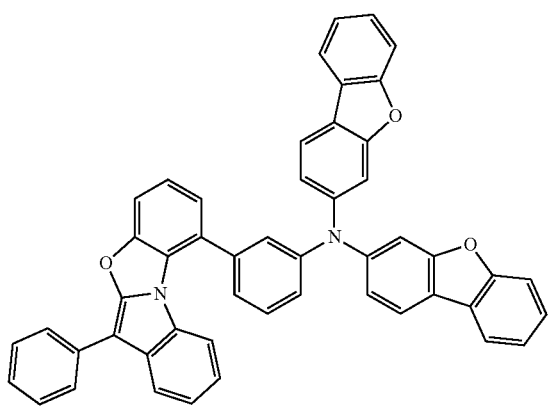
A89
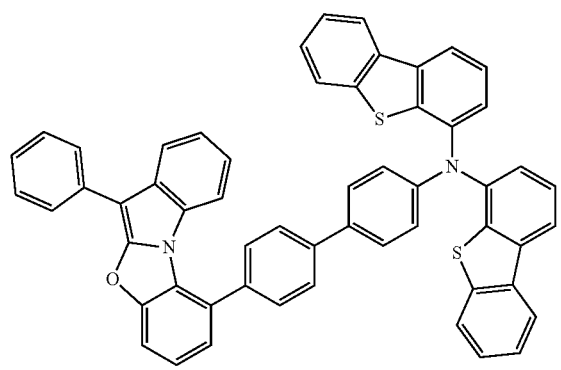
A90
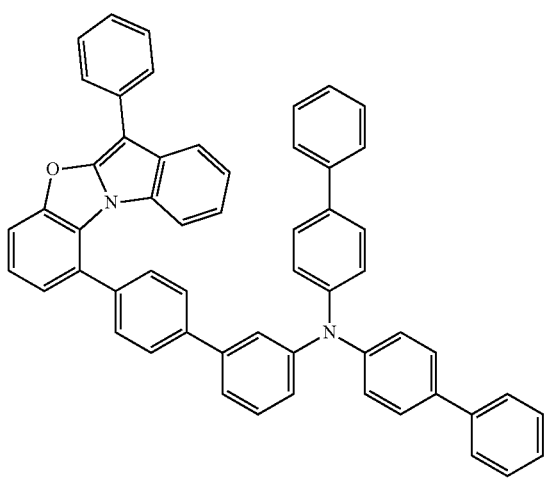
A91
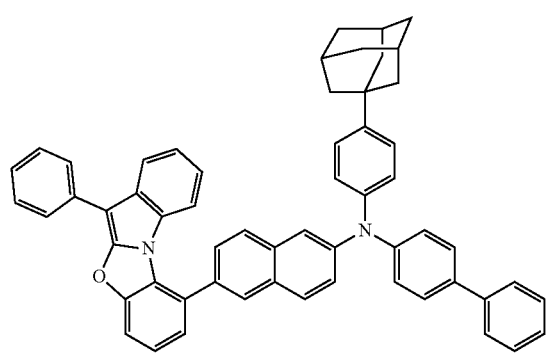
A92
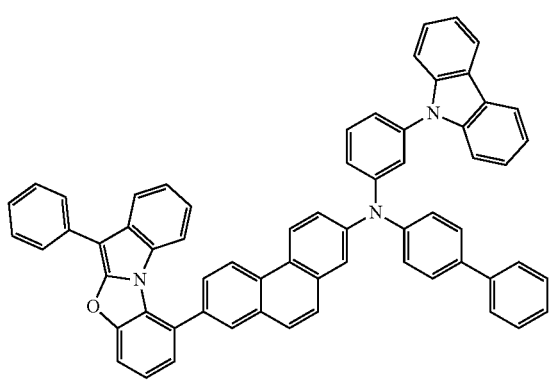

-continued
A93
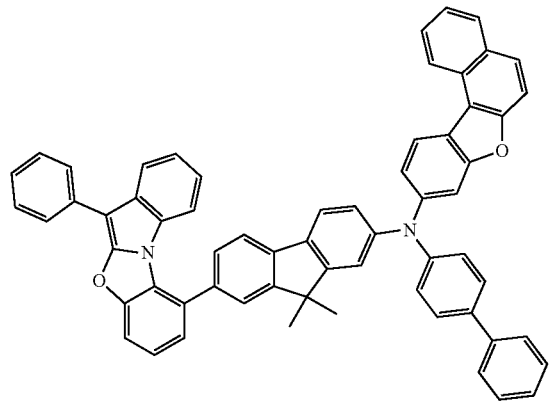
A94
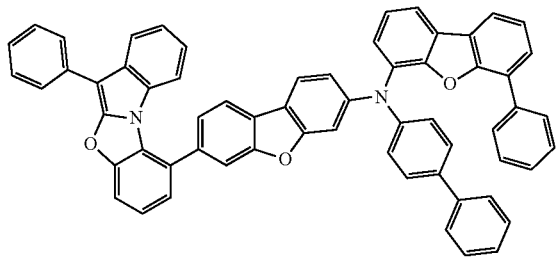
A95
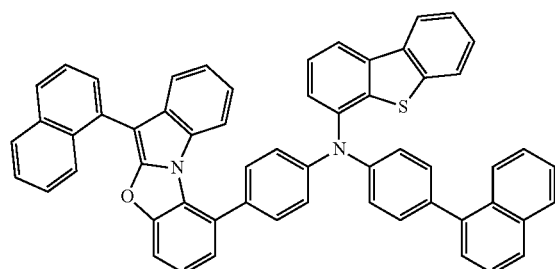
A96
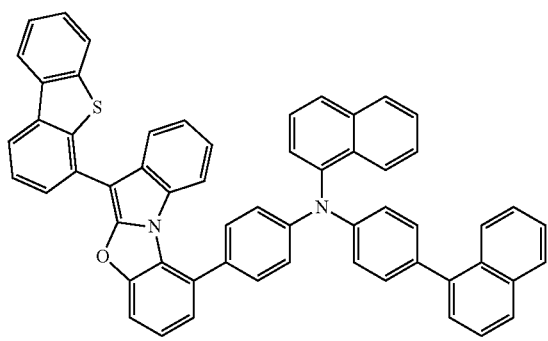
A97
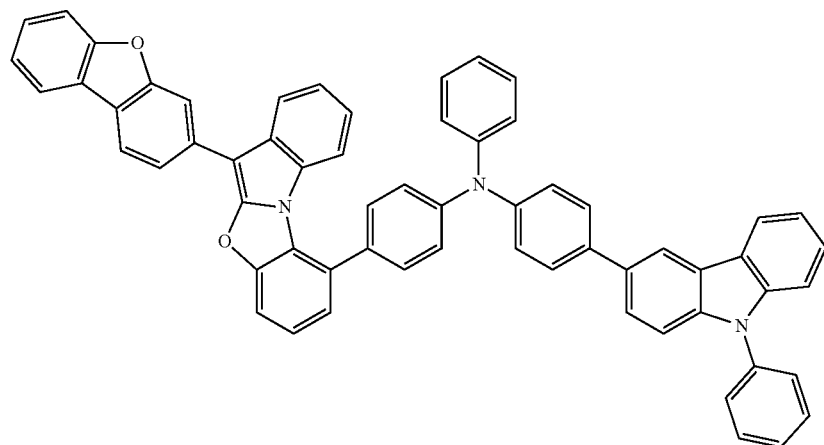
A98
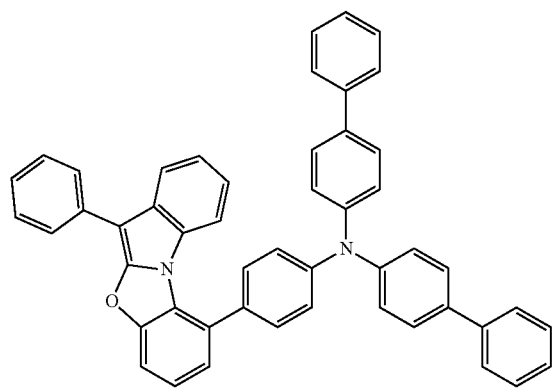
A99
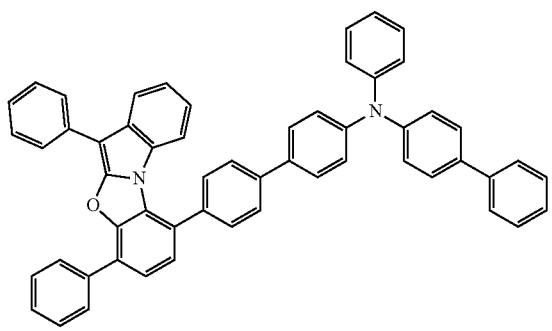

-continued
A100
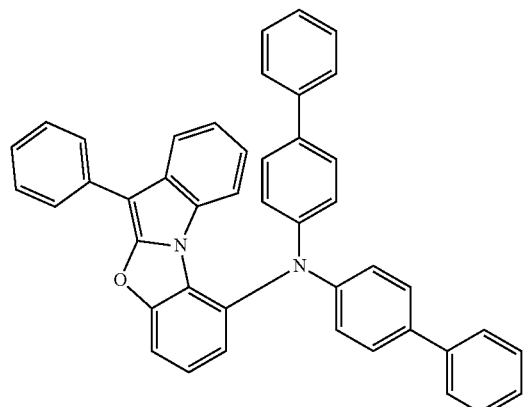
A101
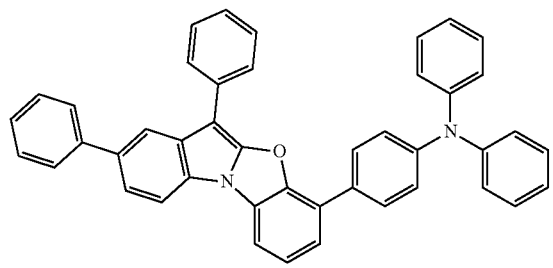
A102
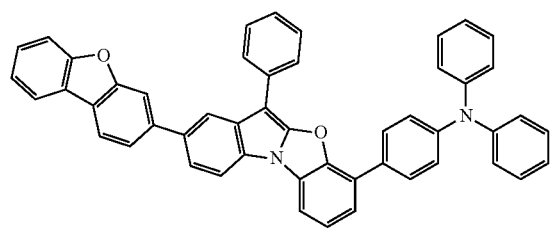
A103
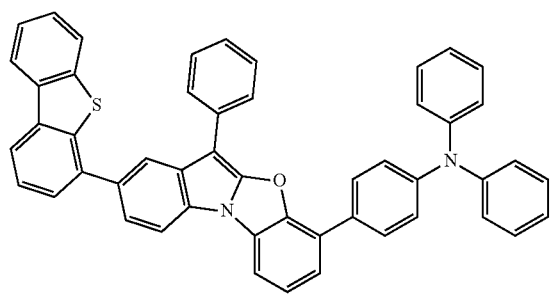
A104
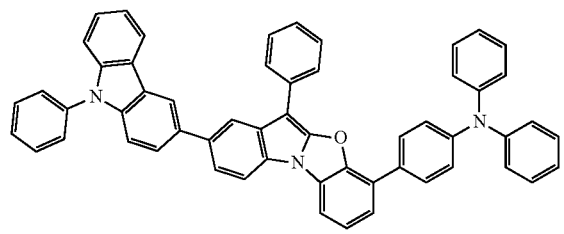
A105
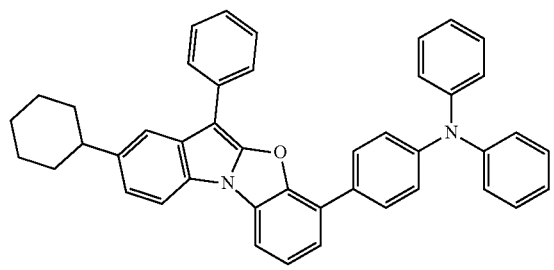
A106
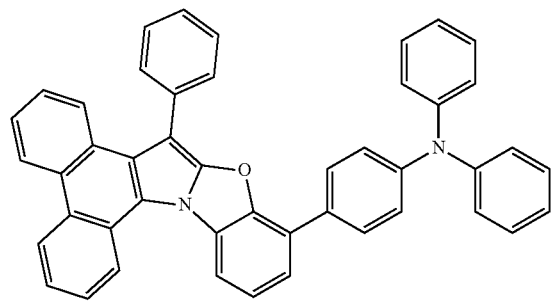
A107
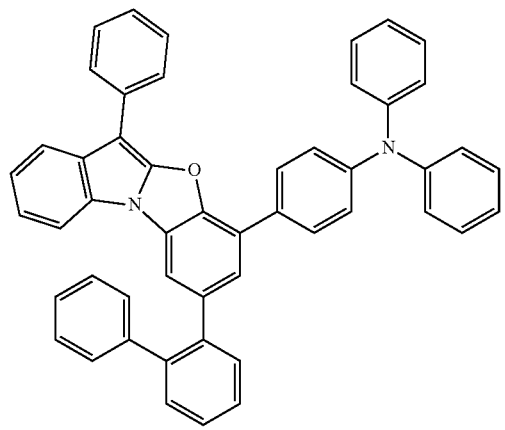

-continued
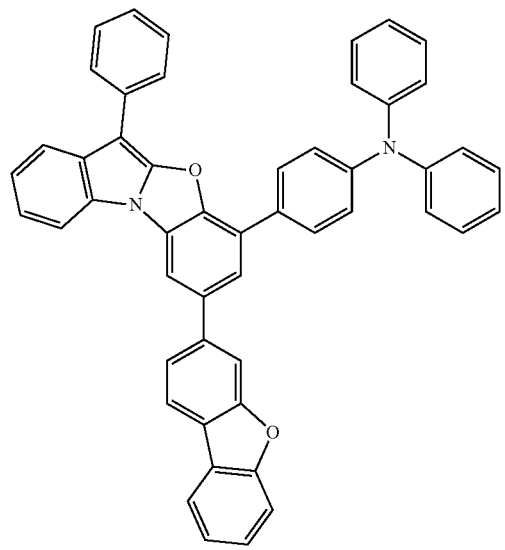
A108
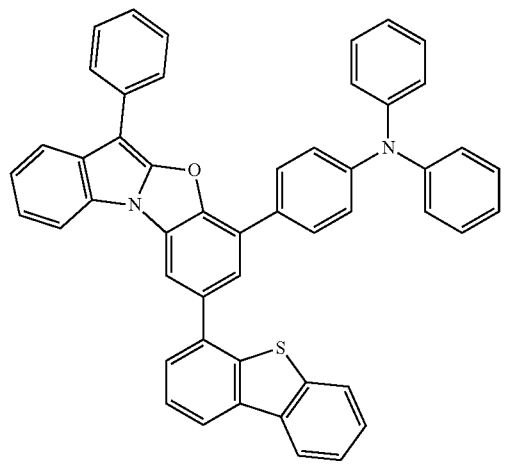
A109
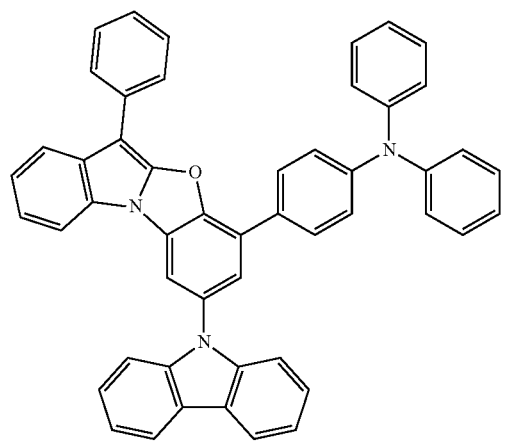
A110
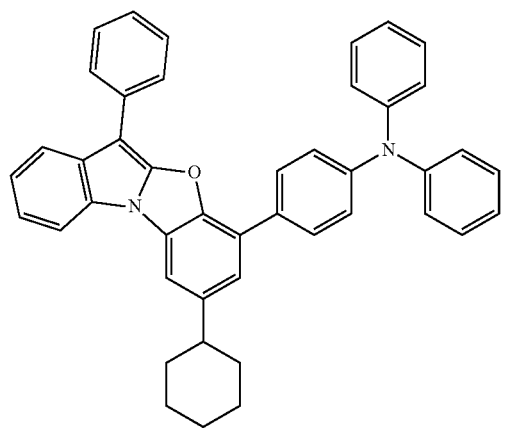
A111
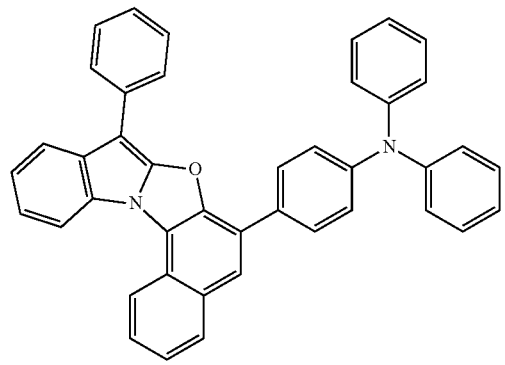
A112

-continued
[Compound Group B]
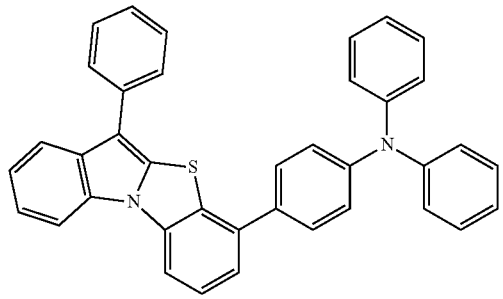
B1
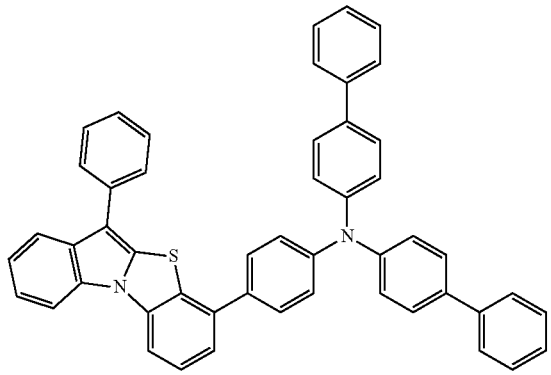
B2
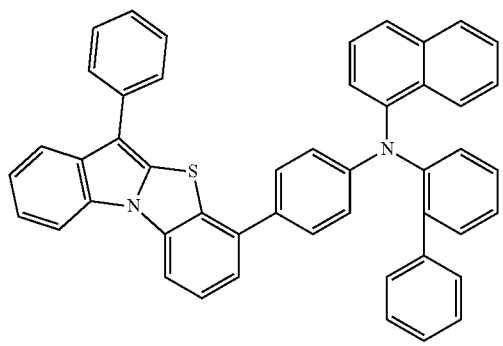
B3
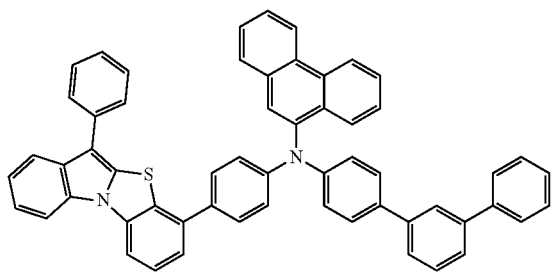
B4
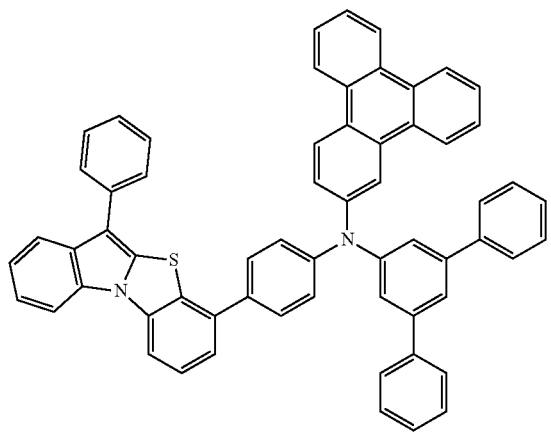
B5
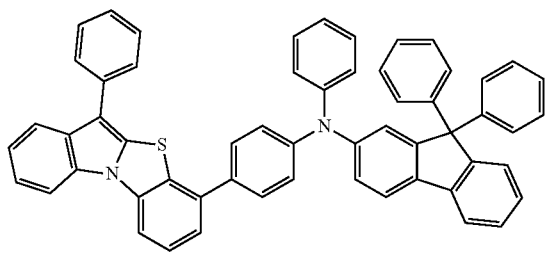
B6
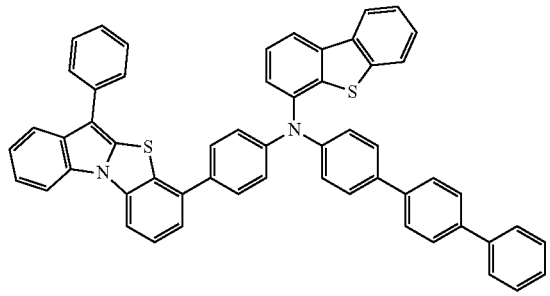
B8
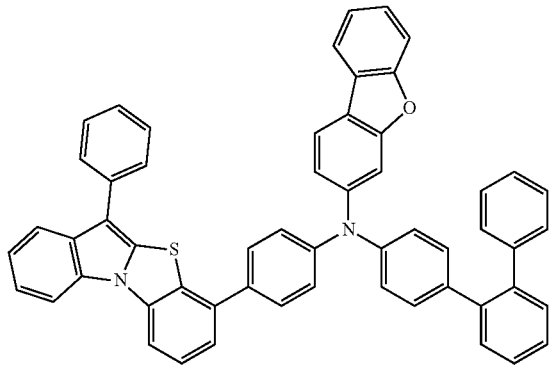
B9

-continued
B10
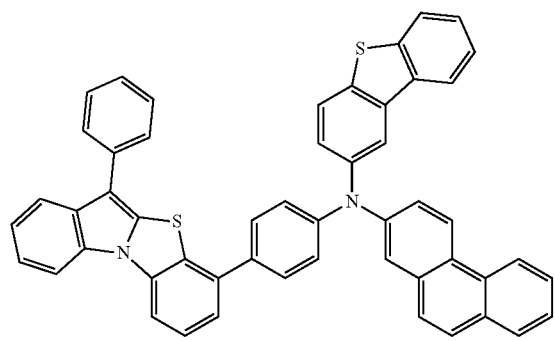
B11
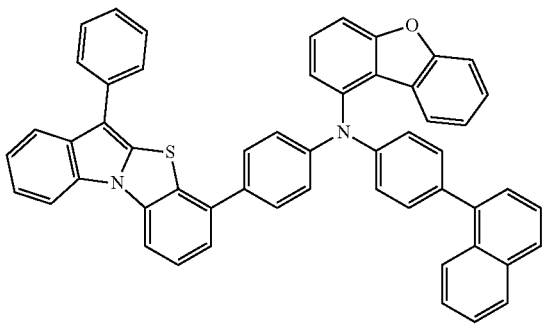
B12
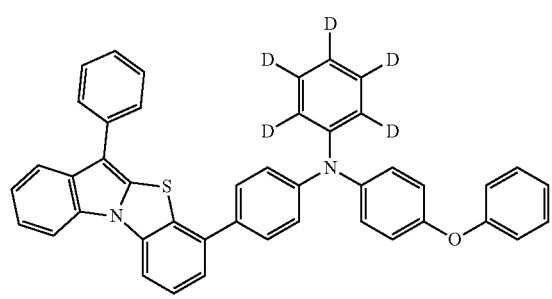
B13
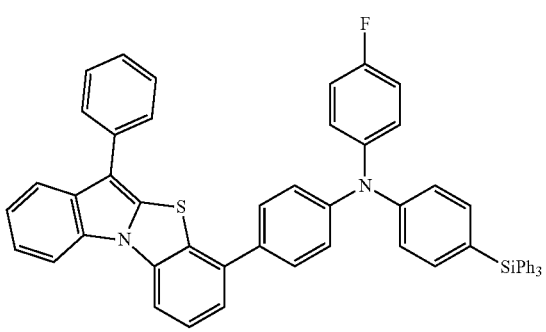
B13
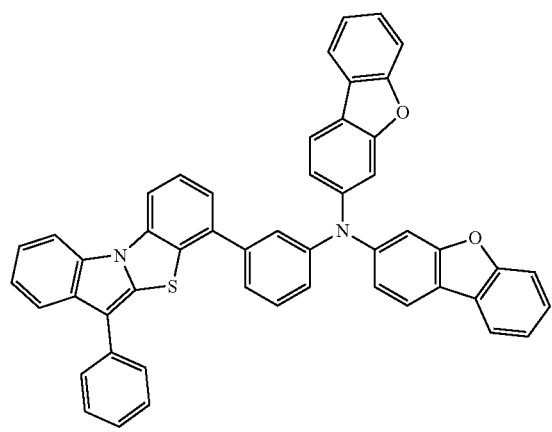
B14
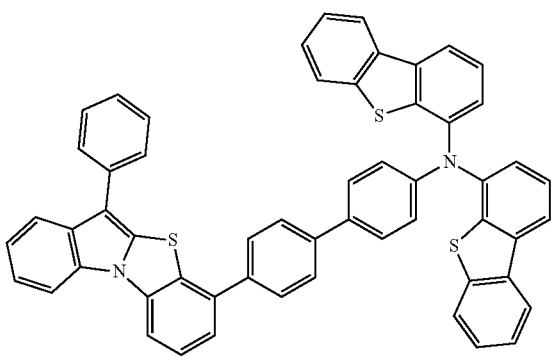
B15
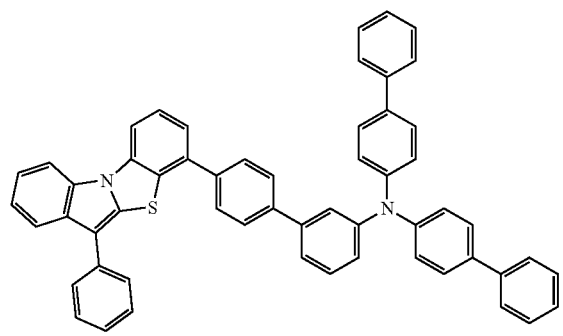
B16
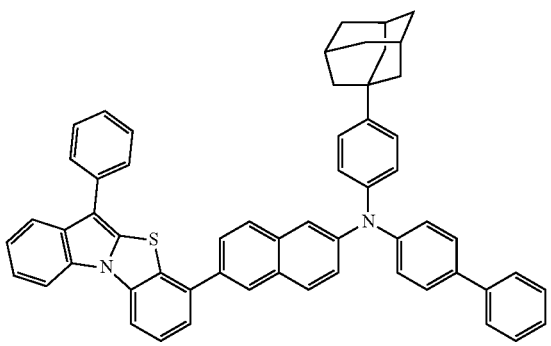

-continued
B17
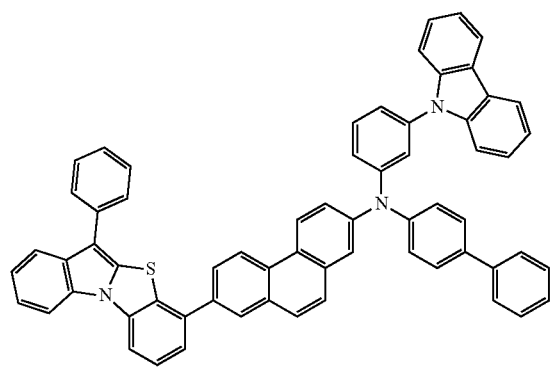
B18
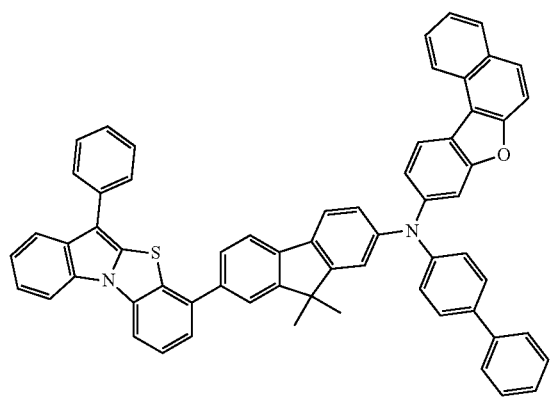
B19
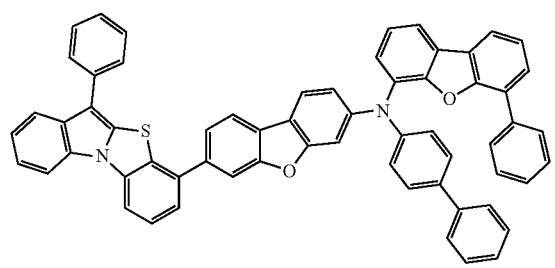
B20
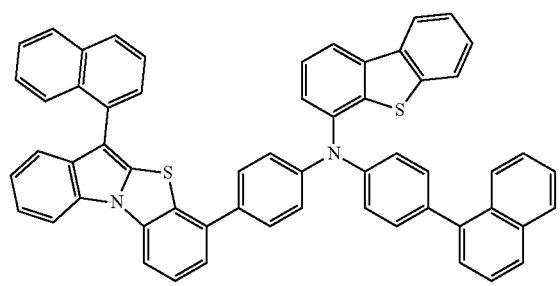
B21
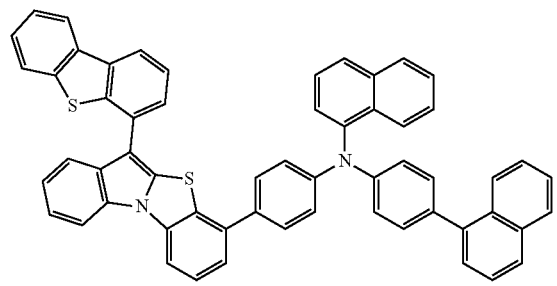
B22
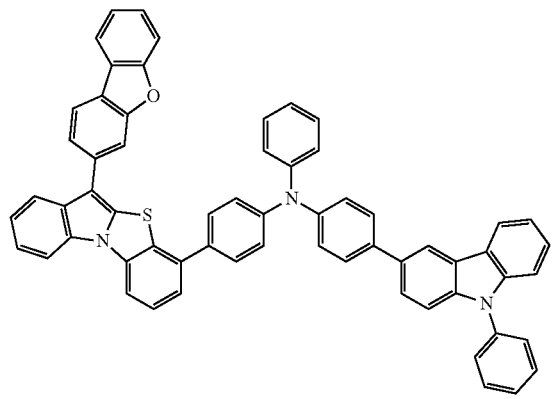
B23
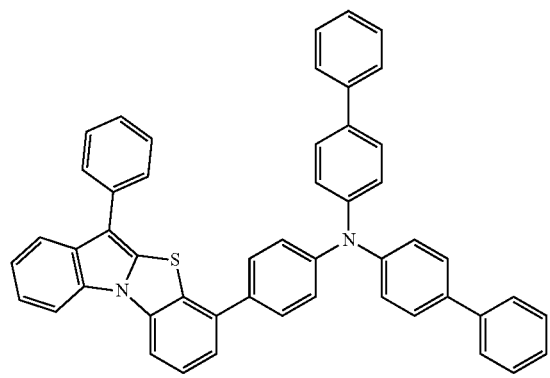
B24
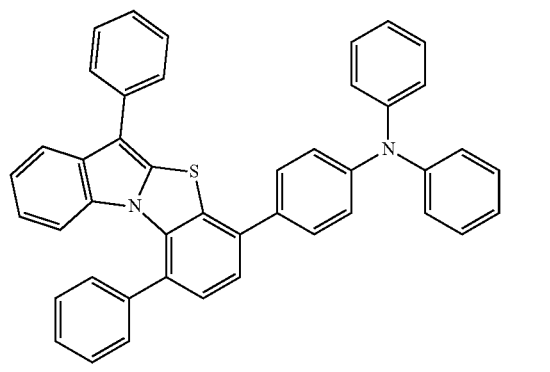

-continued
B25
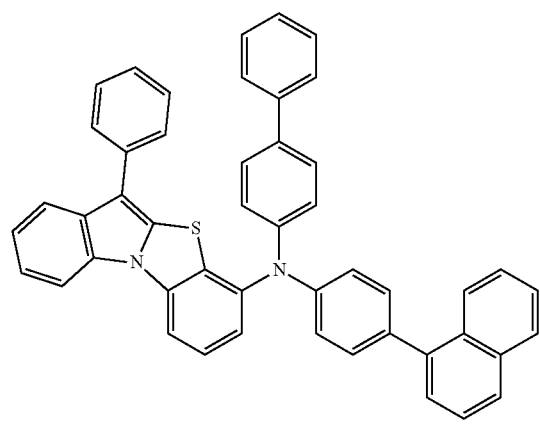
B26
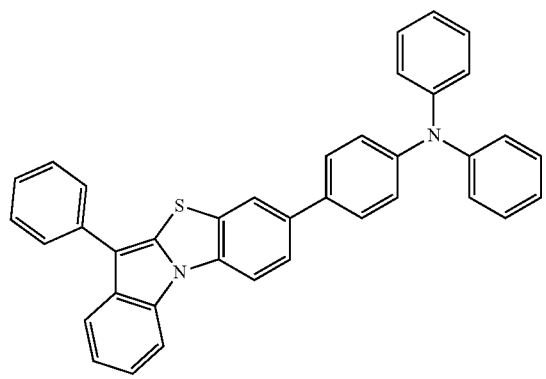
B27
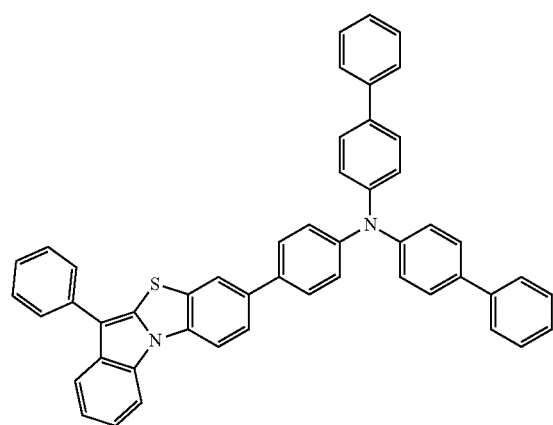
B28
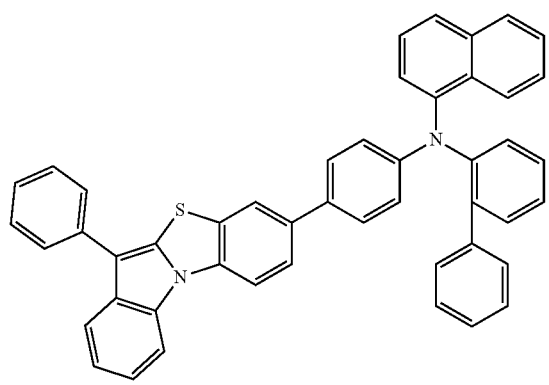
B29
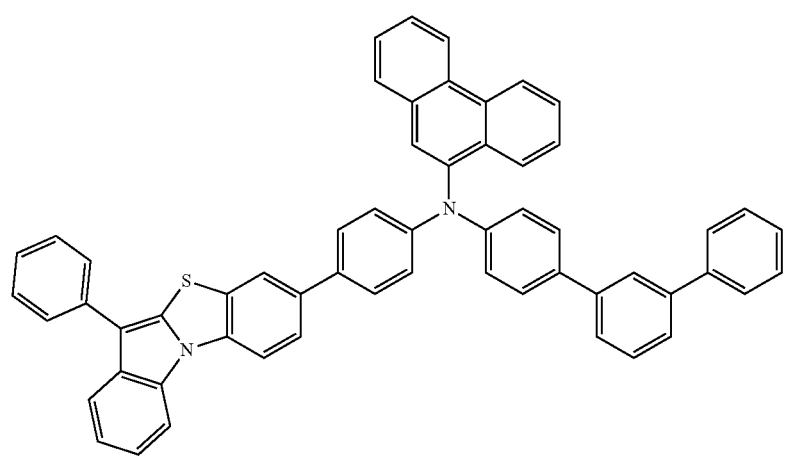

-continued
B30
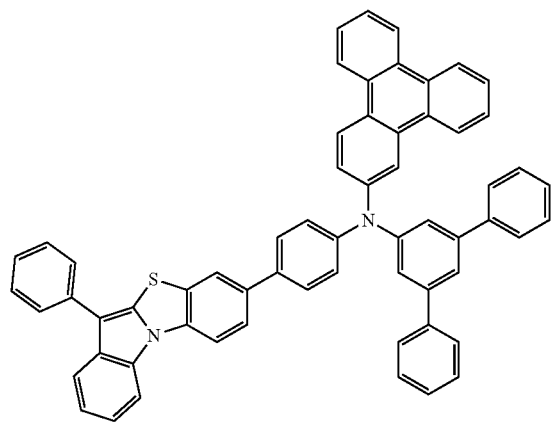
B31
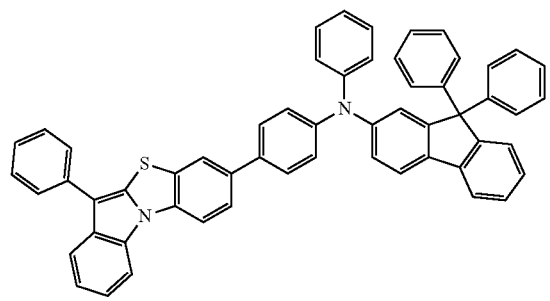
B32
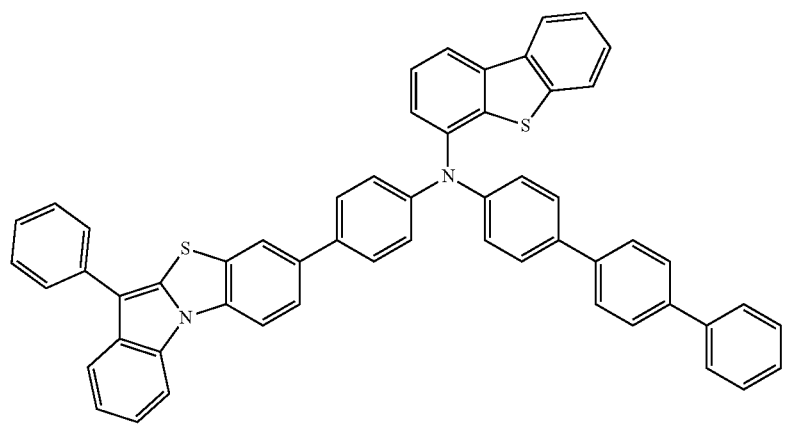
B33
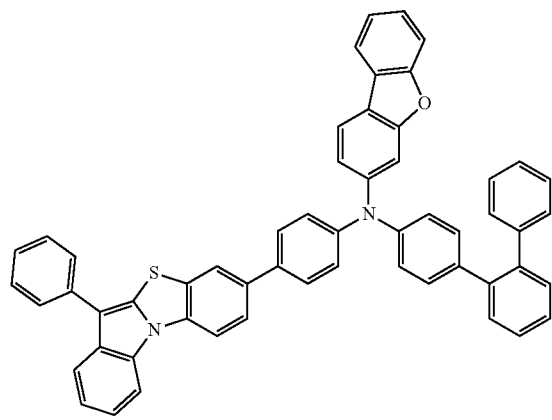
B34
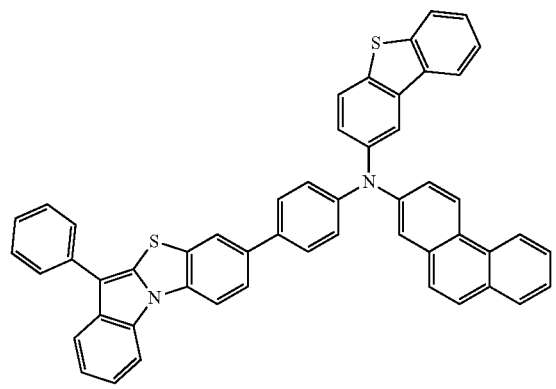

-continued
B35
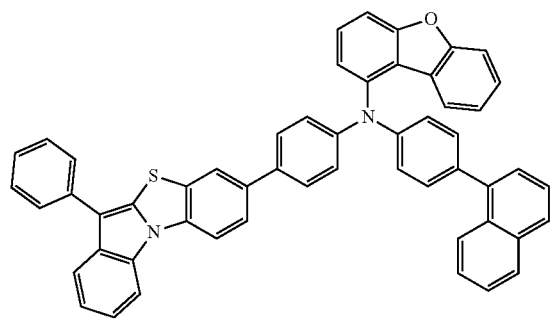
B36
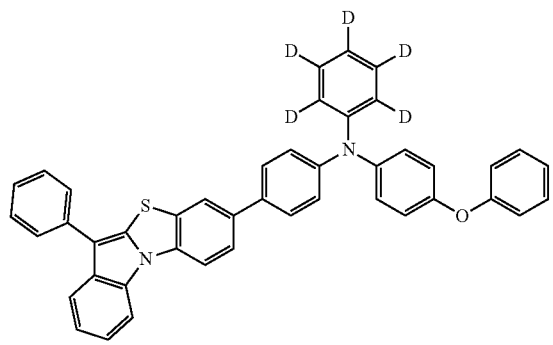
B37
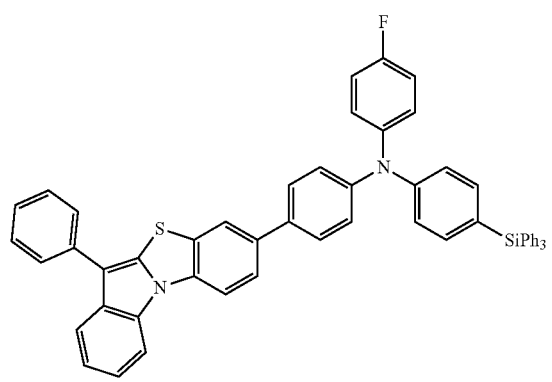
B38
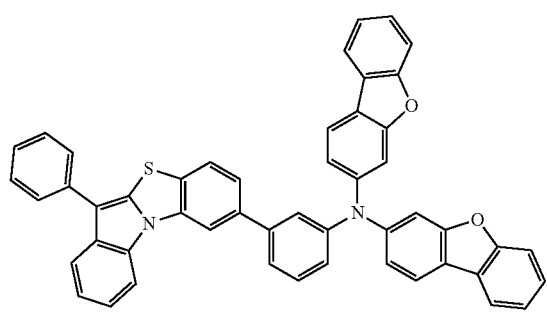
B39
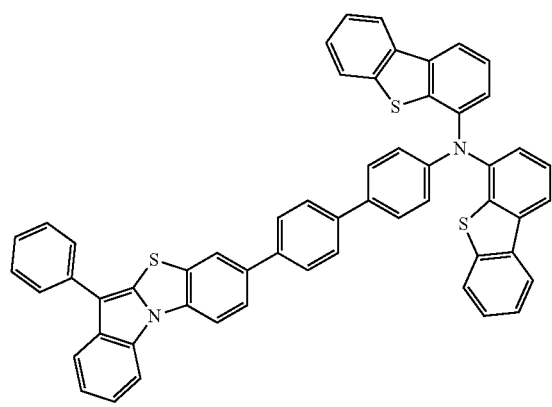
B40
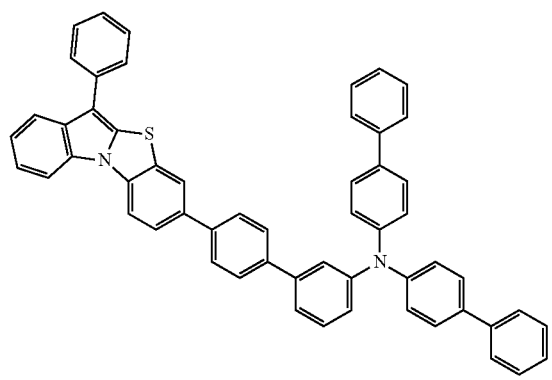

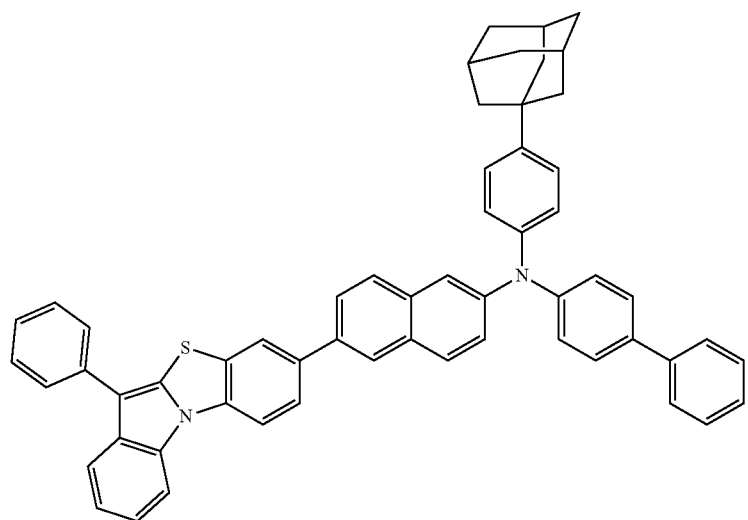
B41
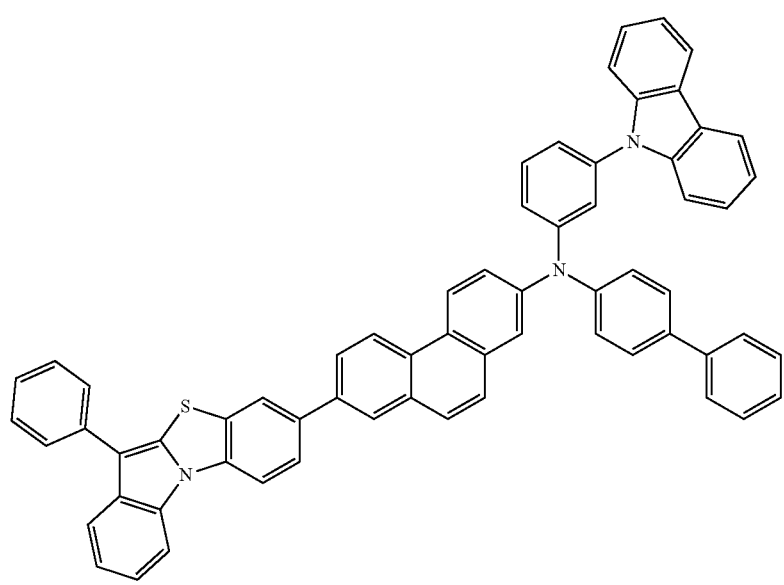
B42
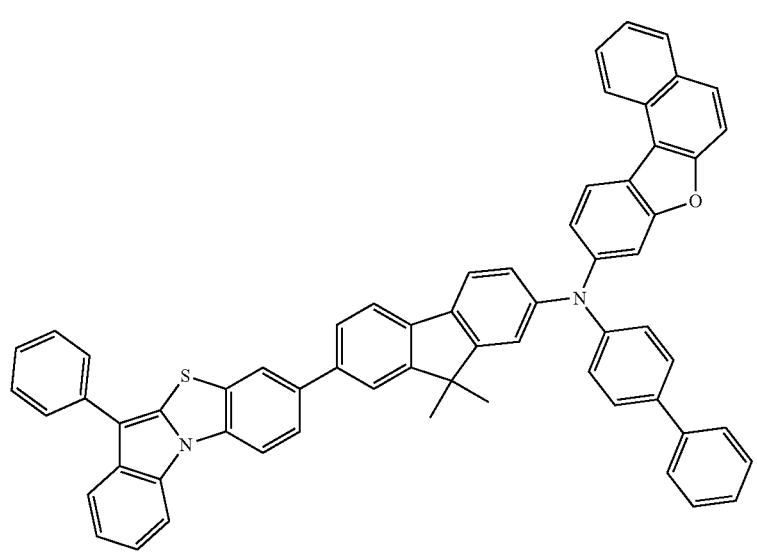
B43

-continued
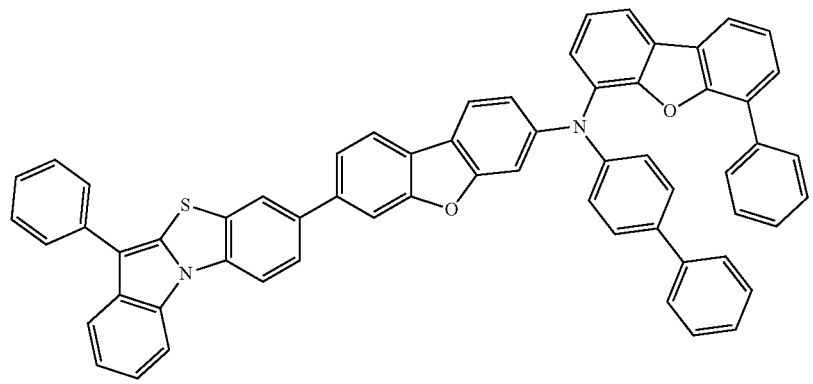
B44
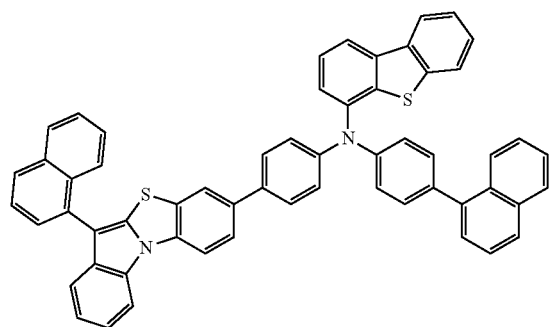
B45
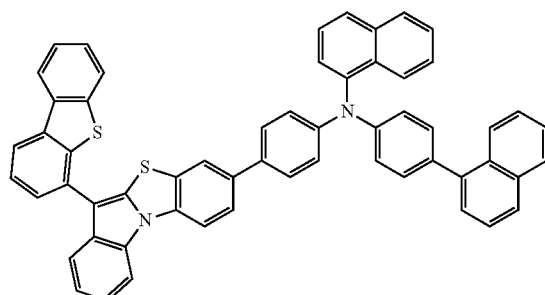
B46
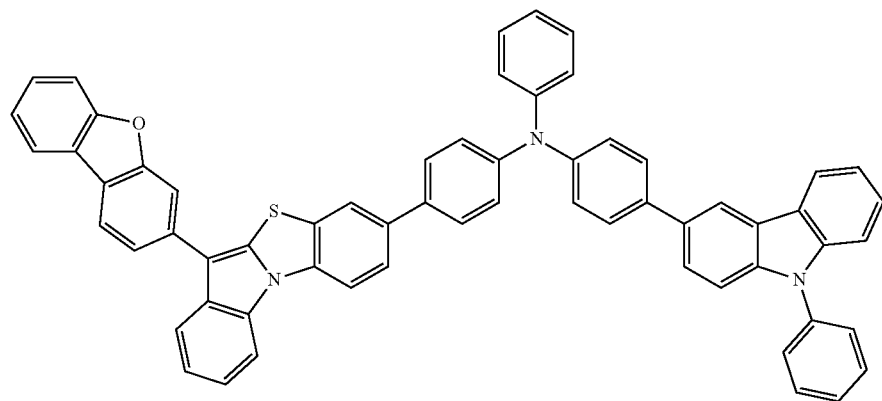
B47
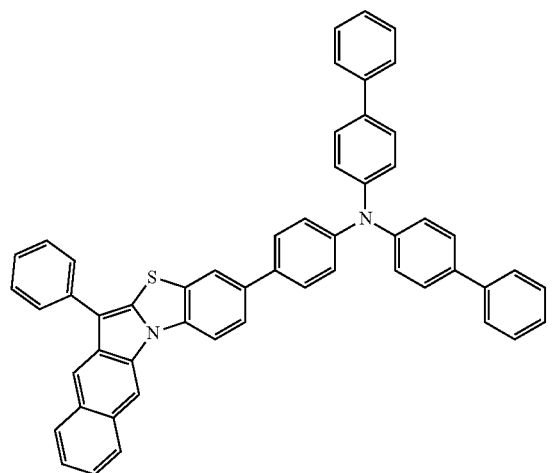
B48
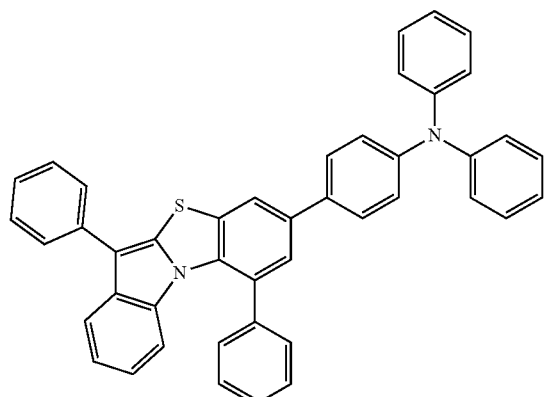
B49

-continued
B50
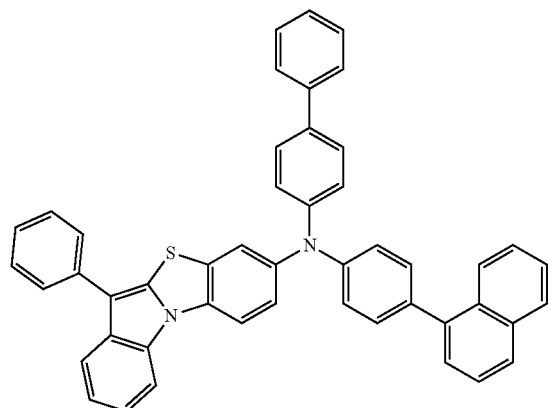
B51
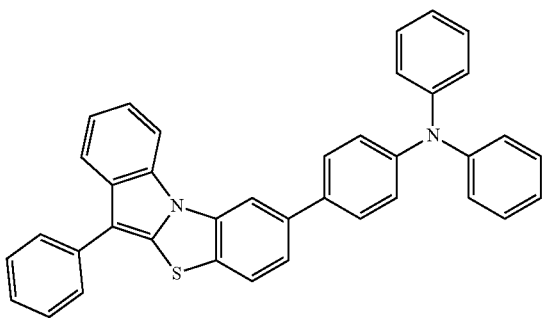
B52
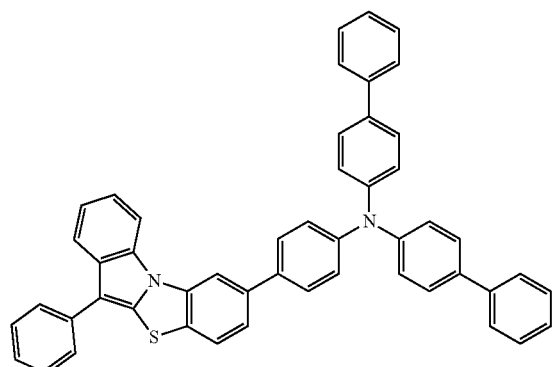
B53
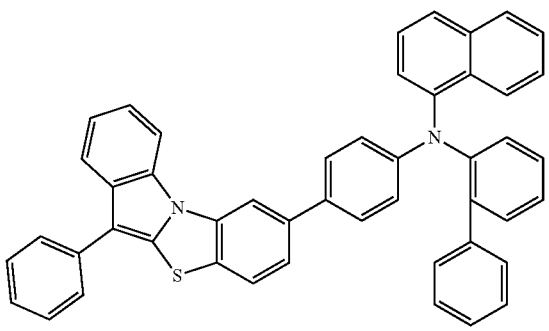
B54
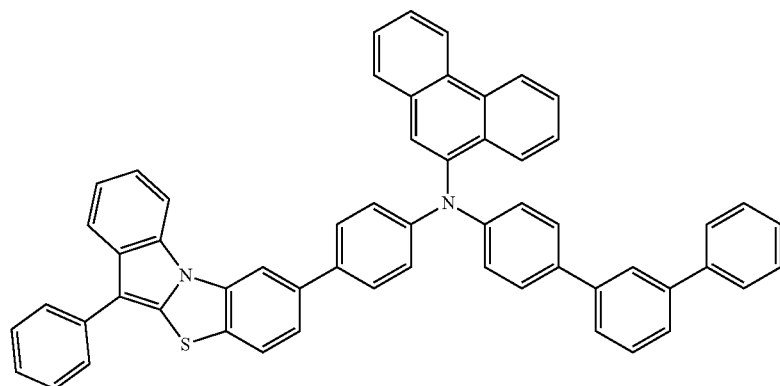
B55
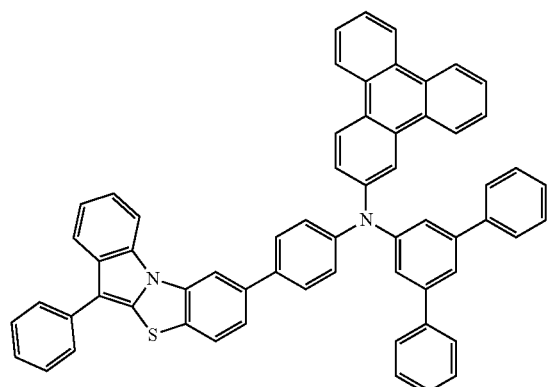
B56
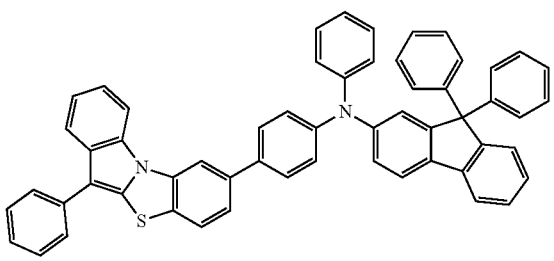

-continued
B57
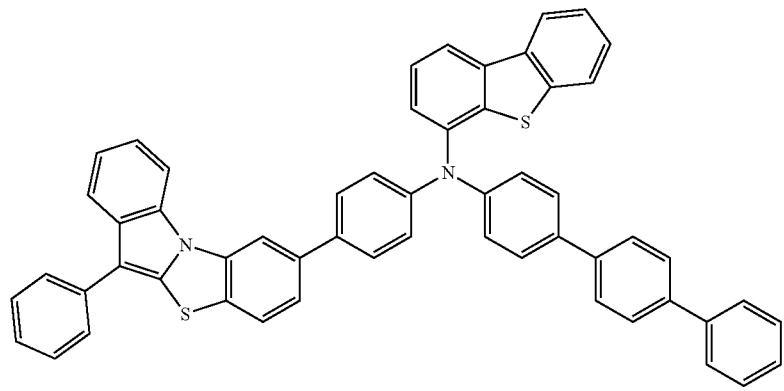
B58
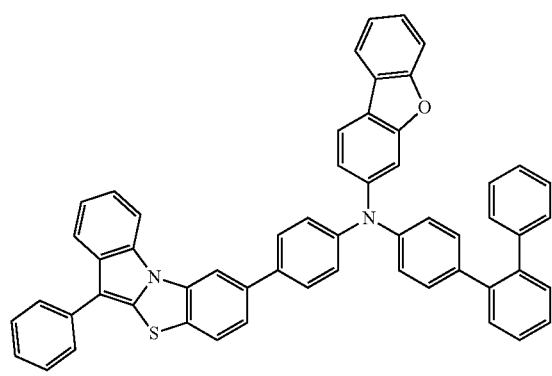
B59
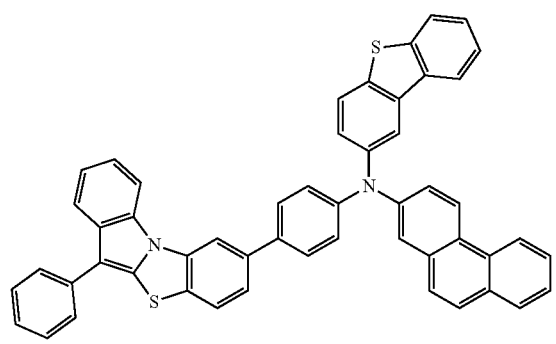
B60
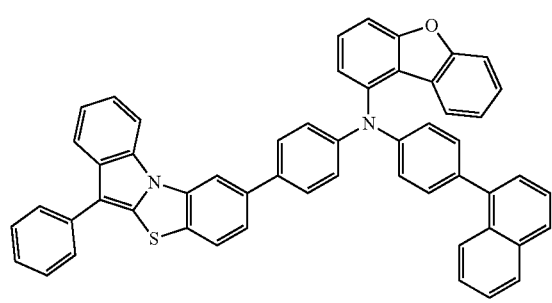
B61
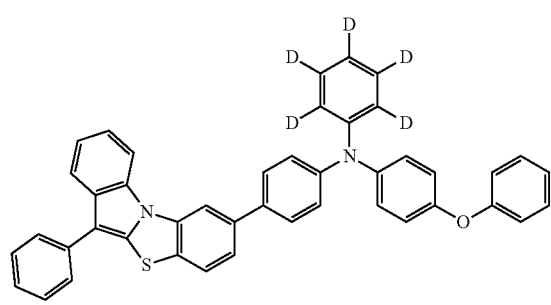
B62
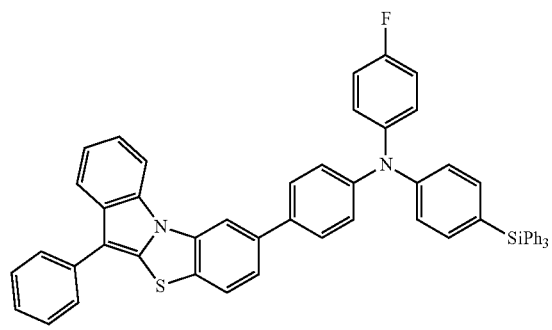
B63
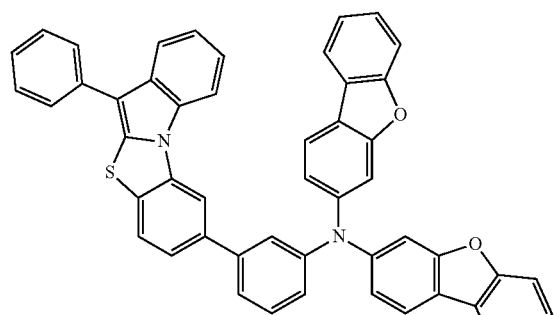

-continued
B64
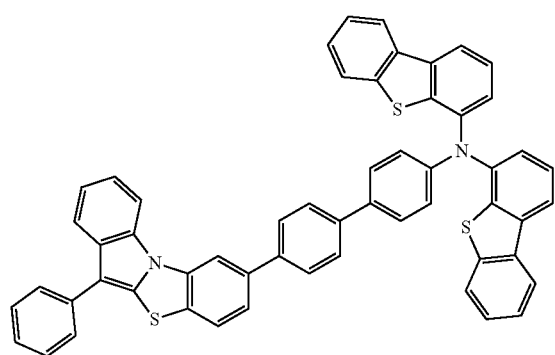
B65
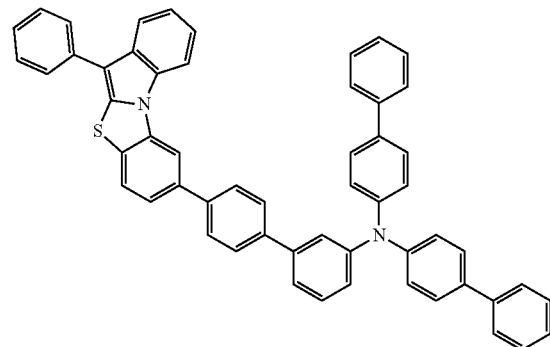
B66
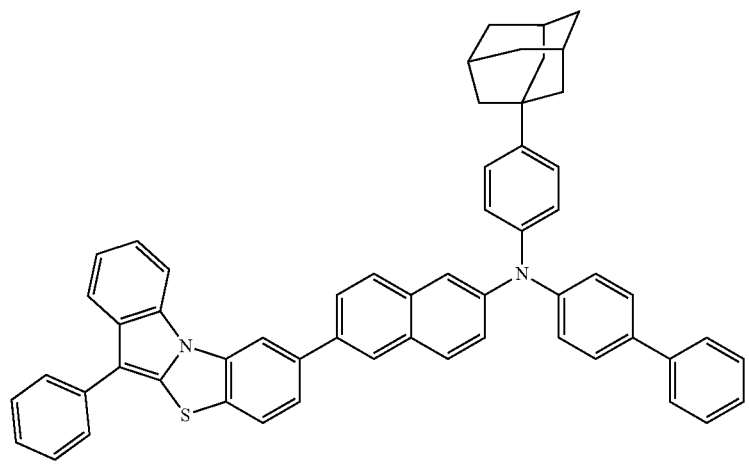
B67
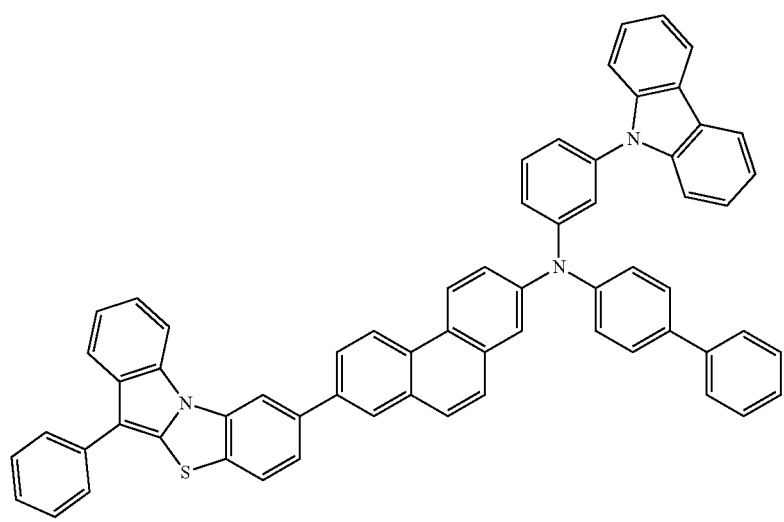

-continued
B68
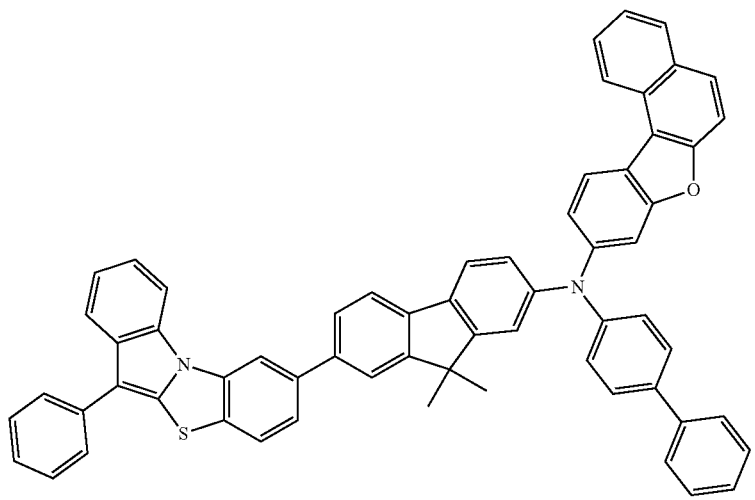
B69
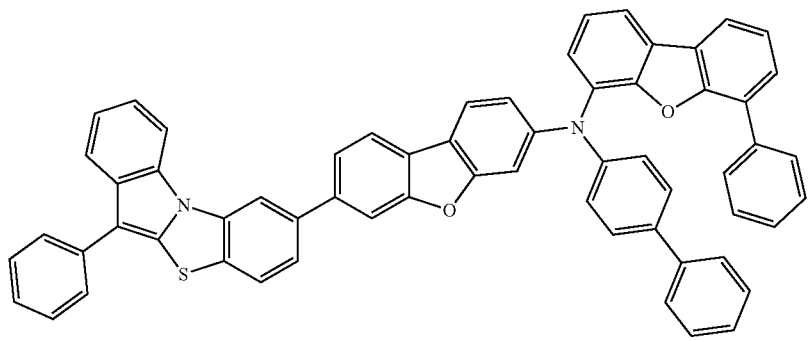
B70
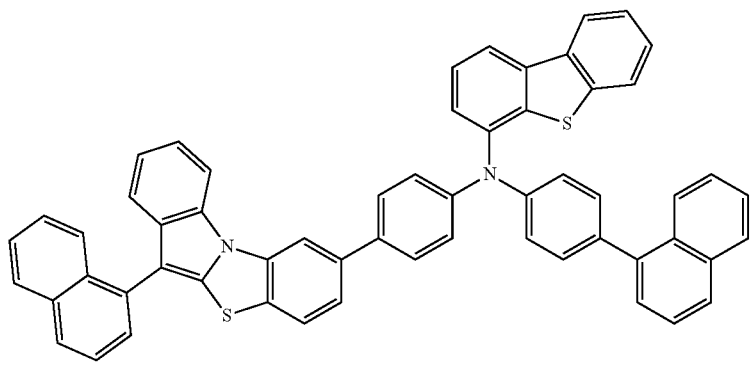
B71
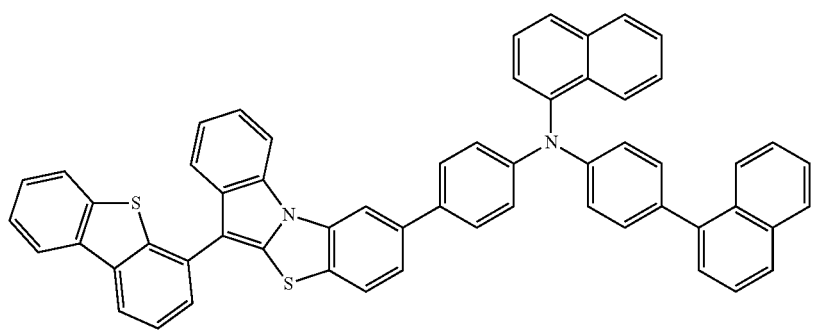

-continued
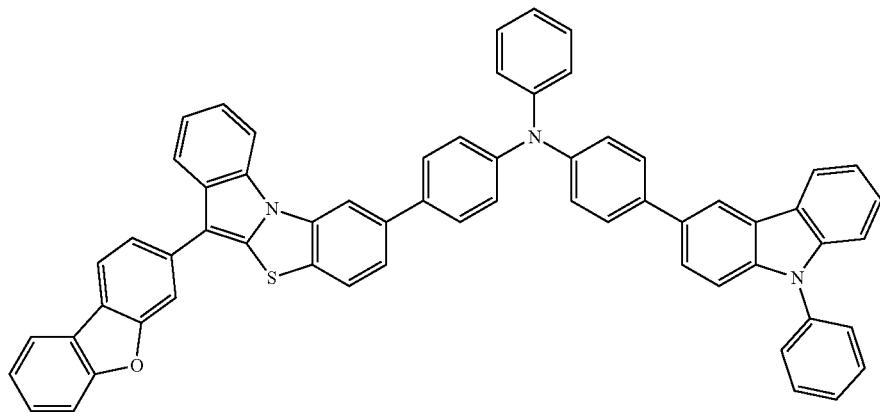
B72
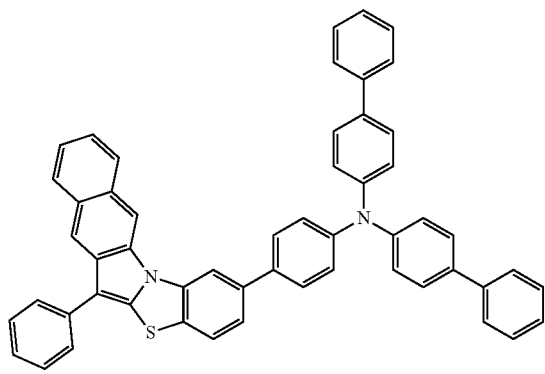
B73
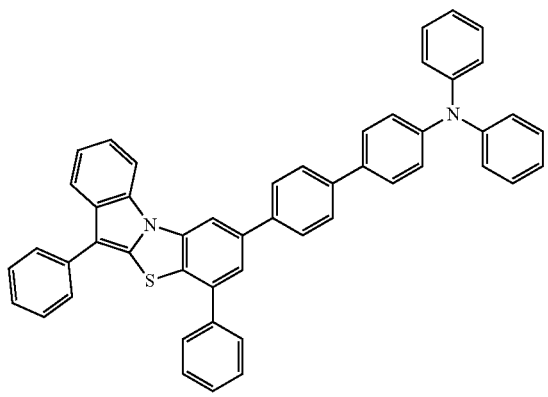
B74
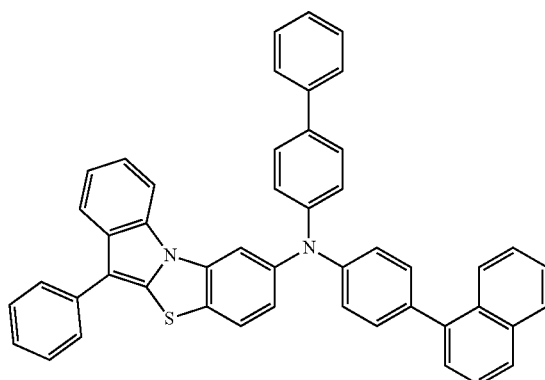
B75
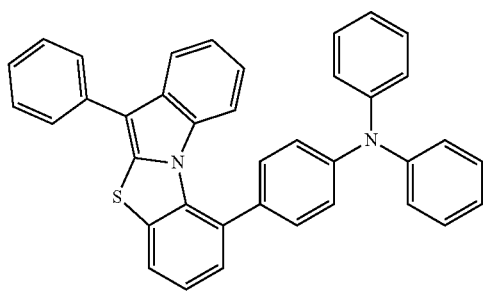
B76
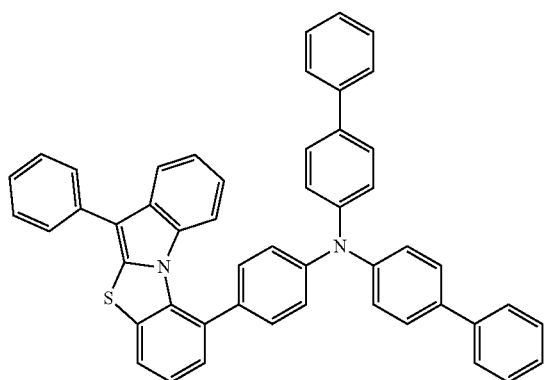
B77
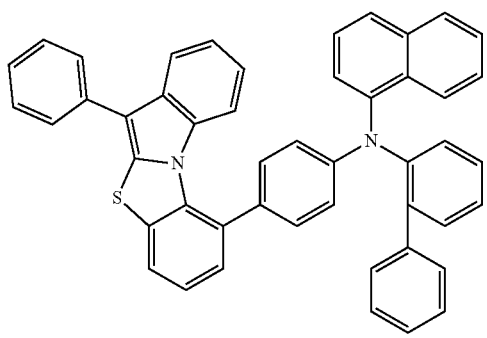
B78

-continued
| B79 | B80 |
|---|---|
| 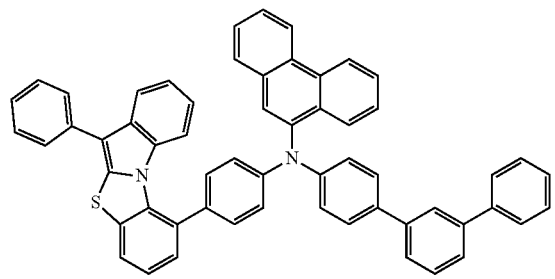 | 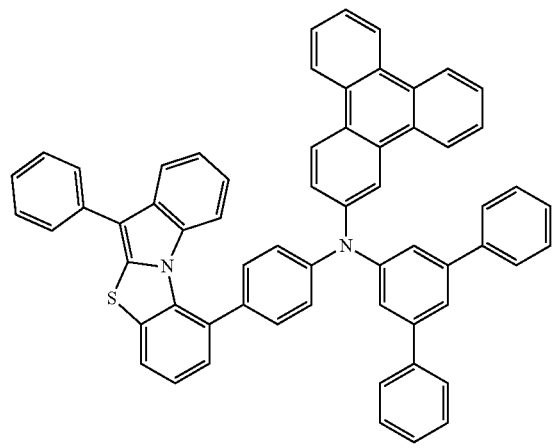 |
| B81 | B82 |
| 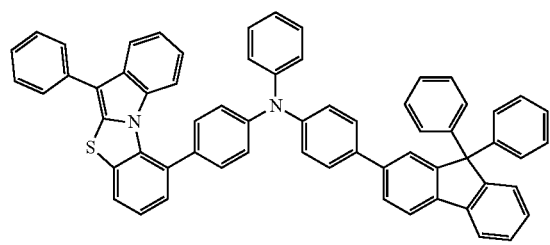 | 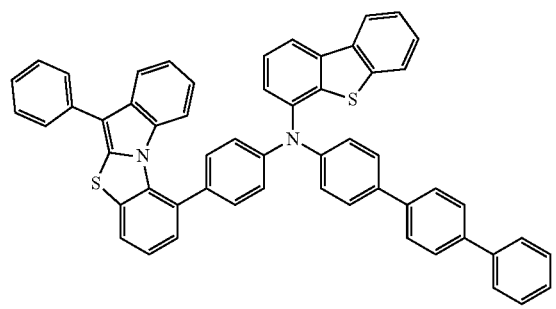 |
| B83 | B84 |
| 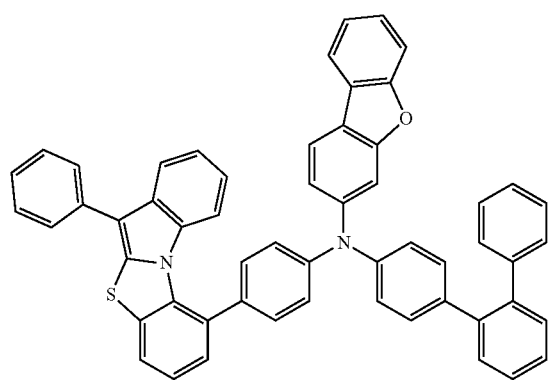 | 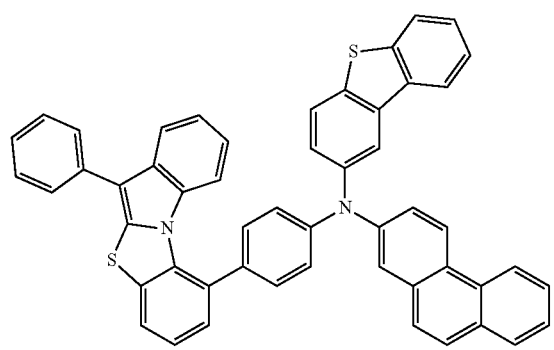 |
| B85 | B86 |
| 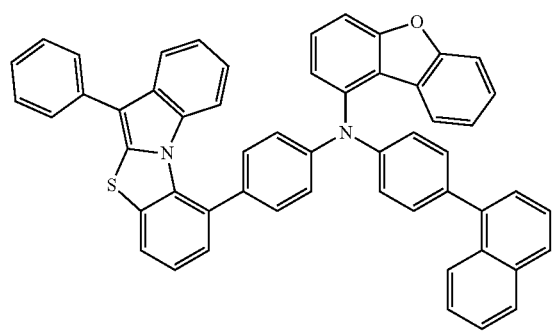 | 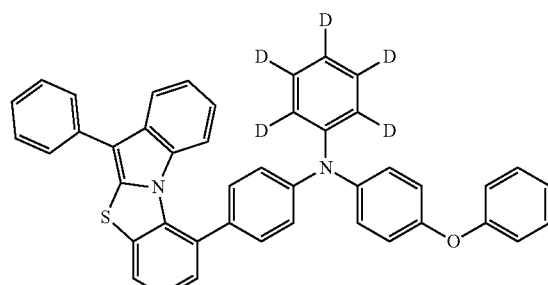 |

-continued
B87
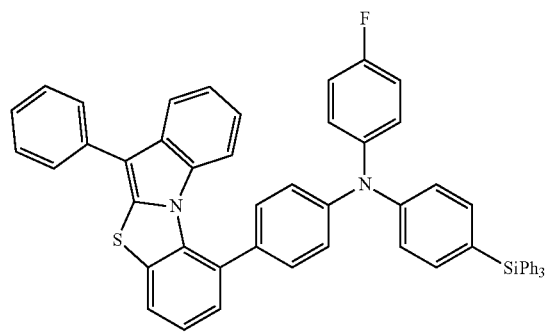
B88
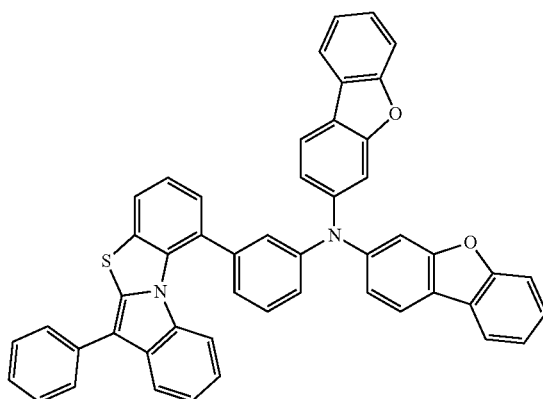
B89
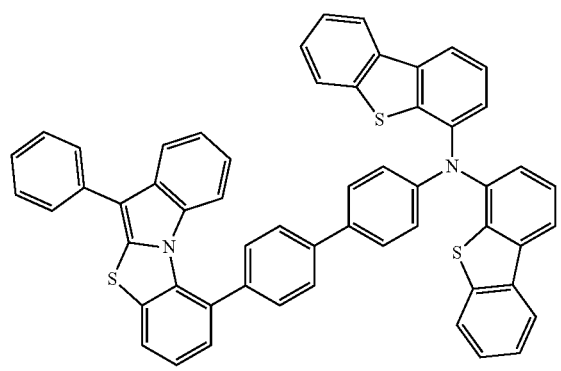
B90
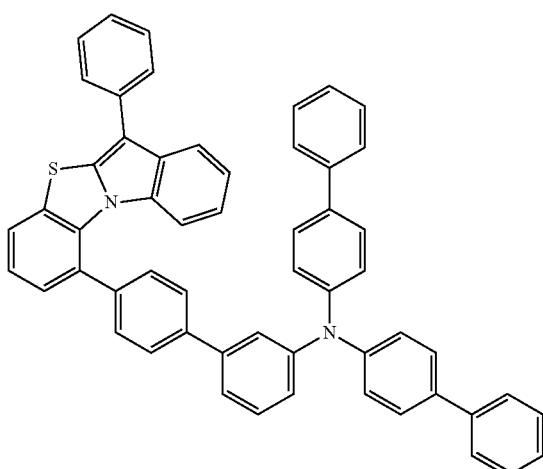
B91
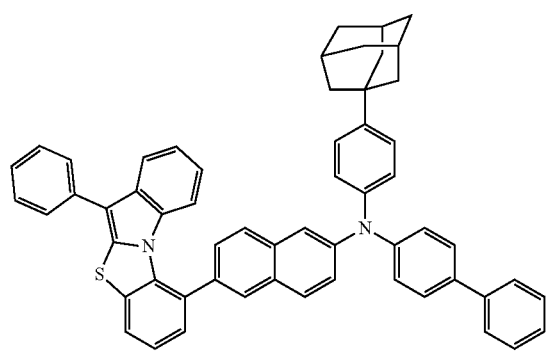
B92
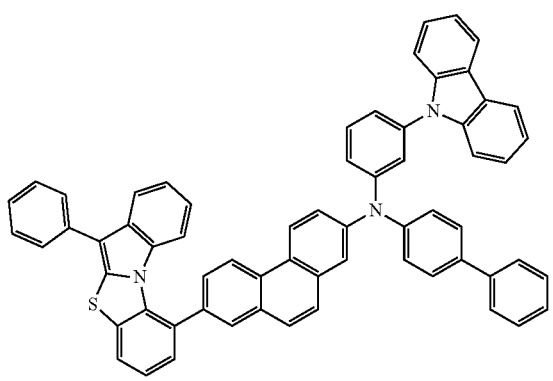

-continued
B93
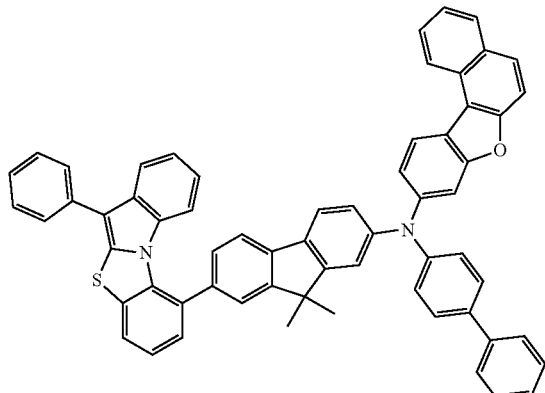
B94
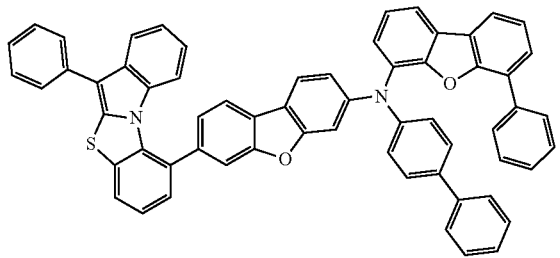
B95
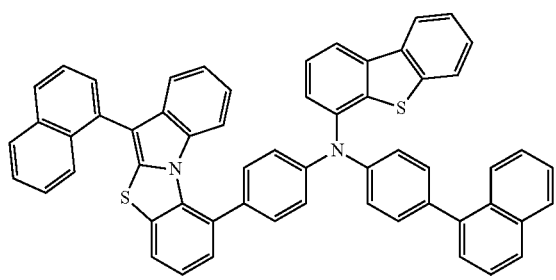
B96
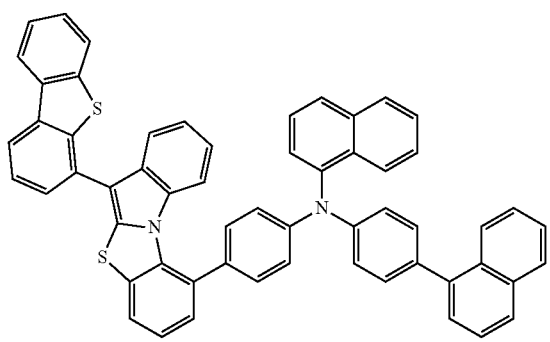
B97
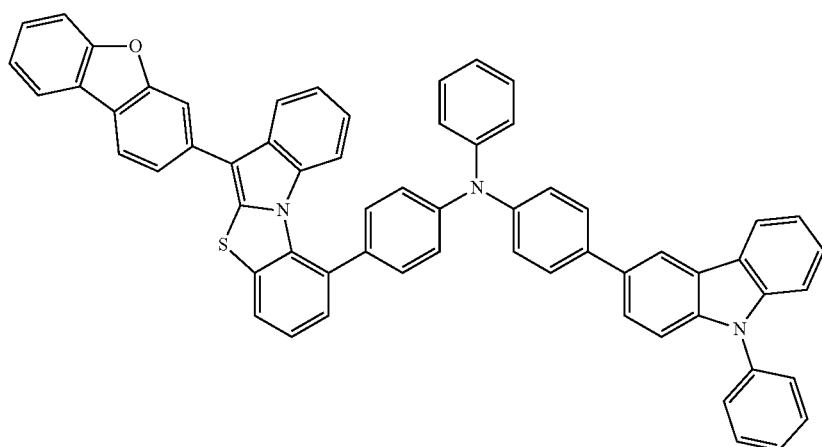
B98
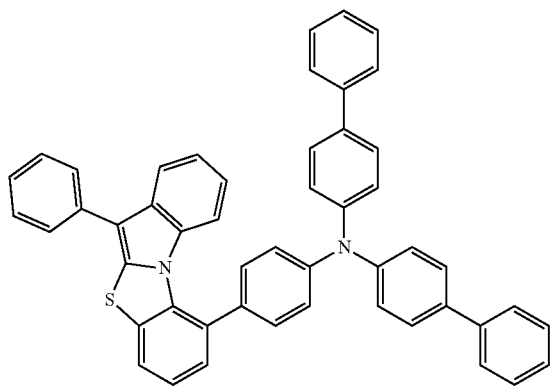
B99
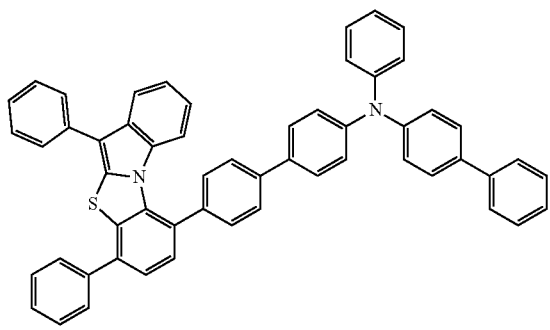

-continued
B100
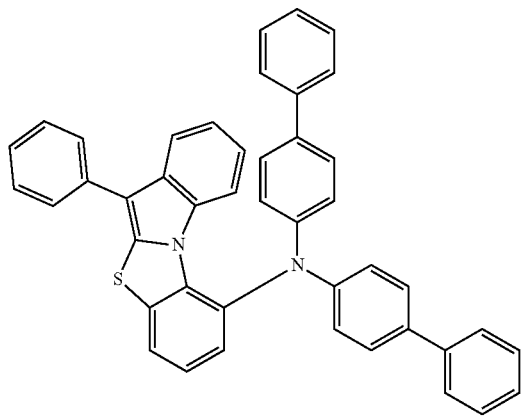
B101
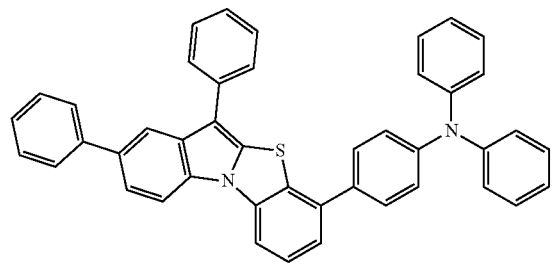
B102
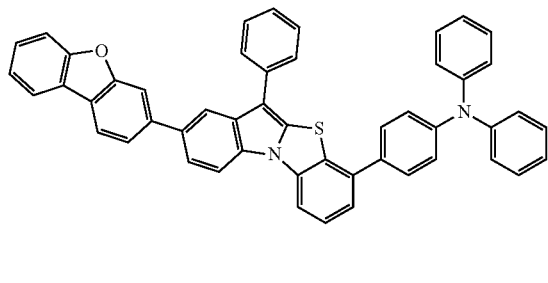
B103
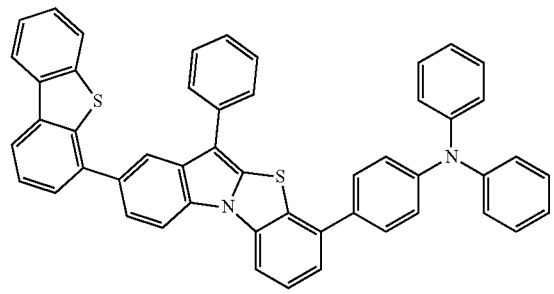
B104
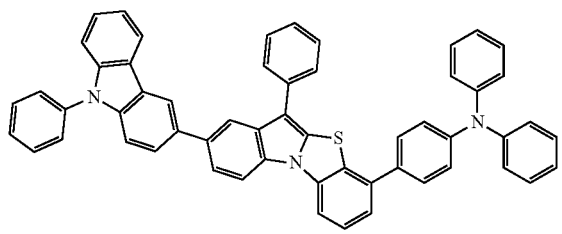
B105
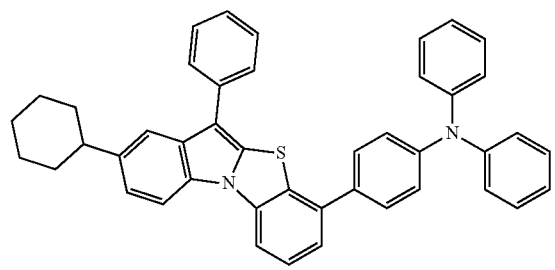
B106
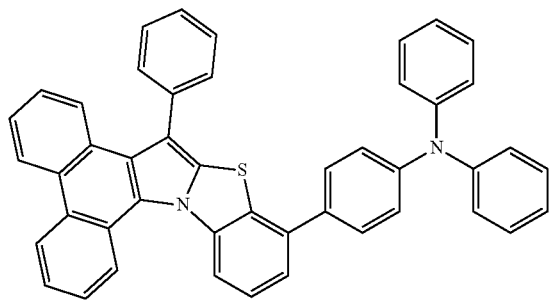
B107
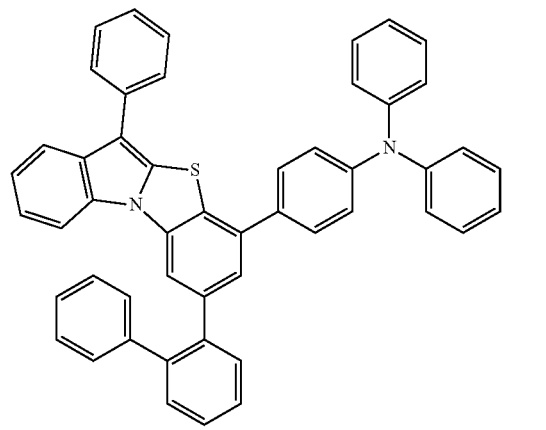

-continued

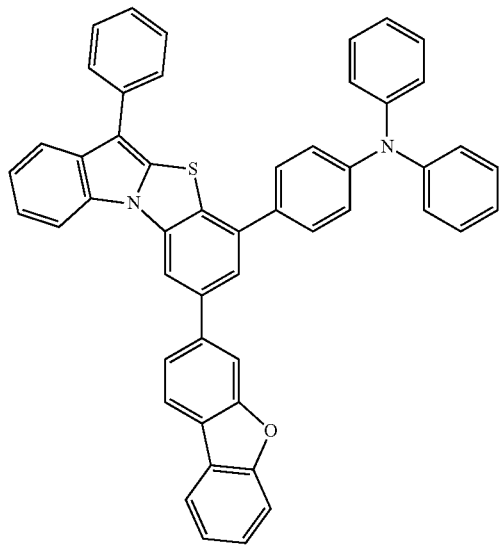
B108

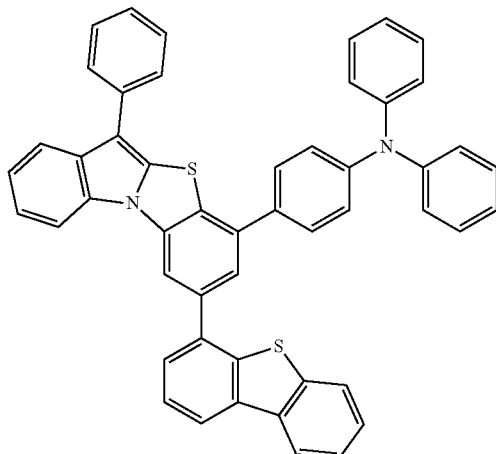
B109

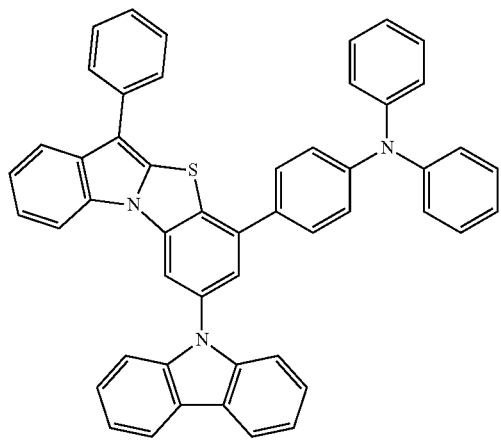
B110

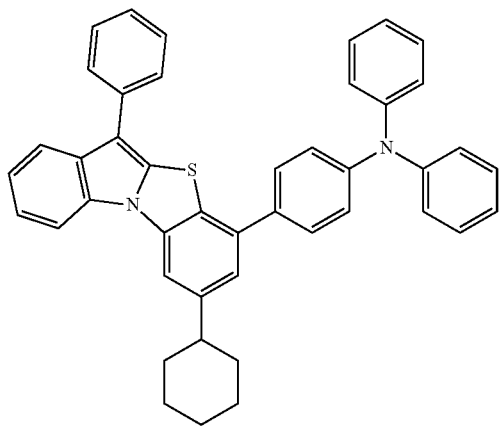
B111

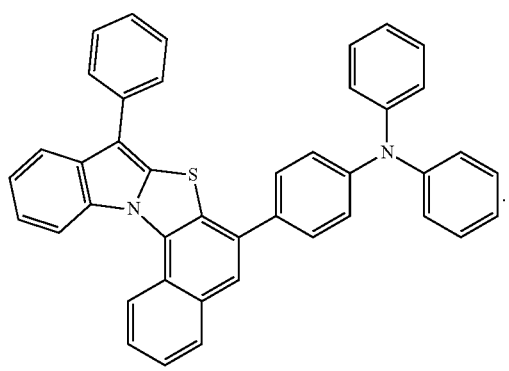
B112

In the description, Ph refers to a phenyl group.

The amine compound may be included, for example, in a hole transport region HTR among the organic layers (HTR, EML and ETR), For example, the amine compound may be included in a hole transport layer HTL in the hole transport region HTR.

In the organic electroluminescence devices 10 of embodiments, as shown in FIGS. 1 to 3, the hole transport region may include one or two or more kinds of the amine compounds represented in Compound Group A and Compound Group B. The hole transport region HTR may further include a known material in addition to the amine compound in Compound Group A and Compound Group B.

The hole transport region HTR of the organic electroluminescence device 10 of an embodiment may include the amine compound. If the hole transport region HTR is composed of a plurality of organic layers, the amine compound of an embodiment may be included in an organic layer that is adjacent to an emission layer EML. For example, the amine compound may be included in a hole transport layer HTL of the hole transport region HTR.

If the hole transport region HTR of the organic electroluminescence device 10 of an embodiment includes a hole injection layer HIL and a hole transport layer HTL, the amine compound may be included in the hole transport layer HTL.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 1,000 Å to about 1,500 Å

The hole transport region HTR may have a single layer structure formed using a single material, a single layer structure formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In some implementations, the hole transport region HTR may have a single layer structure formed using a plurality of different materials, or a laminated structure including, as laminated from the first electrode EL1, hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, as examples.

The hole transport region HTR may be formed using a suitable method such as a vacuum deposition method, a spin coating method, a cast method, a Langmuir-Blodgett (LB) method, an inkjet printing method, a laser printing method, or a laser induced thermal imaging (LITI) method.

In the organic electroluminescence device 10, when the hole transport layer HTL includes the amine compound, the hole injection layer HIL may include a well-known hole injection material. For example, the hole injection layer HIL may include a phthalocyanine compound such as copper phthalocyanine; N,N'-diphenyl-N,N'-bis-[4-(phenyl-m-tolyl-amino)-phenyl]-phenyl-4,4'-diamine (DNTPD), 4,4',4"-tris(3-methylphenylphenylamino)triphenyl amine (m-MTDATA), 4,4',4"-tris(N,N-diphenylamino)triphenylamine (TDATA), 4,4',4"-tris{N-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL of the organic electroluminescence device 10 may further include a known hole transport material in addition to the amine compound. For example, the hole transport layer HTL may include carbazole derivatives such as N-phenylcarbazole and polyvinylcarbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, or, for example, from about 100 Å to about 5,000 Å. The thickness of the hole injection region HIL may be, for example, from about 30 Å to about 1,000 Å, and the thickness of the hole transport layer HTL may be from about 30 Å to about 1,000 Å. The thickness of the electron blocking layer EBL may be, for example, from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be a quinone derivative, a metal oxide, or a cyano group-containing compound, as examples. For example, the p-dopant may include a quinone derivative such as tetracyanoquinodimethane (TCNQ) or 2,3,5,6-tetrafluoro-7,7,8,8-tetracyanoquinodimethane (F4-TCNQ), or a metal oxide such as tungsten oxide, or molybdenum oxide.

As described above, the hole transport region HTR may further include at least one of a hole buffer layer and an electron blocking layer EBL in addition to the hole injection layer HIL and the hole transport layer ITL. The hole buffer layer may compensate an optical resonance distance according to the wavelength of light emitted from an emission layer EML and may increase light emission efficiency. Materials that are included in a hole transport region HTR may be used as materials included in a hole buffer layer. The term "hole blocking layer EBL" refers to a layer that helps to prevent the injection of electrons from the electron transport region ETR into the hole transport region HTR.

The emission layer EML may be provided on the hole transport region HTR. The emission layer EML may have a thickness of, for example, from about 100 Å to about 1,000 Å, or from about 100 Å to about 300 Å. The emission layer EML may have a single layer structure formed using a single material, a single layer structure formed using a plurality of different materials, or a multilayer structure having a plurality of layers formed using a plurality of different materials.

In the organic electroluminescence device 10 of an embodiment, the emission layer EML may include an anthracene derivative, a pyrene derivative, a fluoranthene derivative, a chrysene derivative, a dihydrobenzanthracene derivative, or a triphenylene derivative. For example, the emission layer EML may include an anthracene derivative or a pyrene derivative.

The emission layer EML may include an anthracene derivative represented by Formula C, below.

[Formula C]

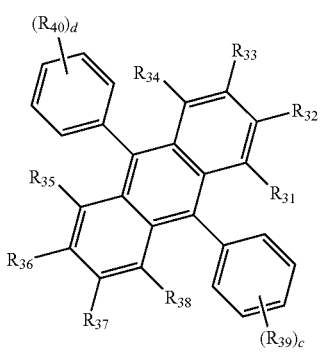

In Formula C, $R_{31}$ to $R_{40}$ may be each independently a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring carbon atoms, or a substituted or unsubstituted heteroaryl group of 2 to 30 ring carbon atoms, or may be combined with an adjacent group to form a ring. $R_{31}$ to $R_{40}$ may be combined with an adjacent group to form a saturated hydrocarbon ring or an unsaturated hydrocarbon ring.

In Formula C, "c" and "d" may be each independently an integer of 0 to 5.

Formula C may be represented by any one among Formula 3-1 to Formula 3-12, below.

3-1

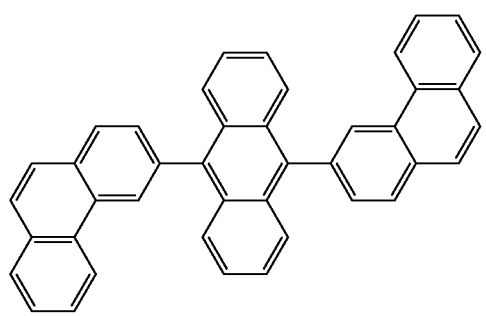

3-2

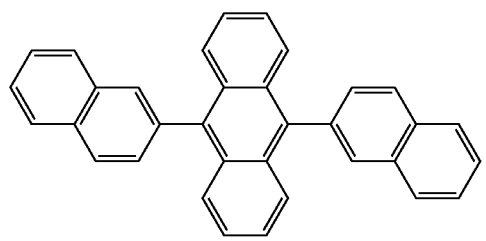

3-3

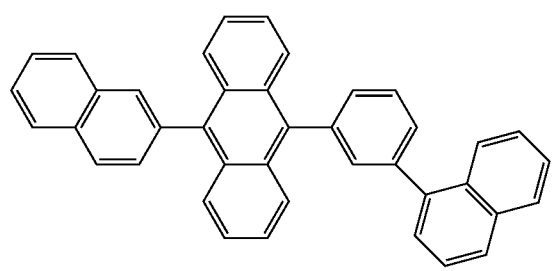

3-4

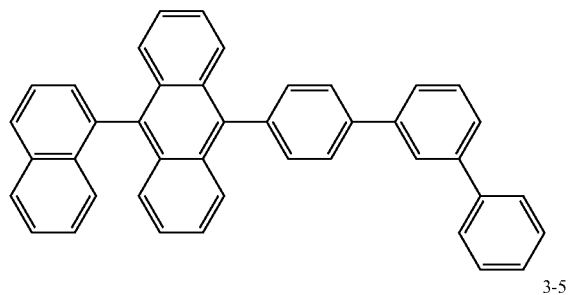

3-5

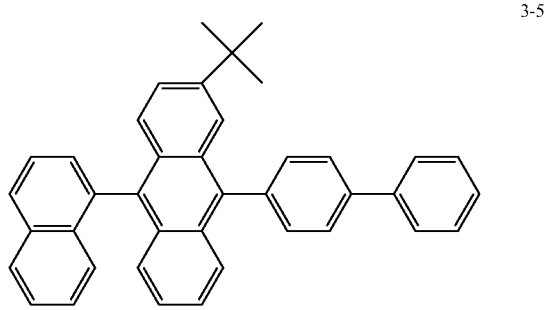

3-6

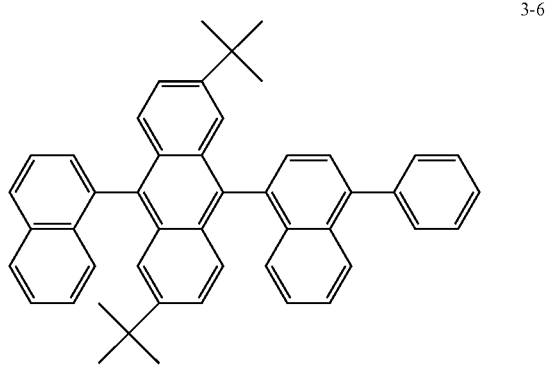

3-7

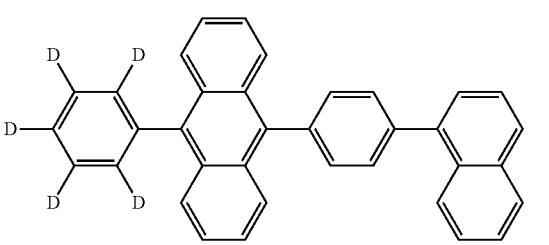

3-8

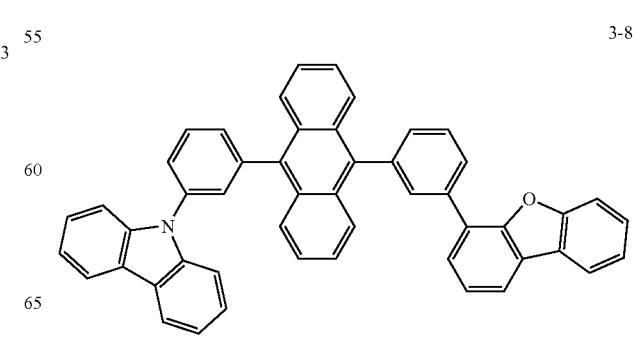

-continued 3-9
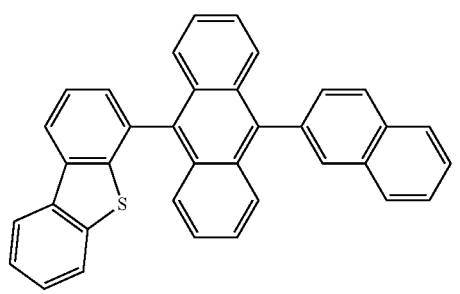

3-10
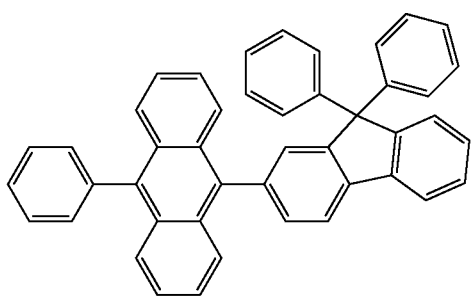

3-11
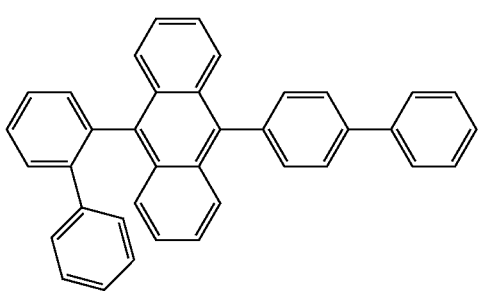

3-12
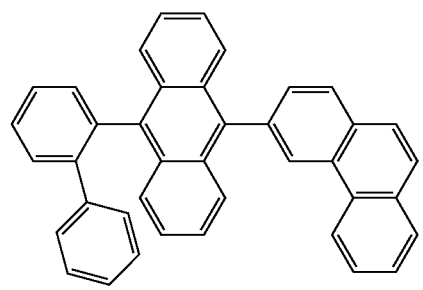

In the organic electroluminescence devices 10 shown in FIG. 1 to FIG. 3, the emission layer EML may include a host and a dopant, and the emission layer EML may include the compound represented by Formula C as a host material.

The emission layer EML may further include a suitable material as the host material. For example, the emission layer EML may include as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TcTa) or 1,3,5-tris(N-phenylbenzimidazole-2-yl)benzene (TPBi). For example, tris(8-hydroxyquinolino)aluminum (Alq$_3$), 4,4'-bis(N-carbazolyl)-1,1'-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzofuran (PPF), etc.

In an embodiment, the emission layer EML may include as a known dopant material, a styryl derivative (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene or derivatives thereof (for example, 2,5,8,11-tetra-t-butylperylene (TBP)), pyrene or the derivatives thereof (for example, 1,1-dipyrene, 1,4-dipyrenylbenzene, 1,4-bis(N,N-diphenylamino)pyrene), etc.

The emission layer may emit any one among blue light and green light. For example, the emission layer may emit blue light or green light having a wavelength region of about 440 nm to about 560 nm.

In the organic electroluminescence devices 10 as shown in FIGS. 1 to 3, the electron transport region ETR may be provided on the emission layer EML. The electron transport region ETR may include, for example, at least one of a hole blocking layer HBL, an electron transport layer ETL or an electron injection layer EIL.

The electron transport region ETR may have a single layer structure formed using a single material, a single layer structure formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. The electron transport region ETR may have a single layer structure composed of a plurality of different materials, or a laminated structure, laminated from the emission layer EML, of electron transport layer ETL/electron injection layer EIL, or hole blocking layer HBL/electron transport layer ETL/electron injection layer EIL, without limitation. The thickness of the electron transport region ETR may be, for example, from about 100 Å to about 1,500 Å.

The electron transport region ETR may be formed using a suitable method such as a vacuum deposition method, a spin coating method, a cast method, a Langmuir-Blodgett (LB) method, an inkjet printing method, a laser printing method, or a laser induced thermal imaging (LITI) method.

If the electron transport region ETR includes an electron transport layer ETL, the electron transport region ETR may include an anthracene-based compound. The hole transport region may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10- phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), or a mixture thereof. The thickness of the electron transport layer ETL may be from about 100 Å to about 1,000 Å or, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, for example, LiF, lithium quinolate (LiQ), $Li_2O$, BaO, NaCl, CsF, a lanthanide metal such as Yb, or a metal halide such as RbCl, and RbI. The electron injection layer EIL may be also formed using a mixture material of an electron transport material and an insulating organo metal salt. The organo metal salt may be a material having an energy band gap of about 4 eV or more. For example, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, or from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound or a mixture including thereof (for example, a mixture of Ag and Mg). The second electrode EL2 may have a multilayered structure including a reflective layer or a transflective layer formed using the above-described materials, and a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may be recombined in the emission layer EML to produce excitons. The excitons may emit light via transition from an excited state to a ground state.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

1. SYNTHETIC EXAMPLES

The amine compound of an embodiment may be synthesized, for example, as follows. In the synthetic examples, FAB-MS measurement was performed using JMS-700V of JEOL Co.

1-1. Synthesis of Compound A2

Amine Compound A2 according to an embodiment may be synthesized, for example, by the following Reaction 1:

Reaction 1

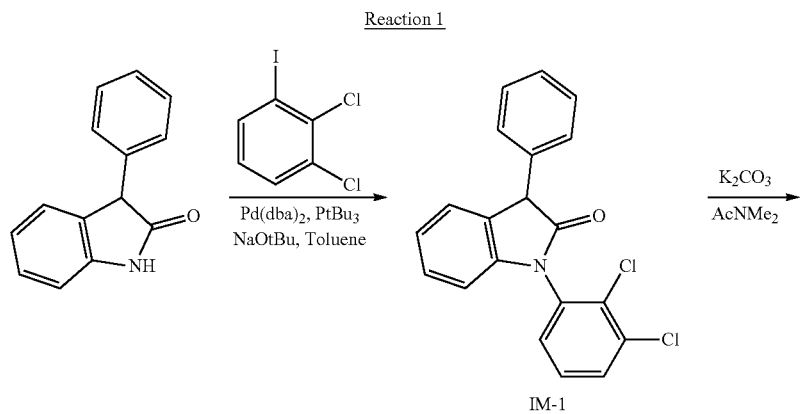

IM-1

-continued

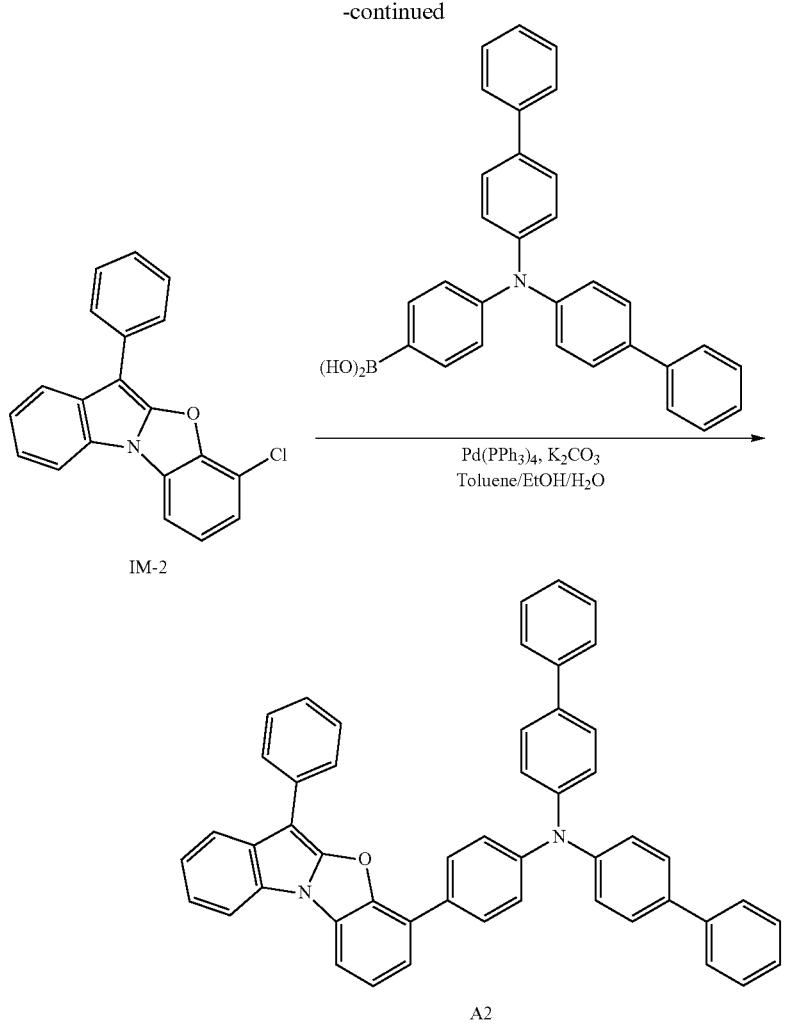

Synthesis of Intermediate IM-1

Under an argon (Ar) atmosphere, to a 500 ml, three-neck flask, 15.00 g (71.7 mmol) of 3-phenyl-1H-oxindole, 1.24 g (0.03 eq, 2.2 mmol) of Pd(dba)$_2$, 10.22 g (1.5 eq, 107.5 mmol) of NaOtBu, 358 ml of toluene, 21.52 g (1.1 eq, 78.9 mmol) of 1,2-dichloro-3-iodo-benzene and 1.45 g (0.1 eq, 7.2 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a saturated brine solution and dried with MgSO$_4$. After filtering MgSO$_4$, an organic layer was concentrated to obtain a crude product. The crude product thus obtained was separated by silica gel column chromatography using a mixture solvent of hexane and toluene as a developing solution to obtain Intermediate IM-1 (19.04 g, yield 75%). The molecular weight of Intermediate IM-1 measured by FAB-MS was 354.

Synthesis of Intermediate IM-2

Under an argon (Ar) atmosphere, to a 300 ml, three-neck flask, 15.00 g (42.3 mmol) of Intermediate IM-1, 212 ml of N,N-dimethylacetamide and 23.41 g (4 eq, 169.4 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated to obtain a crude product. The crude product thus obtained was separated by silica gel column chromatography using a mixture solvent of hexane and toluene as a developing solution to obtain Intermediate IM-2 (10.90 g, yield 81%). The molecular weight of Intermediate IM-2 measured by FAB-MS was 317.

Synthesis of Compound A2

Under an argon (Ar) atmosphere, to a 300 ml, three-neck flask, 5.00 g (15.7 mmol) of Intermediate IM-2, 7.64 g (1.1 eq, 17.3 mmol) of 4-{di[(1,1'-biphenyl)-4-yl]amino}phenylboronic acid, 6 52 g (3.0 eq, 47.2 mmol) of K$_2$CO$_3$, 0.91 g (0.05 eq, 0.8 mmol) of Pd(PPh$_3$)$_4$ and 110 ml of a mixture solution of toluene/EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated to obtain a crude product. The crude product thus obtained was separated by silica gel column chromatography using a mixture solvent of hexane and toluene as a developing solution to obtain Compound A2 (9.08 g, yield 85%). The molecular weight of Compound A2 measured by FAB-MS was 678.
1-2. Synthesis of Compound A14
Amine Compound A14 according to an embodiment may be synthesized, for example, by the following Reaction 2:
Reaction 2
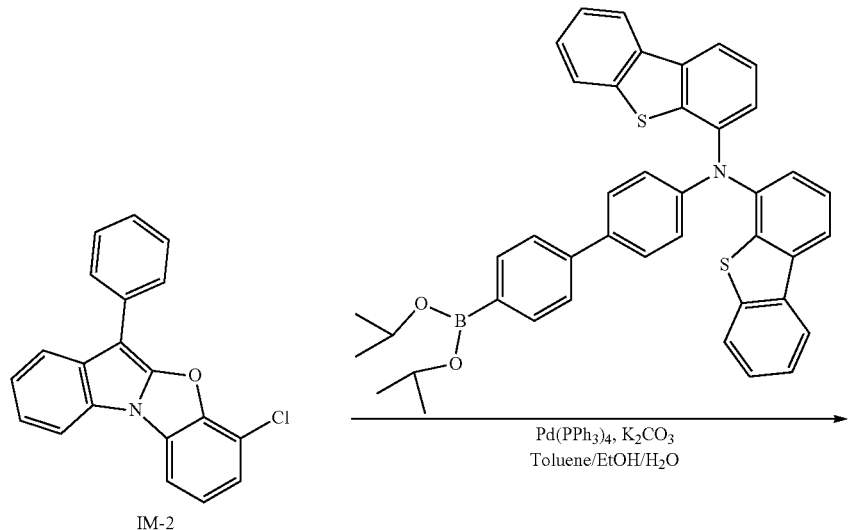
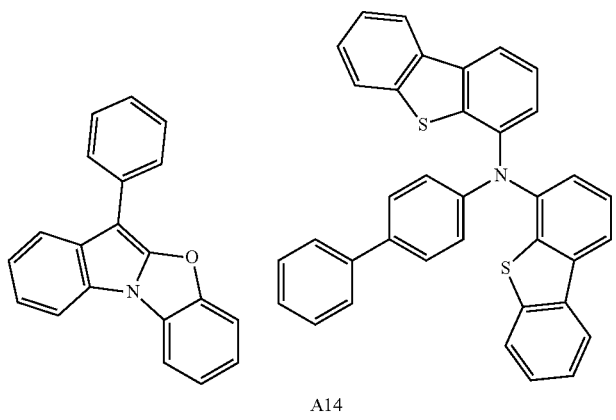

Under an argon (Ar) atmosphere, to a 300 ml, three-neck flask, 5.00 g (15.7 mmol) of Intermediate IM-2, 11.42 g (1.1 eq, 17.3 mmol) of N-(dibenzothiophen-4-yl)-N-[4'-(4,4,5,5-tetramethyl-1,3,2-dioxaborolan-2-yl)-(1,1'-biphenyl)-4-yl]dibenzothiophen-4-amine, 6 52 g (3.0 eq, 47.2 mmol) of $K_2CO_3$, 0.91 g (0.05 eq, 0.8 mmol) of $Pd(PPh_3)_4$ and 110 ml of a mixture solution of toluene/EtOH/$H_2O$ with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with $MgSO_4$. After filtering $MgSO_4$, an organic layer was concentrated to obtain a crude product. The crude product thus obtained was separated by silica gel column chromatography using a mixture solvent of hexane and toluene as a developing solution to obtain Compound A14 (10.00 g, yield 78%). The molecular weight of Compound A14 measured by FAB-MS was 815.

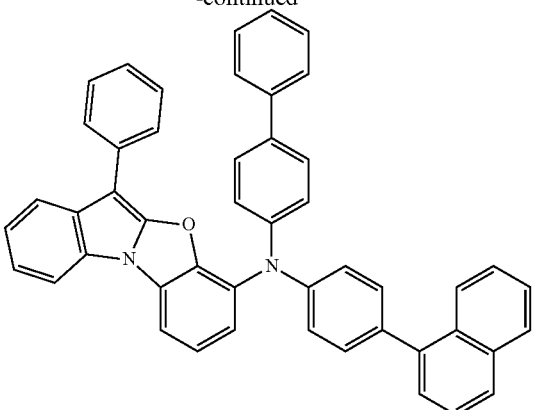

A25

1-3. Synthesis of Compound A25

Amine Compound A25 according to an embodiment may be synthesized, for example, by the following Reaction 3:

Reaction 3

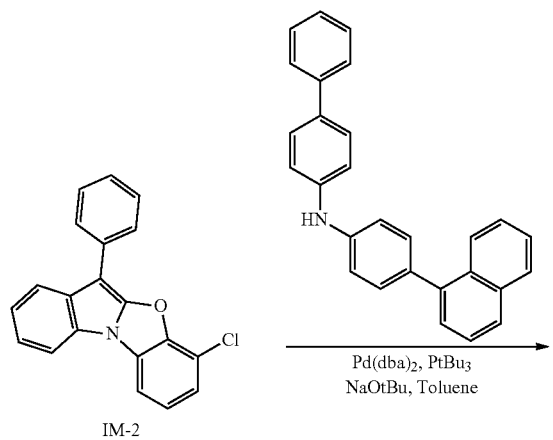

Under an argon (Ar) atmosphere, to a 200 ml, three-neck flask, 5.00 g (15.7 mmol) of Intermediate IM-2, 0.27 g (0.03 eq, 0.5 mmol) of $Pd(dba)_2$, 3.02 g (2.0 eq, 31.5 mmol) of NaOtBu, 78 ml of toluene, 6.43 g (1.1 eq, 17.3 mmol) of N-[4-(naphthalen-1-yl)phenyl]-(1,1'-biphenyl)-4-amine, and 0.32 g (0.1 eq, 1.6 mmol) of $tBu_3P$ were added one by one, followed by heating to about 120° C. and stirring. After cooling to room temperature in the air, water was added to the reaction solution and an organic layer was separately taken. Toluene was added to an aqueous layer, and an organic layer was additionally extracted. Organic layers were put together and washed with a saturated brine solution and dried with $MgSO_4$. After filtering $MgSO_4$, an organic layer was concentrated to obtain a crude product. The crude product thus obtained was separated by silica gel column chromatography using a mixture solvent of hexane and toluene as a developing solution to obtain Compound A25 (8.32 g, yield 81%). The molecular weight of Compound A25 measured by FAB-MS was 652.

1-4. Synthesis of Compound A46

Amine Compound A46 according to an embodiment may be synthesized, for example, by the following Reaction 4:

Reaction 4

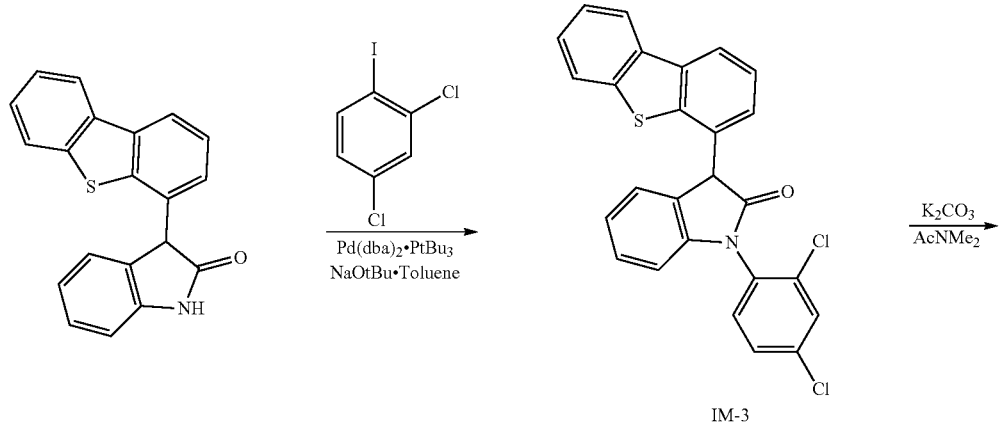

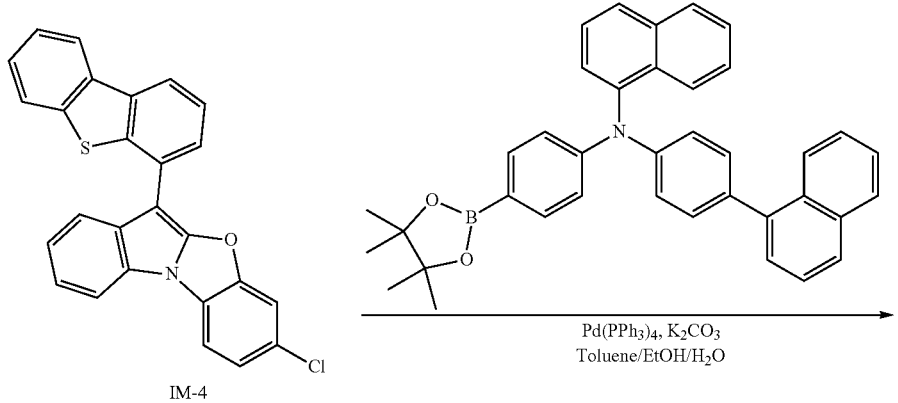

IM-4

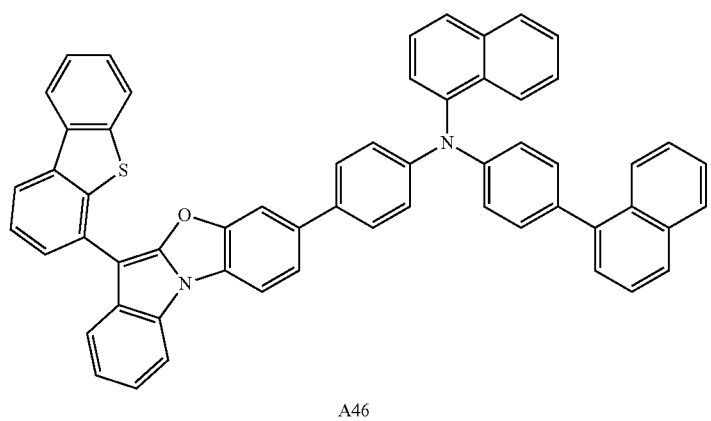

A46

Synthesis of Intermediate IM-3

Under an argon (Ar) atmosphere, to a 500 ml, three-neck flask, 15.00 g (47.6 mmol) of 3-bibenzothiophen-4-yl)-1H-oxindole, 0.82 g (0.03 eq, 1.4 mmol) of Pd(dba)$_2$, 6.86 g (1.5 eq, 71.3 mmol) of NaOtBu, 238 ml of toluene, 14.28 g (1.1 eq, 52.3 mmol) of 2,4-dichloro-1-iodobenzene and 0.96 g (0.1 eq, 4.8 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated to obtain a crude product. The crude product thus obtained was separated by silica gel column chromatography using a mixture solvent of hexane and toluene as a developing solution to obtain Intermediate IM-3 (15.77 g, yield 72%). The molecular weight of Intermediate IM-3 measured by FAB-MS was 460.

Synthesis of Intermediate IM-4

Under an argon (Ar) atmosphere, to a 300 ml, three-neck flask, 15.00 g (32.6 mmol) of Intermediate IM-3, 163 ml of N,N-dimethylacetamide and 18.01 g (4 eq, 130.3 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-4 (10.36 g, yield 75%). The molecular weight of Intermediate IM-4 measured by FAB-MS was 423.

Synthesis of Compound A46

Under an argon (Ar) atmosphere, to a 300 ml, three-neck flask, 5.00 g (11.8 mmol) of Intermediate IM-4, 7.10 g (1.1 eq, 13.0 mmol) of N-(4-(naphthalen-1-yl)phenyl)-N-(4-(4,4,5,5-tetramethyl-1,3,2-dioxaborolan-2-yl)phenyl)naphthalen-1-amine, 4 89 g (3.0 eq, 35.4 mmol) of K$_2$CO$_3$, 0.68 g (0.05 eq, 0.6 mmol) of Pd(PPh$_3$)$_4$ and 83 ml of a mixture solution of toluene/EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound A46 (7.54 g, yield 79%). The molecular weight of Compound A46 measured by FAB-MS was 809.

1-5. Synthesis of Compound A50

Amine Compound A50 according to an embodiment may be synthesized, for example, by the following Reaction 5:

Reaction 5

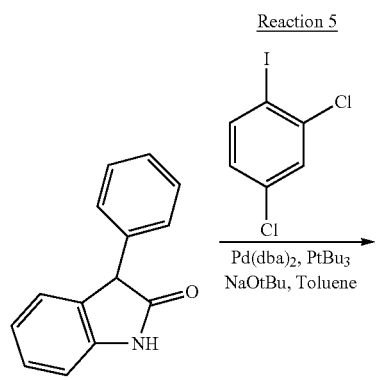

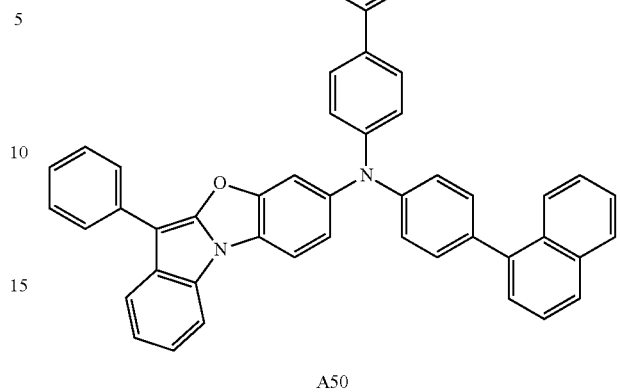

A50

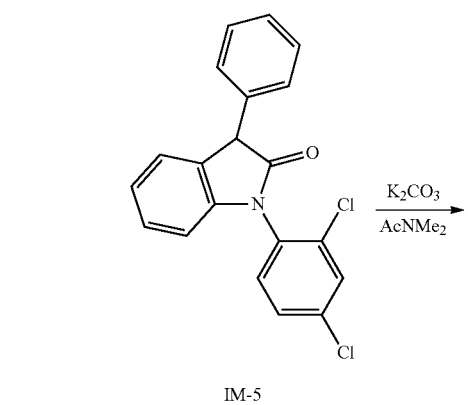
IM-5

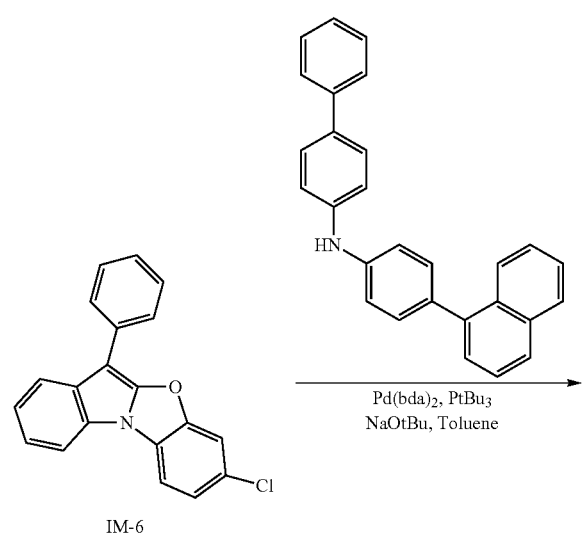
IM-6

Synthesis of Intermediate IM-5

Under an argon (Ar) atmosphere, to a 500 ml, three-neck flask, 15.00 g (71.7 mmol) of 3-phenyl-1H-oxindole, 1.24 g (0.03 eq, 2.2 mmol) of Pd(dba)$_2$, 10.22 g (1.5 eq, 107.5 mmol) of NaOtBu, 358 ml of toluene, 21.52 g (1.1 eq, 78.9 mmol) of 2,4-dichloro-1-iodo-benzene and 1.45 g (0.1 eq, 7.2 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-5 (19.55 g, yield 77%). The molecular weight of Intermediate IM-5 measured by FAB-MS was 354.

Synthesis of Intermediate IM-6

Under an argon (Ar) atmosphere, to a 300 ml, three-neck flask, 15.00 g (42.3 mmol) of Intermediate IM-5. 212 ml of N,N-dimethylacetamide and 23.41 g (4 eq. 169.4 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-6 (10.23 g, yield 76%). The molecular weight of Intermediate IM-6 measured by FAB-MS was 317.

Synthesis of Compound A50

Under an argon (Ar) atmosphere, to a 200 ml, three-neck flask, 5.00 g (15.7 mmol) of Intermediate IM-6, 0.27 g (0.03 eq, 0.5 mmol) of Pd(dba)$_2$, 3.02 g (2.0 eq, 31.5 mmol) of NaOtBu, 78 ml of toluene, 6.43 g (1.1 eq, 17.3 mmol) of N-[4-(naphthalen-1-yl)phenyl[-(1,1'-biphenyl)-4-amine and 0.32 g (0.1 eq, 1.6 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound A50 (7.60 g, yield 74%). The molecular weight of Compound A50 measured by FAB-MS was 652.

1-6. Synthesis of Compound A63

Amine Compound A63 according to an embodiment may be synthesized, for example, by the following Reaction 6:

Reaction 6

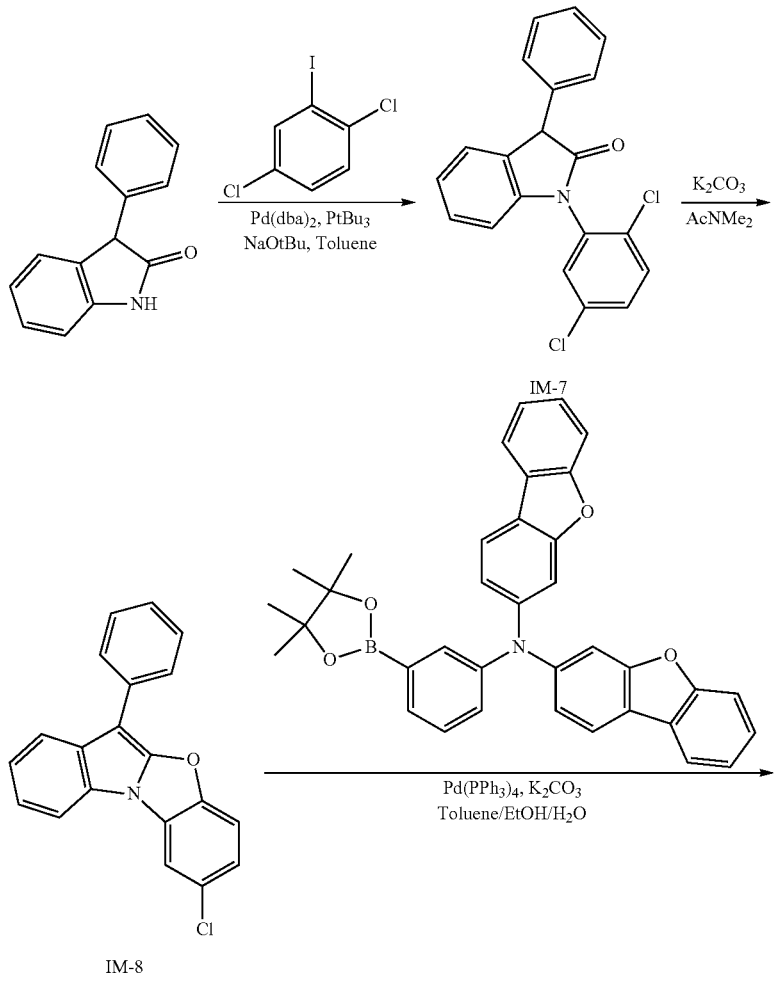

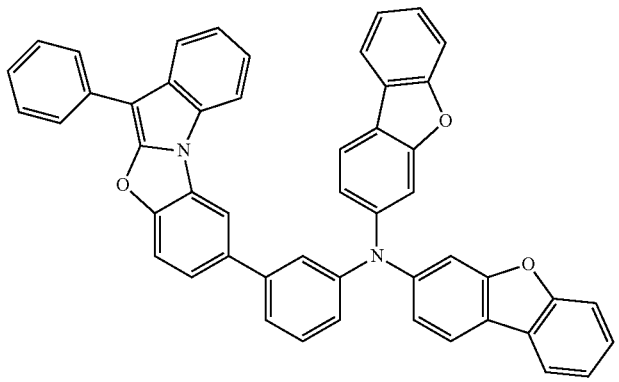

A63

Synthesis of Intermediate IM-7

Under an argon (Ar) atmosphere, to a 500 ml, three-neck flask, 15.00 g (71.7 mmol) of 3-phenyl-1H-oxindole, 1.24 g (0.03 eq, 2.2 mmol) of Pd(dba)$_2$, 10.22 g (1.5 eq, 107.5 mmol) of NaOtBu, 358 ml of toluene, 21.52 g (1.1 eq, 78.9 mmol) of 1,4-dichloro-2-iodobenzene and 1.45 g (0.1 eq, 7.2 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-7 (21.33 g. yield 84%). The molecular weight of Intermediate IM-7 measured by FAB-MS was 354.

Synthesis of Intermediate IM-8

Under an argon (Ar) atmosphere, to a 300 ml, three-neck flask, 15.00 g (42.3 mmol) of Intermediate IM-7, 212 ml of N,N-dimethylacetamide and 23.41 g (4 eq, 169.4 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-8 (10.76 g, yield 80%).

The molecular weight of Intermediate IM-8 measured by FAB-MS was 317.

Synthesis of Compound A63

Under an argon (Ar) atmosphere, to a 300 ml, three-neck flask, 5.00 g (15.7 mmol) of Intermediate IM-8, 7.36 g (1.1 eq, 17.3 mmol) of N-(dibenzofuran-3-yl)-N-[3-(4,4,5,5-tetramethyl-1,3,2-dioxaborolan-2-yl)phenyl]dibenzofuran-3-amine, 6.52 g (3.0 eq, 47.2 mmol) of K$_2$CO$_3$, 0.91 g (0.05 eq, 0.8 mmol) of Pd(PPh$_3$)$_4$ and 110 ml of a mixture solution of toluene/EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound A63 (6.50 g, yield 78%). The molecular weight of Compound A63 measured by FAB-MS was 706.

1-7. Synthesis of Compound A70

Amine Compound A70 according to an embodiment may be synthesized, for example, by the following Reaction 7:

Reaction 7

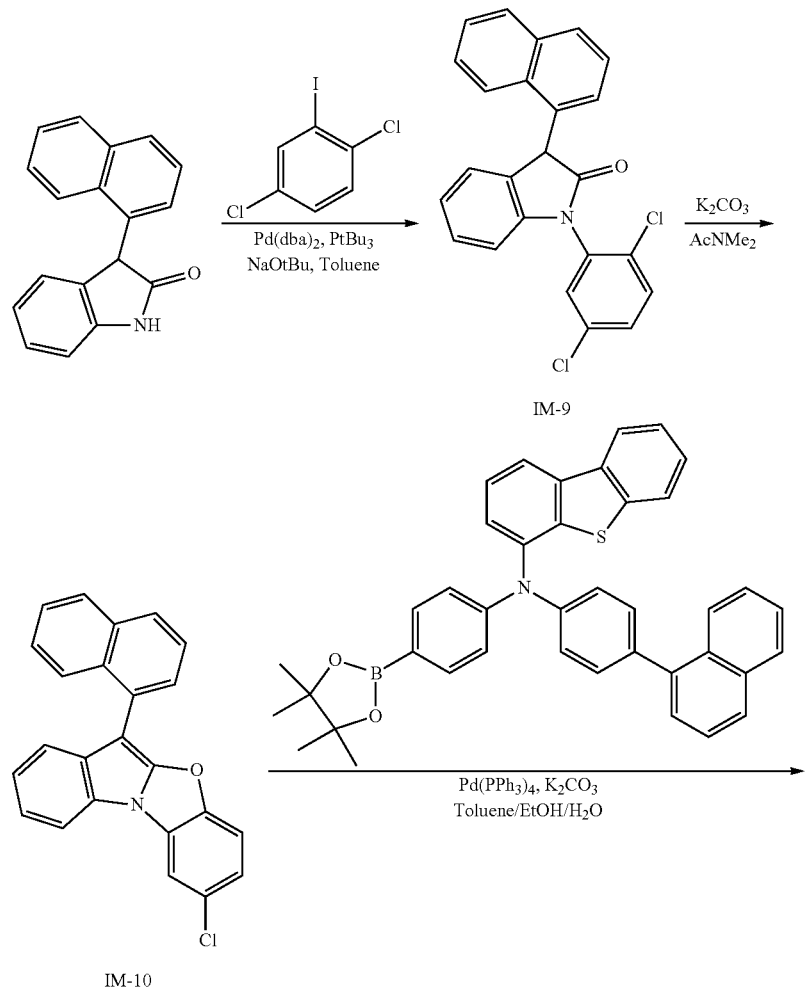

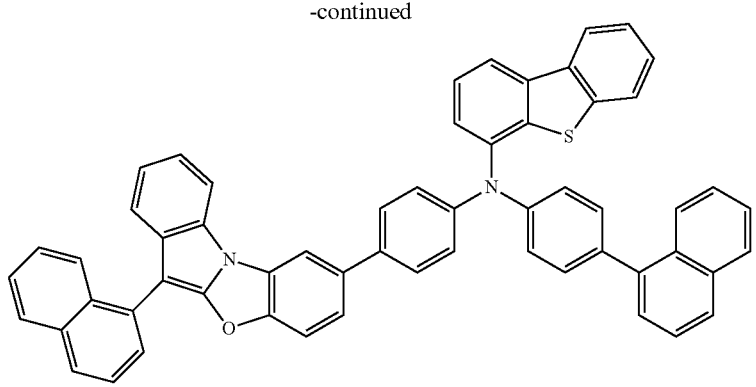

A70

Synthesis of Intermediate IM-9

Under an argon (Ar) atmosphere, to a 500 ml, three-neck flask, 15.00 g (57.85 mmol) of 3-(1-naphthyl)-1H-oxindole, 1.00 g (0.03 eq, 1.7 mmol) of Pd(dba)$_2$, 8.34 g (1.5 eq, 86.8 mmol) of NaOtBu, 289 ml of toluene, 17.36 g (1.1 eq, 63.6 mmol) of 1,4-dichloro-2-iodobenzene and 1.17 g (0.1 eq, 5.8 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-9 (19.41 g, yield 83%). The molecular weight of Intermediate IM-9 measured by FAB-MS was 404.

Synthesis of Intermediate IM-10

Under an argon (Ar) atmosphere, to a 300 ml, three-neck flask, 15.00 g (37.1 mmol) of Intermediate IM-9, 185 ml of N,N-dimethylacetamide and 20.51 g (4 eq, 148.4 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-10 (10.24 g, yield 75%). The molecular weight of Intermediate IM-10 measured by FAB-MS was 367.

Synthesis of Compound A70

Under an argon (Ar) atmosphere, to a 300 ml, three-neck flask, 5.00 g (13.6 mmol) of Intermediate IM-10, 9.27 g (1.1 eq, 15.0 mmol) of N-[4-(naphthalen-1-yl)phenyl]-N-[4-(4,4,5,5-tetramethyl-1,3,2-dioxaborolan-2-yl)phenyl]dibenzothiophen-4-amine, 5.64 g (3.0 eq, 40.8 mmol) of K$_2$CO$_3$, 0.79 g (0.05 eq, 0.7 mmol) of Pd(PPh$_3$)$_4$ and 95 ml of a mixture solution of toluene/EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound A70 (8.03 g, yield 73%). The molecular weight of Compound A70 measured by FAB-MS was 809.

1-8. Synthesis of Compound A85

Amine Compound A85 according to an embodiment may be synthesized, for example, by the following Reaction 8:

Reaction 8

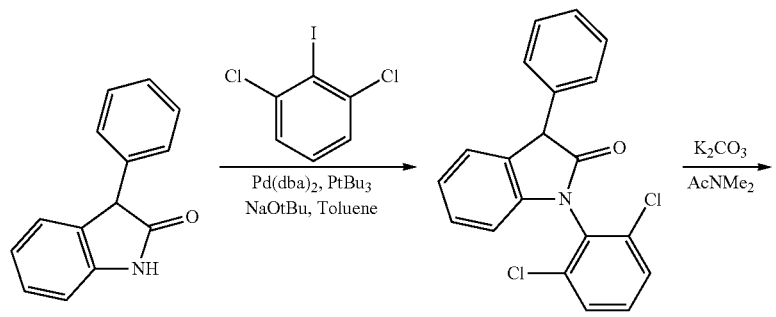

IM-11

-continued

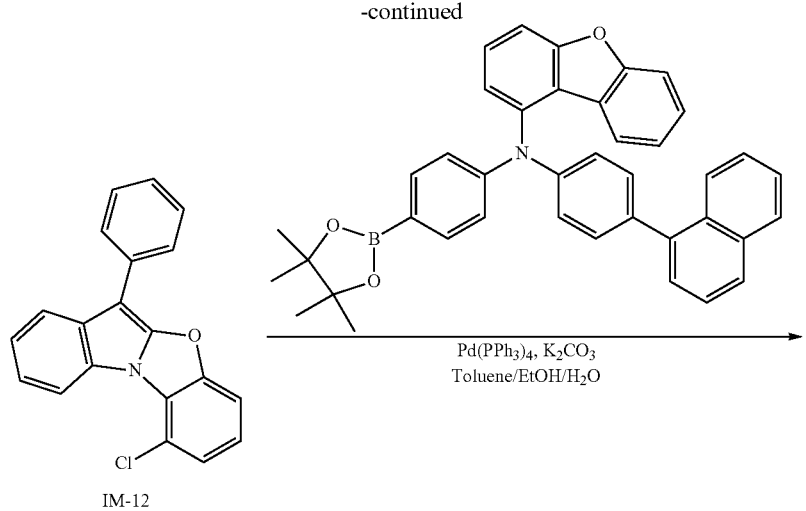

IM-12

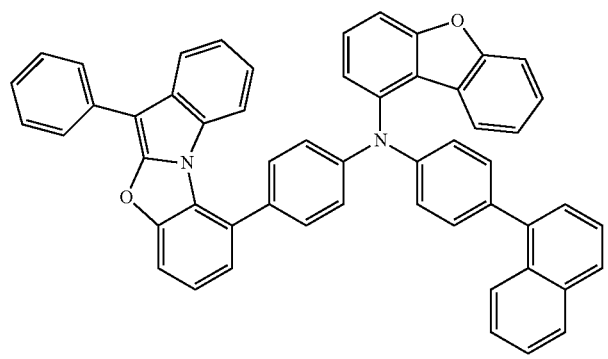

A85

Synthesis of Intermediate IM-11

Under an argon (Ar) atmosphere, to a 500 ml, three-neck flask, 15.00 g (71.7 mmol) of 3-(1-naphthyl)-1H-oxindole, 1.24 g (0.03 eq, 2.2 mmol) of Pd(dba)$_2$, 10.22 g (1.5 eq, 107.5 mmol) of NaOtBu, 358 ml of toluene, 21.52 g (1.1 eq, 78.9 mmol) of 1,3-dichloro-2-iodobenzene and 1.45 g (0.1 eq, 7.2 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-11 (18.79 g, yield 74%). The molecular weight of Intermediate IM-11 measured by FAB-MS was 354.

Synthesis of Intermediate IM-12

Under an argon (Ar) atmosphere, to a 300 ml, three-neck flask, 15.00 g (42.3 mmol) of Intermediate IM-11, 212 ml of N,N-dimethylacetamide and 23.41 g (4 eq, 169.4 mmol) of K$_2$CO$_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-12 (10.90 g, yield 81%). The molecular weight of Intermediate IM-12 measured by FAB-MS was 317.

Synthesis of Compound A85

Under an argon (Ar) atmosphere, to a 300 ml, three-neck flask, 5.00 g (15.7 mmol) of Intermediate IM-12, 7.83 g (1.1 eq, 17.3 mmol) of N-[4-(naphthalen-1-yl)phenyl]-N-[4-(4,4,5,5-tetramethyl-1,3,2-dioxaborolan-2-yl)phenyl]dibenzo-furan-1-amine, 6.52 g (3.0 eq, 47.2 mmol) of K$_2$CO$_3$, 0.91 g (0.05 eq, 0.8 mmol) of Pd(PPh$_3$)$_4$ and 110 ml of a mixture solution of toluene/EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound A85 (6.05 g, yield 69%). The molecular weight of Compound A85 measured by FAB-MS was 742.

1-9. Synthesis of Compound B7

Amine Compound B7 according to an embodiment may be synthesized, for example, by the following Reaction 9:

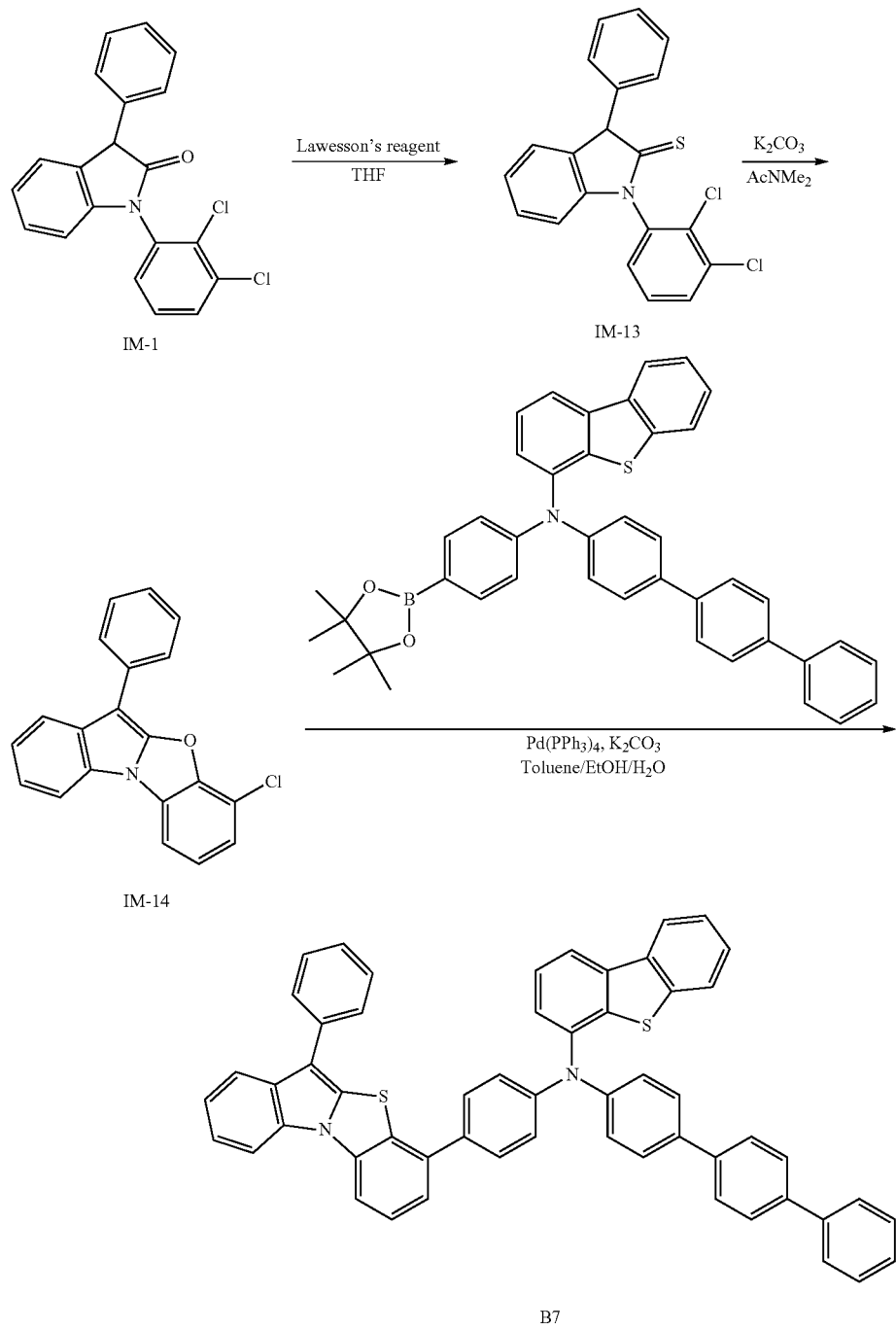

Synthesis of Intermediate IM-13

Under an argon (Ar) atmosphere, to a 300 ml, three-neck flask, 20.00 g (56.5 mmol) of Intermediate IM-1, 188 ml of THF, and 12.56 g (0.55 eq, 31.3 mmol) of Lawesson's reagent (2,4-bis(4-methoxyphenyl)-1,3,2,4-dithiadiphosphetane-2,4-disulfide, (hereinafter, this compound name will be omitted)) were added one by one, followed by stirring at room temperature. After concentrating the reaction solution, the crude product thus obtained was separated by silica gel column chromatography using a mixture solvent of hexane and toluene as a developing solution to obtain Intermediate IM-13 (16.73 g, yield 80%). The molecular weight of Intermediate IM-13 measured by FAB-MS was 370.

Synthesis of Intermediate IM-14

Under an argon (Ar) atmosphere, to a 300 ml, three-neck flask, 15.00 g (40.5 mmol) of Intermediate IM-13, 202 ml of N,N-dimethylacetamide and 22.39 g (4 eq, 162.0 mmol) of $K_2CO_3$ were added one by one, followed by heating to about 120° C. and stirring. After cooling to room temperature in the air, water was added to the reaction solution, and extraction with AcOEt was performed. An organic layer was washed with a saturated brine solution and dried with MgSO₄. After filtering MgSO₄, an organic layer was concentrated. The crude product thus obtained was separated by silica gel column chromatography using a mixture solvent of hexane and toluene as a developing solution to obtain Intermediate IM-14 (11.09 g, yield 82%). The molecular weight of Intermediate IM-14 measured by FAB-MS was 333.

Synthesis of Compound B7

Under an argon (Ar) atmosphere, to a 300 ml, three-neck flask, 5.00 g (15.0 mmol) of Intermediate IM-14, 10.37 g (1.1 eq, 16.5 mmol) of N-[(1,1': 4',1"-terphenyl)-4-yl]-N-[4-(4,4,5,5-tetramethyl-1,3,2-dioxaborolan-2-yl)phenyl]dibenzothiophen-4-amine, 6.20 g (3.0 eq, 44.9 mmol) of K₂CO₃, 0.87 g (0.05 eq, 0.7 mmol) of Pd(PPh₃)₄ and 105 ml of a mixture solution of toluene/EtOH/H₂O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO₄. After filtering MgSO₄, an organic layer was concentrated. The crude product thus obtained was separated by silica gel column chromatography using a mixture solvent of hexane and toluene as a developing solution to obtain Compound B7 (9.48 g, yield 79%). The molecular weight of Compound B7 measured by FAB-MS was 801.

1-10. Synthesis of Compound B31

Amine Compound B31 according to an embodiment may be synthesized, for example, by the following Reaction 10:

[Reaction 10]

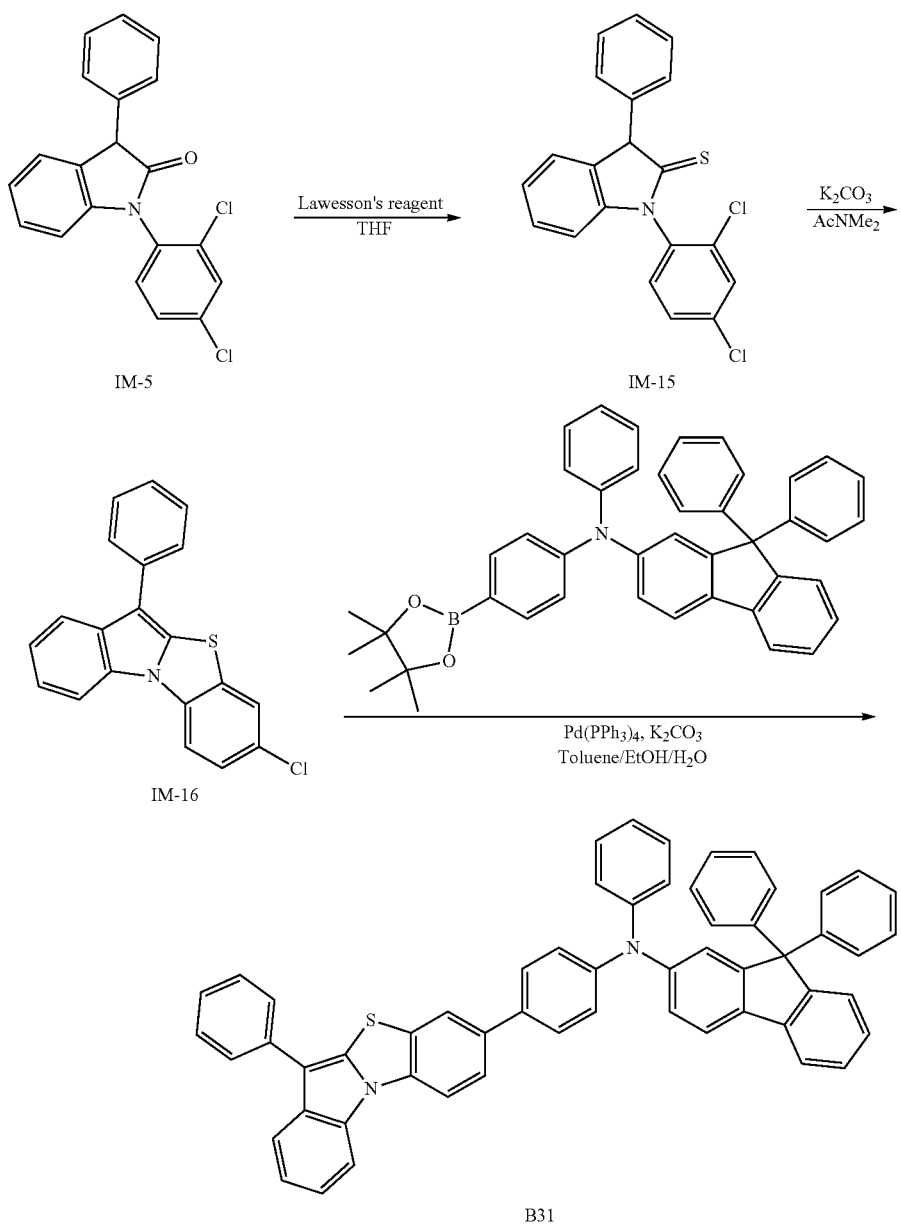

Synthesis of Intermediate IM-15

Under an argon (Ar) atmosphere, to a 300 ml, three-neck flask, 20.00 g (56.5 mmol) of Intermediate IM-5, 188 ml of THF, and 12.56 g (0.55 eq, 31.1 mmol) of Lawesson's reagent were added one by one, followed by stirring at room temperature. After concentrating the reaction solution, the crude product thus obtained was separated by silica gel column chromatography using a mixture solvent of hexane and toluene as a developing solution to obtain Intermediate IM-15 (16.52 g, yield 79%). The molecular weight of Intermediate IM-15 measured by FAB-MS was 370.

Synthesis of Intermediate IM-16

Under an argon (Ar) atmosphere, to a 300 ml, three-neck flask, 15.00 g (40.5 mmol) of Intermediate IM-15, 202 ml of N,N-dimethylacetamide and 22.39 g (4 eq, 162.0 mmol) of $K_2CO_3$ were added one by one, followed by heating to about 120° C. and stirring. After cooling to room temperature in the air, water was added to the reaction solution, and extraction with AcOEt was performed. An organic layer was washed with a saturated brine solution and dried with $MgSO_4$. After filtering $MgSO_4$, an organic layer was concentrated. The crude product thus obtained was separated by silica gel column chromatography using a mixture solvent of hexane and toluene as a developing solution to obtain Intermediate IM-16 (11.49 g, yield 85%). The molecular weight of Intermediate IM-16 measured by FAB-MS was 333.

Synthesis of Compound B31

Under an argon (Ar) atmosphere, to a 300 ml, three-neck flask, 5.00 g (15.0 mmol) of Intermediate IM-16, 10.08 g (1.1 eq, 16.5 mmol) of N,9,9-triphenyl-N-[4-(4,4,5,5-tetramethyl-1,3,2-dioxaborolan-2-yl)phenyl]-9H-fluoren-2-amine, 6.20 g (3.0 eq, 44.9 mmol) of $K_2CO_3$, 0.87 g (0.05 eq, 0.7 mmol) of $Pd(PPh_3)_4$ and 105 ml of a mixture solution of toluene/EtOH/$H_2O$ with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with $MgSO_4$. After filtering $MgSO_4$, an organic layer was concentrated. The crude product thus obtained was separated by silica gel column chromatography using a mixture solvent of hexane and toluene as a developing solution to obtain Compound B31 (9.03 g, yield 77%). The molecular weight of Compound B31 measured by FAB-MS was 783.

1-11. Synthesis of Compound B65

Amine Compound B65 according to an embodiment may be synthesized, for example, by the following Reaction 11:

[Reaction 11]

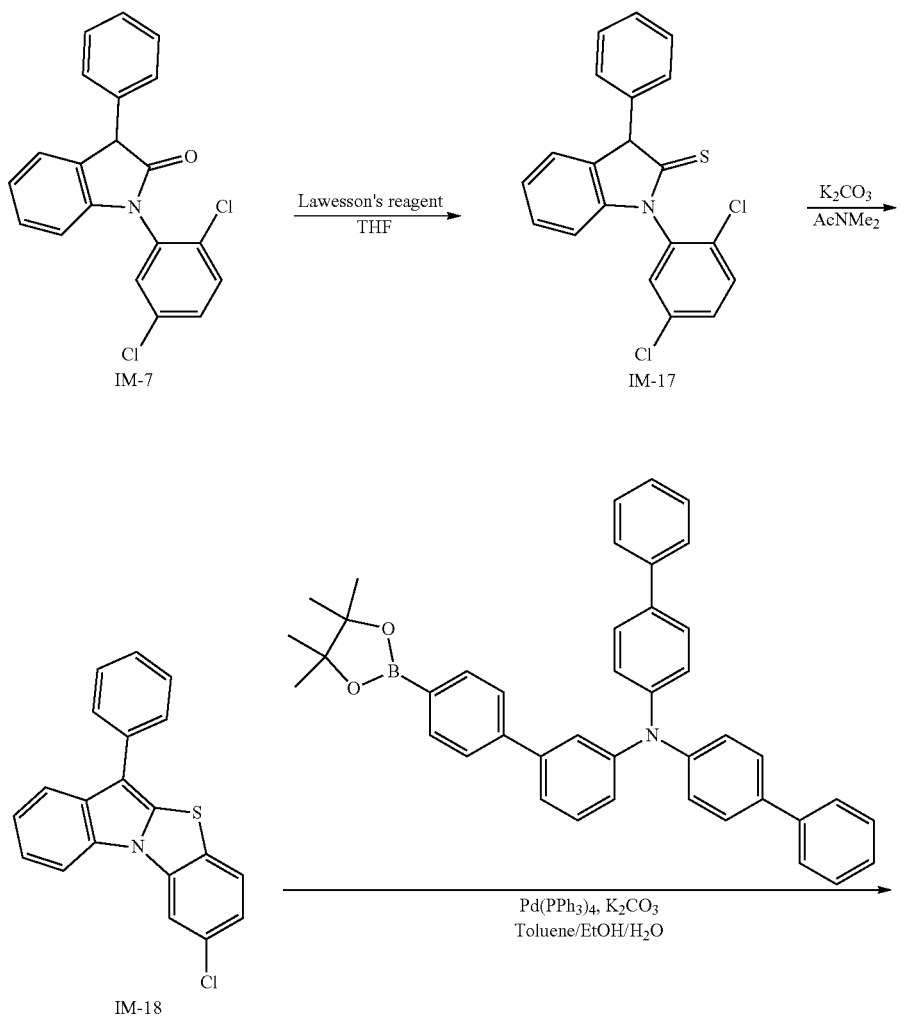

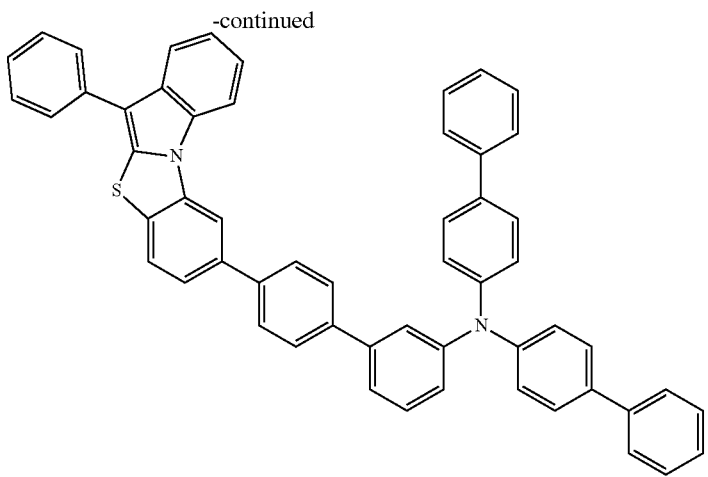

B65

Synthesis of Intermediate IM-17

Under an argon (Ar) atmosphere, to a 300 ml, three-neck flask, 20.00 g (56.5 mmol) of Intermediate IM-7, 188 ml of THF, and 12.56 g (0.55 eq, 31.1 mmol) of Lawesson's reagent were added one by one, followed by stirring at room temperature. After concentrating the reaction solution, the crude product thus obtained was separated by silica gel column chromatography using a mixture solvent of hexane and toluene as a developing solution to obtain Intermediate IM-17 (16.31 g, yield 78%). The molecular weight of Intermediate IM-17 measured by FAB-MS was 370.

Synthesis of Intermediate IM-18

Under an argon (Ar) atmosphere, to a 300 ml, three-neck flask, 15.00 g (40.5 mmol) of Intermediate IM-17, 202 ml of N,N-dimethylacetamide and 22.39 g (4 eq, 162.0 mmol) of $K_2CO_3$ were added one by one, followed by heating to about 120° C. and stirring. After cooling to room temperature in the air, water was added to the reaction solution, and extraction with AcOEt was performed. An organic layer was washed with a saturated brine solution and dried with $MgSO_4$. After filtering $MgSO_4$, an organic layer was concentrated. The crude product thus obtained was separated by silica gel column chromatography using a mixture solvent of hexane and toluene as a developing solution to obtain Intermediate IM-18 (11.49 g, yield 85%). The molecular weight of Intermediate IM-18 measured by FAB-MS was 333.

Synthesis of Compound B65

Under an argon (Ar) atmosphere, to a 300 ml, three-neck flask, 5.00 g (15.0 mmol) of Intermediate IM-18, 10.14 g (1.1 eq, 16.5 mmol) of N,N-di[(1,1'-biphenyl)-4-yl]-4'-(4,4,5,5-tetramethyl-1,3,2-dioxaborolan-2-yl)-(1,1'-biphenyl)-3-amine, 6.20 g (3.0 eq, 44.9 mmol) of $K_2CO_3$, 0.87 g (0.05 eq, 0.7 mmol) of $Pd(PPh_3)_4$ and 105 ml of a mixture solution of toluene/EtOH/$H_2O$ with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with $MgSO_4$. After filtering $MgSO_4$, an organic layer was concentrated. The crude product thus obtained was separated by silica gel column chromatography using a mixture solvent of hexane and toluene as a developing solution to obtain Compound B65 (8.66 g, yield 75%). The molecular weight of Compound B65 measured by FAB-MS was 770.

1-12. Synthesis of Compound B67

Amine Compound B67 according to an embodiment may be synthesized, for example, by the following Reaction 12:

Reaction 12

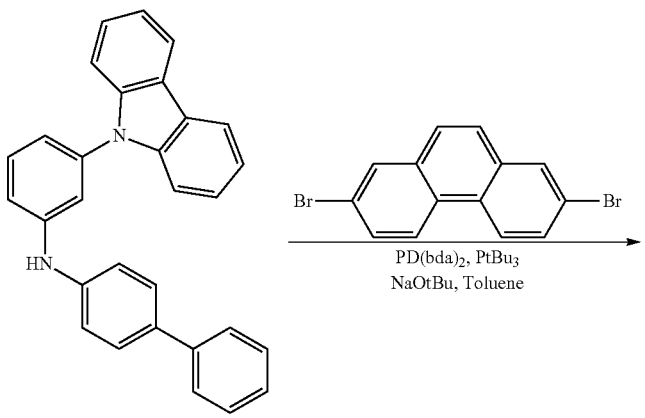

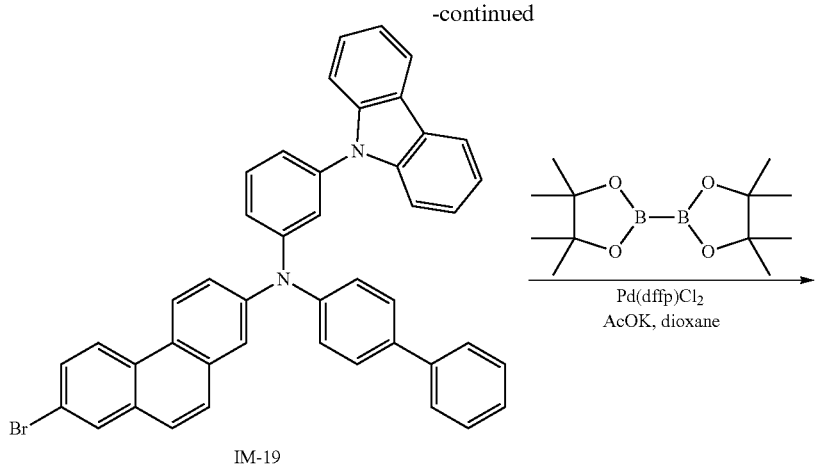
IM-19
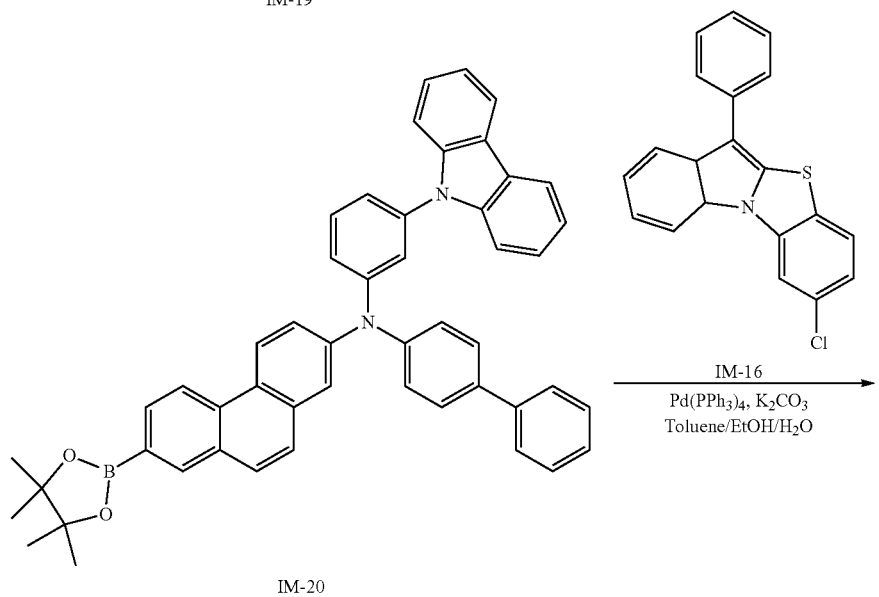
IM-20
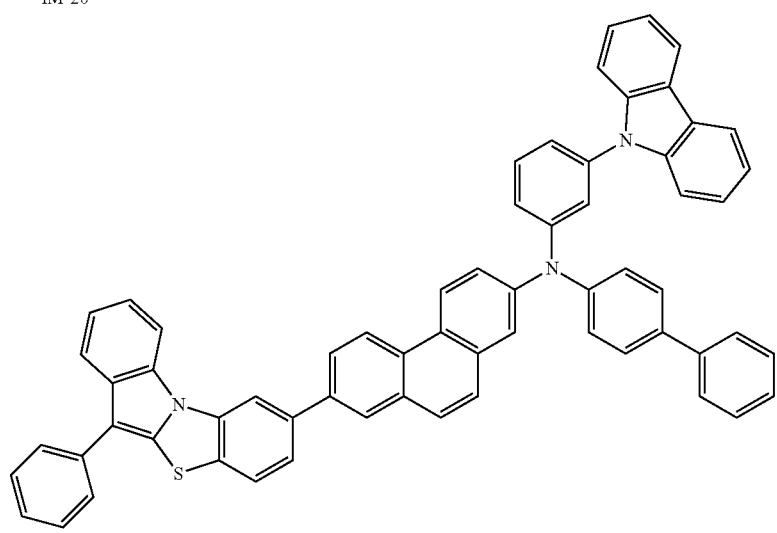
B67
Synthesis of Intermediate IM-19
Under an argon (Ar) atmosphere, to a 500 ml, three-neck flask, 15.00 g (36.5 mmol) of N-(3-(9H-carbazol-9-yl)phenyl)-[1,1'-biphenyl]-4-amine, 0.63 g (0.03 eq, 1.1 mmol) of Pd(dba)$_2$, 3.86 g (2.0 eq, 40.2 mmol) of NaOtBu, 183 ml of toluene, 18.42 g (1.5 eq, 54.8 mmol) of 2,7-dibromophenanthrene and 0.74 g (0.1 eq, 3.7 mmol) of tBu$_3$P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-19 (18.00 g, yield 74%). The molecular weight of Intermediate IM-19 measured by FAB-MS was 665.

Synthesis of Intermediate IM-20

Under an argon (Ar) atmosphere, to a 300 ml, three-neck flask, 10.00 g (15.0 mmol) of Intermediate IM-19, 1.23 g (0.1 eq, 1.5 mmol) of Pd(dppf)Cl$_2$.CH$_2$Cl$_2$ complex, 2.95 g (2.0 eq. 30.0 mmol) of KOAc, 4.58 g (1.2 eq, 18.0 mmol) of bis(pinacolato)diboron and 75 ml of 1,4-dioxane were added one by one, followed by heating to about 100° C. and stirring. After cooling to room temperature in the air, water was added to the reaction solution and an organic layer was separately taken. Toluene was added to an aqueous solution, and an organic layer was additionally extracted. Organic layers were put together and washed with a brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Intermediate IM-20 (8.46 g, yield 79%). The molecular weight of Intermediate IM-20 measured by FAB-MS was 712.

Synthesis of Compound B67

Under an argon (Ar) atmosphere, to a 300 ml, three-neck flask, 5.00 g (15.0 mmol) of Intermediate IM-16, 11.74 g (1.1 eq, 16.5 mmol) of Intermediate IM-20, 6.20 g (3.0 eq, 44.9 mmol) of K$_2$CO$_3$, 0.87 g (0.05 eq, 0.7 mmol) of Pd(PPh$_3$)$_4$ and 105 ml of a mixture solution of toluene/ EtOH/H$_2$O with 4:2:1 were added one by one, followed by heating to about 80° C. and stirring. After cooling to room temperature in the air, the reaction solution was extracted with toluene. An aqueous layer was removed, and an organic layer was washed with a saturated brine solution and dried with MgSO$_4$. After filtering MgSO$_4$, an organic layer was concentrated. The crude product thus obtained was separated by silica gel column chromatography using a mixture solvent of hexane and toluene as a developing solution to obtain Compound B67 (10.20 g, yield 77%). The molecular weight of Compound B67 measured by FAB-MS was 884.

1-13. Synthesis of Compound B100

Amine Compound B100 according to an embodiment t may be synthesized, for example, by the following Reaction 13:

Reaction 13

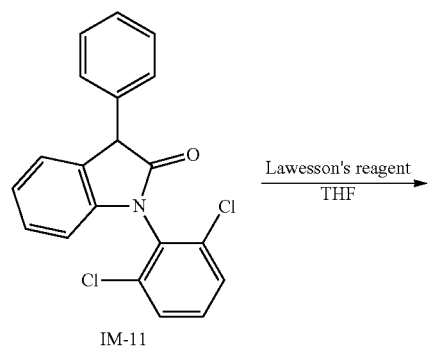

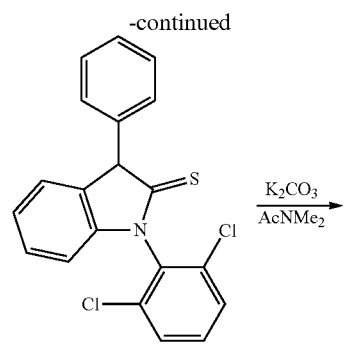

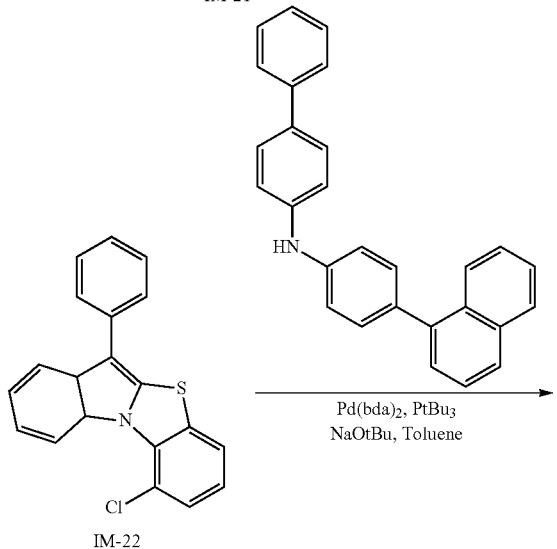

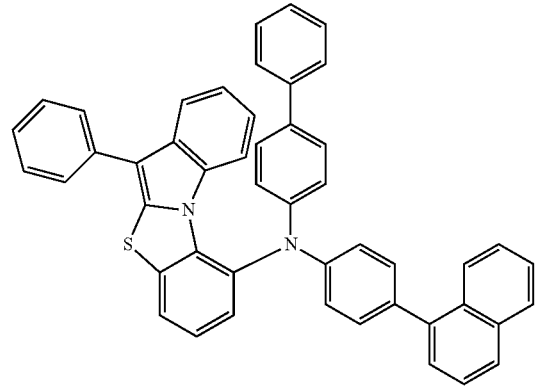

Synthesis of Intermediate IM-21

Under an argon (Ar) atmosphere, to a 300 ml, three-neck flask, 20.00 g (56.5 mmol) of Intermediate IM-11, 188 ml of THF, and 12.56 g (0.55 eq, 31.1 mmol) of Lawesson's reagent were added one by one, followed by stirring at room temperature. After concentrating the reaction solution, the crude product thus obtained was separated by silica gel column chromatography using a mixture solvent of hexane and toluene as a developing solution to obtain Intermediate IM-21 (15.89 g, yield 76%). The molecular weight of Intermediate IM-21 measured by FAB-MS was 370.

Synthesis of Intermediate IM-22

Under an argon (Ar) atmosphere, to a 300 ml, three-neck flask, 15.00 g (40.5 mmol) of Intermediate IM-21, 202 ml of N,N-dimethylacetamide and 22.39 g (4 eq, 162.0 mmol) of K₂CO₃ were added one by one, followed by heating to about 120° C. and stirring. After cooling to room temperature in the air, water was added to the reaction solution, and extraction with AcOEt was performed. An organic layer was washed with a saturated brine solution and dried with MgSO₄. After filtering MgSO₄, an organic layer was concentrated. The crude product thus obtained was separated by silica gel column chromatography using a mixture solvent of hexane and toluene as a developing solution to obtain Intermediate IM-22 (10.55 g, yield 78%). The molecular weight of Intermediate IM-22 measured by FAB-MS was 333.

Synthesis of Compound B100

Under an argon (Ar) atmosphere, to a 200 ml, three-neck flask, 5.00 g (15.0 mmol) of Intermediate IM-22, 0.26 g (0.03 eq, 0.4 mmol) of Pd(dba)₂, 2.88 g (2.0 eq, 30.0 mmol) of NaOtBu, 75 ml of toluene, 6.12 g (1.1 eq, 16.5 mmol) of N-[4-(naphthalen-1-yl)phenyl]-(1,1'-biphenyl)-4-amine and 0.30 g (0.1 eq, 1.5 mmol) of tBu₃P were added one by one, followed by heating to about 120° C. and stirring. After cooling to room temperature in the air, water was added to the reaction solution, and an organic layer was separately taken. Toluene was added to an aqueous layer, and an organic layer was additionally extracted. Organic layers were put together and washed with a brine solution and dried with MgSO₄. After filtering MgSO₄, an organic layer was concentrated. The crude product thus obtained was separated by silica gel column chromatography using a mixture solvent of hexane and toluene as a developing solution to obtain Compound B100 (8.01 g, yield 80%). The molecular weight of Compound B10 measured by FAB-MS was 668.

2. MANUFACTURE AND EVALUATION OF ORGANIC ELECTROLUMINESCENCE DEVICES INCLUDING AN AMINE COMPOUND 2-1. Examples of Organic Electroluminescence Devices Including an Amine Compound Organic electroluminescence devices of Examples 1 to 13 and Comparative Examples 1 to 5 were manufactured using Example Compounds A2, A14, A25, A46, A50, A63, A70, A85, B7, B31, B65, B67 and B100, and Comparative Compounds R1 to R5, respectively, as a material for a hole transport layer.

Example Compounds

A2

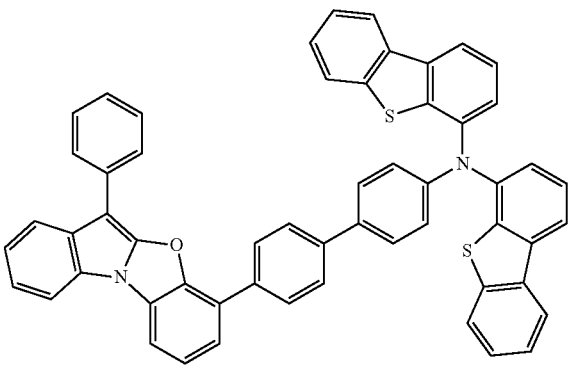

A14

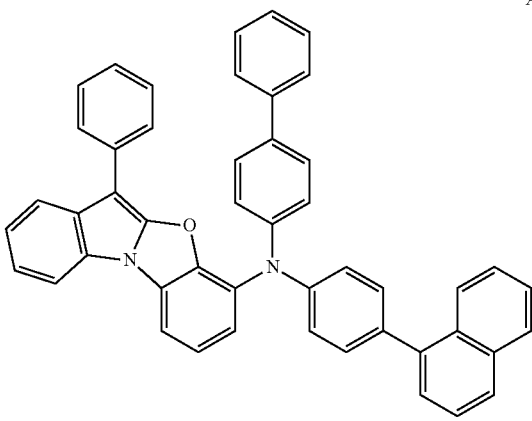

A25

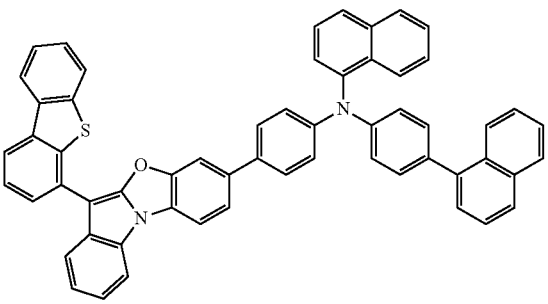

A46

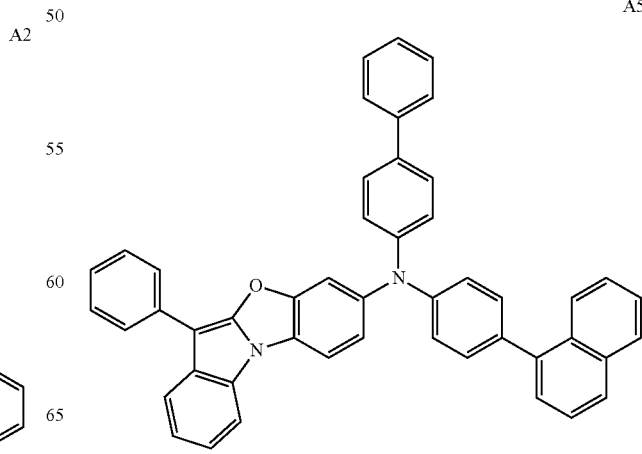

A50

123
-continued
A63
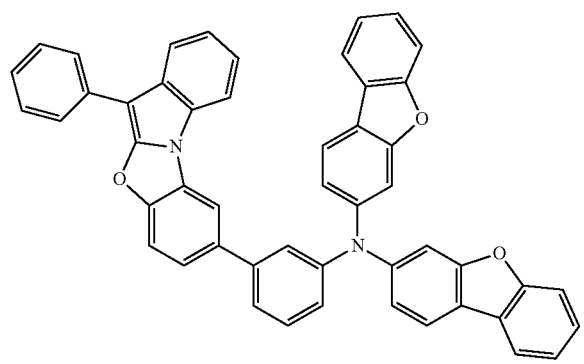
A70
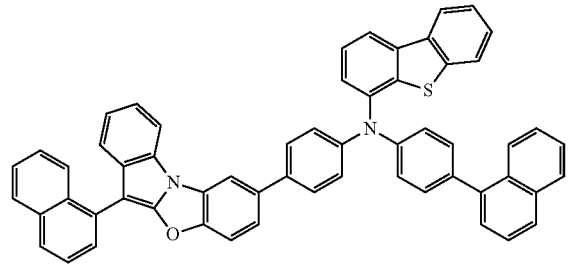
A85
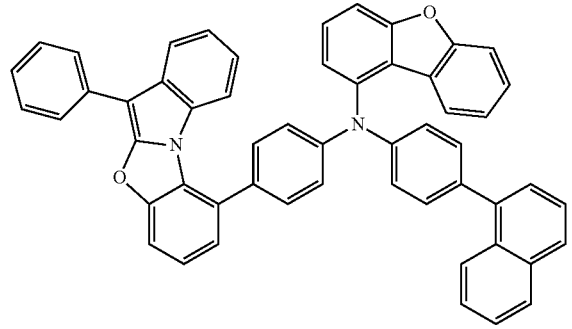
B7
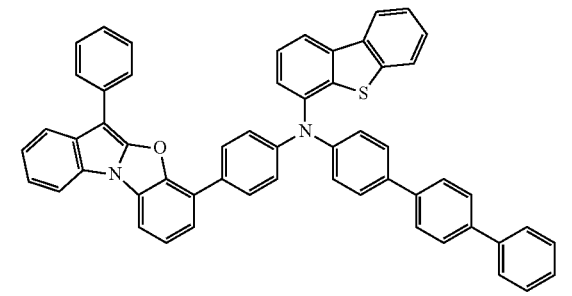
124
-continued
B31
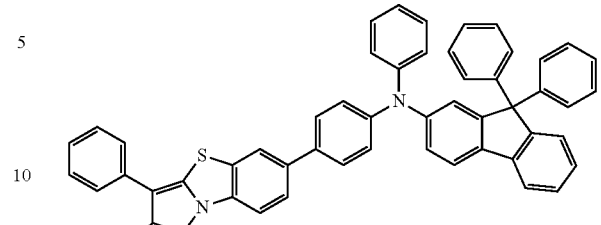
B65
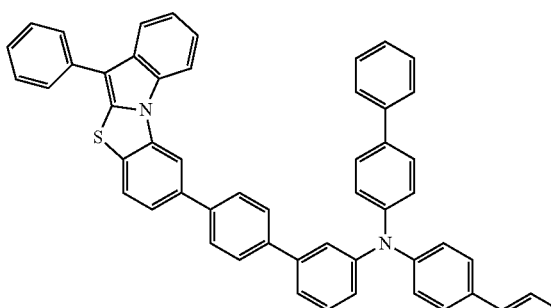
B67
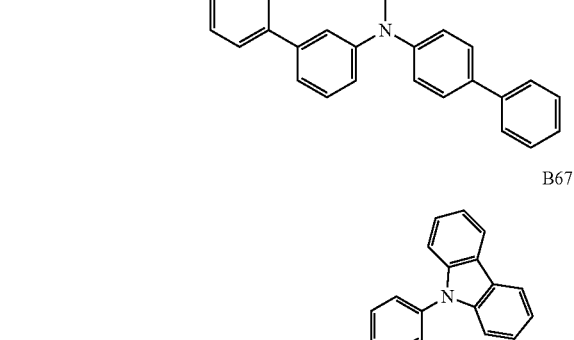
B100
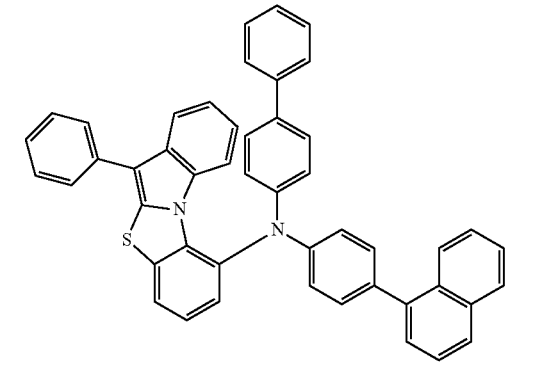

Comparative Compounds

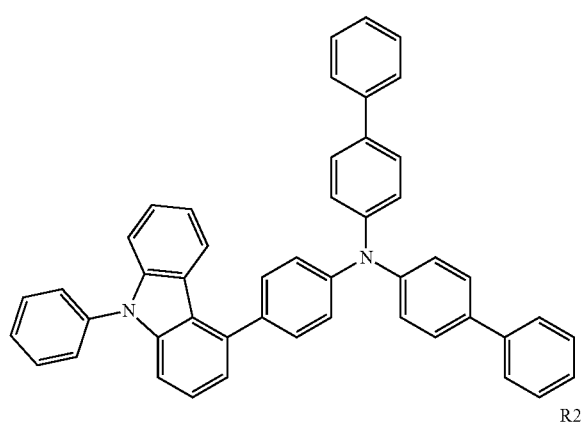
R1

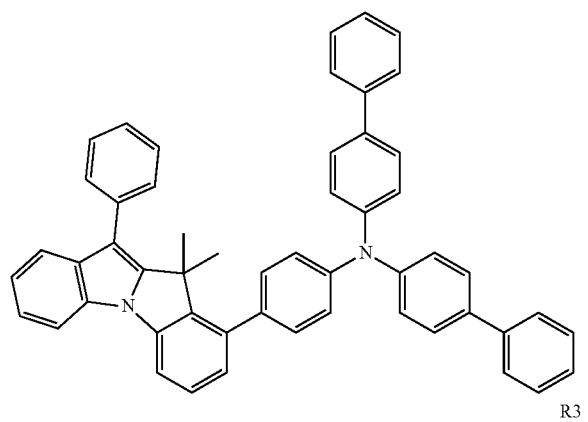
R2

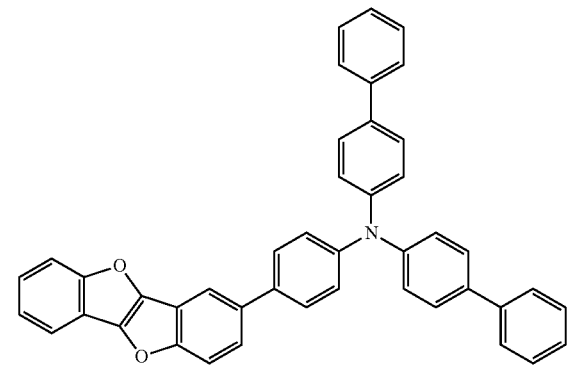
R3

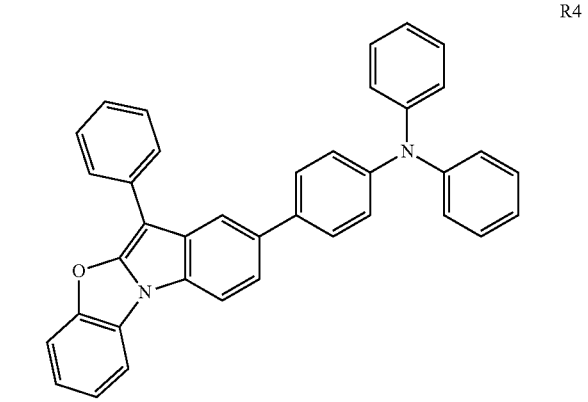
R4

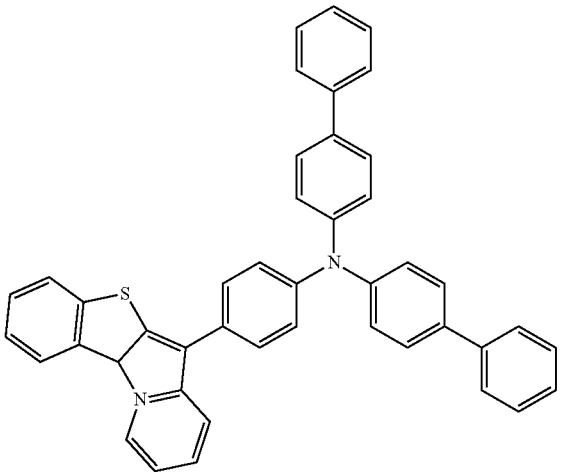
R5

Manufacture of Organic Electroluminescence Devices

Organic electroluminescence devices of Examples 1 to 13 and Comparative Examples 1 to 5 were manufactured as follows. A first electrode EL1 was formed using ITO to a thickness of about 150 nm. A hole injection layer HIL was formed using 2-TNATA to a thickness of about 60 nm, and a hole transport layer HTL was formed using each of the Example Compounds and the Comparative Compounds to a thickness of about 30 nm. An emission layer EML was formed using ADN doped with 3% TBP to a thickness of about 25 nm. An electron transport layer ETL was formed using $Alq_3$ to a thickness of about 25 nm, and an electron injection layer EIL was formed using LiF to a thickness of about 1 nm. A second electrode EL2 was formed using Al to a thickness of about 100 nm. Each layer was formed by using a vacuum deposition method.

Evaluation of Properties of Organic Electroluminescence Devices

The evaluation of the properties of the organic electroluminescence devices thus manufactured were conducted using 2400 series Source Meter of Keithley Instrument Co., a luminous brightness measurement apparatus, CS-200 of Konica Minolta Co., and PC Program LabVIEW 2.0 for measurement of National Instrument Co., in a dark room.

In order to evaluate the properties of the organic electroluminescence devices according to the Examples and the Comparative Examples, a driving voltage, current efficiency and luminance half life were measured. The current efficiency means a value with respect to a current density of about 10 $mA/cm^2$. In addition, the initial current density of the half-life of the luminance was about 1.0 $mA/cm^2$. The evaluation results in Table 1 are shown as relative values with respect to reference (100%) of the maximum emission efficiency and half-life of Comparative Example 1 in which DPEPO was used as a host material.

TABLE 1

| Device manufacturing example | Hole transport layer | Driving voltage (V) | Current efficiency (cd/A) | Luminance half life (h) |
|---|---|---|---|---|
| Example 1 | Example Compound A2 | 5.4 | 7.8 | 2050 |
| Example 2 | Example Compound A14 | 5.5 | 8.0 | 2000 |

TABLE 1-continued

| Device manufacturing example | Hole transport layer | Driving voltage (V) | Current efficiency (cd/A) | Luminance half life (h) |
|---|---|---|---|---|
| Example 3 | Example Compound A25 | 5.7 | 8.3 | 2000 |
| Example 4 | Example Compound A46 | 5.7 | 7.7 | 2150 |
| Example 5 | Example Compound A50 | 5.6 | 8.0 | 2100 |
| Example 6 | Example Compound A63 | 5.6 | 7.9 | 2050 |
| Example 7 | Example Compound A70 | 5.7 | 7.8 | 2200 |
| Example 8 | Example Compound A85 | 5.6 | 8.2 | 1950 |
| Example 9 | Example Compound B7 | 5.6 | 7.9 | 2000 |
| Example 10 | Example Compound B31 | 5.5 | 8.0 | 2250 |
| Example 11 | Example Compound B65 | 5.5 | 8.0 | 2100 |
| Example 12 | Example Compound B67 | 5.6 | 7.6 | 2050 |
| Example 13 | Example Compound B100 | 5.7 | 8.3 | 2000 |
| Comparative Example 1 | Comparative Compound R1 | 6.3 | 6.0 | 1550 |
| Comparative Example 2 | Comparative Compound R2 | 6.4 | 6.5 | 1500 |
| Comparative Example 3 | Comparative Compound R3 | 6.1 | 5.8 | 1500 |
| Comparative Example 4 | Comparative Compound R4 | 5.9 | 6.8 | 1600 |
| Comparative Example 5 | Comparative Compound R5 | 6.0 | 6.7 | 1650 |

Referring to the results of Table 1, it was found that if the amine compound according to an embodiment is applied as a material for a hole transport layer in the organic electroluminescence device, a low driving voltage, high efficiency and long life could be achieved. For example, Example 1 to Example 13 accomplished higher efficiency and longer life when compared with Comparative Example 1 to Comparative Example 5. Example 1 to Example 13 showed a driving voltage of about 5.4 V to about 5.7 V, current efficiency of about 7.6 cd/A to about 8.3 cd/A, and luminance half life of about 1950 hours to about 2200 hours, and a low driving voltage, high efficiency and long life were achieved. Comparative Example 1 to Comparative Example 5 showed a driving voltage of about 5.9 V to about 6.4 V, current efficiency of about 5.86 cd/A to about 6.8 cd/A, and luminance half life of about 1500 hours to about 1650 hours, and a higher driving voltage, lower efficiency and shorter life were achieved when compared with the Example Compounds.

The Example Compounds are considered to achieve high efficiency and a low driving voltage while keeping the long-life characteristics of amine by introducing an amine to a benzoxazoleindole or benzothiazoleindole skeleton, which has excellent heat tolerance and charge tolerance.

In the benzoxazoleindole skeleton or the benzothiazoleindole skeleton, position A1 and position A2 may be defined as follows.

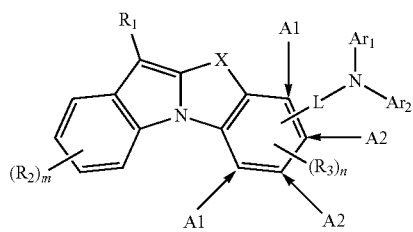

If an amine group is substituted at position A1, a conformation in which the benzoxazoleindole skeleton or the benzothiazoleindole skeleton is bent toward the nitrogen atom of the amine group is obtained. Accordingly, the volume of a whole molecule may increase, and crystallinity may be restrained. Thus, a hole transport degree may be appropriately controlled and the recombination probability of holes and electrons in an emission layer may increase. Therefore, Examples 1, 2, 3, 8, 9 and 13 are thought to achieve excellent current efficiency.

If the amine group is substituted at position A2, the highest occupied molecular orbital (HOMO) around the nitrogen atom of the amine group is delocalized to the benzoxazoleindole skeleton or the benzothiazoleindole skeleton, and the stability in a radical state may be improved. Accordingly, Examples 4, 5, 6, 7, 10, 11 and 12 are thought to achieve long life.

Comparative Examples 1 and 2 do not include a heteroatom other than a nitrogen atom in a core structure and Comparative Example 3 does not include a nitrogen atom in a core structure. Comparative Examples 1 to 3 may show decreased current efficiency when compared with the Examples, which may be because the number and kind of the heteroatom included in the core structure of Comparative Examples 1 to 3 are changed compared to the Examples such that the carrier balance collapses.

Comparative Examples 4 and 5 have the benzoxazoleindole skeleton or the benzothiazoleindole skeleton, but an amine group is substituted at a position having high reactivity in a core structure. The molecular stability of the compounds of Comparative Examples 4 and 5 in a radical state may be deteriorated. Comparative Examples 4 and 5 showed decreased current efficiency and life when compared with the Examples.

In conclusion, the Examples have the benzoxazoleindole skeleton or the benzothiazoleindole skeleton, and the amine group is substituted at position A1 or A2. A low driving voltage, high efficiency and long life may be achieved at the same time.

By way of summation and review, an organic electroluminescence display device is so-called a self-luminescent display device in which holes and electrons injected from a first electrode and a second electrode recombine in an emission layer, and a light emission material which is an organic compound included in the emission layer emits light to achieve display.

In an electroluminescence display device, holes are injected from the first electrode, and the injected holes move via the hole transport layer and are injected into the emission layer. Meanwhile, electrons are injected from the second electrode, and the injected electrons move via the electron transport layer and are injected into the emission layer. By the recombination of the injected holes and electrons in the emission layer, excitons are produced in the emission layer.

The organic electroluminescence device emits light using light produced during the transition of the excitons to a ground state.

In an organic electroluminescence device of a display device, a decrease of the driving voltage, and an increase of the light-emitting efficiency and life of the organic electroluminescence device are desirable. The development of materials for an organic electroluminescence device stably attaining the requirements is ongoing.

Embodiments provide an organic electroluminescence device and an amine compound used therein.

The organic electroluminescence device according to an embodiment may accomplish a low driving voltage, high efficiency and long life.

The amine compound according to an embodiment may be applied to an organic electroluminescence device and may contribute to the decrease of a driving voltage, and the increase of efficiency and life.

The organic electroluminescence device of an embodiment may accomplish a low driving voltage, high efficiency and long life.

The amine compound of an embodiment may be applied in an organic electroluminescence device and may contribute to the decrease of a driving voltage, and the increase of efficiency and life.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. An organic electroluminescence device, comprising:
a first electrode;
a second electrode on the first electrode; and
a plurality of organic layers between the first electrode and the second electrode,
wherein at least one organic layer among the organic layers includes an amine compound represented by the following Formula 1:

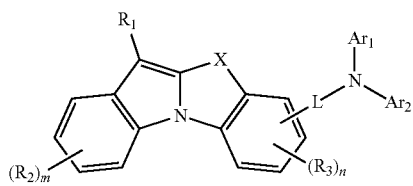

[Formula 1]

in Formula 1,
X is O or S,
$R_1$ is a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms, $R_2$ and $R_3$ are each independently a hydrogen atom, a deuterium atom, a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms, or combined with an adjacent group to form a ring, "m" is an integer of 0 to 4, "n" is an integer of 0 to 3, L is a direct linkage, a substituted or unsubstituted arylene group of 6 to 40 ring carbon atoms, or a substituted or unsubstituted heteroarylene group of 5 to 40 ring carbon atoms, and $Ar_1$ and $Ar_2$ are each independently a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms.

2. The organic electroluminescence device as claimed in claim 1, wherein Formula 1 is represented by the following Formula 2-1 or 2-2:

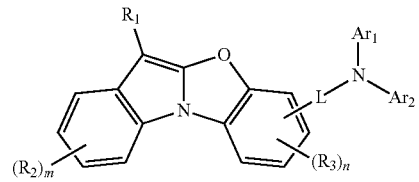

[Formula 2-1]

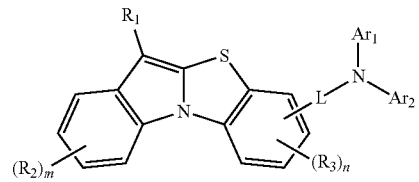

[Formula 2-2]

in Formulae 2-1 and 2-2, $R_1$, $R_2$, $R_3$, $Ar_1$, $Ar_2$ "m", "n" and L are the same as defined in Formula 1.

3. The organic electroluminescence device as claimed in claim 1, wherein Formula 1 is represented by any one among the following Formulae 3-1 to 3-4:

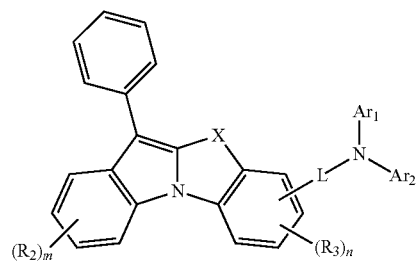

[Formula 3-1]

-continued

[Formula 3-2]

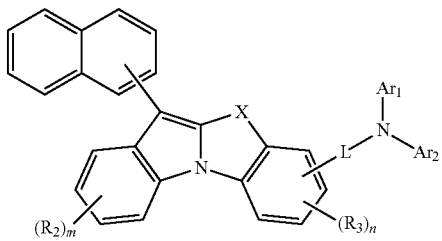

[Formula 3-3]

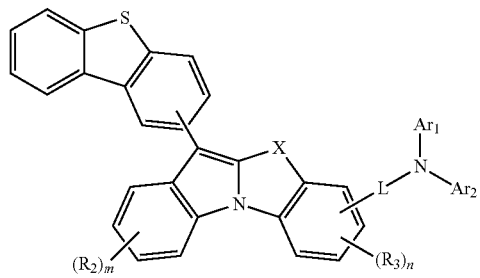

[Formula 3-4]

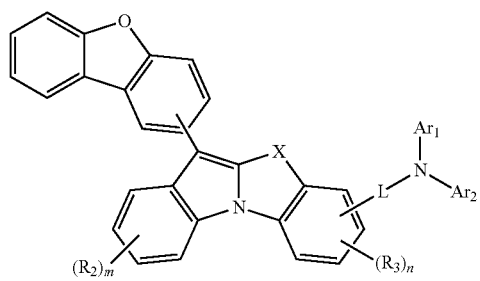

in Formulae 3-1 to 3-4,

X, $R_2$, $R_3$, $Ar_1$, $Ar_2$ "m", "n" and L are the same as defined in Formula 1.

4. The organic electroluminescence device as claimed in claim 1, wherein $R_2$ and $R_3$ are each independently any one of a substituted or unsubstituted cyclohexyl group, a substituted or unsubstituted phenyl group, a substituted or unsubstituted biphenyl group, a substituted or unsubstituted dibenzofuran group, a substituted or unsubstituted dibenzothiophene group and a substituted or unsubstituted carbazole group, or combined with an adjacent group to form a benzene ring.

5. The organic electroluminescence device as claimed in claim 1, wherein "m" and "n" are 0.

6. The organic electroluminescence device as claimed in claim 1, wherein $Ar_1$ and $Ar_2$ are each independently a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted triphenylene group, a substituted or unsubstituted dibenzothiophene group, a substituted or unsubstituted dibenzofuran group, or a substituted or unsubstituted carbazole group.

7. The organic electroluminescence device as claimed in claim 6, wherein $Ar_1$ and $Ar_2$ are each independently unsubstituted or substituted with at least one substituent selected from a hydrogen atom, a deuterium atom, a fluorine atom, an adamantyl group, a triphenylsilyl group, a phenoxy group, an aryl group of 6 to 30 ring carbon atoms, and a heteroaryl group of 5 to 30 ring carbon atoms, or adjacent substituents are combined with each other to form a ring.

8. The organic electroluminescence device as claimed in claim 1, wherein L is a direct linkage, a substituted or unsubstituted phenylene group, a substituted or unsubstituted divalent biphenyl group, a substituted or unsubstituted naphthylene group, a substituted or unsubstituted phenanthrylene group, or a substituted or unsubstituted fluorenylene group.

9. The organic electroluminescence device as claimed in claim 1, wherein the organic layers include:
a hole transport region on the first electrode;
an emission layer on the hole transport region; and
an electron transport region on the emission layer,
wherein the hole transport region includes the amine compound.

10. The organic electroluminescence device as claimed in claim 9, wherein the emission layer emits any one of blue light and green light.

11. The organic electroluminescence device as claimed in claim 1, wherein the amine compound includes at least one among compounds represented in the following Compound Group A and Compound Group B:

[Compound Group A]

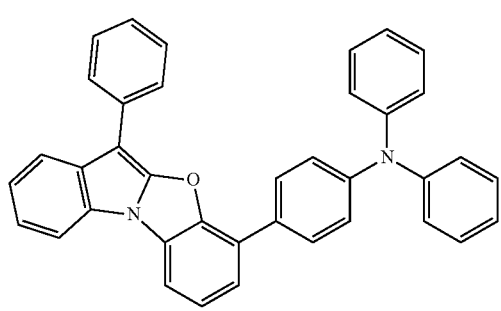

A1

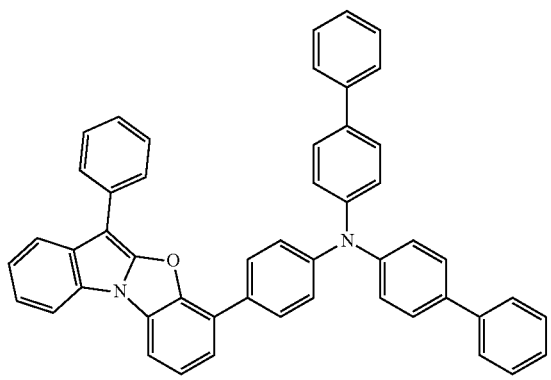

A2

-continued
A3
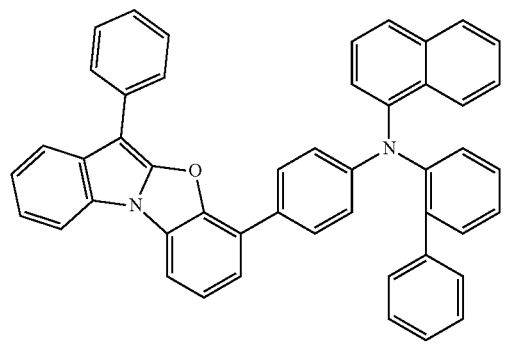
A4
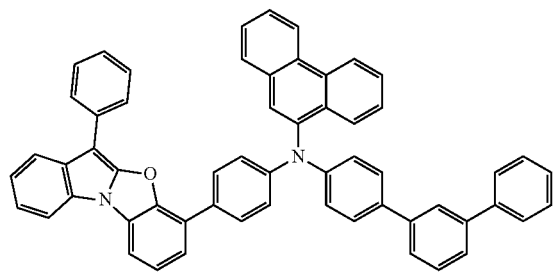
A5
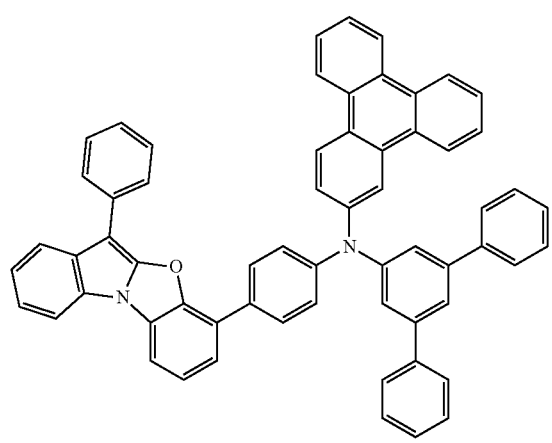
A6
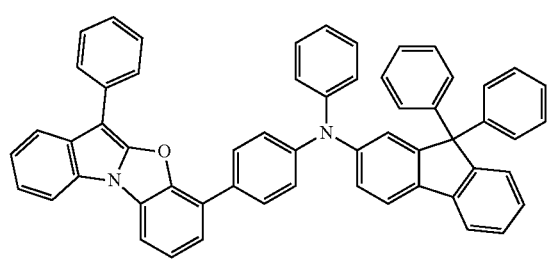
A7
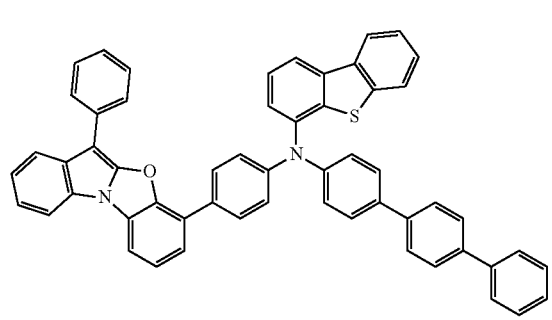
A8
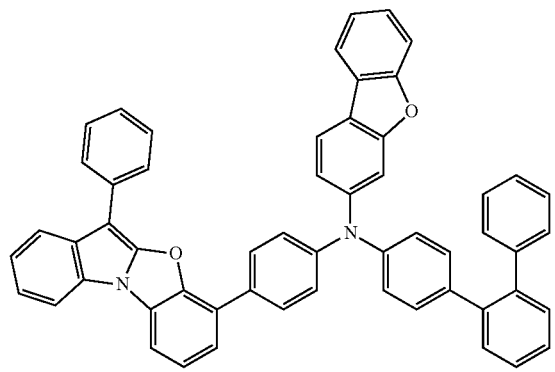
A9
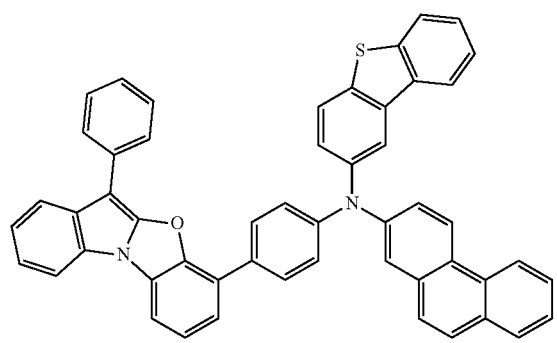
A10
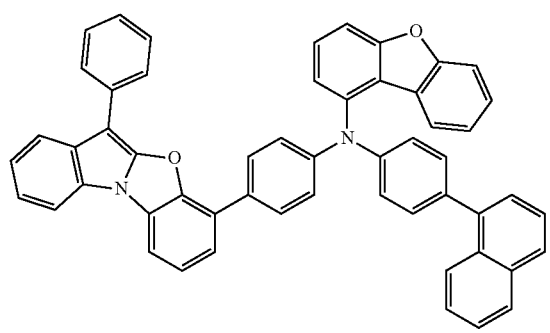

-continued
A11
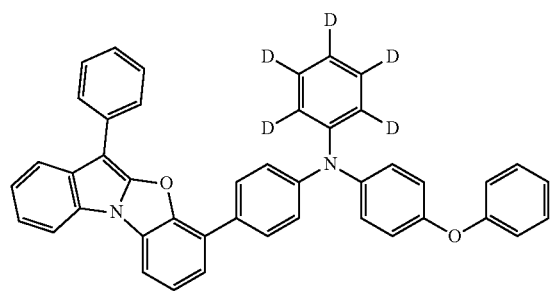
A12
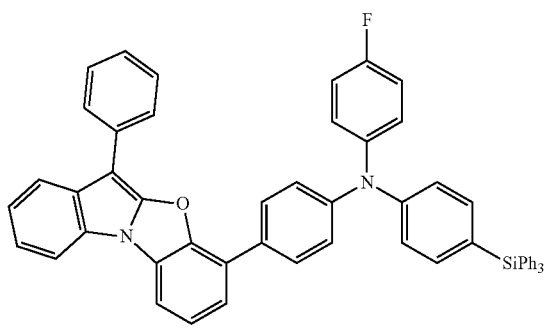
A13
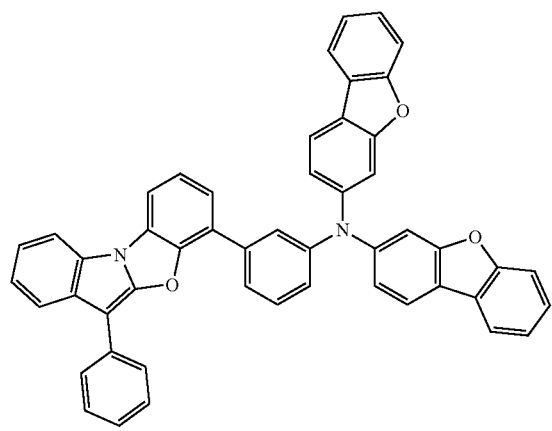
A14
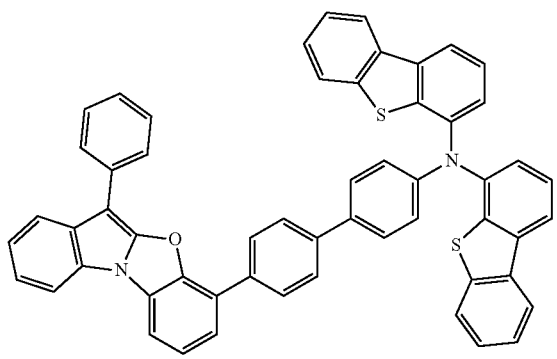
A15
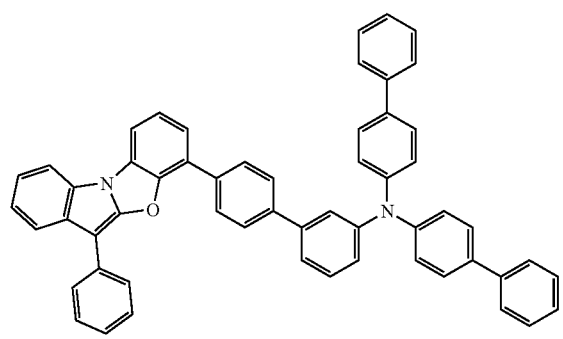
A16
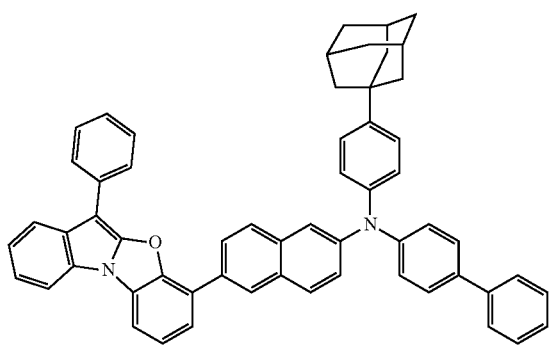
A17
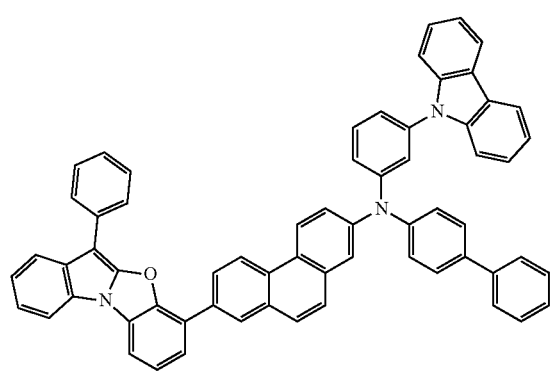
A18
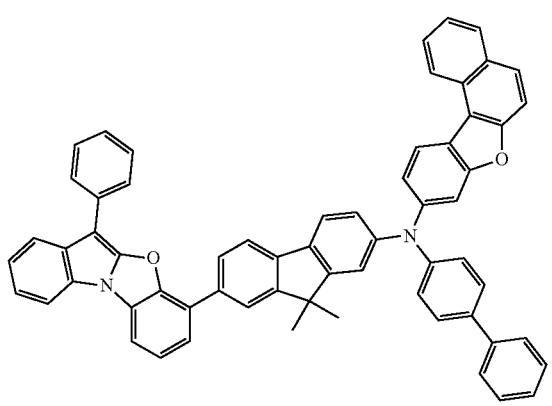

-continued
A19
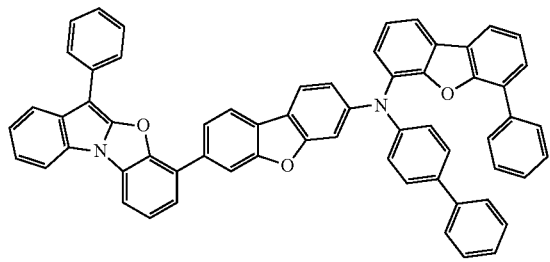
A20
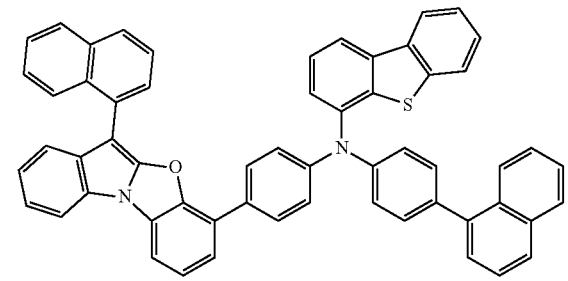
A21
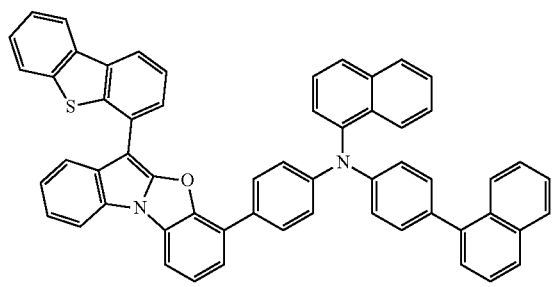
A22
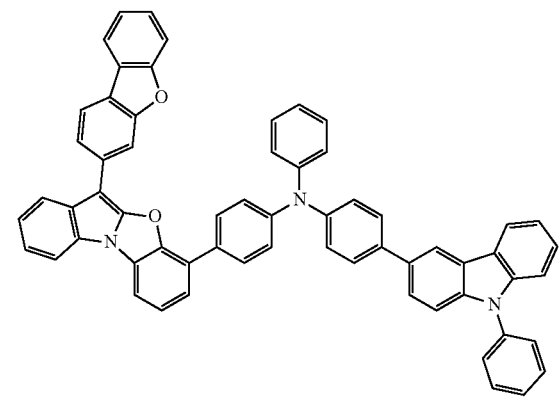
A23
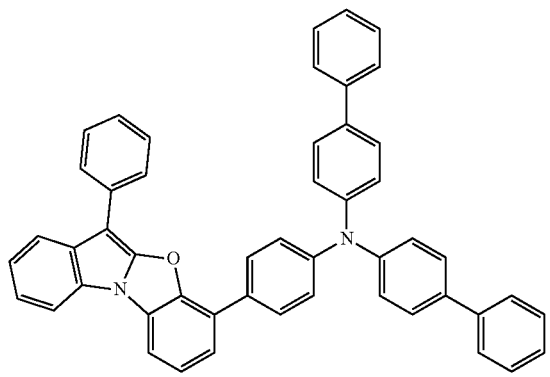
A24
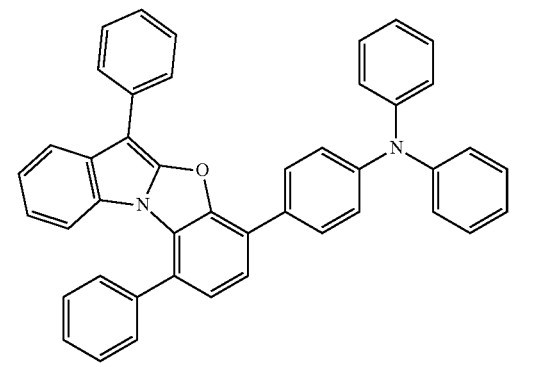
A25
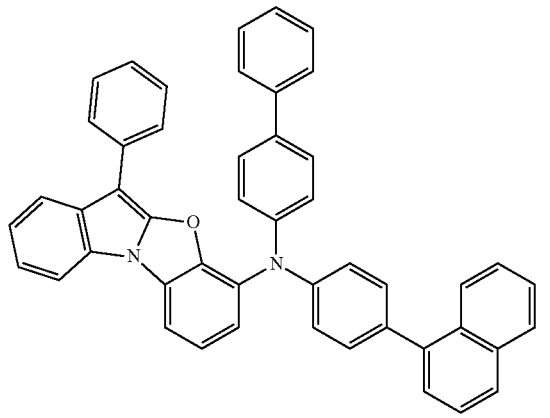
A26
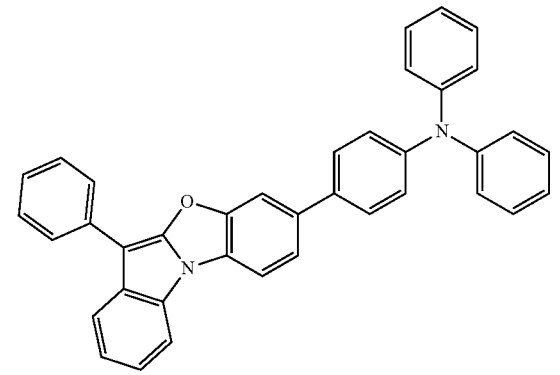

-continued
A27
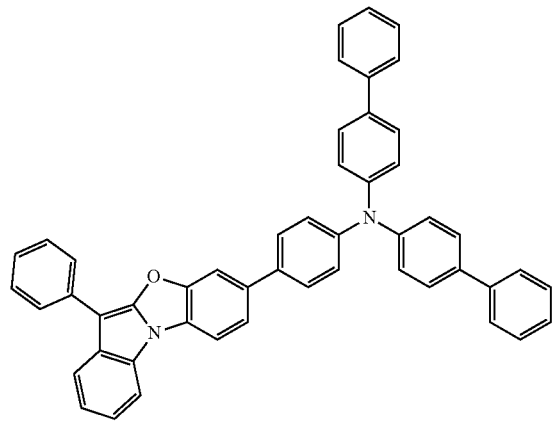
A28
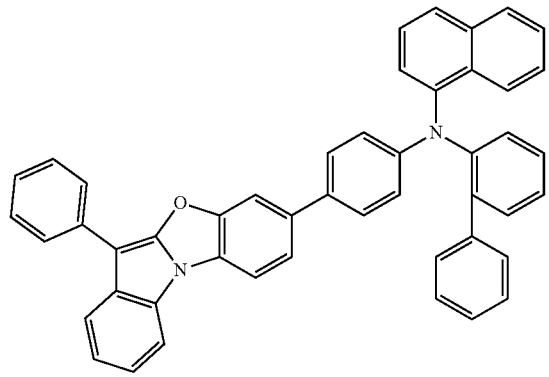
A29
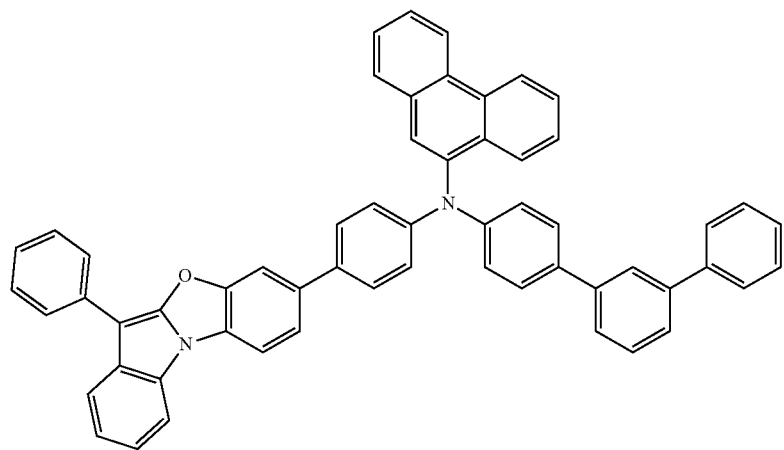
A30
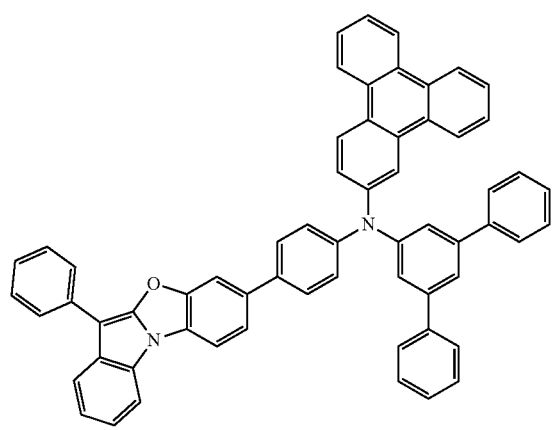
A31
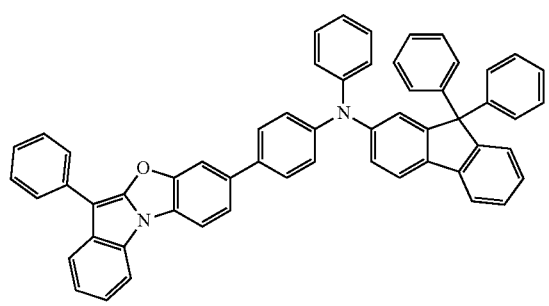

-continued
A32
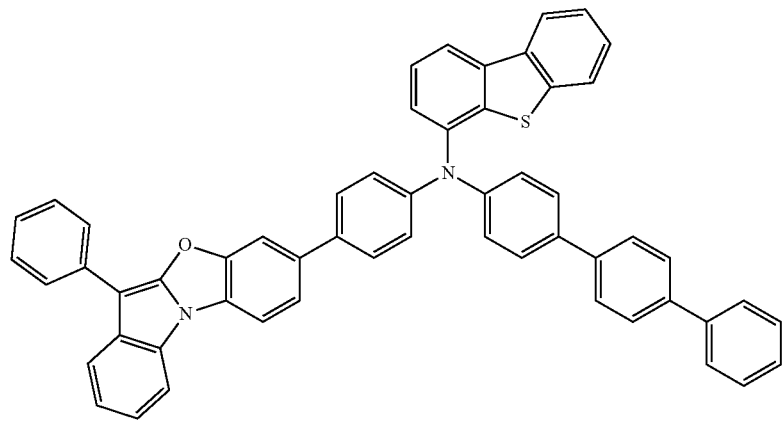
A33
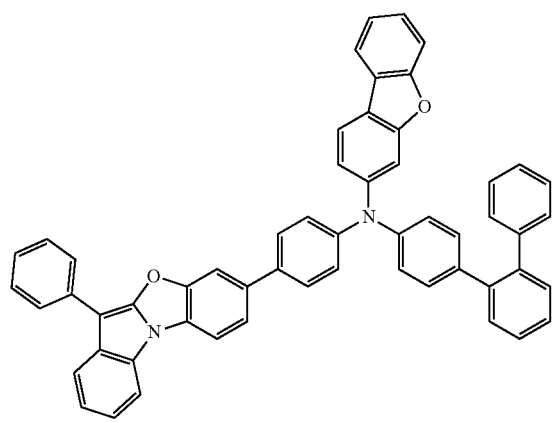
A34
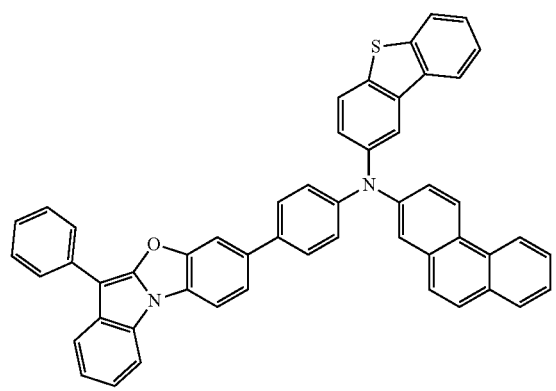
A35
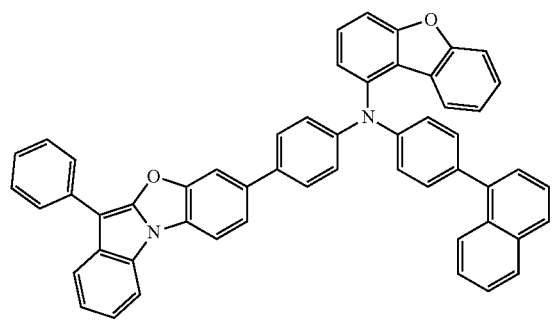
A36
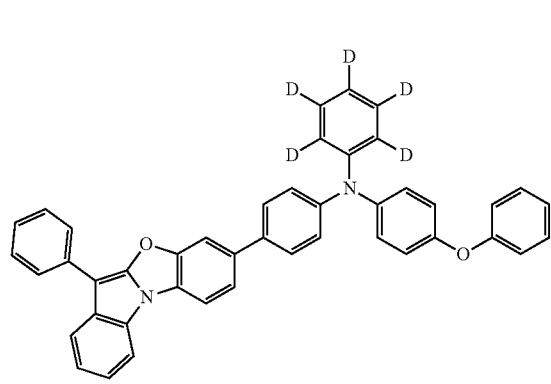
A37
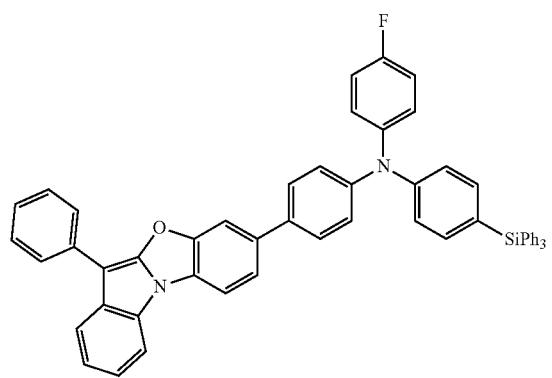
A38
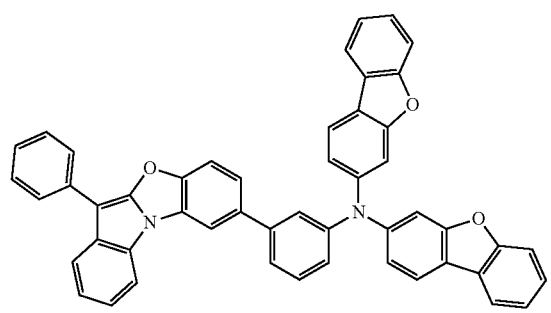

-continued
A39
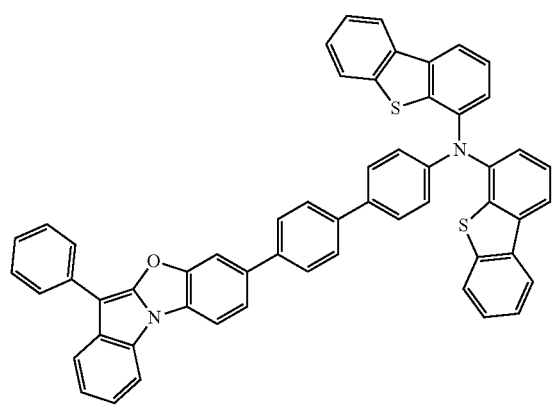
A40
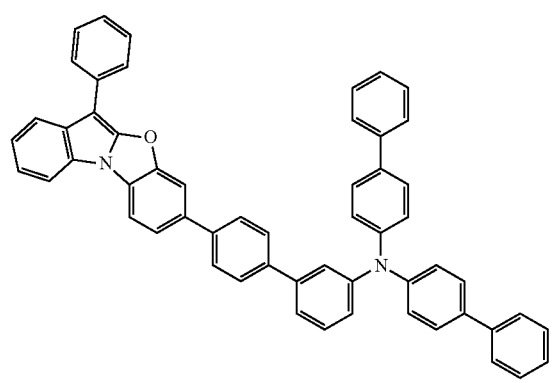
A41
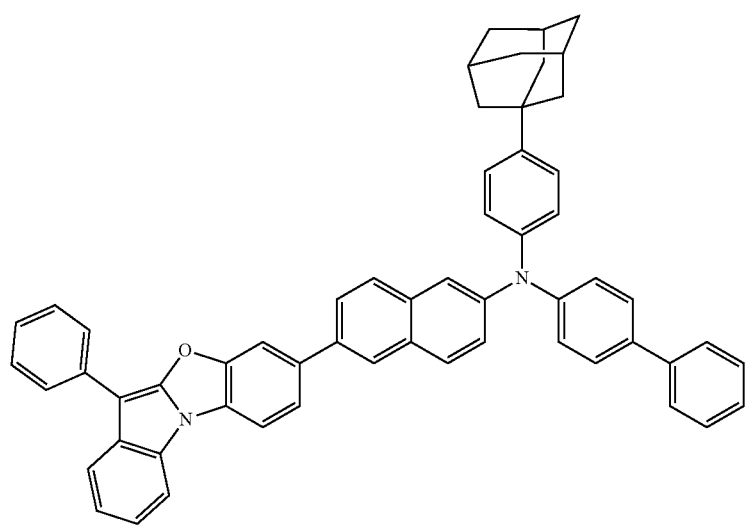
A42
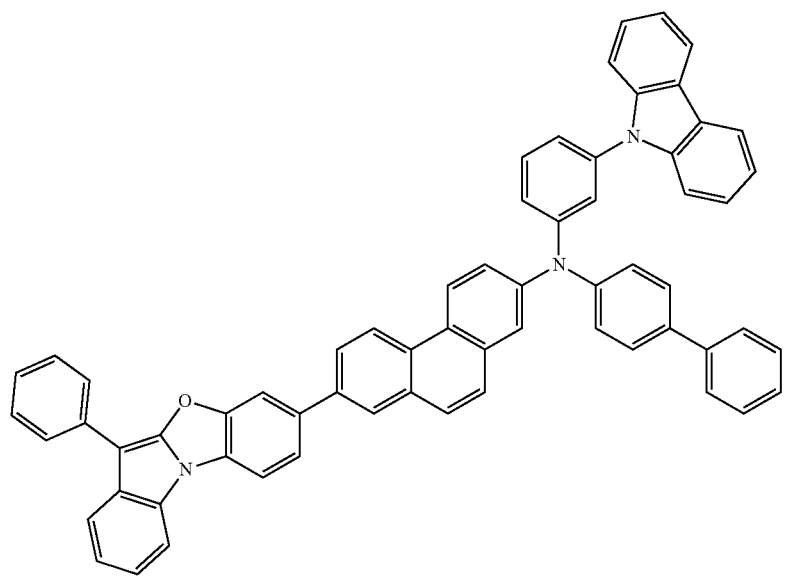

-continued
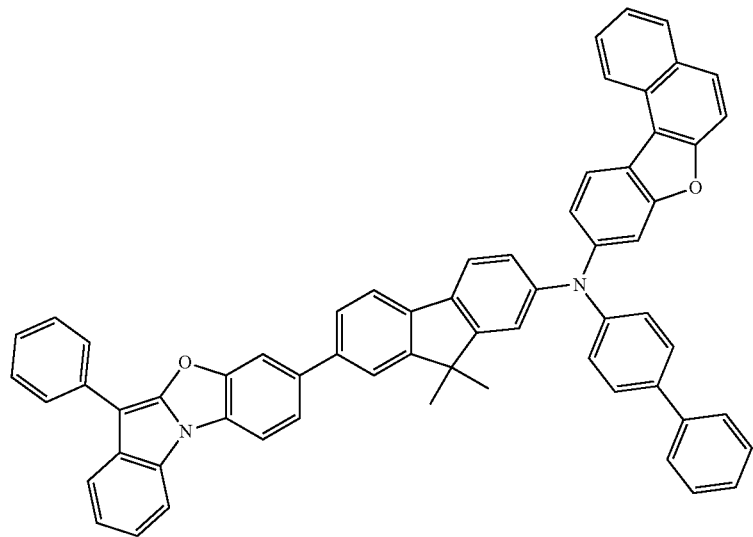
A43
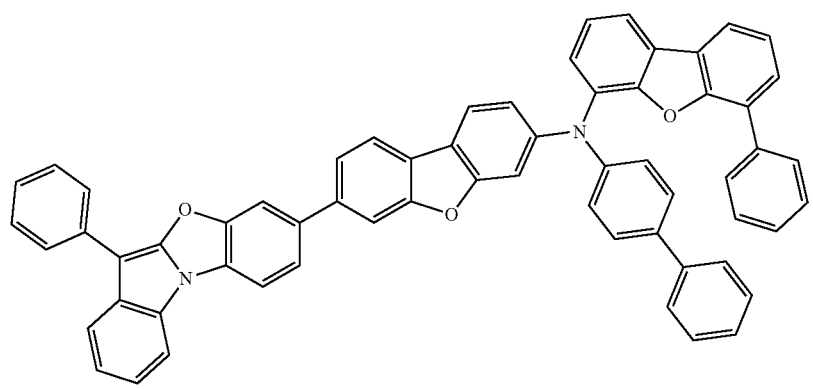
A44
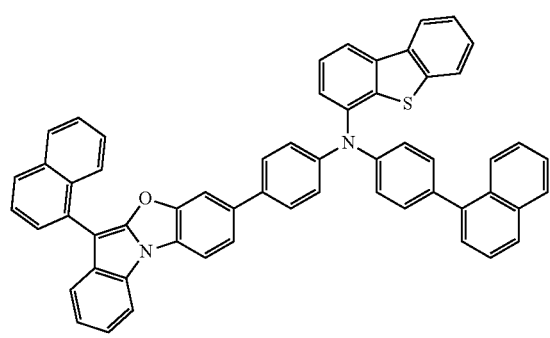
A45
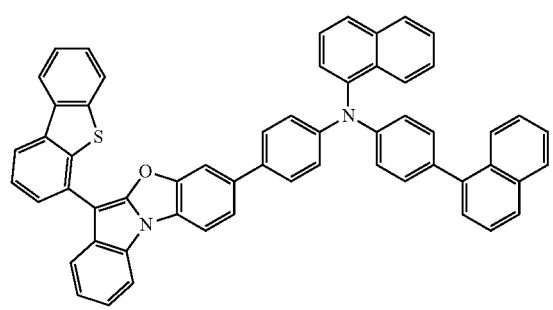
A46

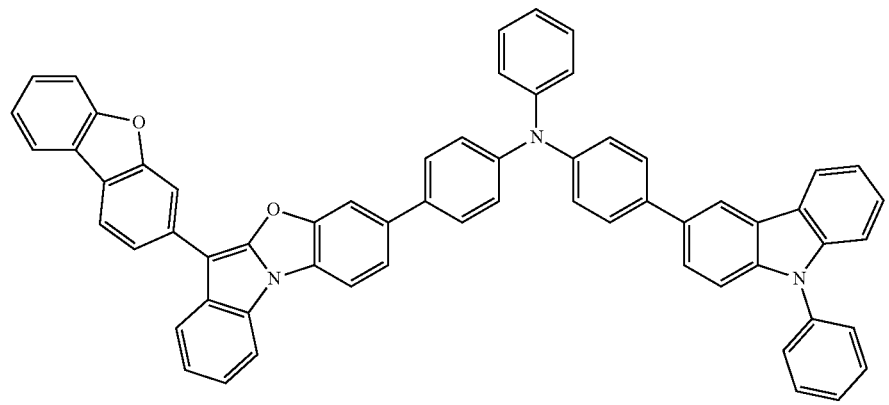
A47
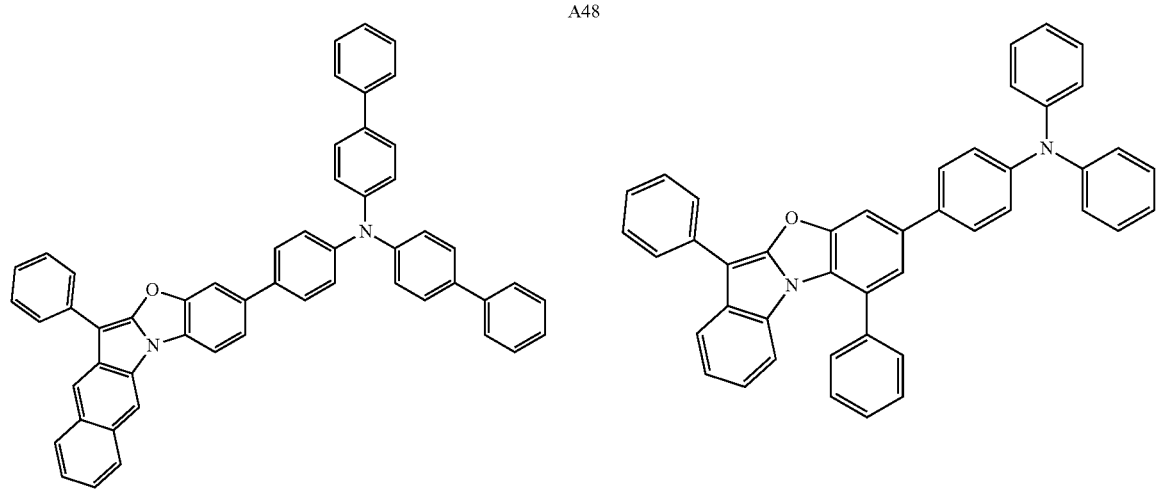
A48
A49
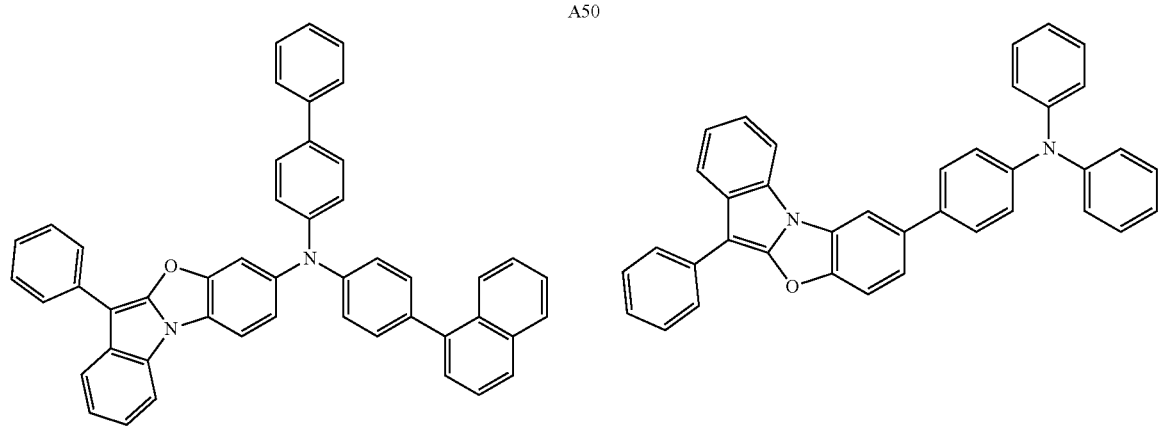
A50
A51

-continued
A52
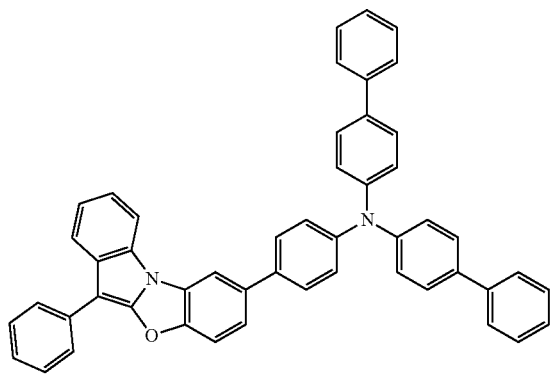
A53
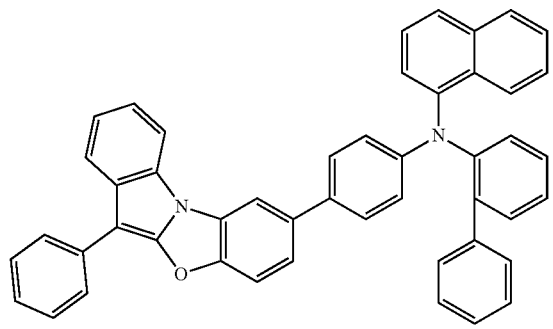
A54
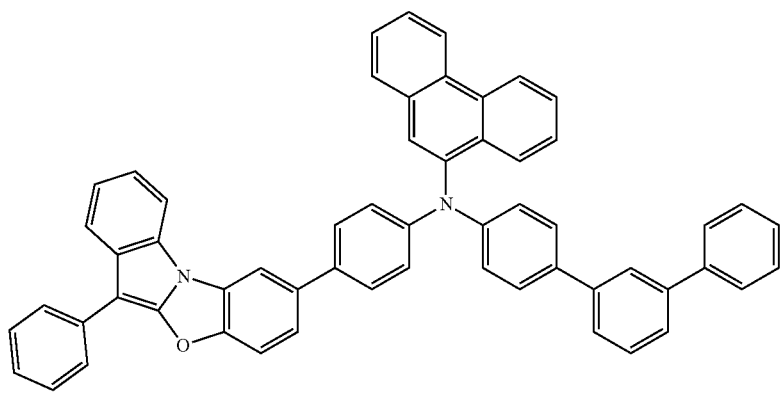
A55
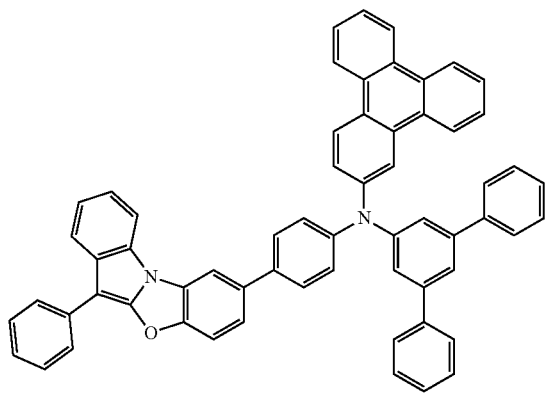
A56
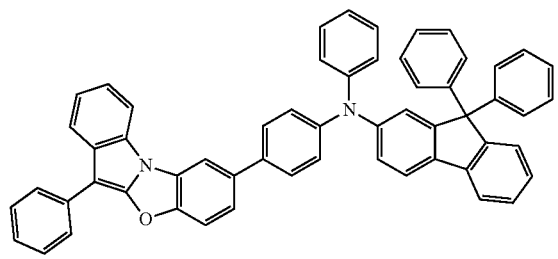
A57
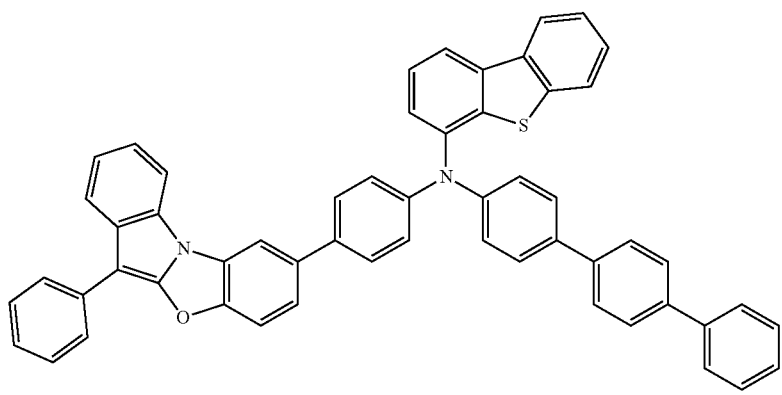

-continued
A58
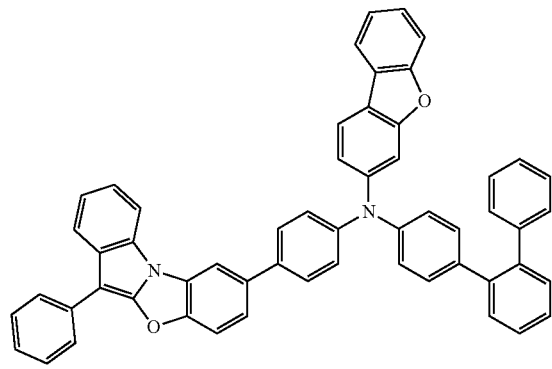
A59
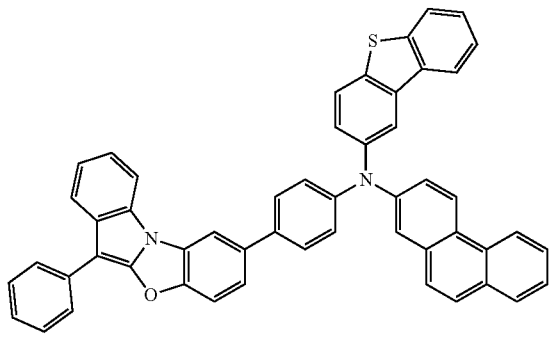
A61
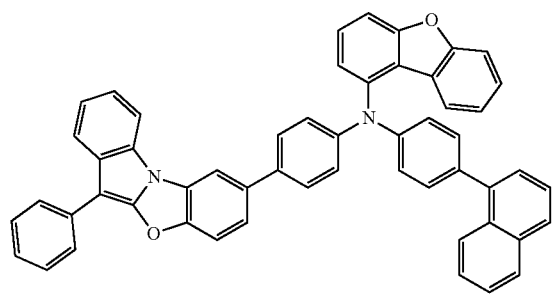
A60
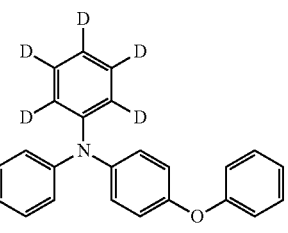
A62
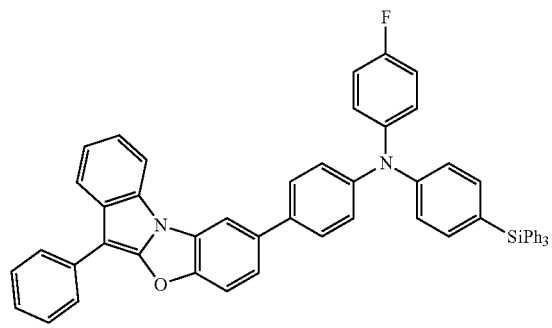
A63
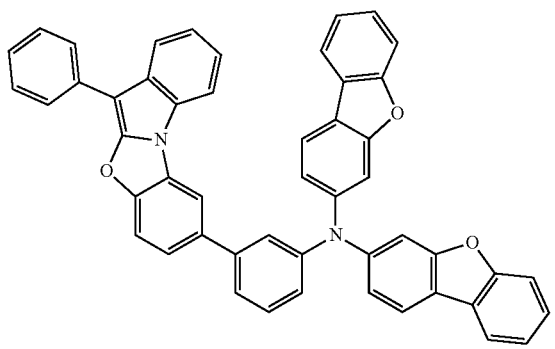
A64
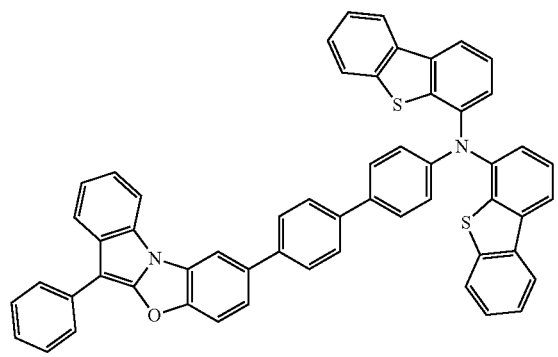
A65
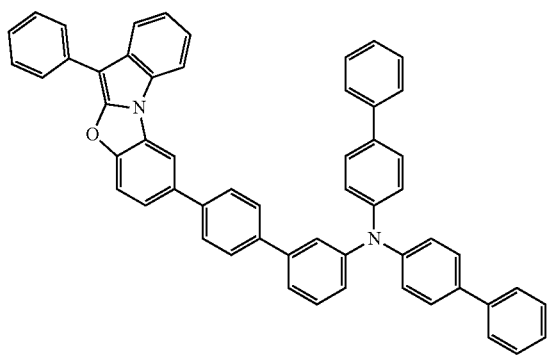

A66
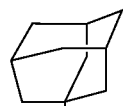
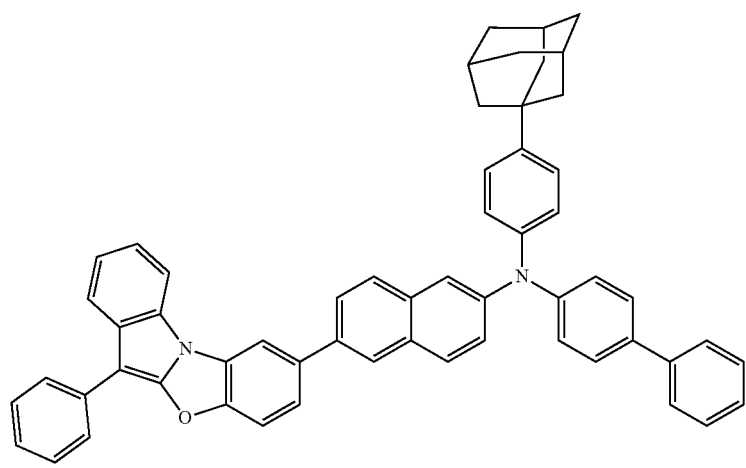
A67
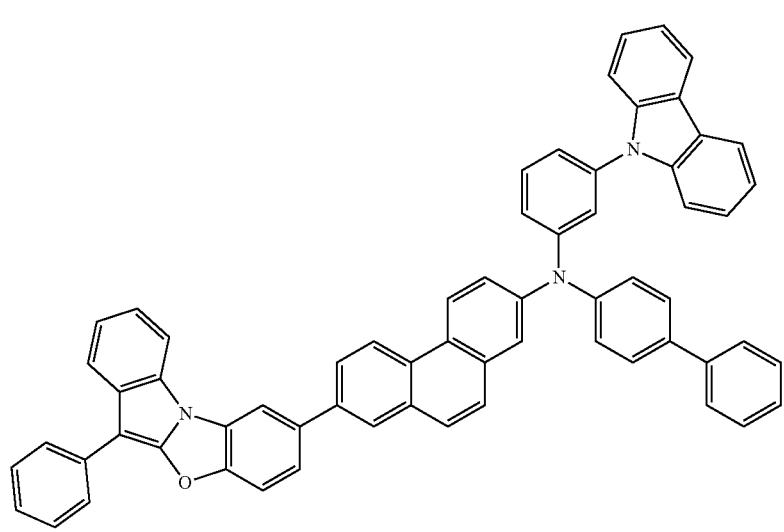
A68
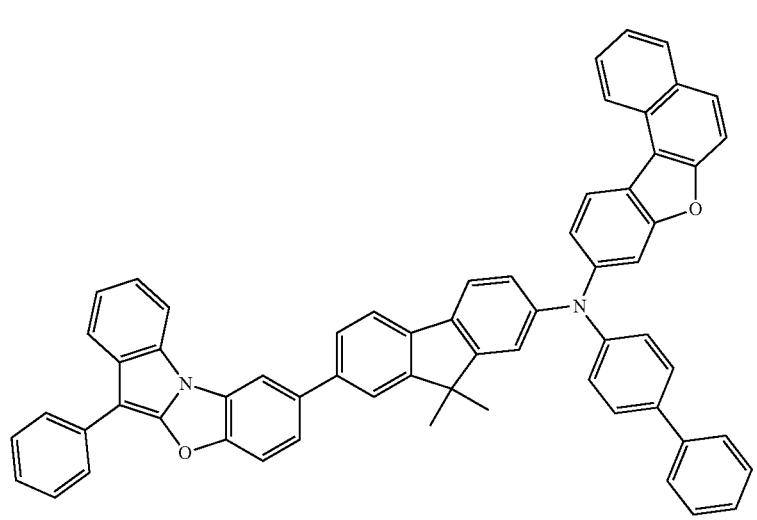

A69
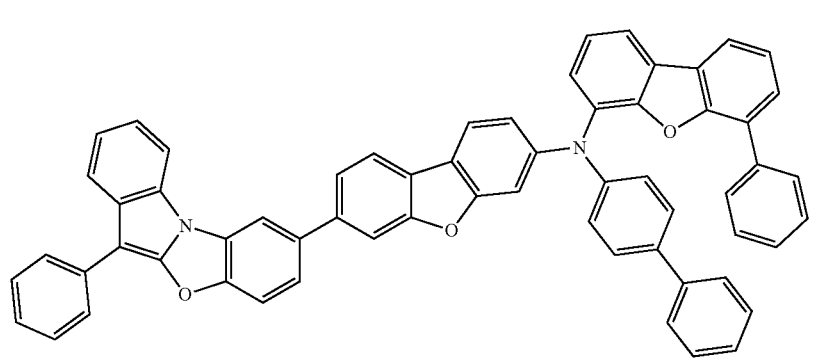
A70
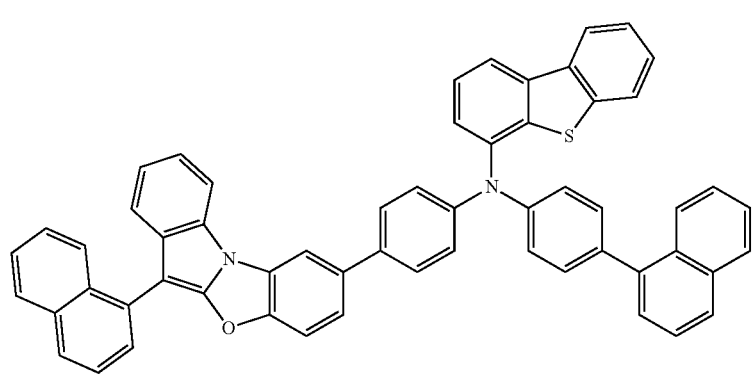
A71
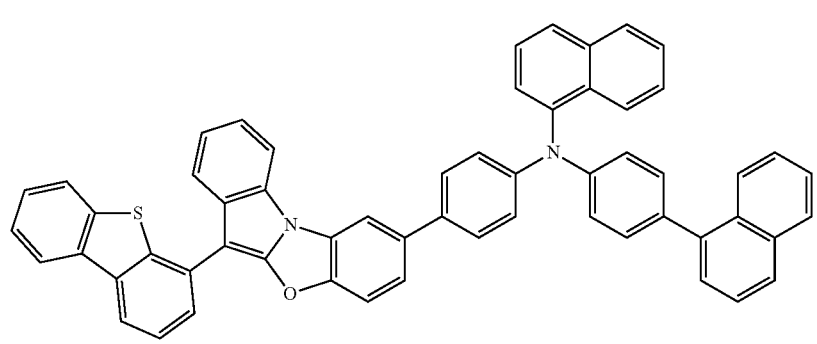
A72
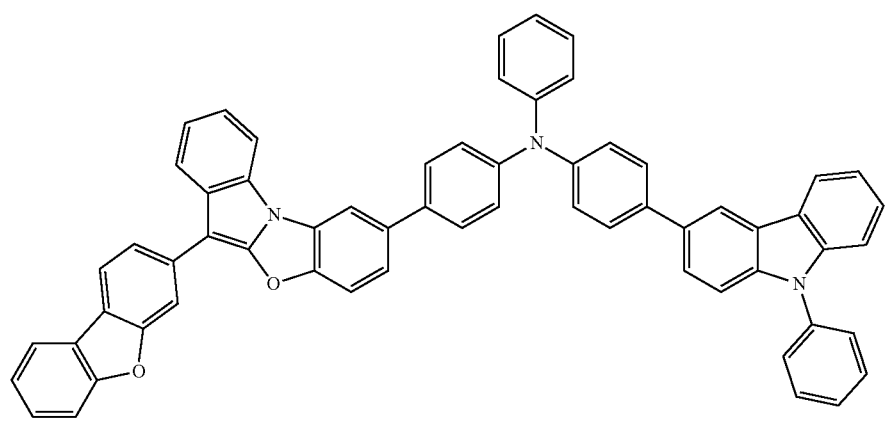

-continued
A73
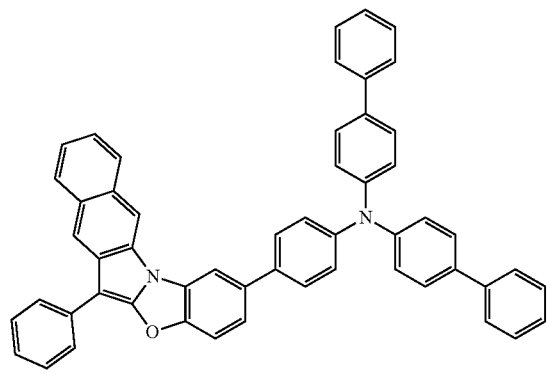
A74
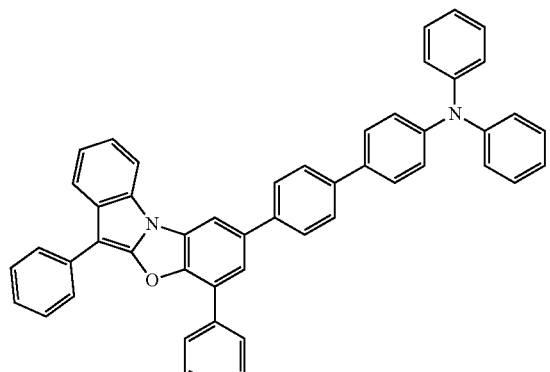
A75
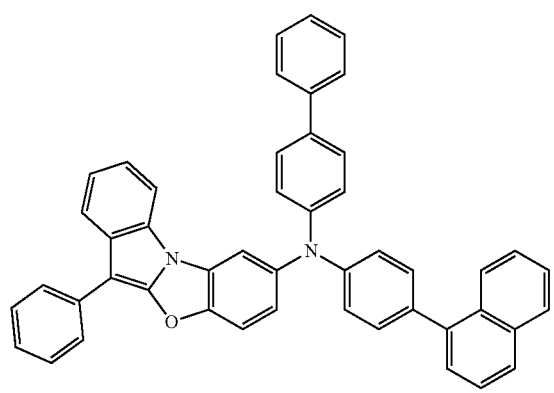
A76
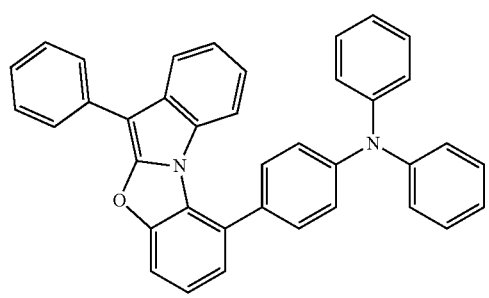
A77
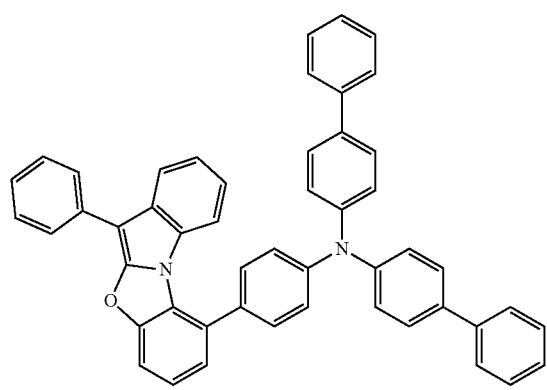
A78
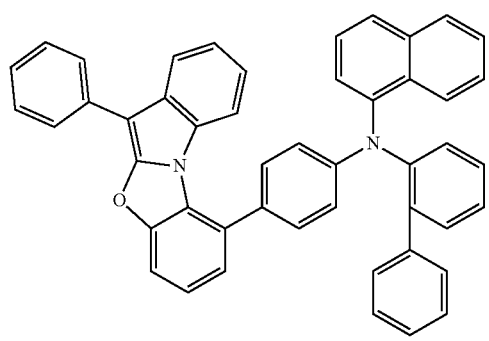
A79
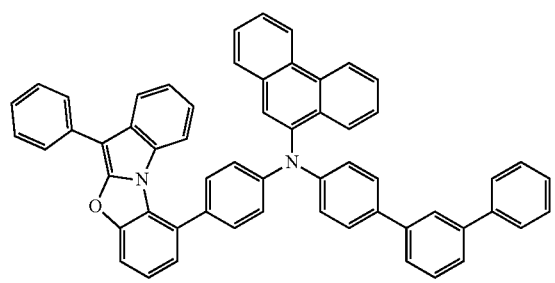
A80
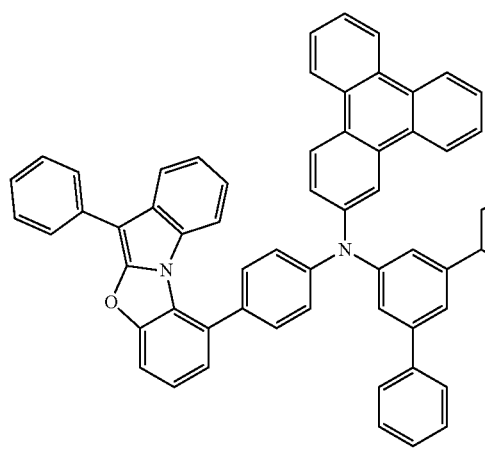

-continued
A81
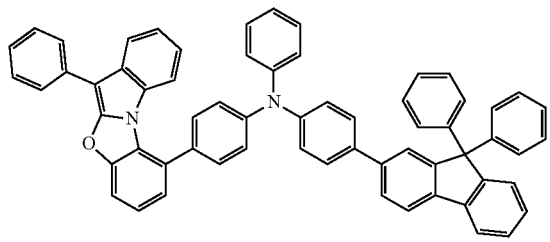
A82
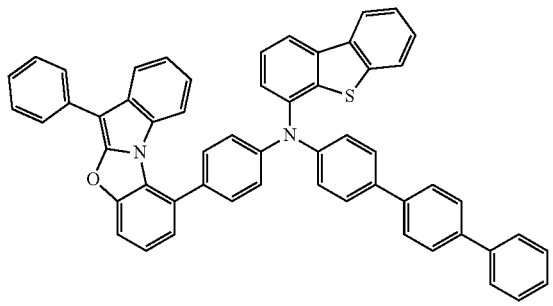
A83
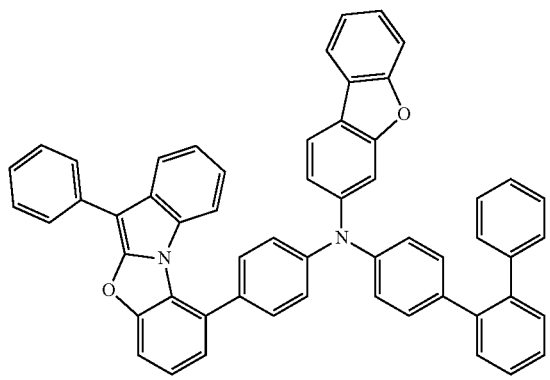
A84
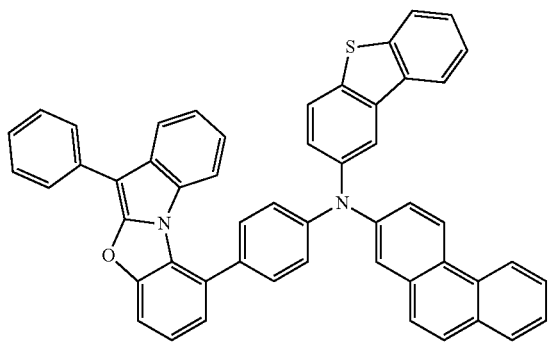
A85
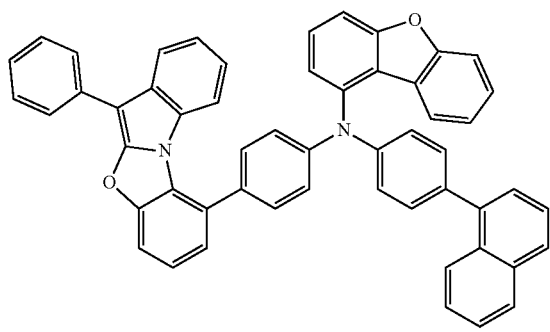
A86
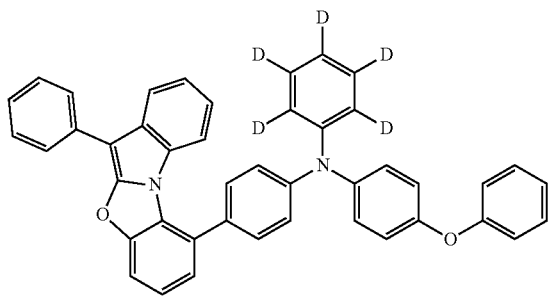
A87
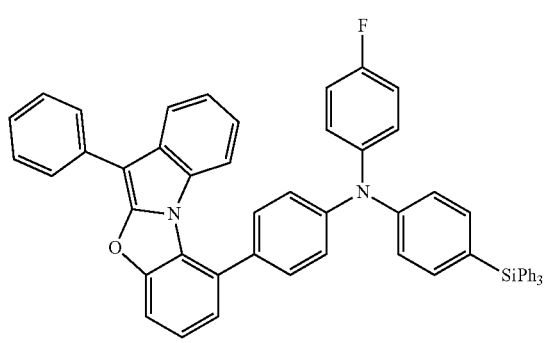
A88
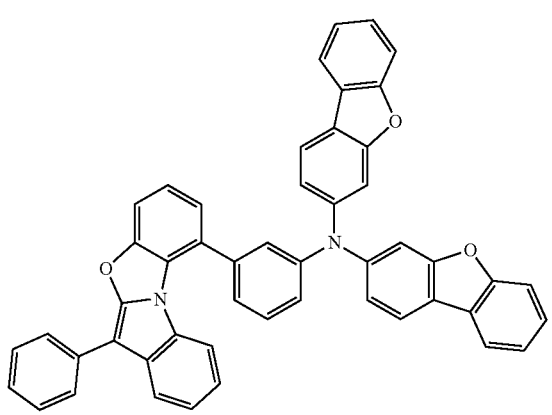

-continued
A89
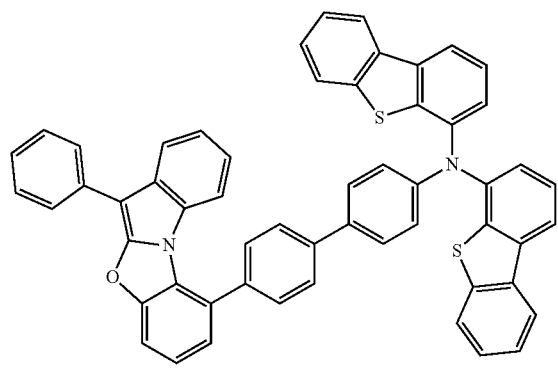
A90
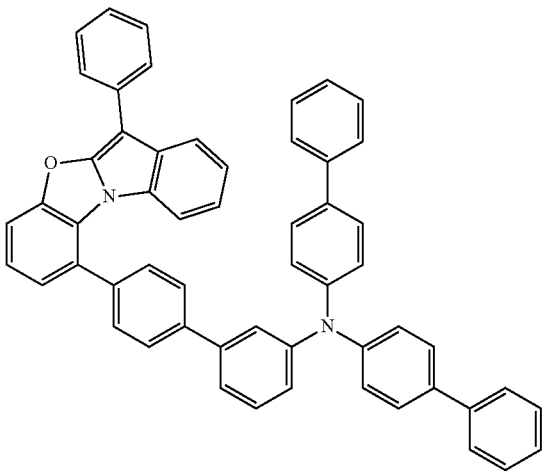
A91
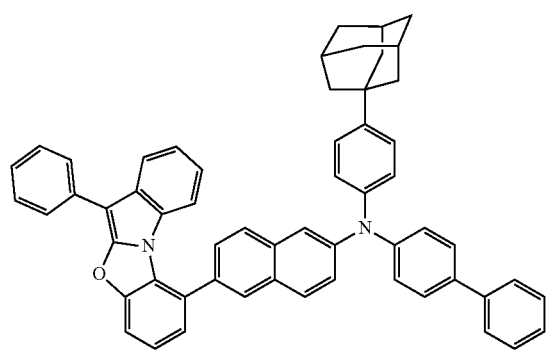
A92
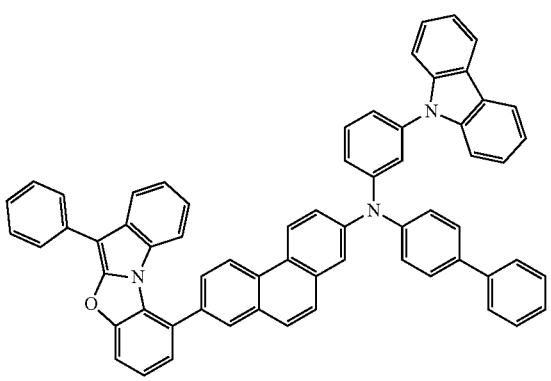
A93
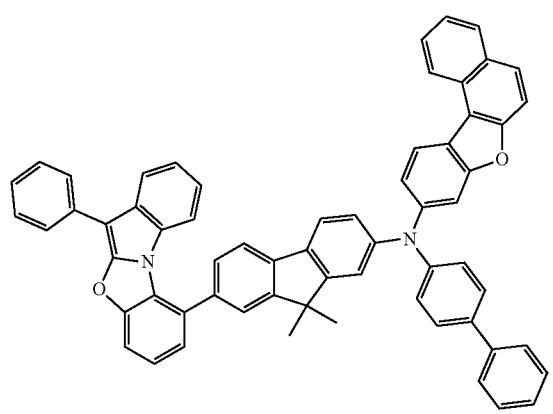
A94
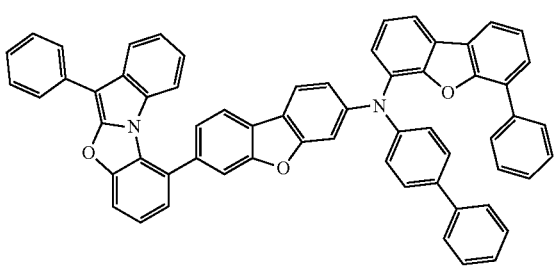

-continued
A95
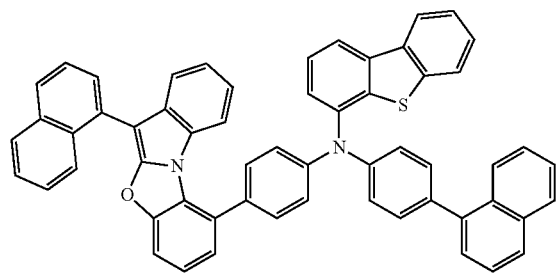
A96
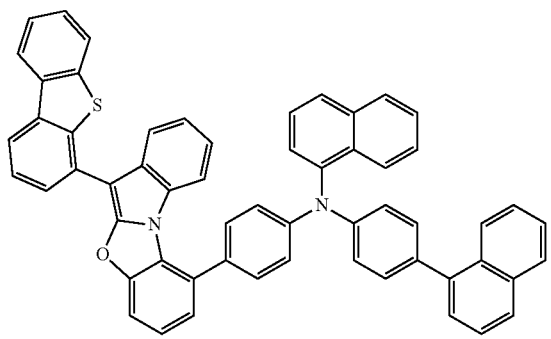
A97
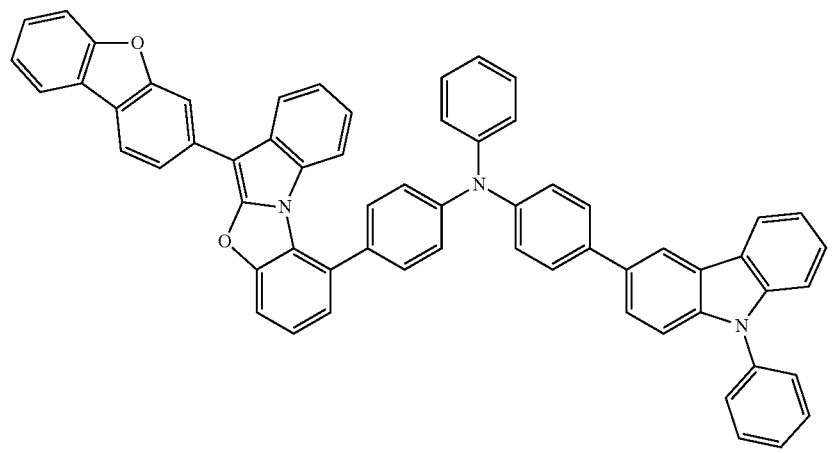
A98
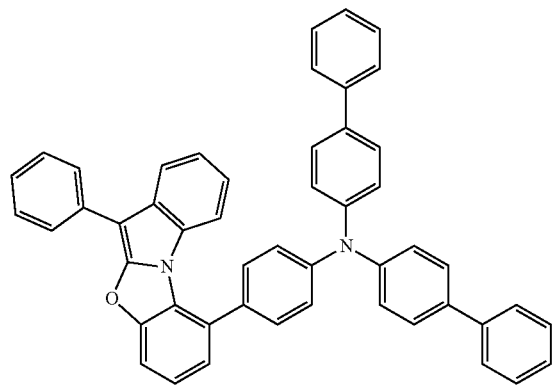
A99
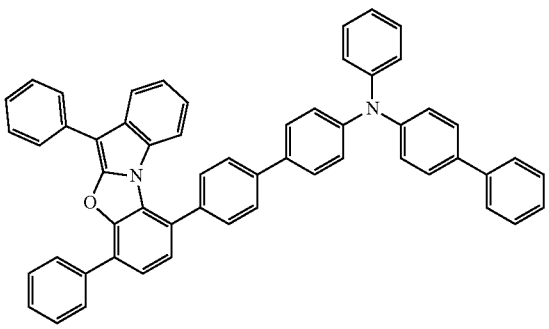
A100
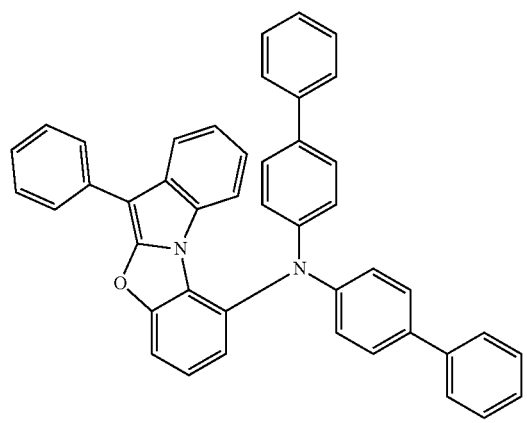
A101
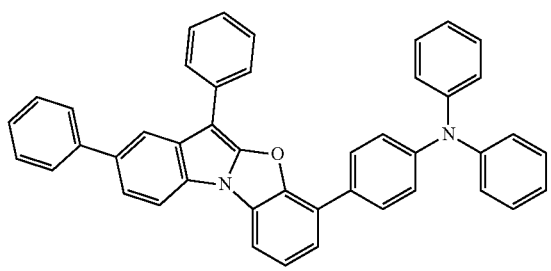

-continued
A102
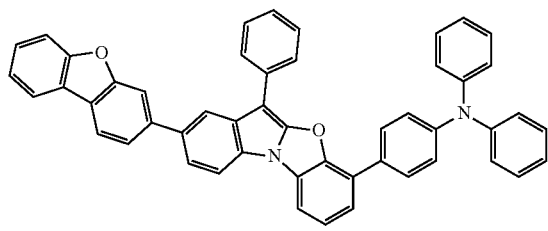
A103
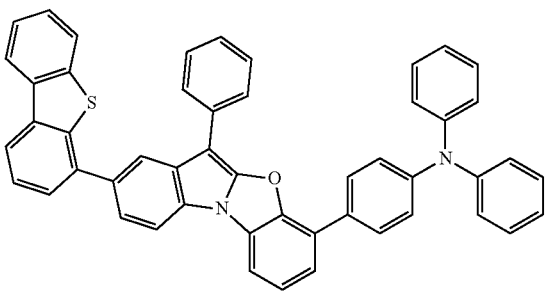
A104
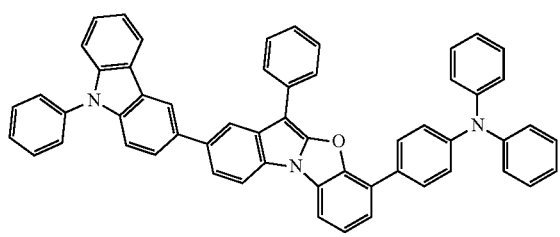
A105
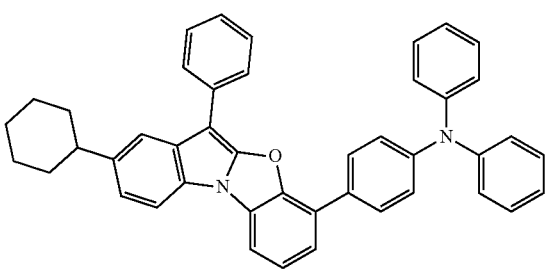
A106
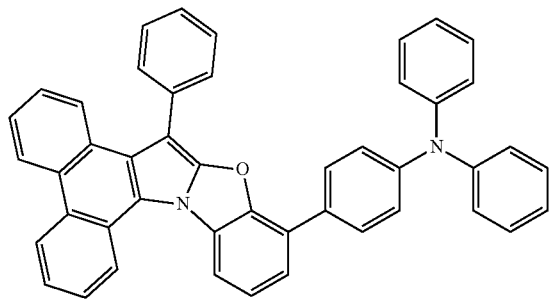
A107
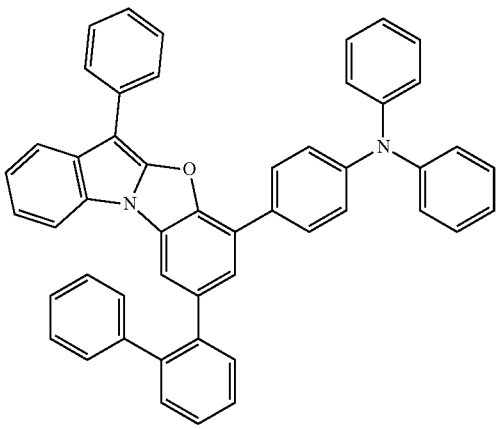
A108
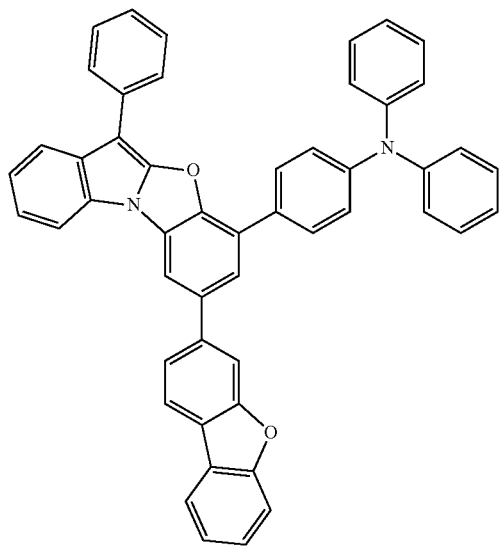
A109
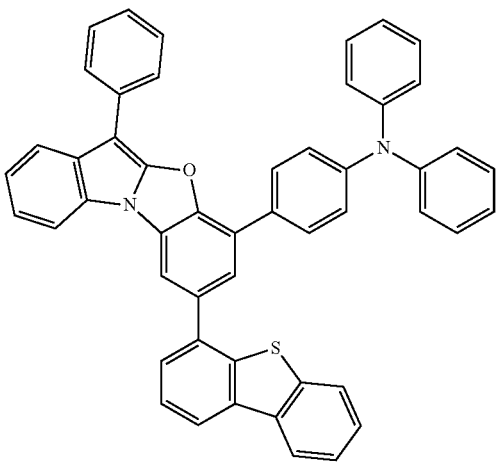

-continued
A110
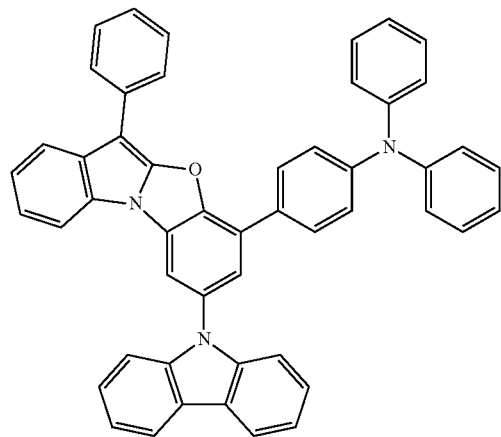
A111
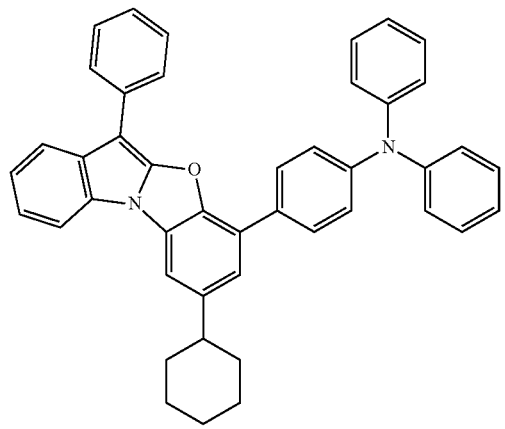
A112
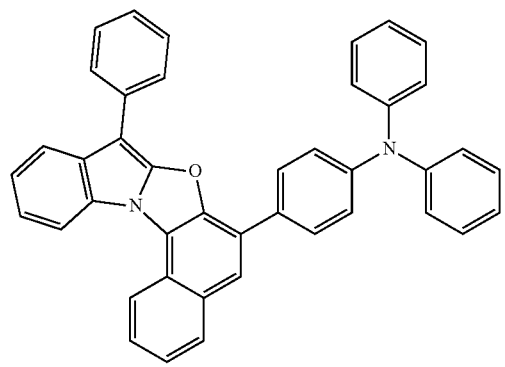
[Compound Group B]
B1
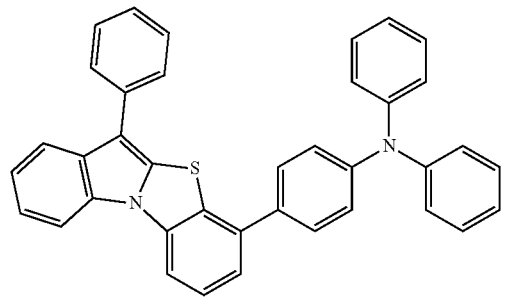
B2
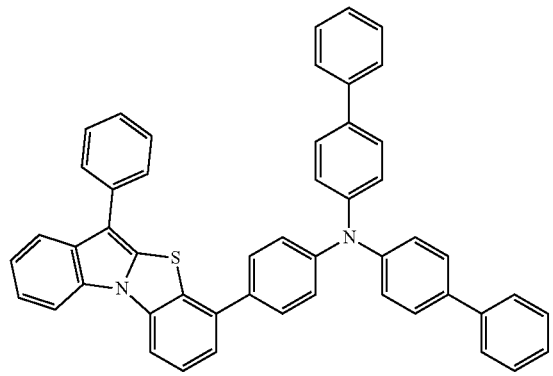
B3
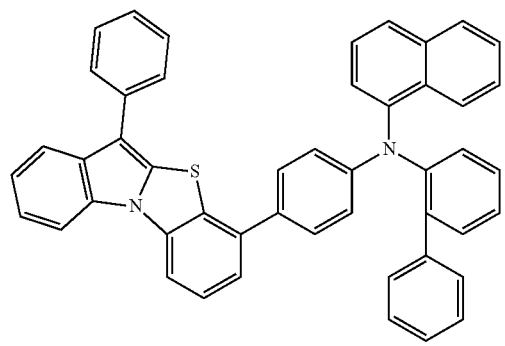
B4
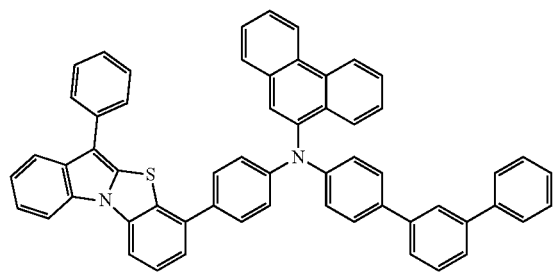

-continued
B5
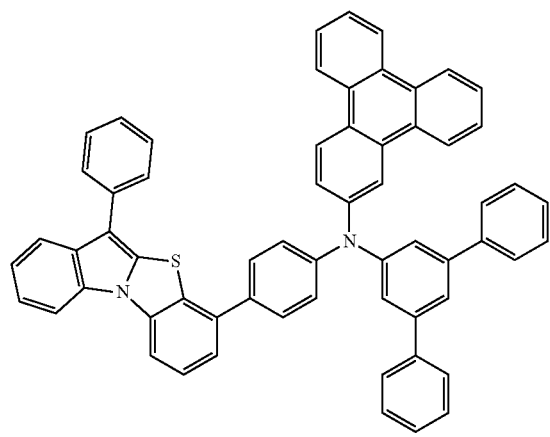
B6
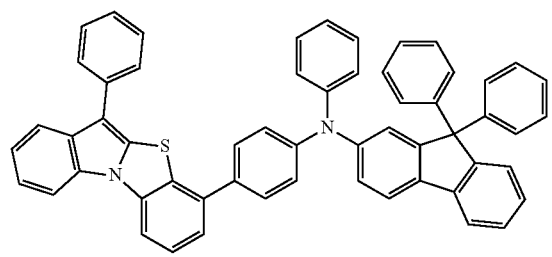
B8
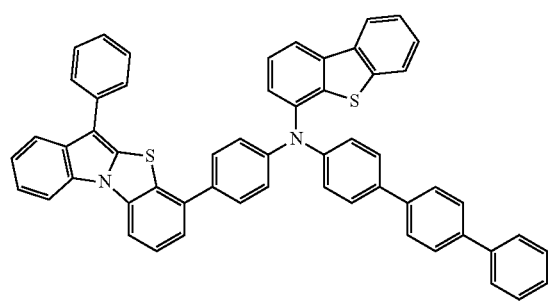
B9
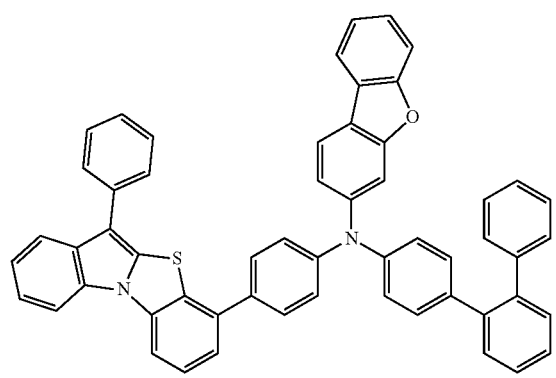
B10
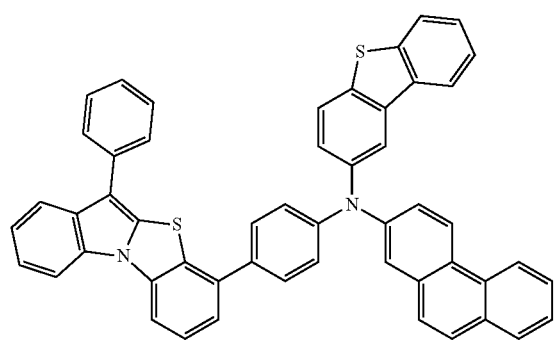
B11
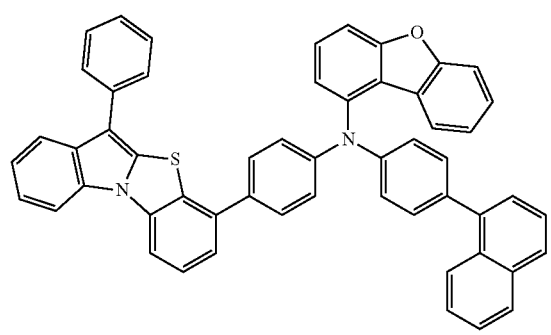
B12
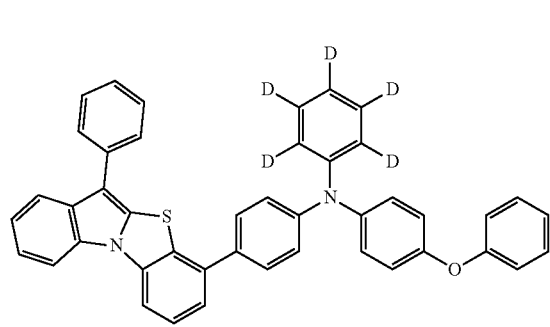
B13
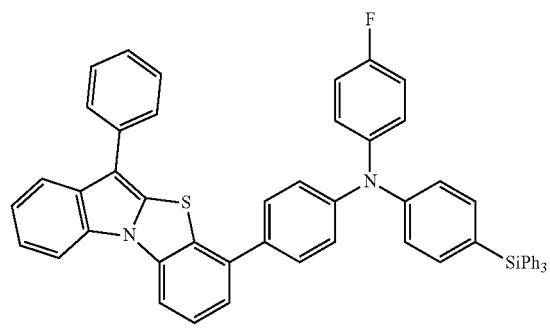

-continued
B13
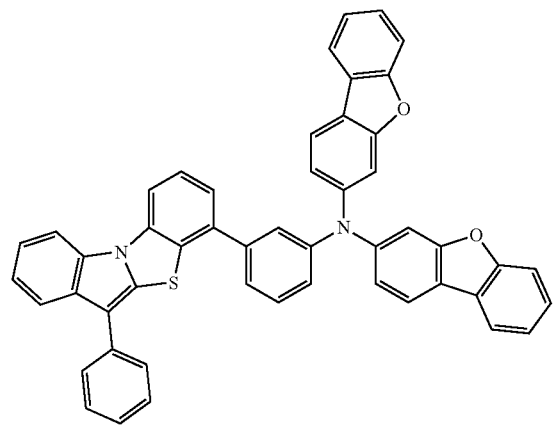
B14
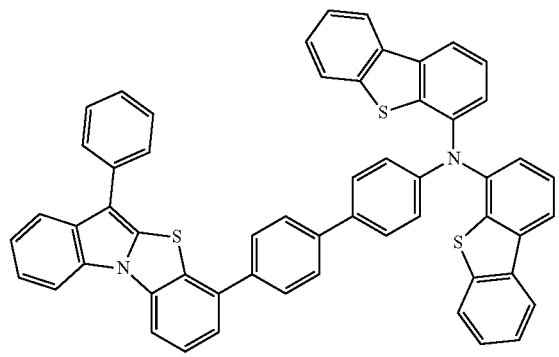
B15
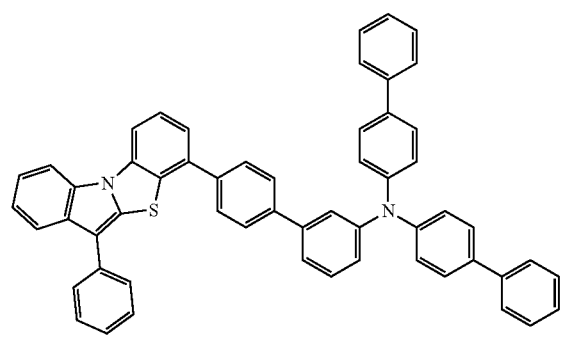
B16
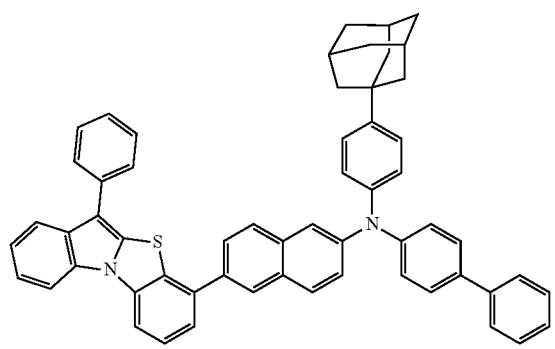
B17
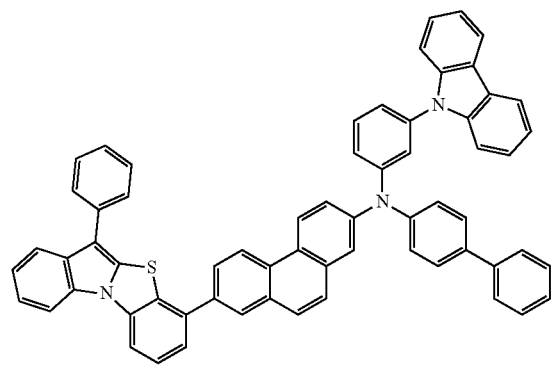
B18
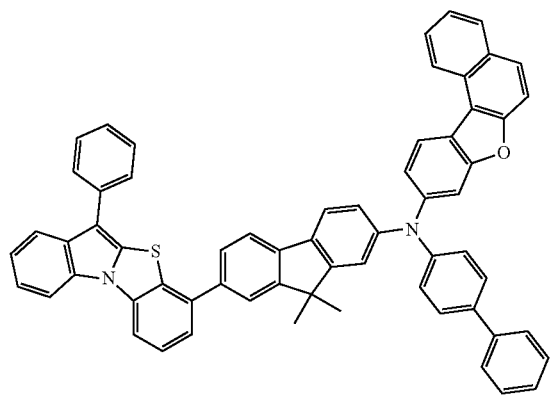
B19
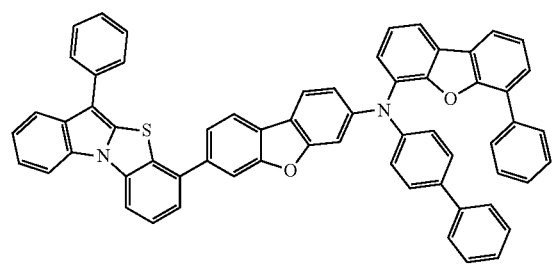
B20
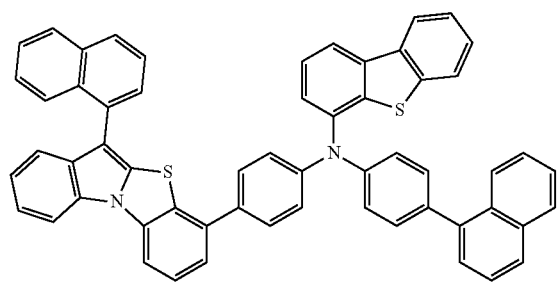

-continued
B21
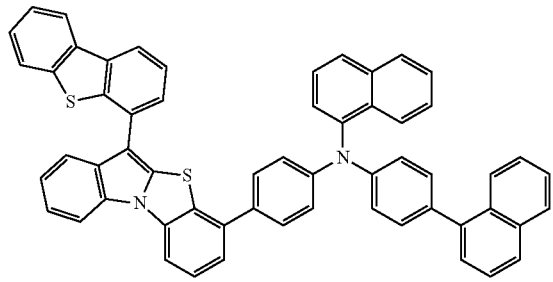
B22
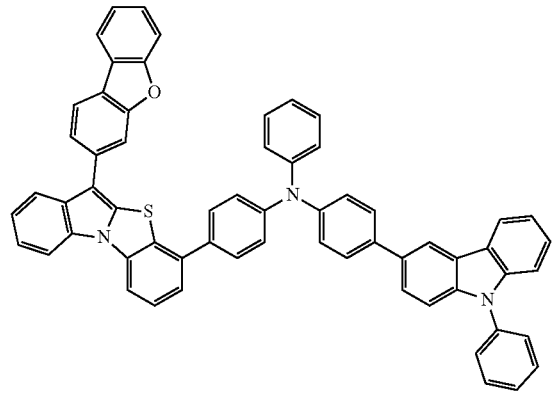
B23
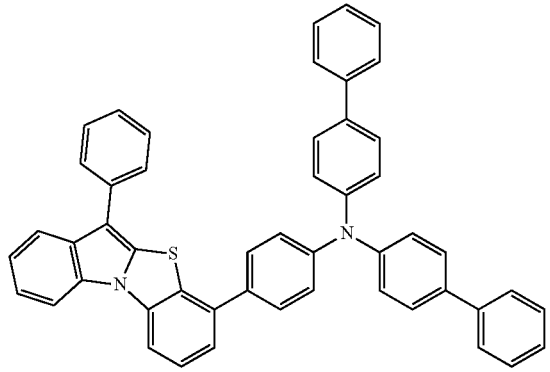
B24
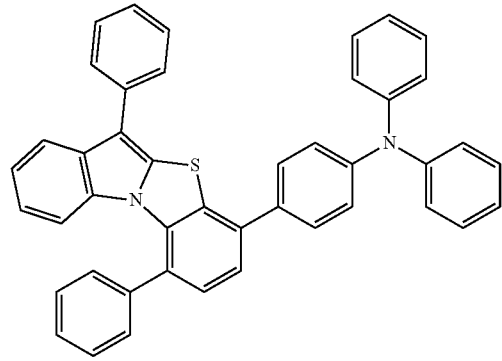
B25
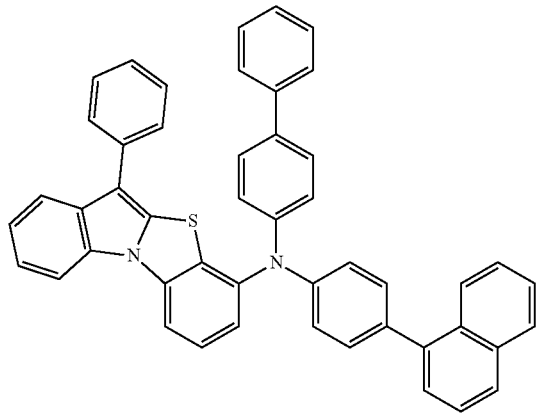
B26
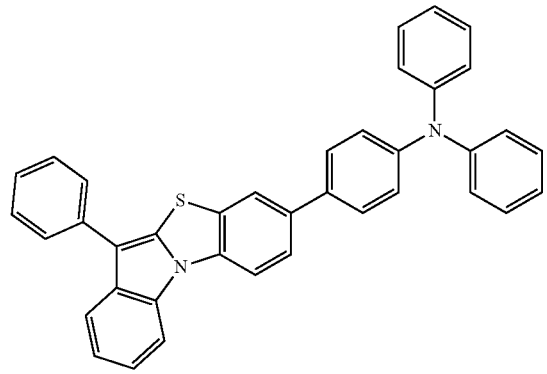
B27
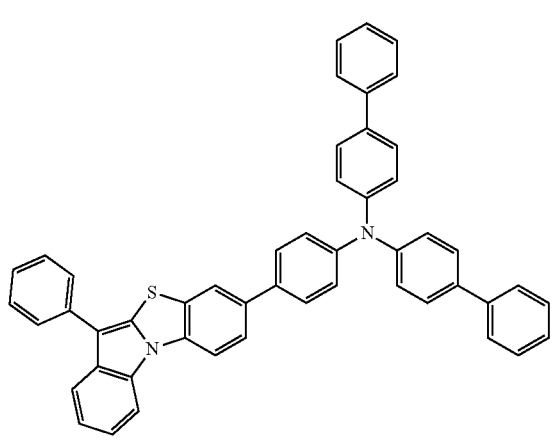
B28
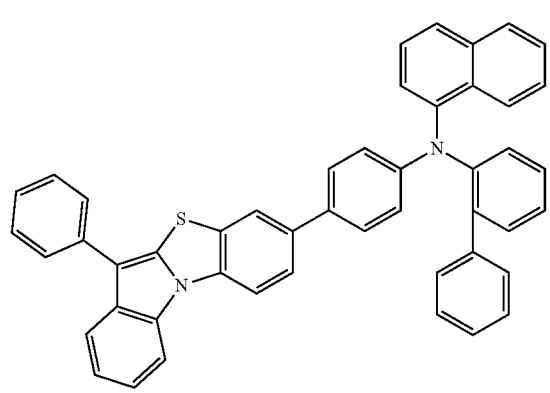

-continued
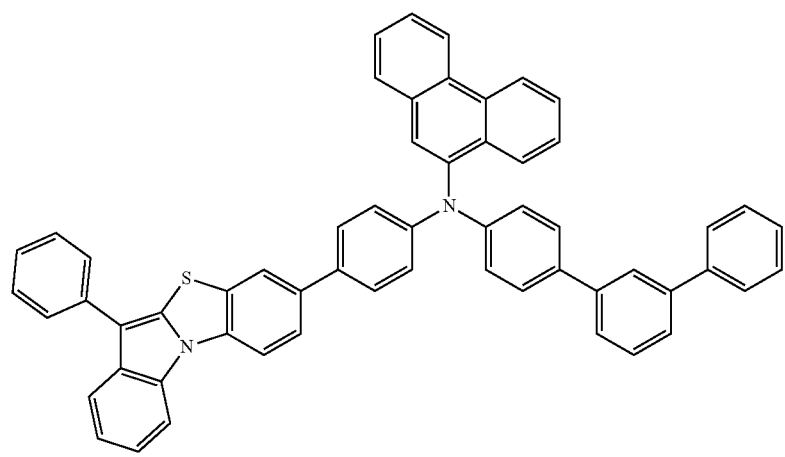
B29
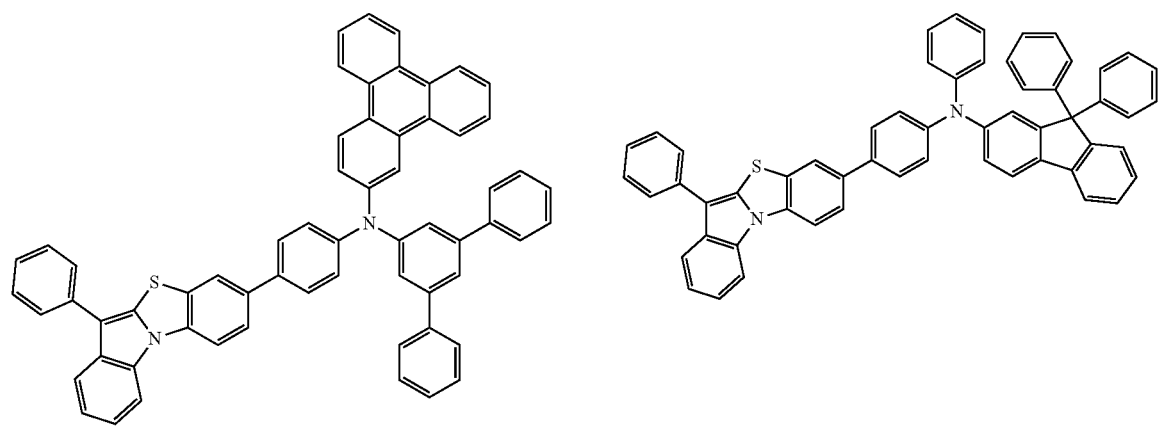
B30
B31
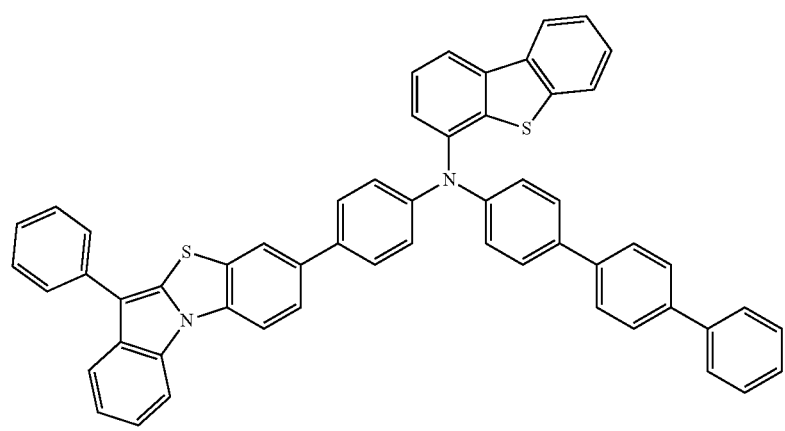
B32

-continued
B33
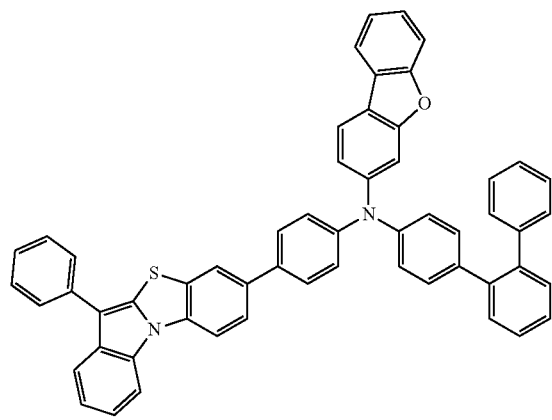
B34
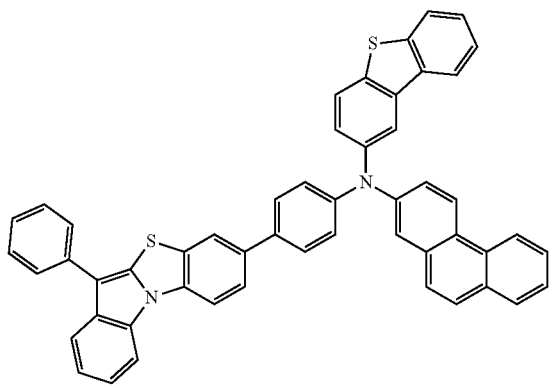
B35
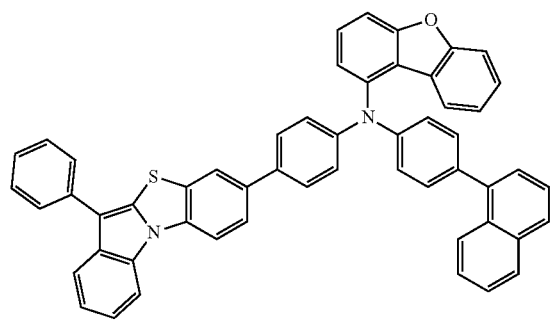
B36
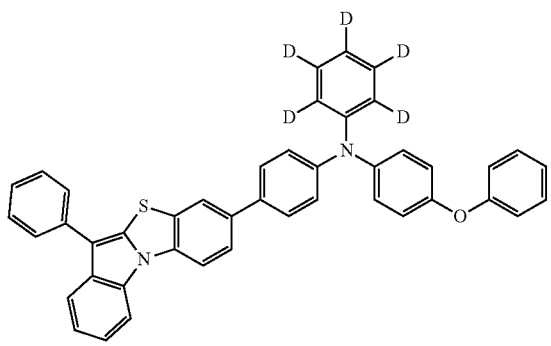
B37
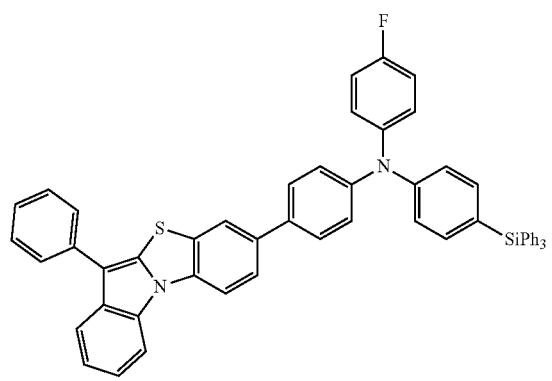
B38
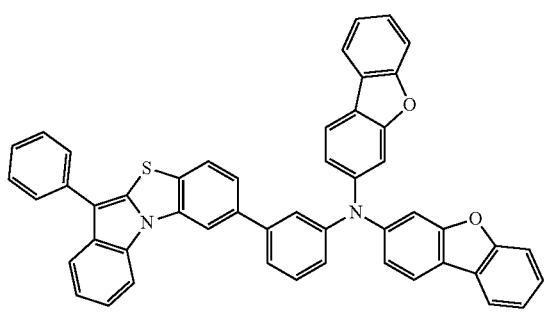
B39
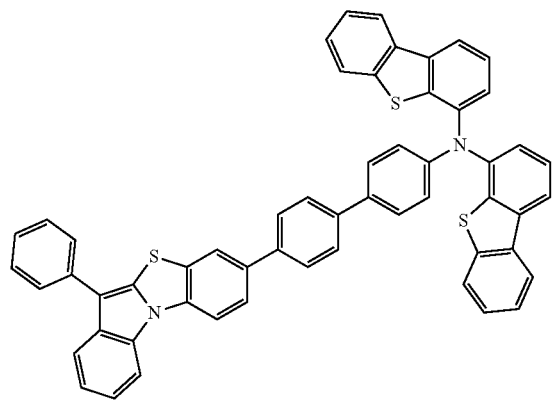
B40
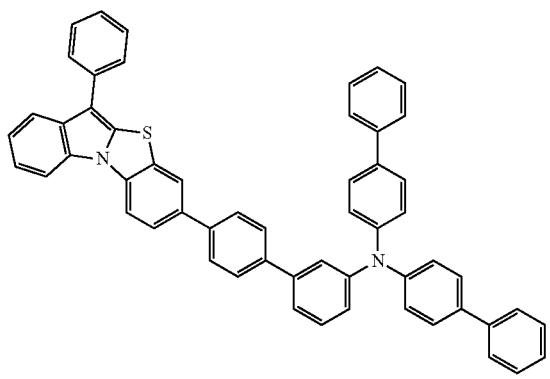

-continued
B41
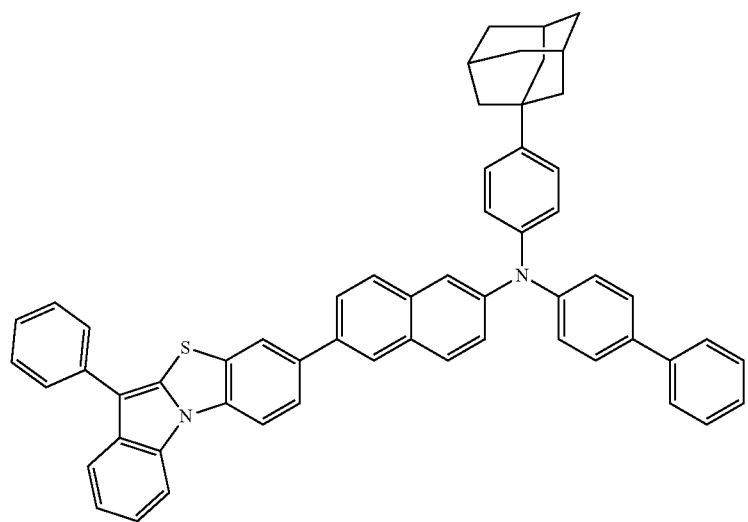
B42
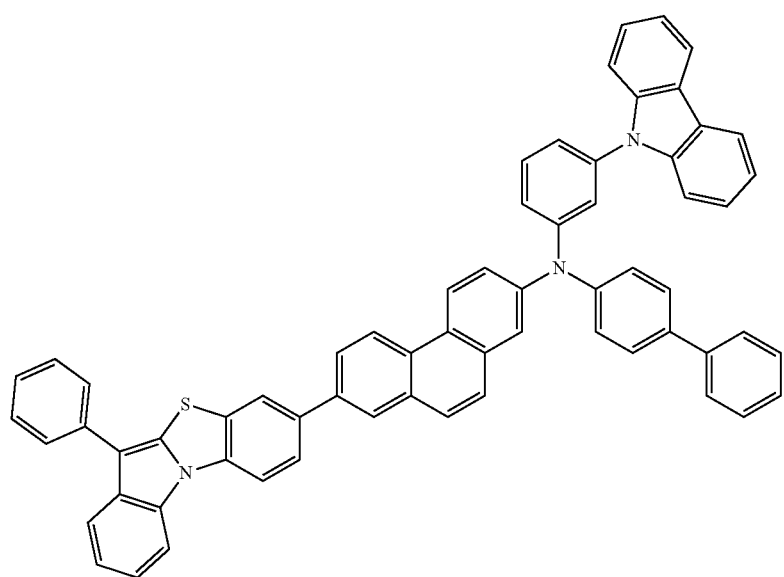
B43
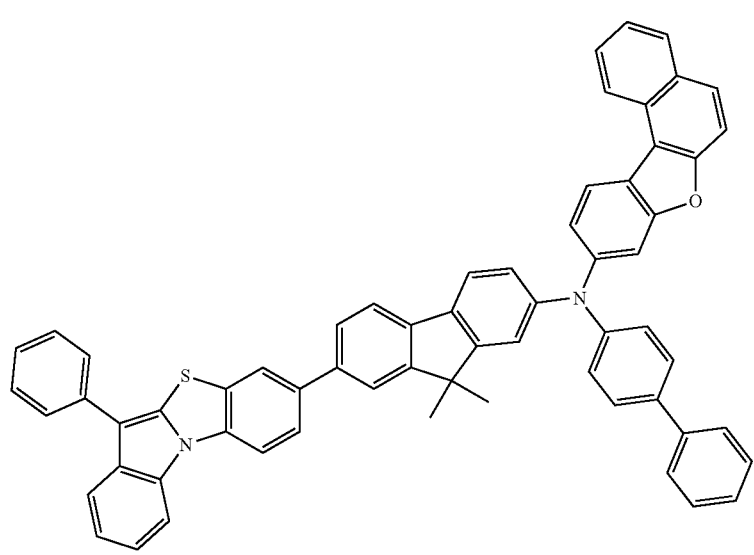

-continued
B44
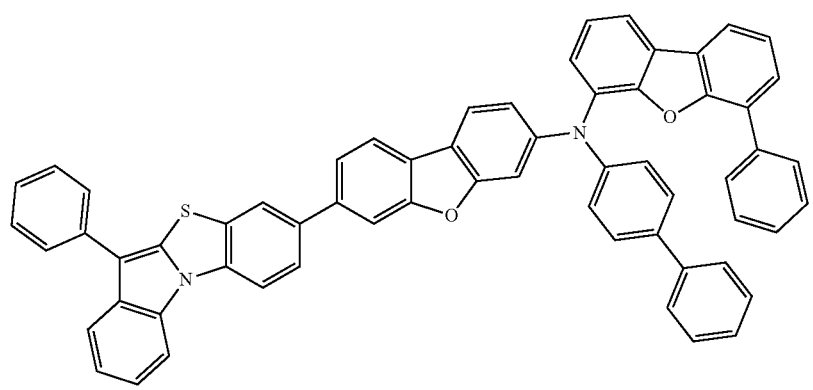
B45
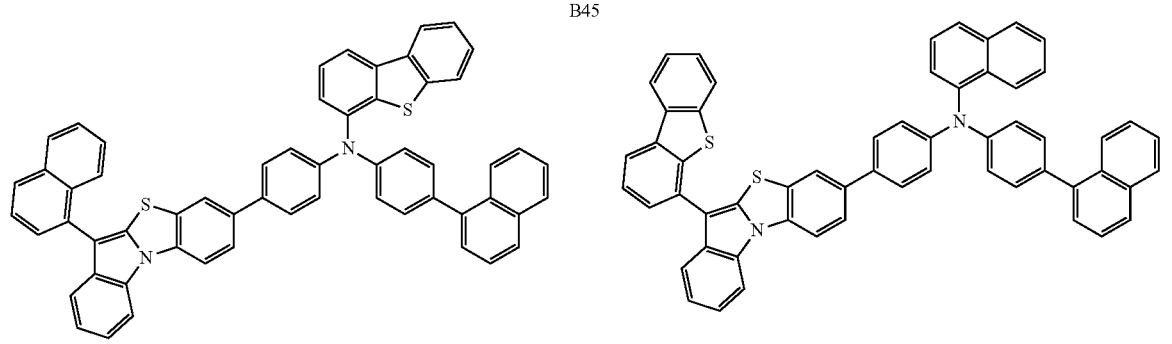
B46
B47
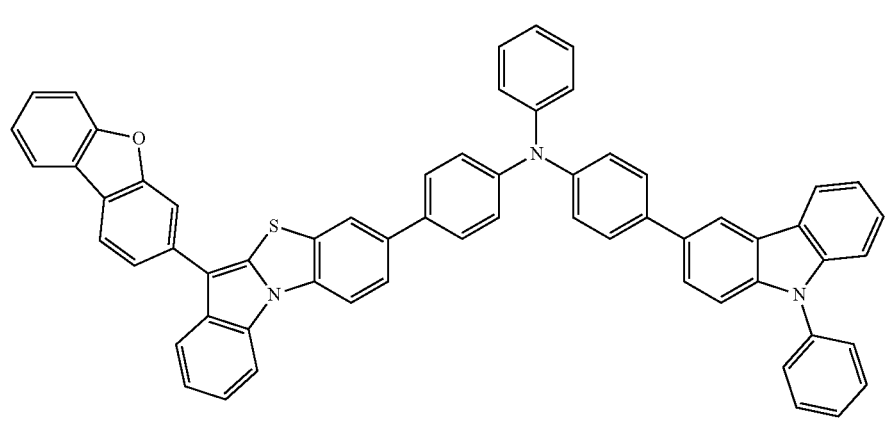
B48
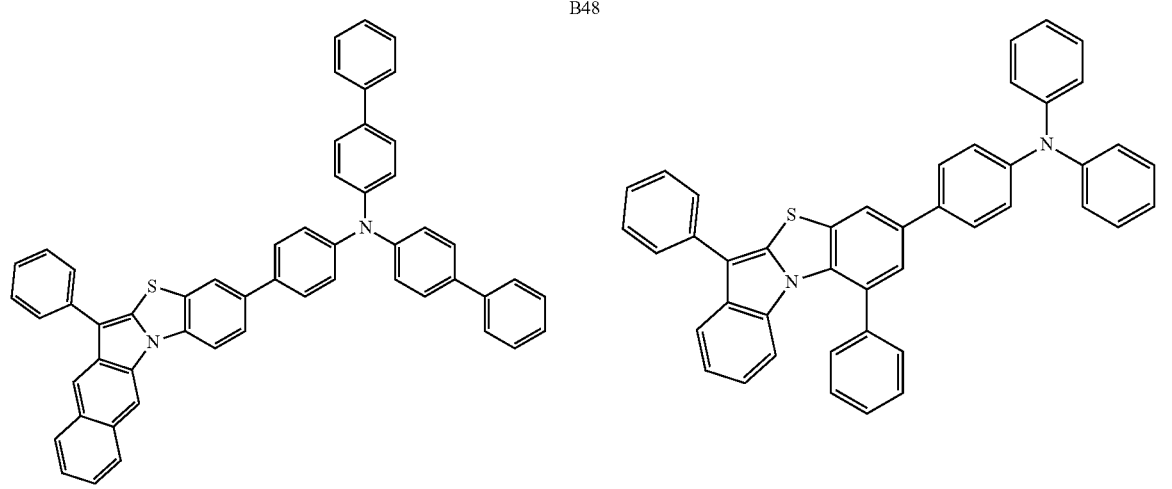
B49

-continued
B50
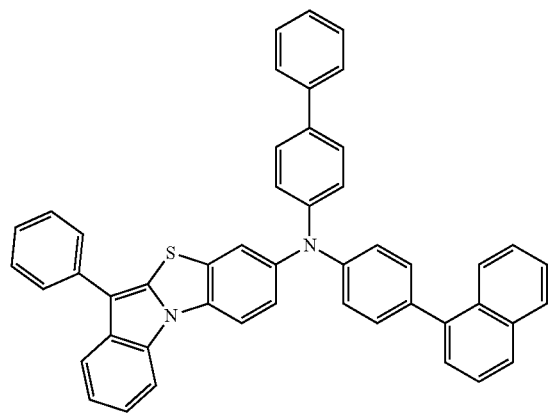
B51
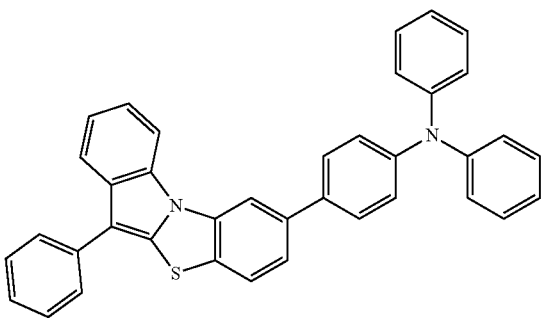
B52
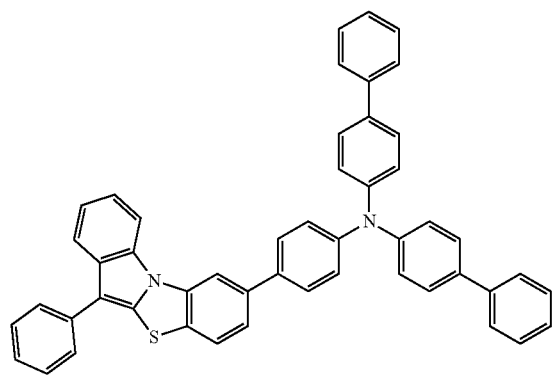
B53
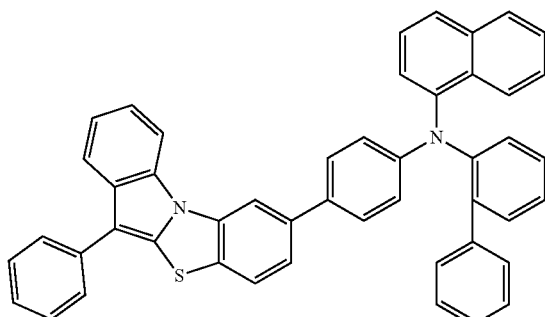
B54
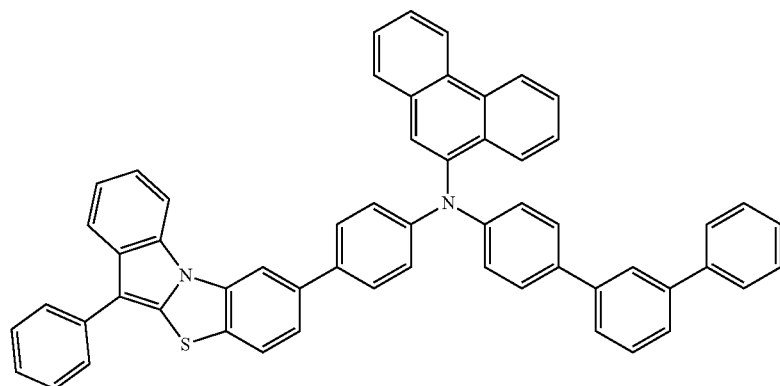
B55
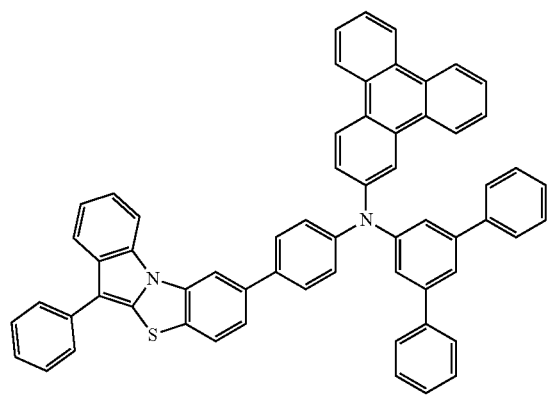
B56
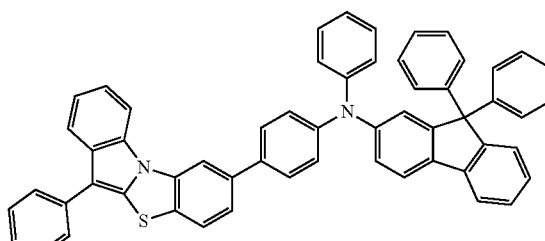

-continued
B57
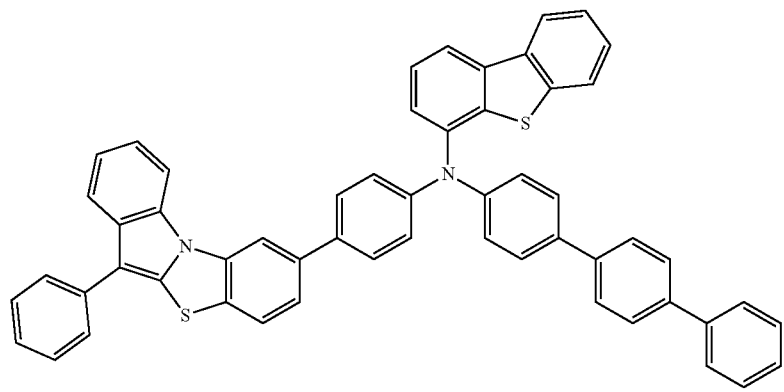
B58 B59
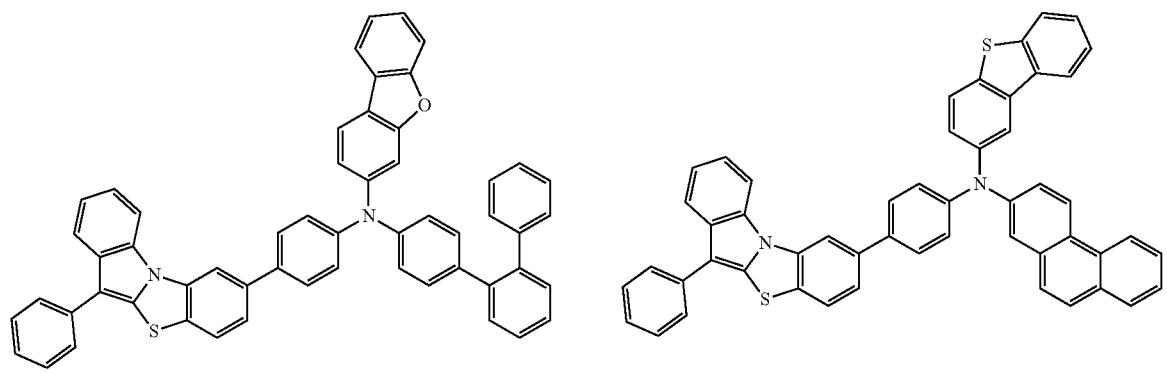
B60 B61
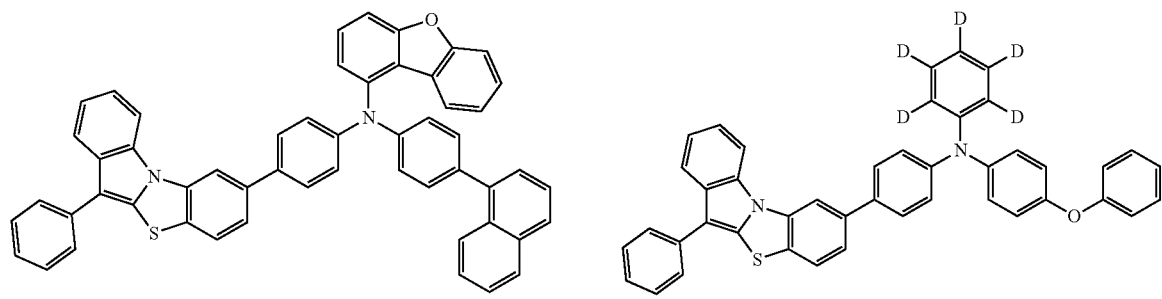
B62 B63
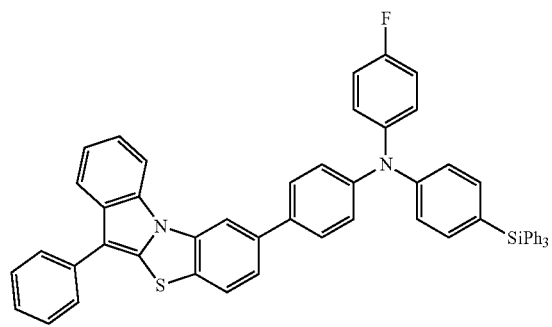
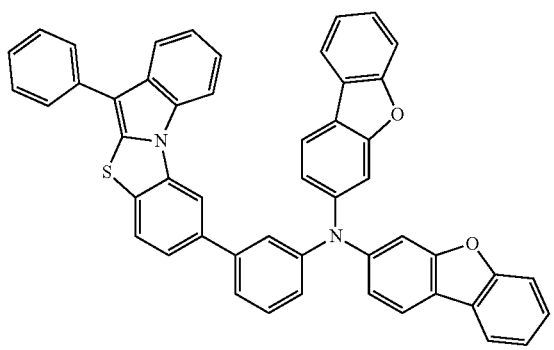

-continued
B64
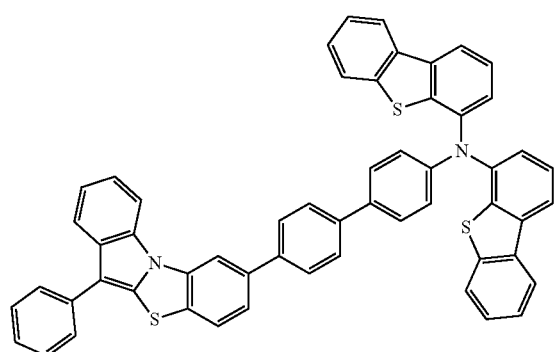
B65
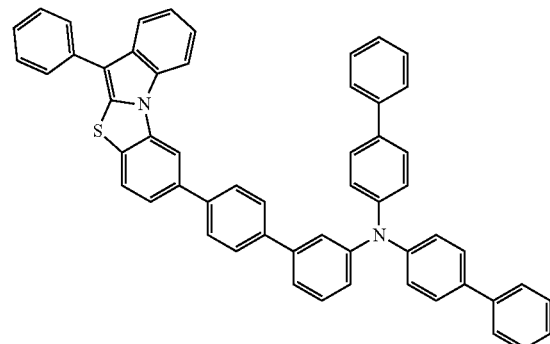
B66
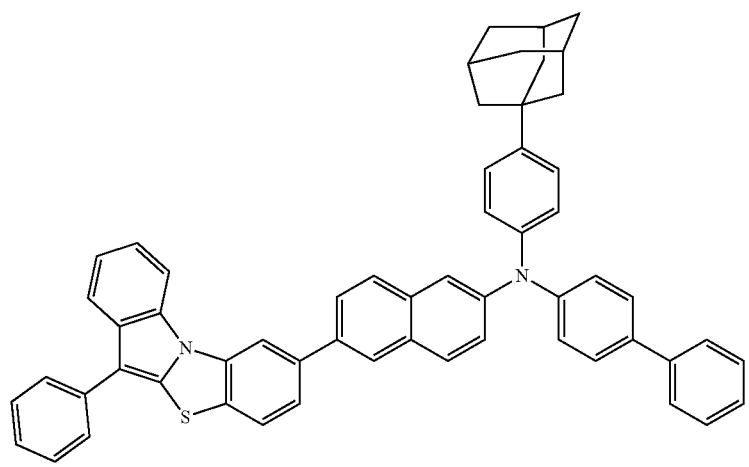
B67
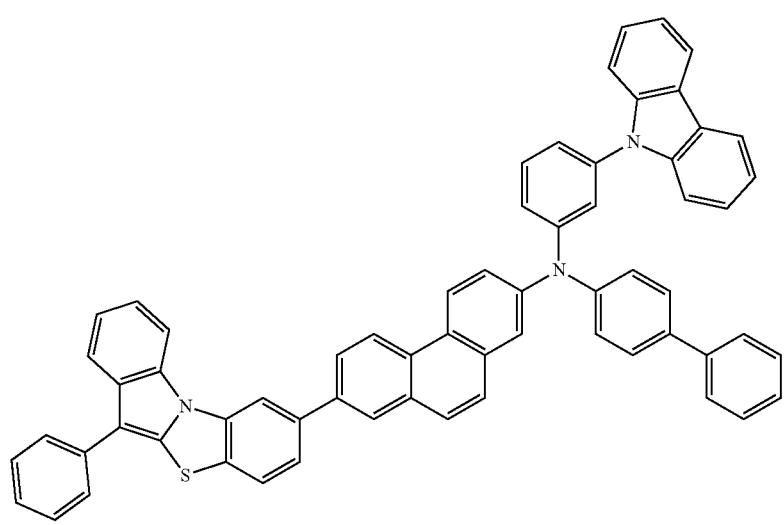

-continued
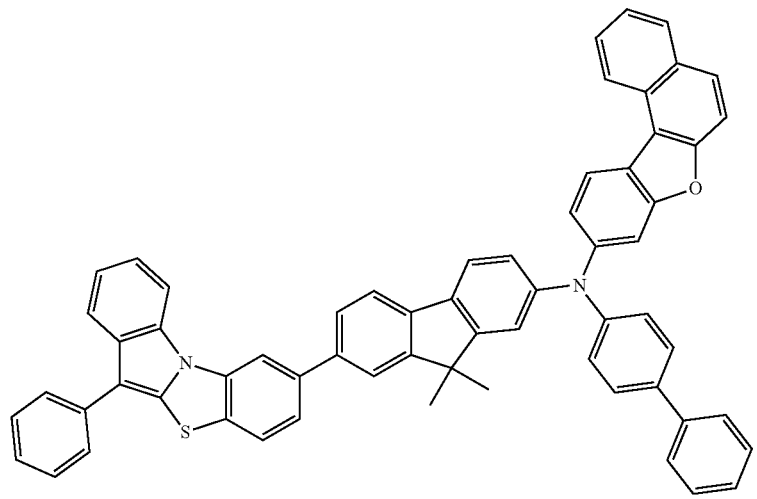
B68
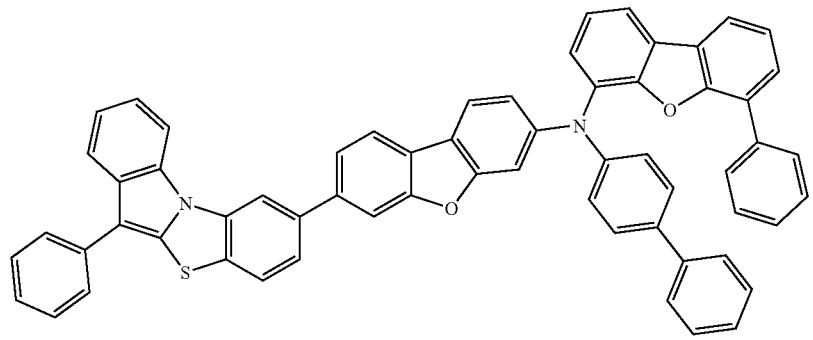
B69
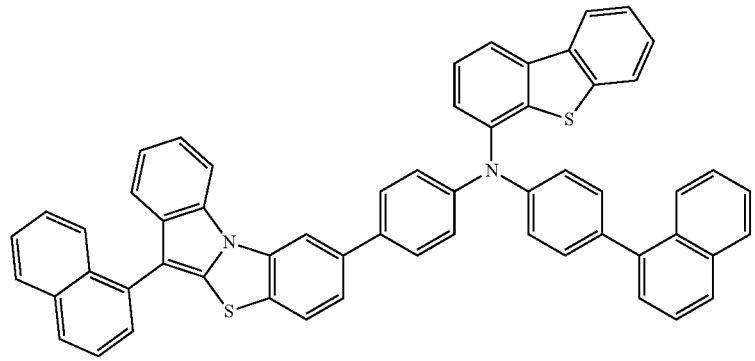
B70
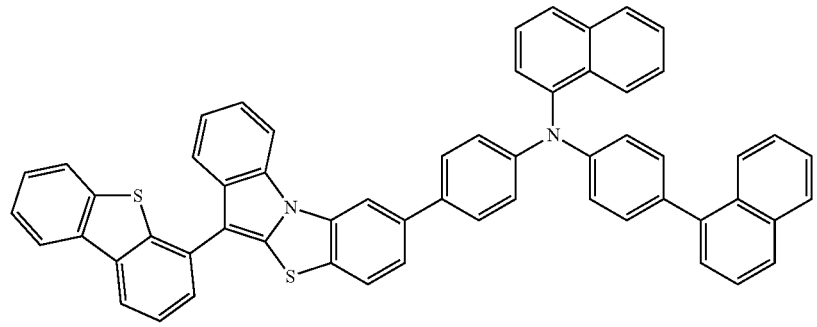
B71

-continued
B72
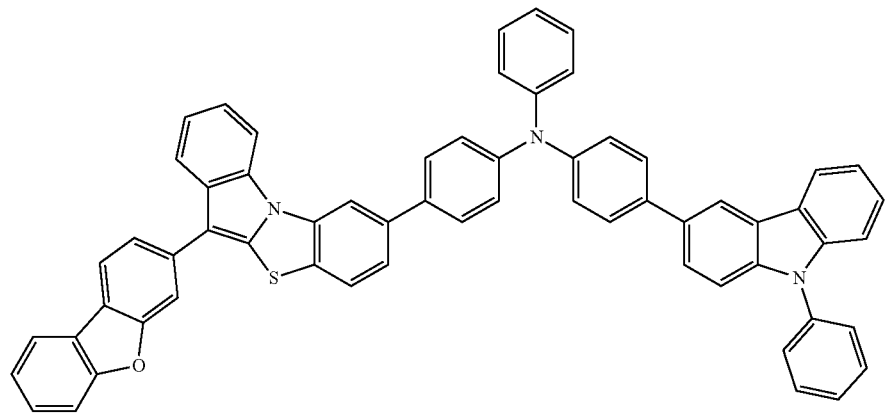
B73
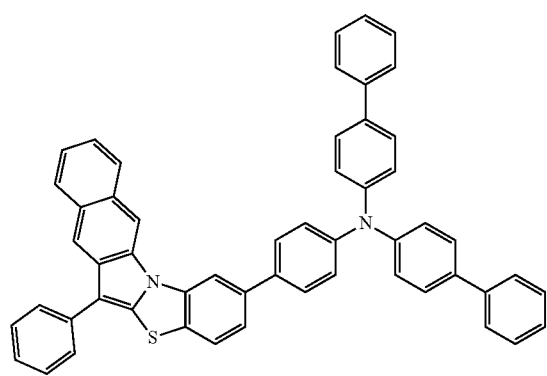
B74
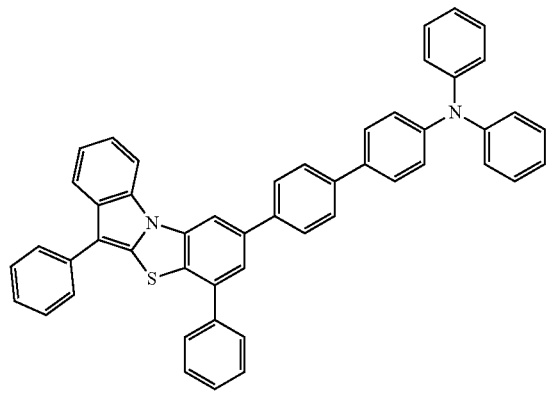
B75
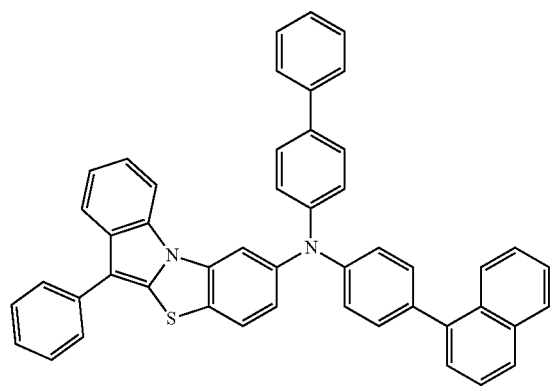
B76
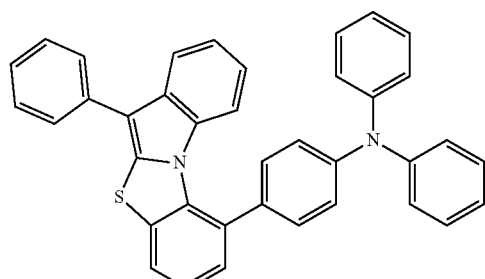
B77
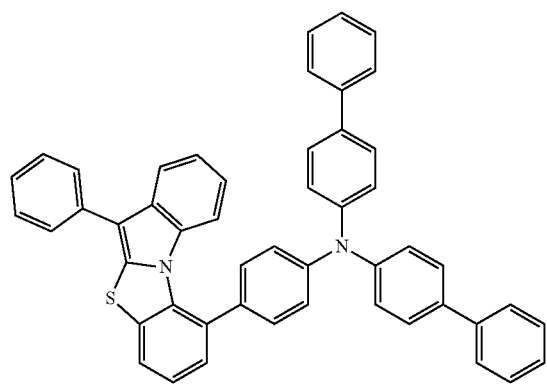
B78
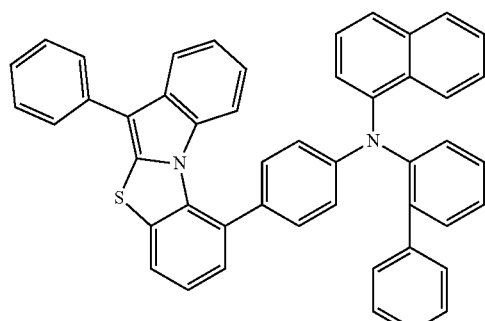

-continued
B79
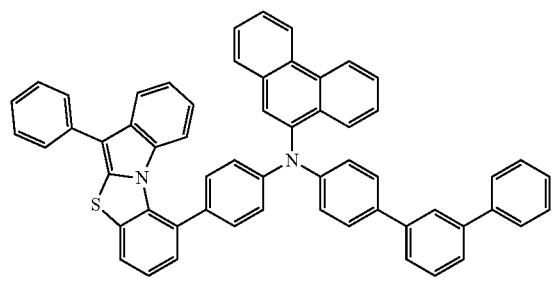
B80
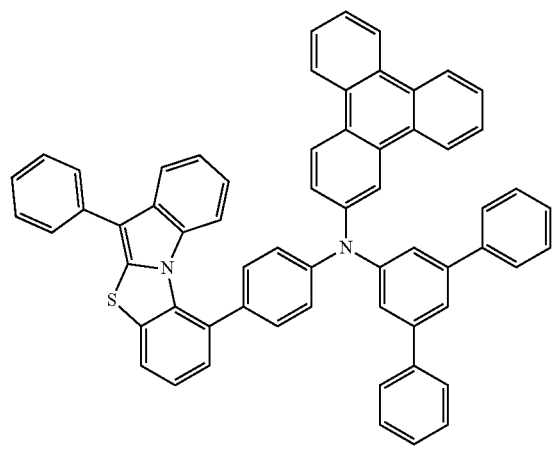
B81
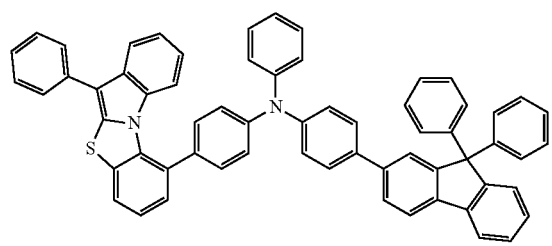
B82
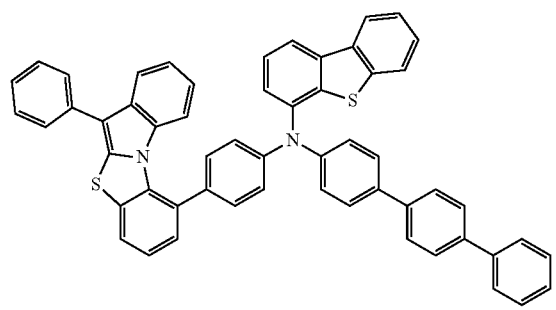
B83
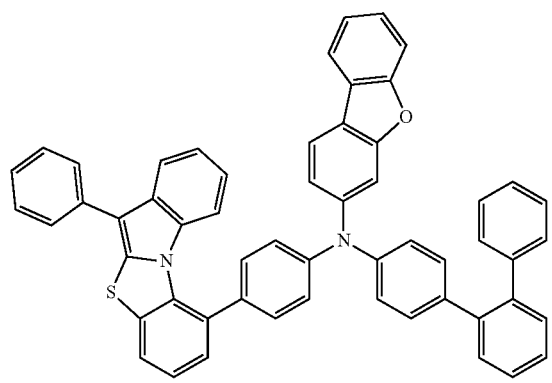
B84
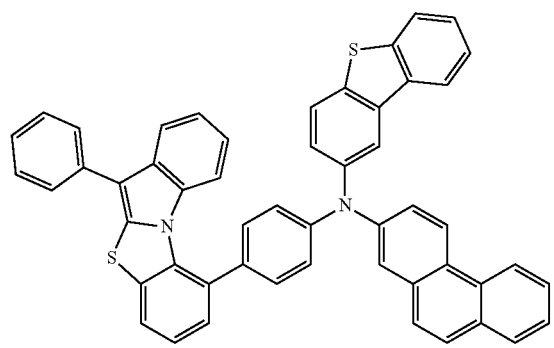
B85
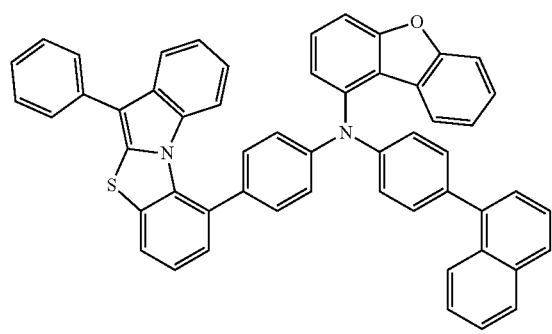
B86
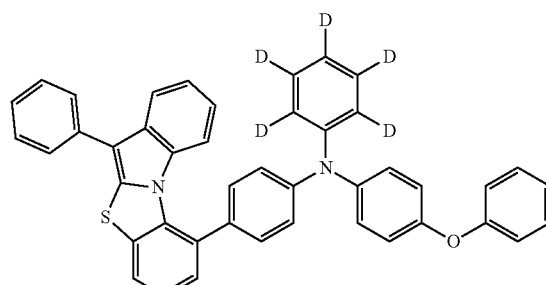

-continued
B87
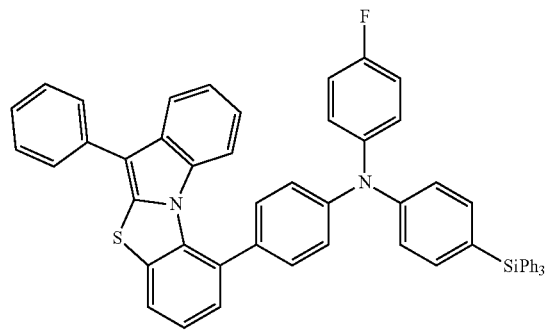
B88
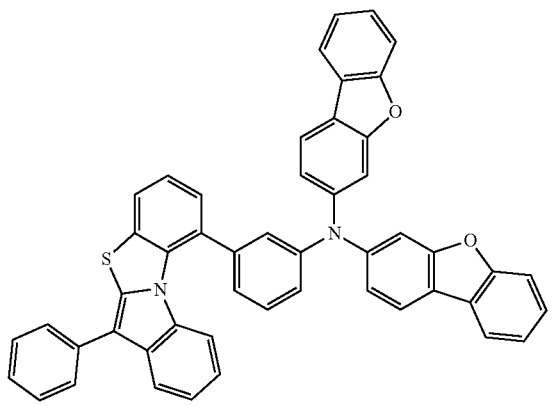
B89
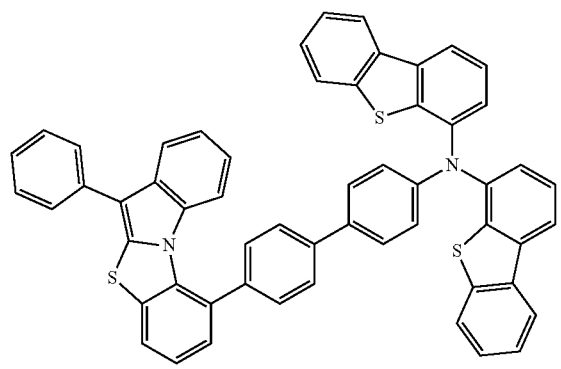
B90
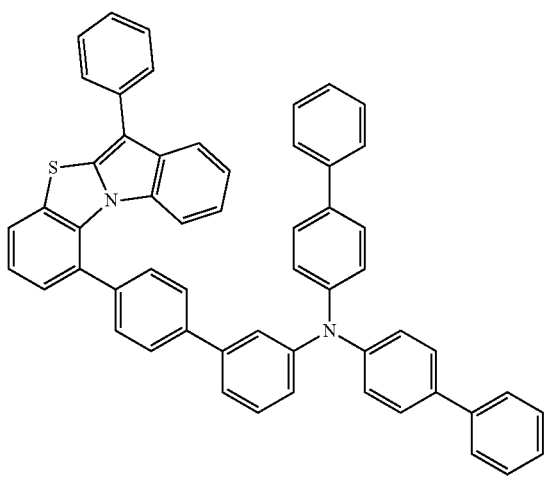
B91
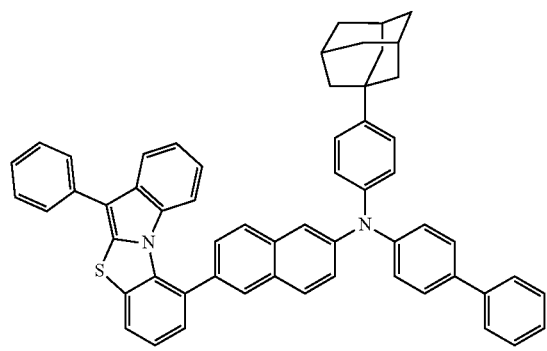
B92
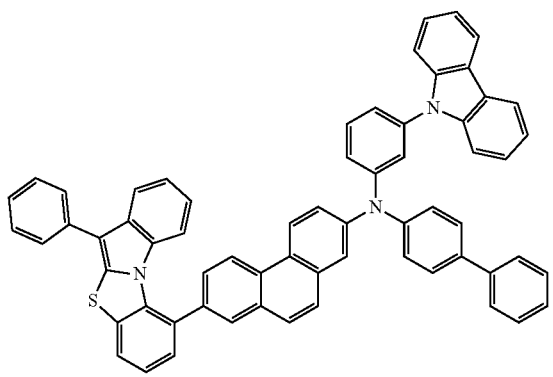

-continued
B93
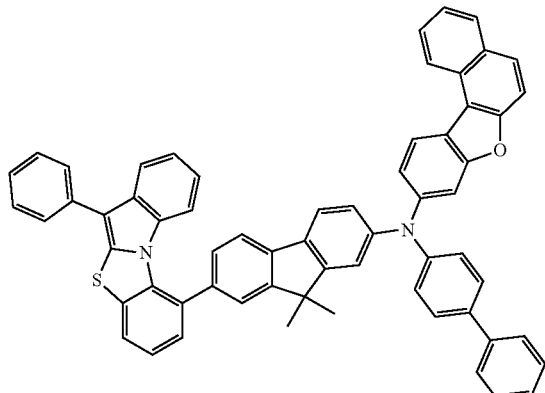
B94
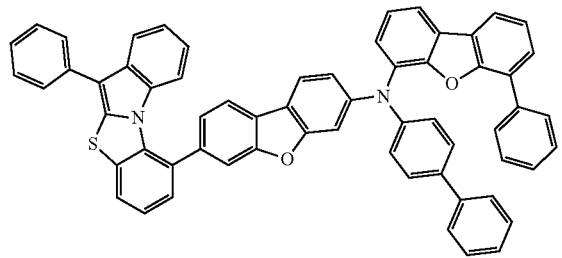
B95
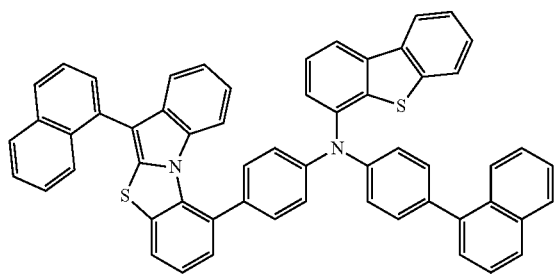
B96
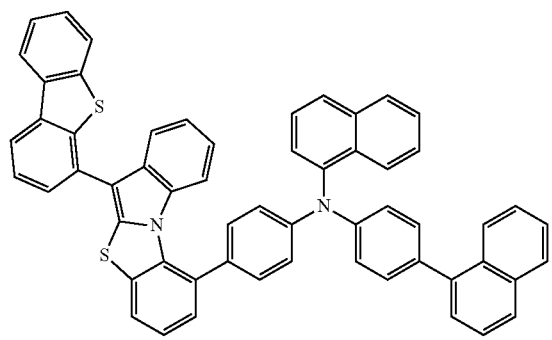
B97
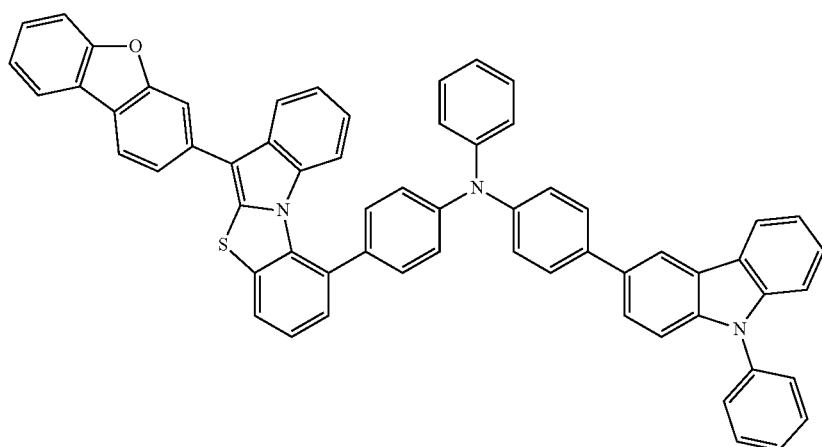
B98
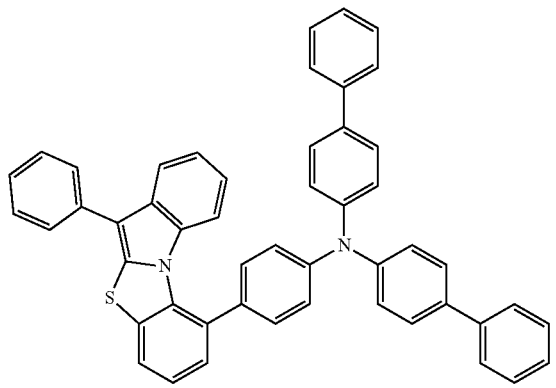
B99
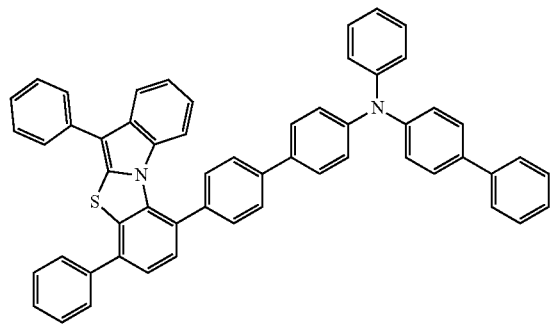

-continued
B100
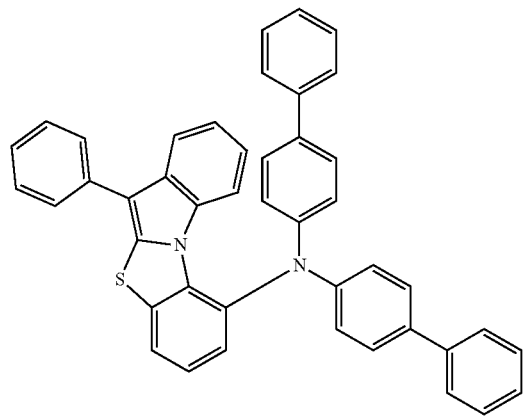
B101
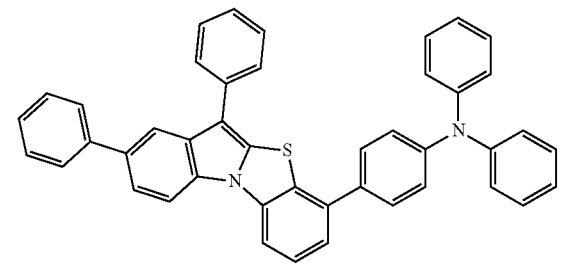
B102
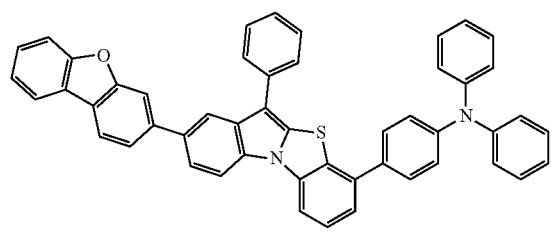
B103
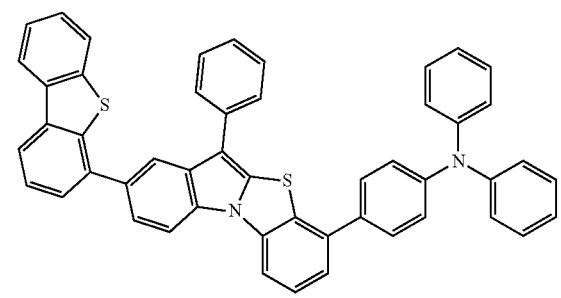
B104
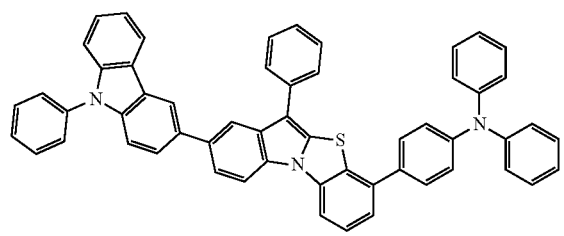
B105
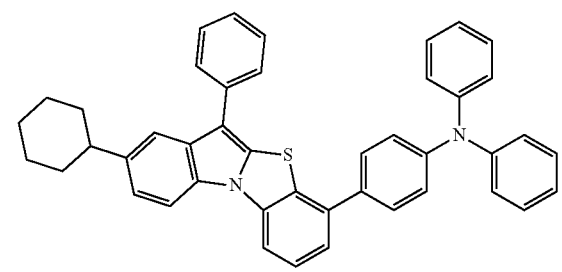
B106
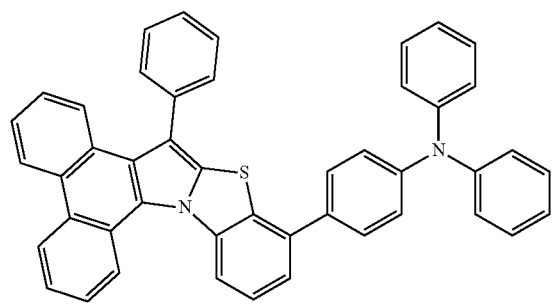
B107
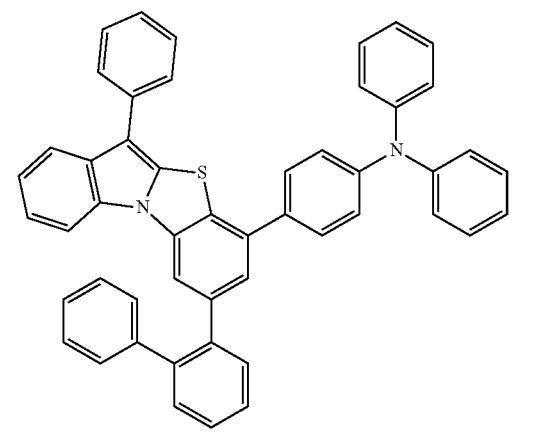

-continued
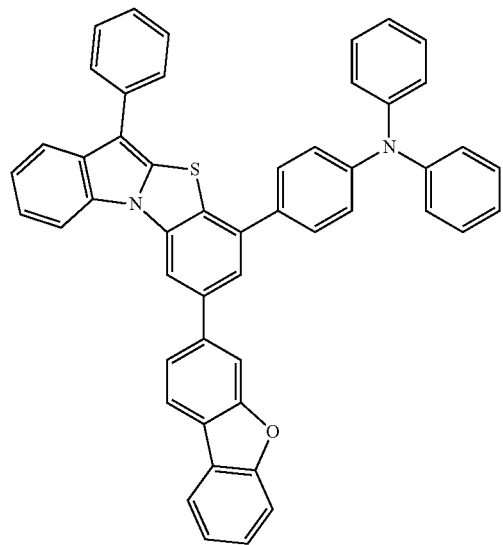
B108
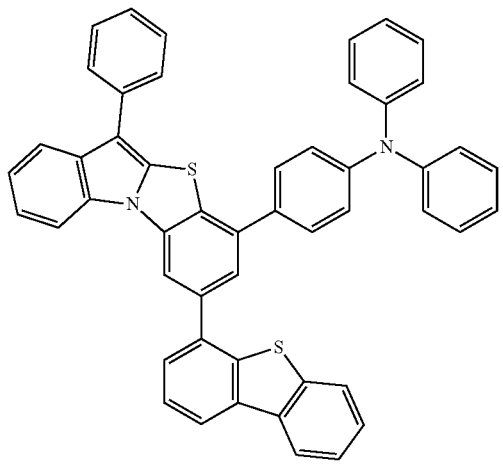
B109
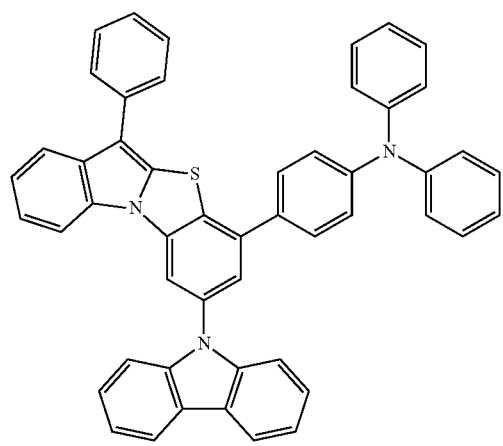
B110
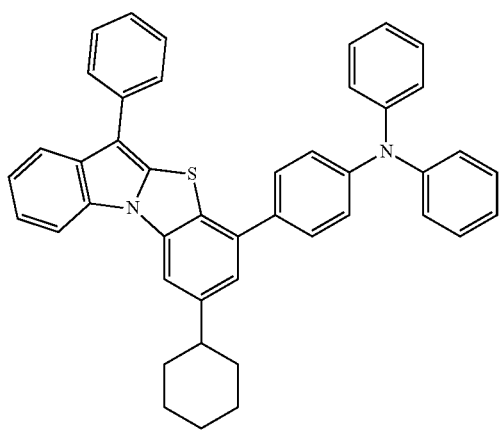
B111
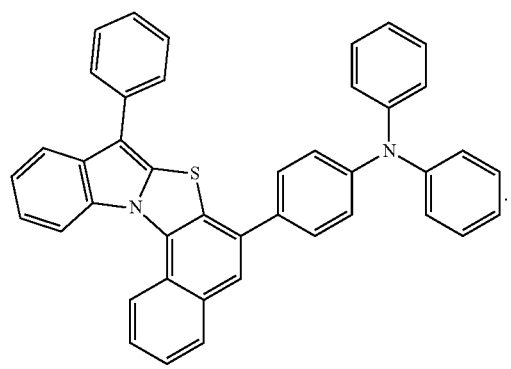
B112

12. An amine compound represented by the following Formula 1:

[Formula 1]

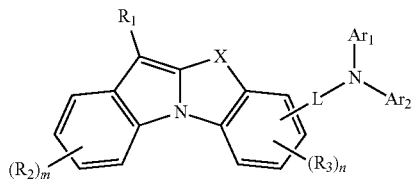

in Formula 1,

X is O or S,

R₁ is a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms, R₂ and R₃ are each independently a hydrogen atom, a deuterium atom, a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms, or combined with an adjacent group to form a ring, "m" is an integer of 0 to 4, "n" is an integer of 0 to 3, L is a direct linkage, a substituted or unsubstituted arylene group of 6 to 40 ring carbon atoms, or a substituted or unsubstituted heteroarylene group of 5 to 40 ring carbon atoms, and Ar₁ and Ar₂ are each independently a substituted or unsubstituted aryl group of 6 to 40 ring carbon atoms, a substituted or unsubstituted heteroaryl group of 5 to 40 ring carbon atoms, or a substituted or unsubstituted alkyl group of 1 to 20 carbon atoms.

13. The amine compound as claimed in claim 12, wherein Formula 1 is represented by the following Formula 2-1 or 2-2:

[Formula 2-1]

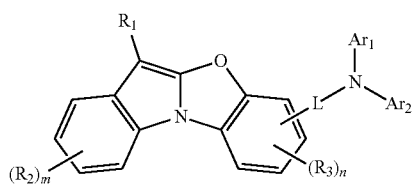

[Formula 2-2]

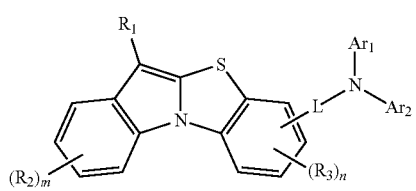

in Formulae 2-1 and 2-2,

R₁, R₂, R₃, Ar₁, Ar₂ "m", "n" and L are the same as defined in Formula 1.

14. The amine compound as claimed in claim 12, wherein Formula 1 is represented by any one among the following Formulae 3-1 to 3-4:

[Formula 3-1]

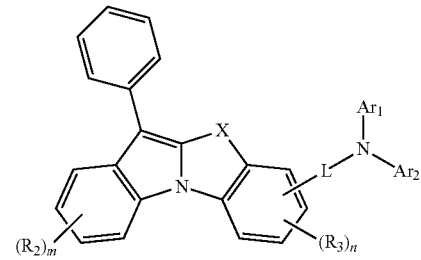

[Formula 3-2]

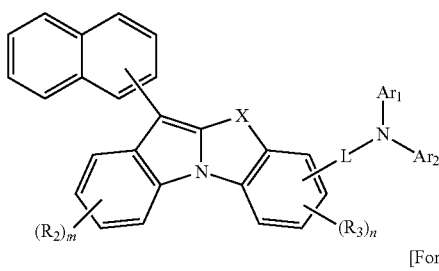

[Formula 3-3]

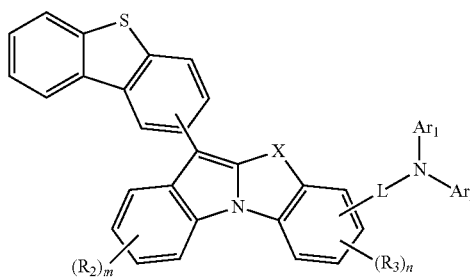

[Formula 3-4]

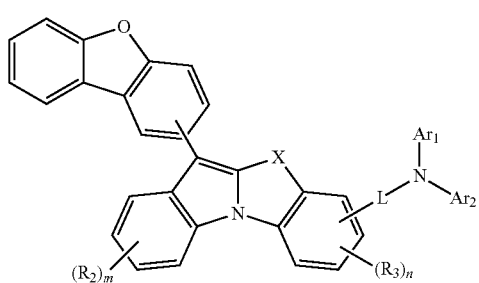

in Formulae 3-1 to 3-4,

X, R₂, R₃, Ar₁, Ar₂ "m", "n" and L are the same as defined in Formula 1.

15. The amine compound as claimed in claim 12, wherein R₂ and R₃ are each independently one selected from a substituted or unsubstituted cyclohexyl group, a substituted or unsubstituted phenyl group, a substituted or unsubstituted biphenyl group, a substituted or unsubstituted dibenzofuran group, a substituted or unsubstituted dibenzothiophene group and a substituted or unsubstituted carbazole group, or combined with an adjacent group to form a benzene ring.

16. The amine compound as claimed in claim 12, wherein "m" and "n" are 0.

17. The amine compound as claimed in claim 12, wherein Ar₁ and Ar₂ are each independently a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted triphenylene group, a substituted or unsubstituted dibenzothiophene group, a substituted or unsubstituted dibenzofuran group, or a substituted or unsubstituted carbazole group.

18. The amine compound as claimed in claim 17, wherein $Ar_1$ and $Ar_2$ are each independently unsubstituted or substituted with at least one substituent selected from a hydrogen atom, a deuterium atom, a fluorine atom, an adamantyl group, a triphenylsilyl group, a phenoxy group, an aryl group of 6 to 30 ring carbon atoms, or a heteroaryl group of 5 to 30 ring carbon atoms, or adjacent substituents are combined with each other to form a ring.

19. The amine compound as claimed in claim 12, wherein L is a direct linkage, a substituted or unsubstituted phenylene group, a substituted or unsubstituted divalent biphenyl group, a substituted or unsubstituted naphthylene group, a substituted or unsubstituted phenanthrylene group, or a substituted or unsubstituted fluorenylene group.

20. The amine compound as claimed in claim 12, wherein the amine compound is one among compounds represented in the following Compound Group A and Compound Group B:

[Compound Group A]

A1
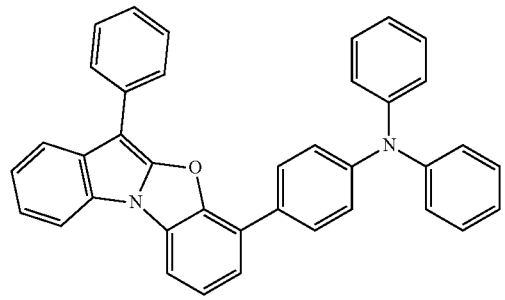

A2
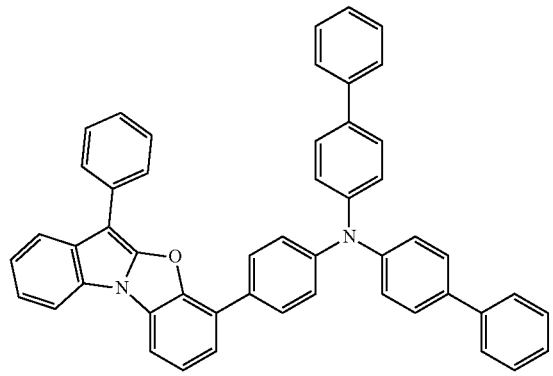

A3
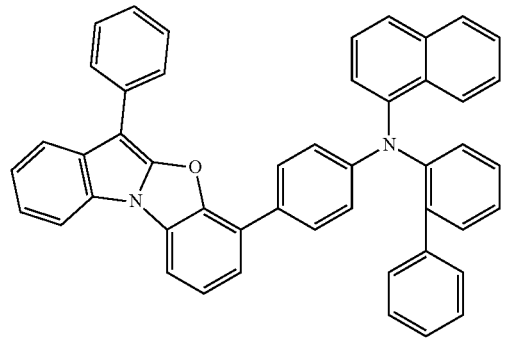

A4
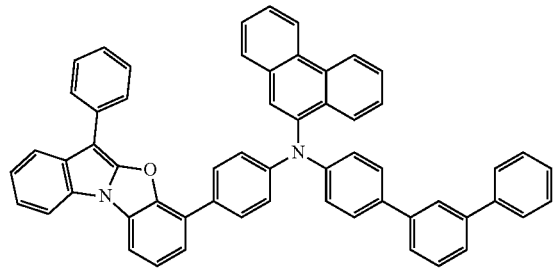

A5
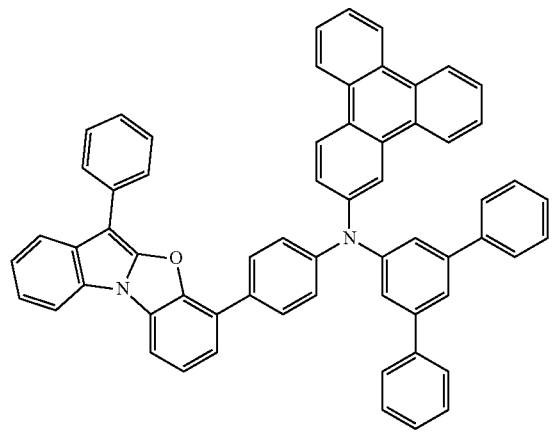

A6
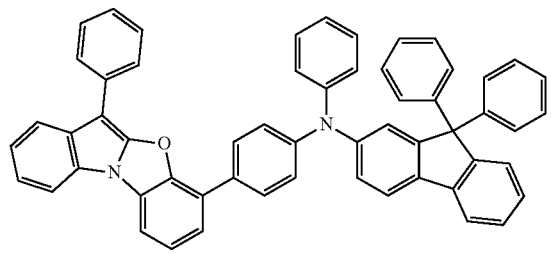

-continued
A7
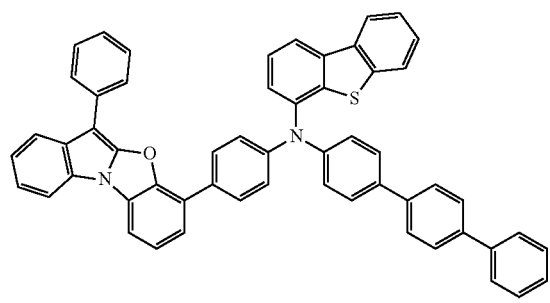
A8
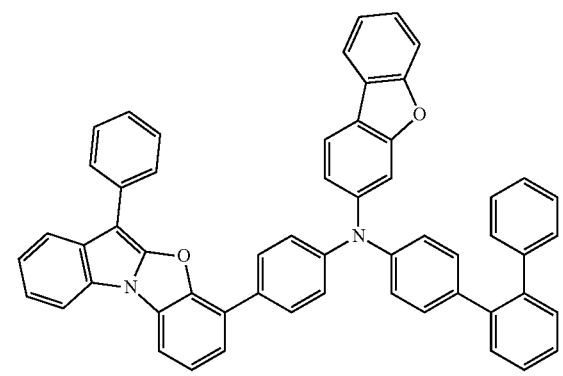
A9
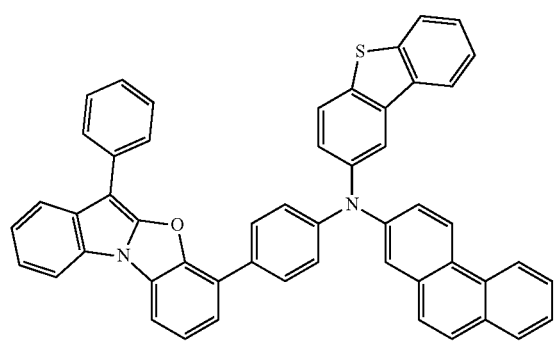
A10
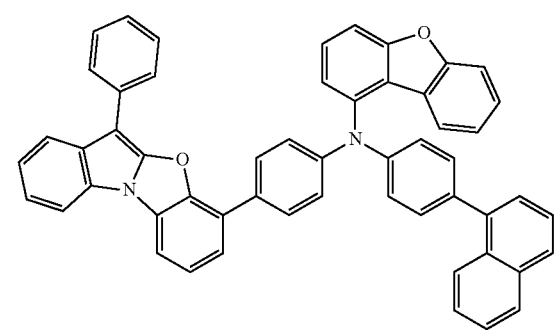
A11
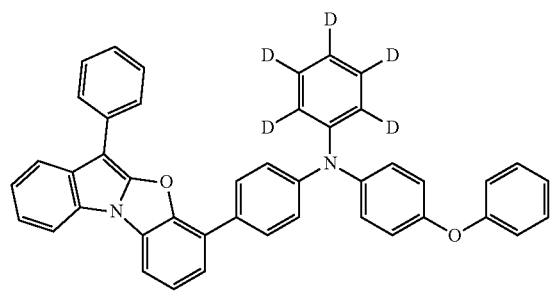
A12
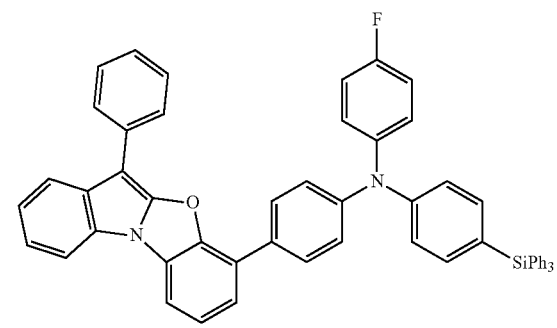
A13
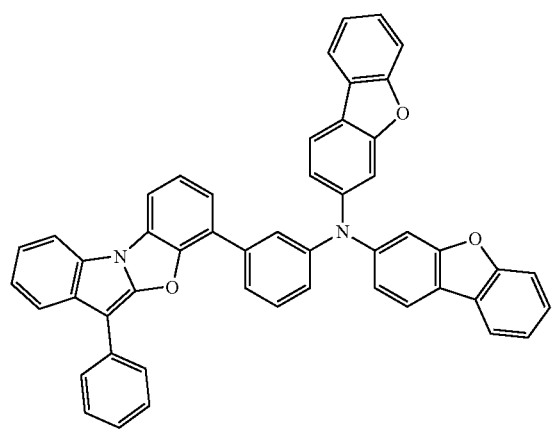
A14
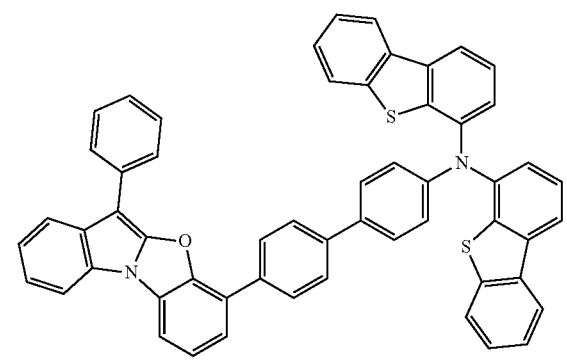

-continued
A15
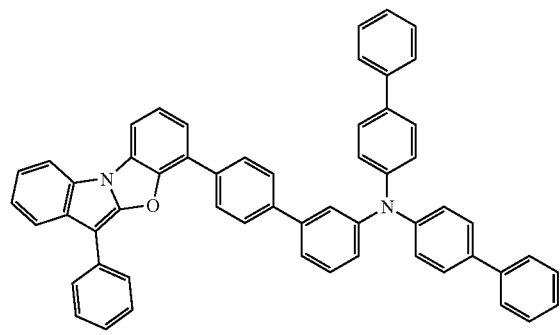
A16
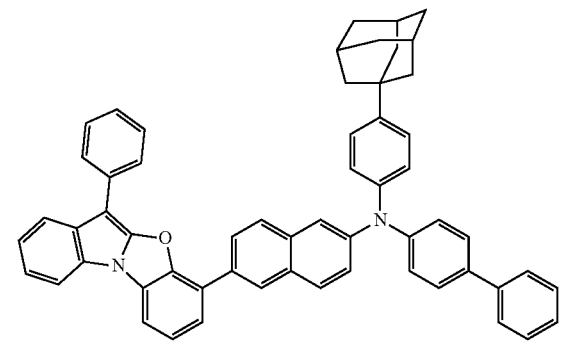
A17
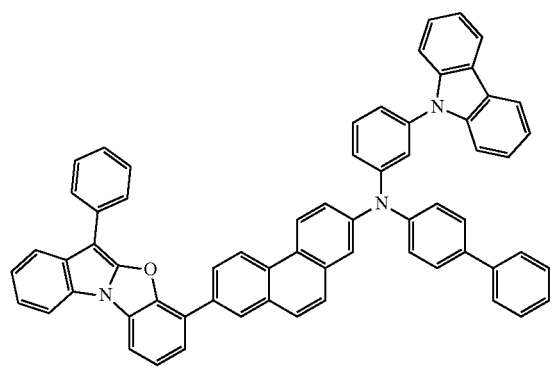
A18
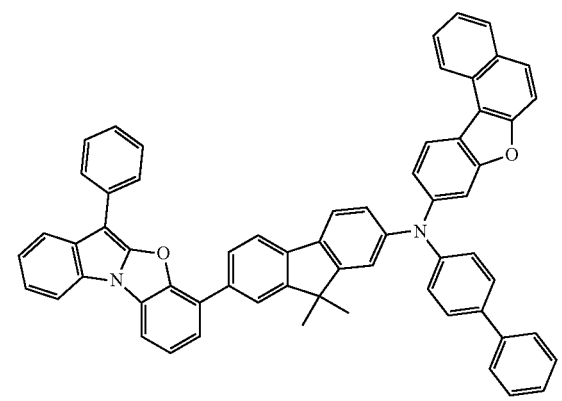
A19
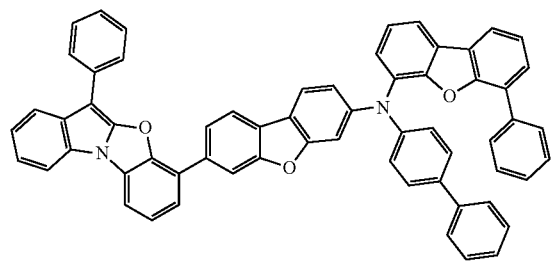
A20
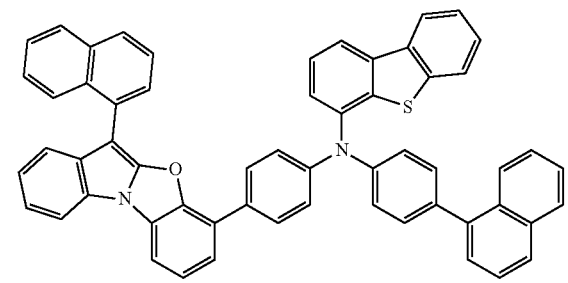
A21
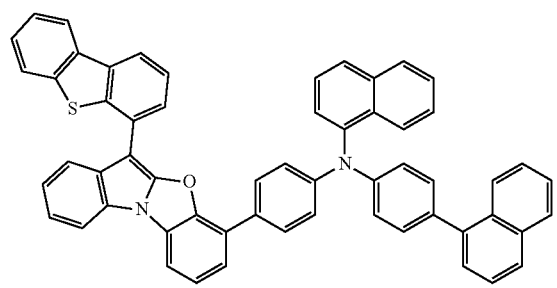
A22
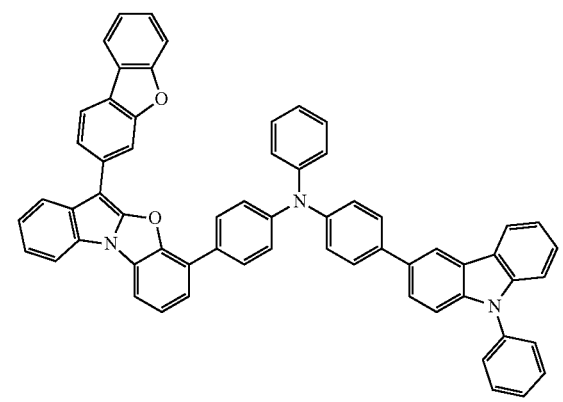

-continued
A23 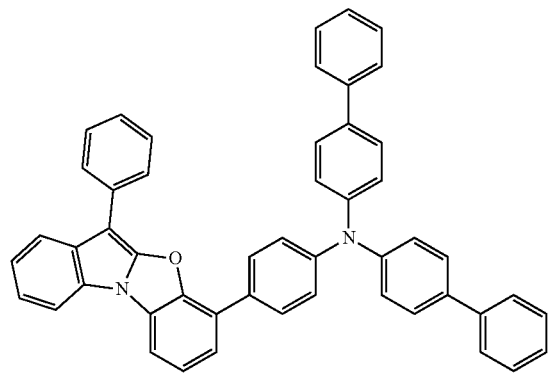
A24 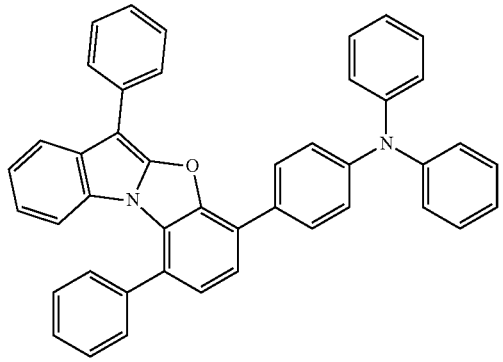
A25 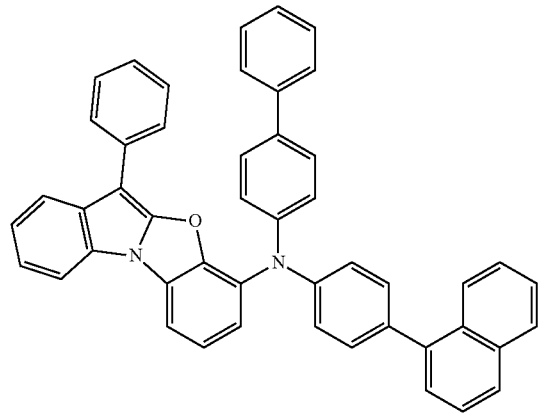
A26 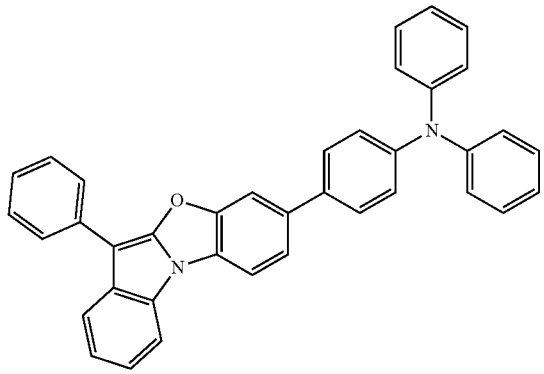
A27 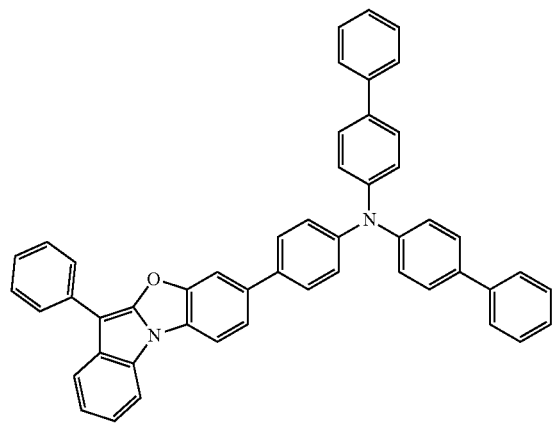
A28 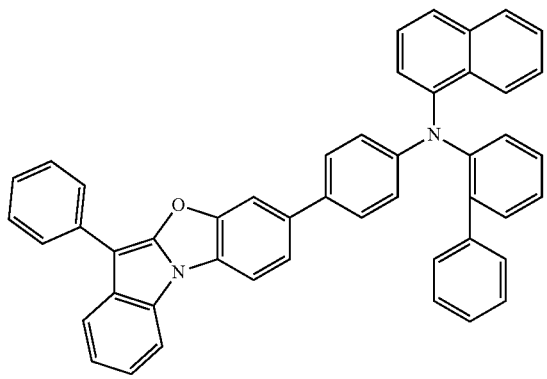

-continued
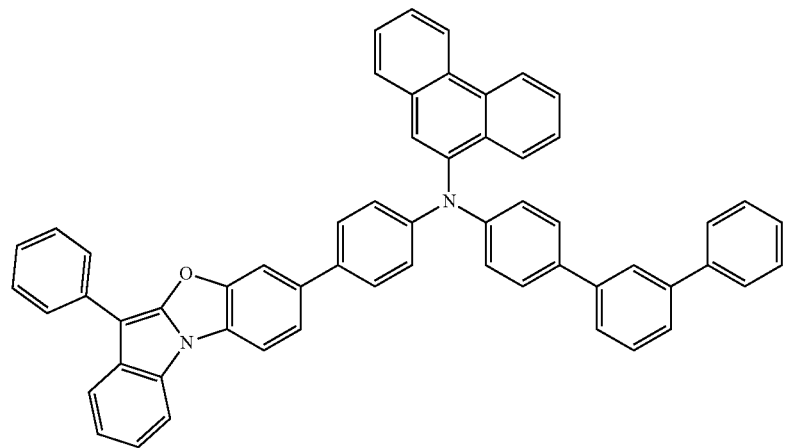
A29
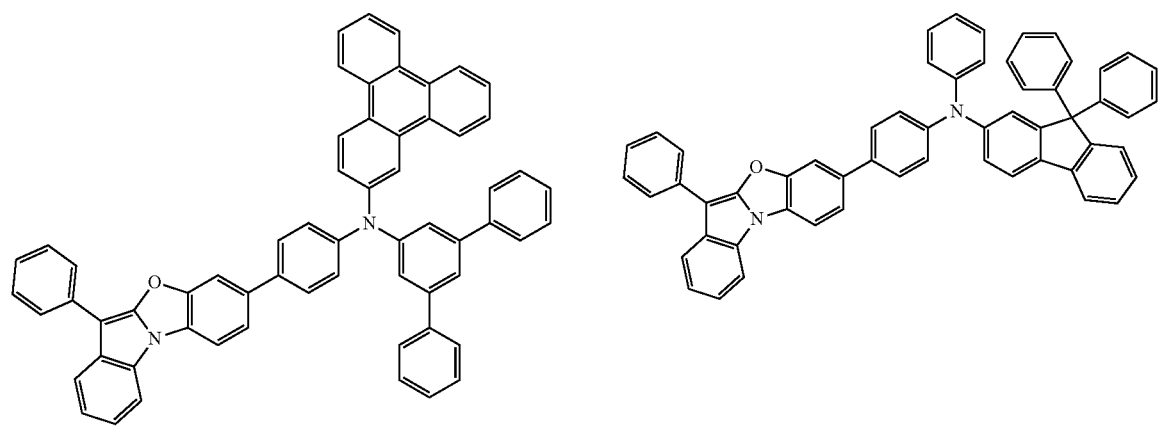
A30    A31
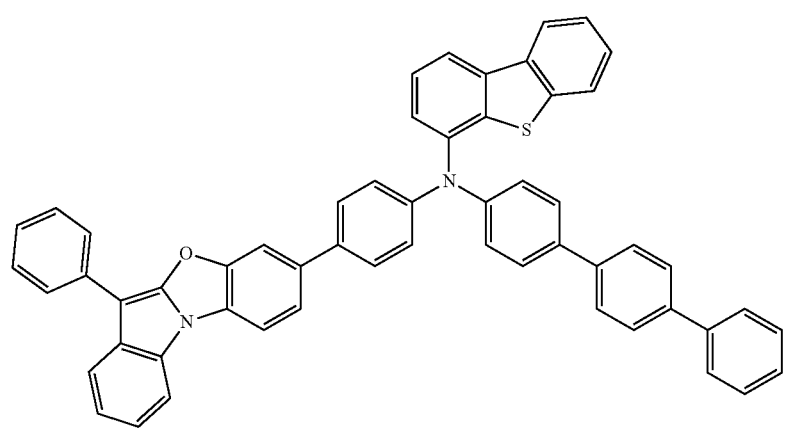
A32

-continued
A33
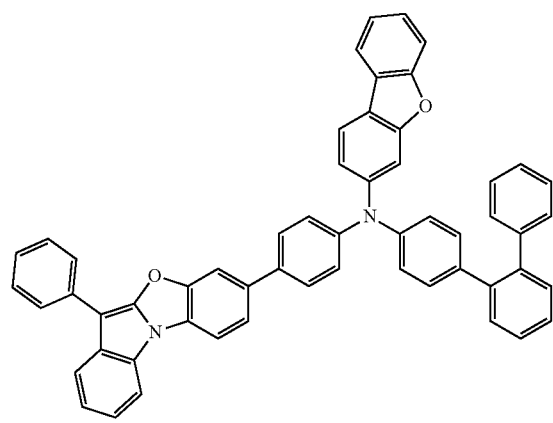
A34
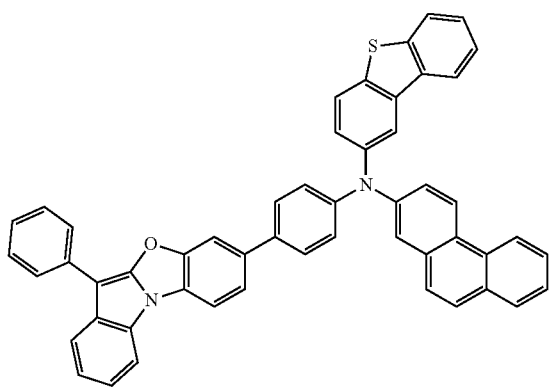
A35
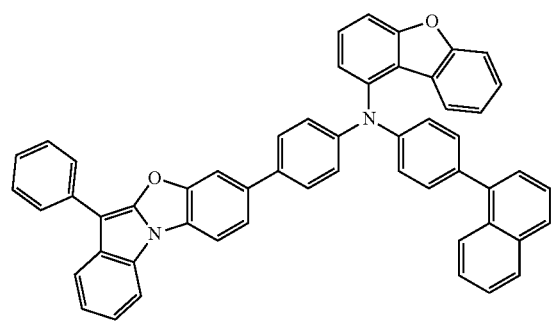
A36
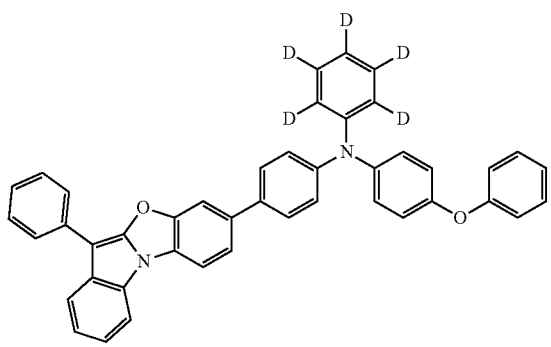
A37
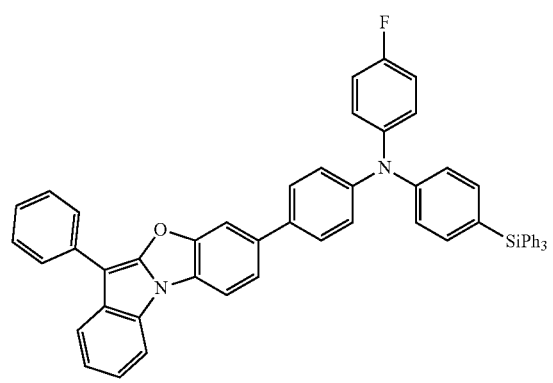
A38
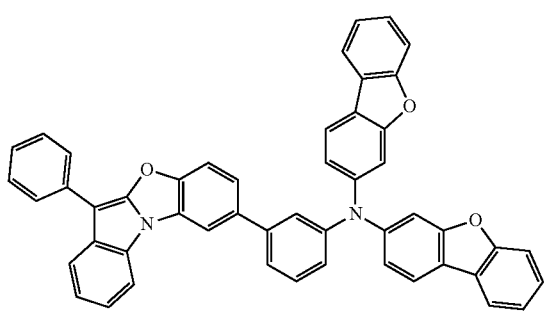
A39
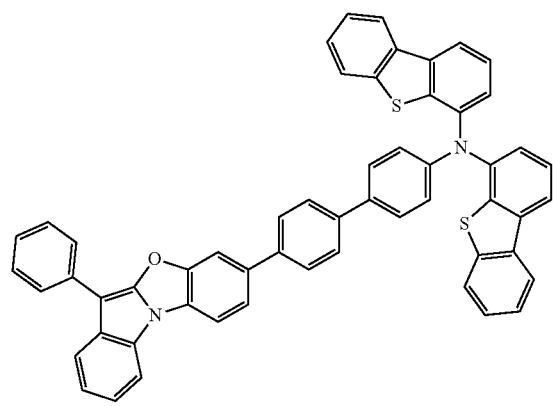
A40
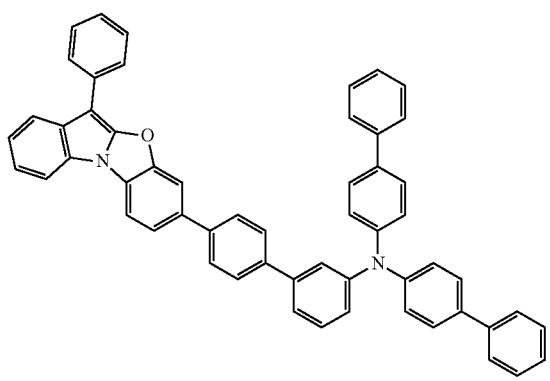

-continued
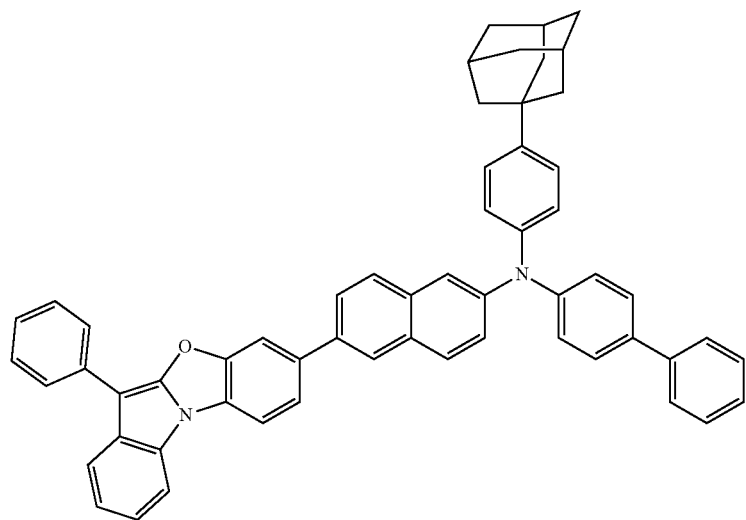
A41
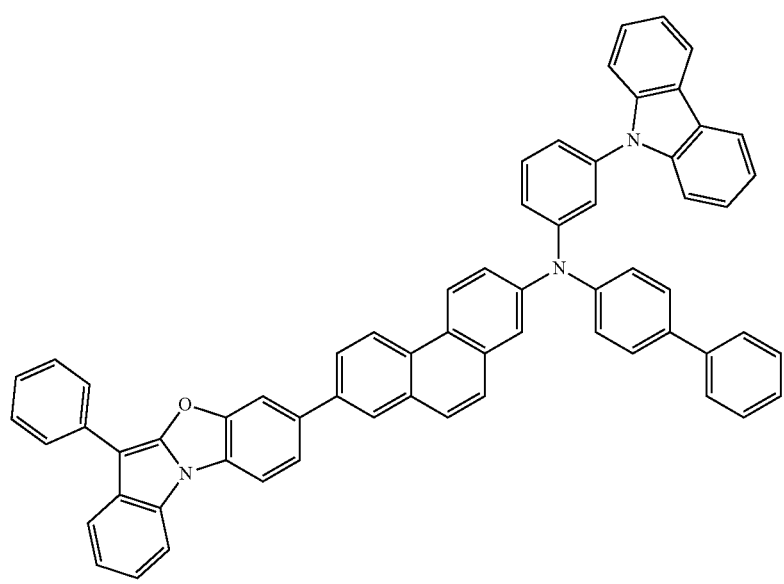
A42
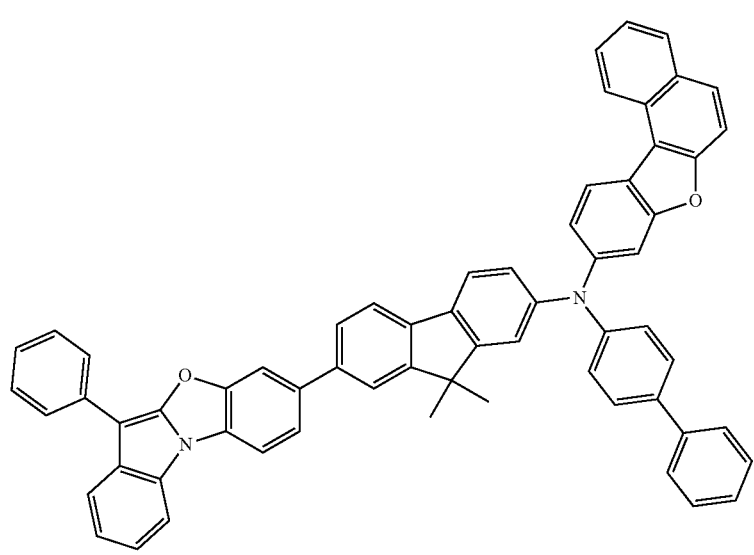
A43

-continued
A44
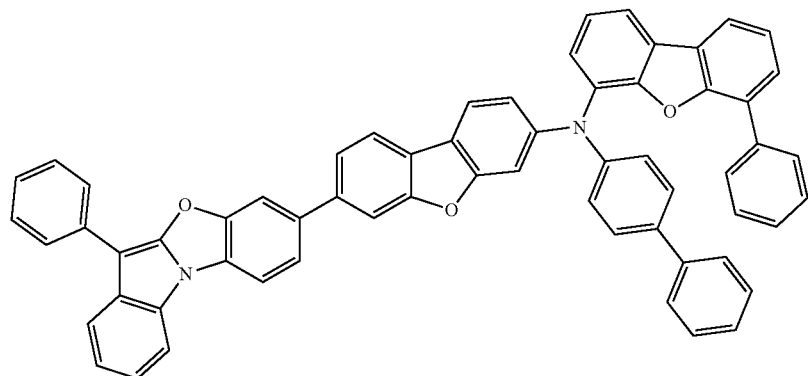
A45
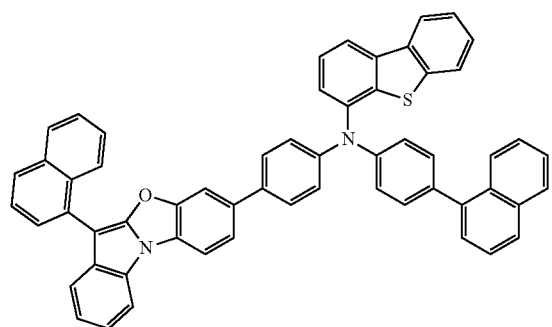
A46
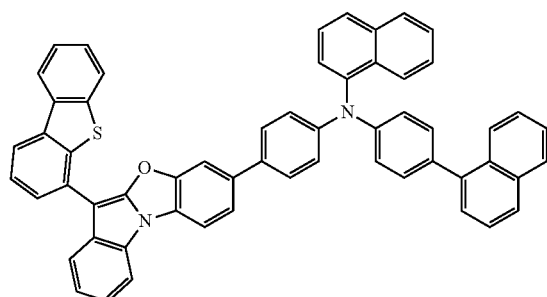
A47
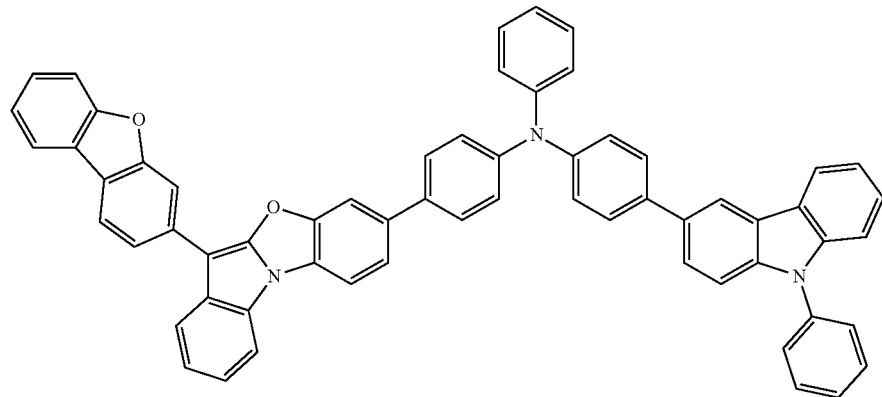
A48
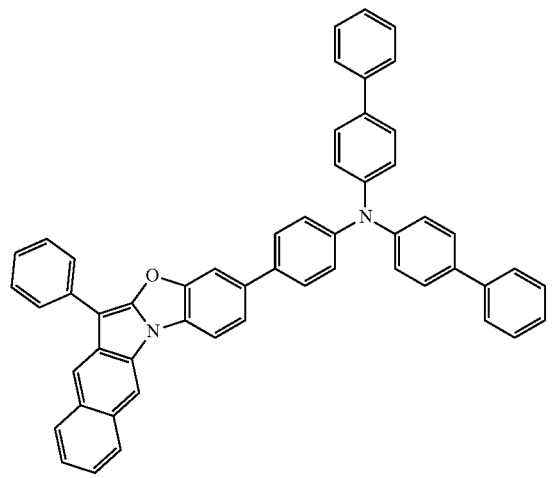
A49
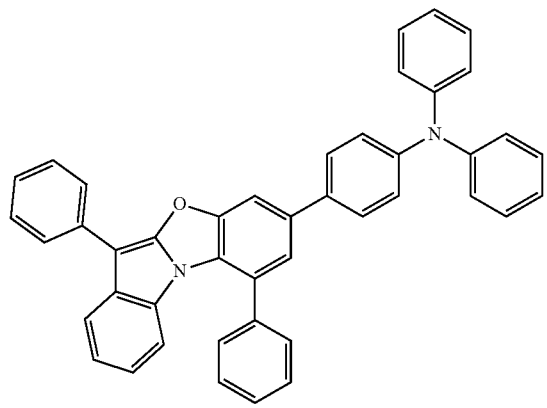

-continued
A50
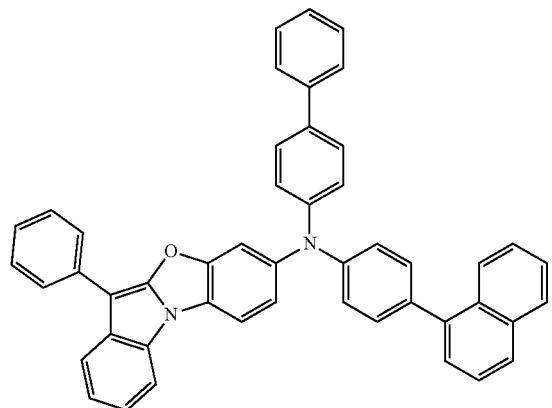
A51
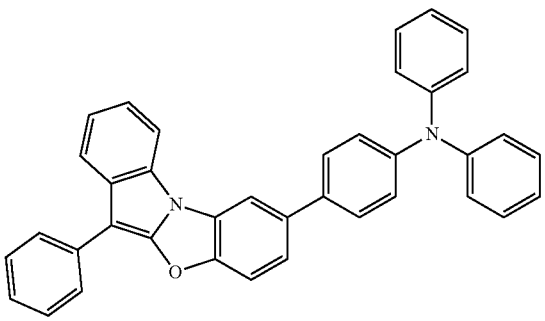
A52
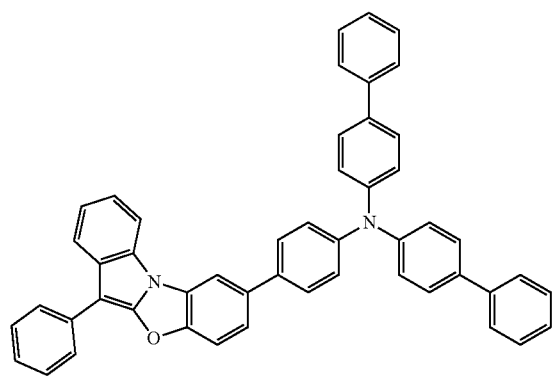
A53
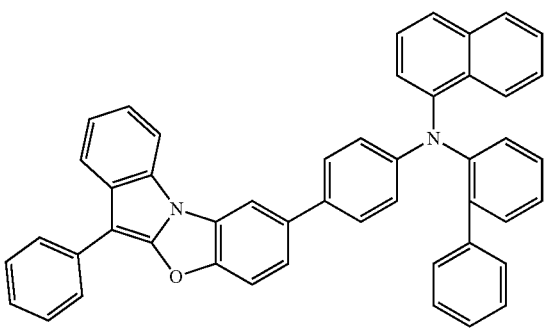
A54
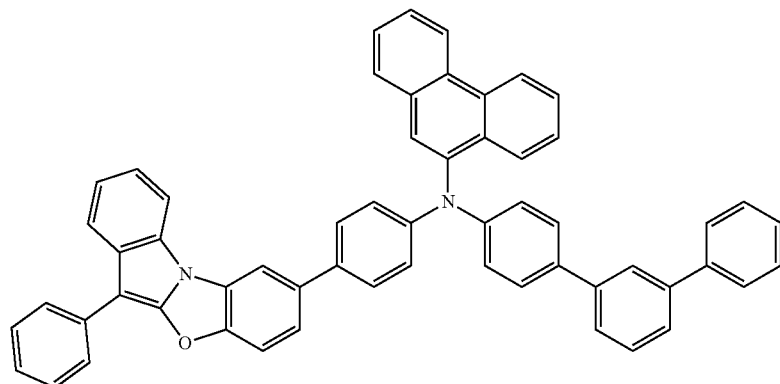
A55
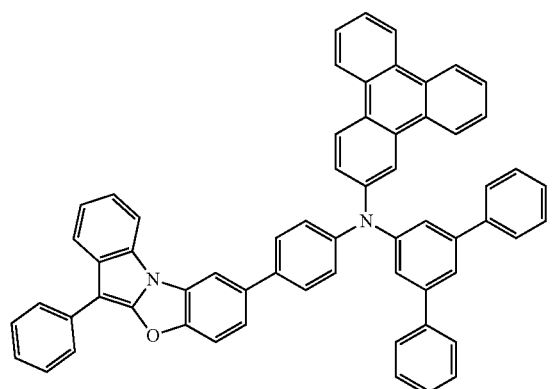
A56
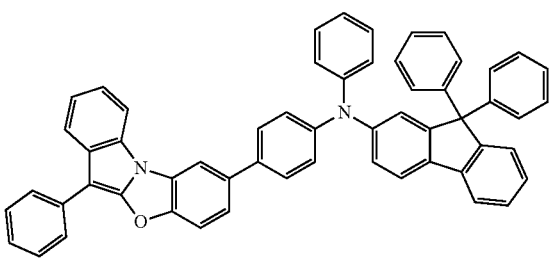

-continued
A57
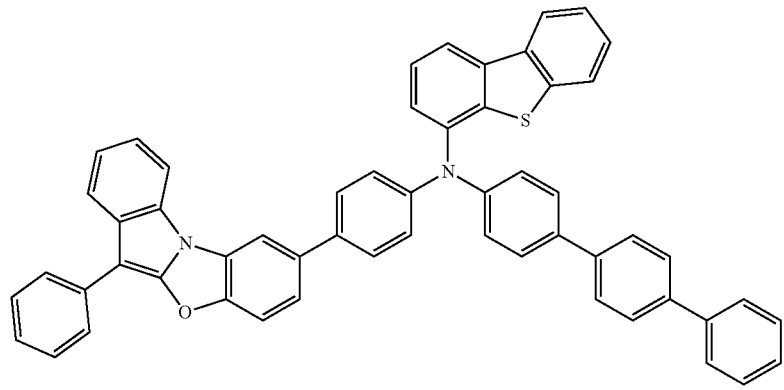
A58
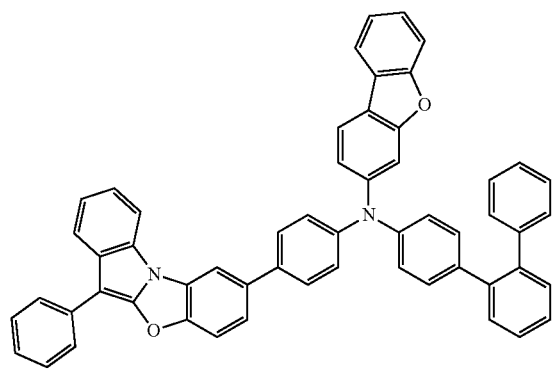
A59
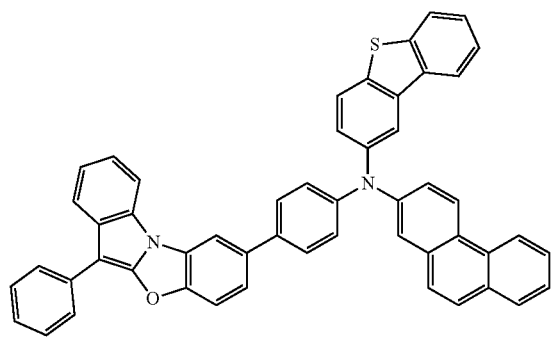
A61
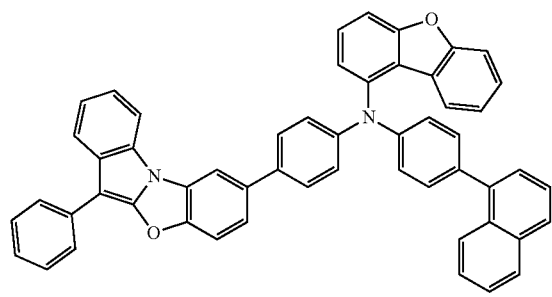
A60
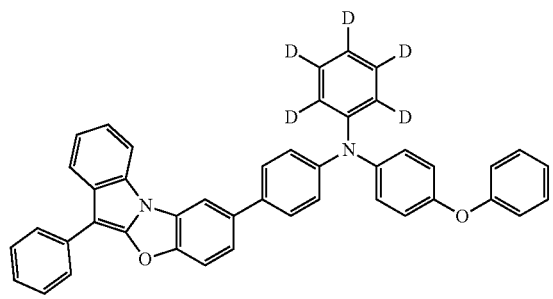
A62
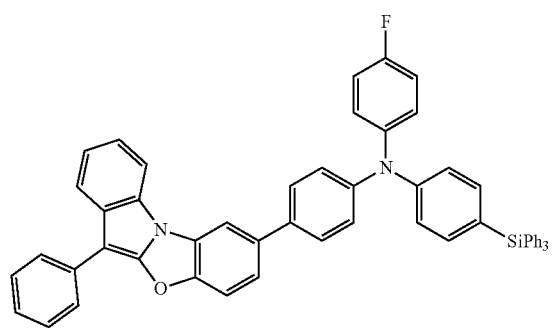
A63
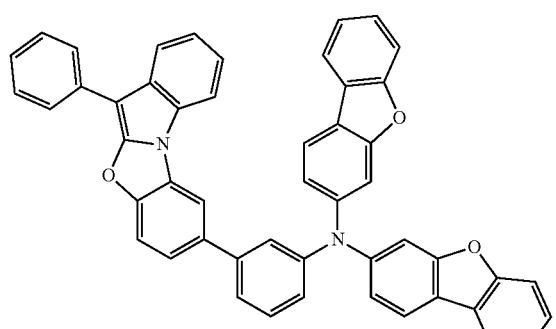

-continued
A64
A65
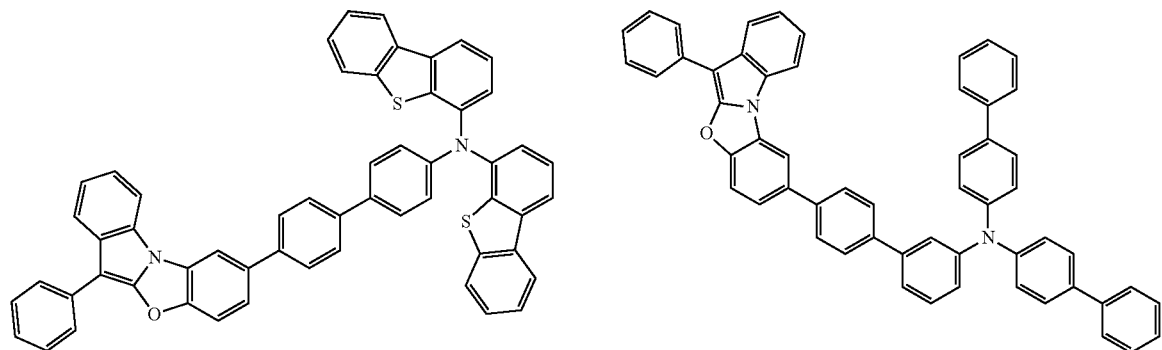
A66
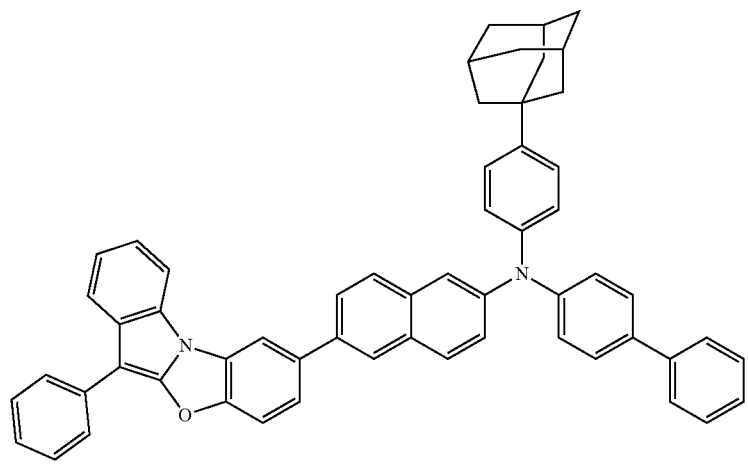
A67
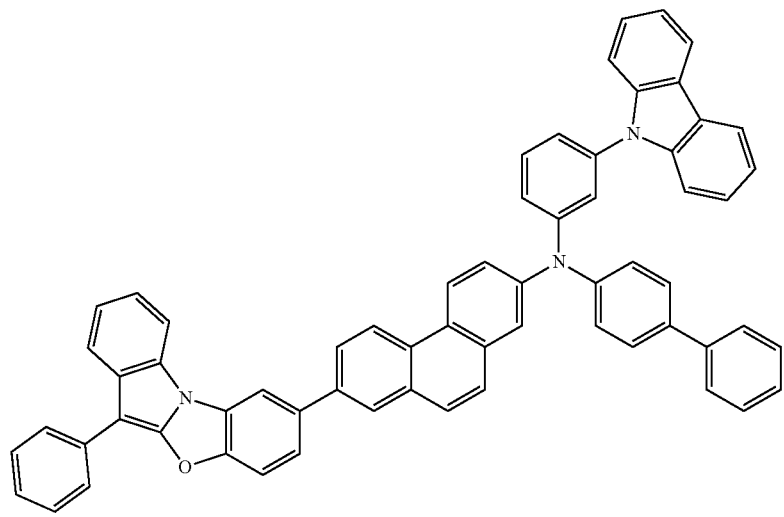

-continued
A68
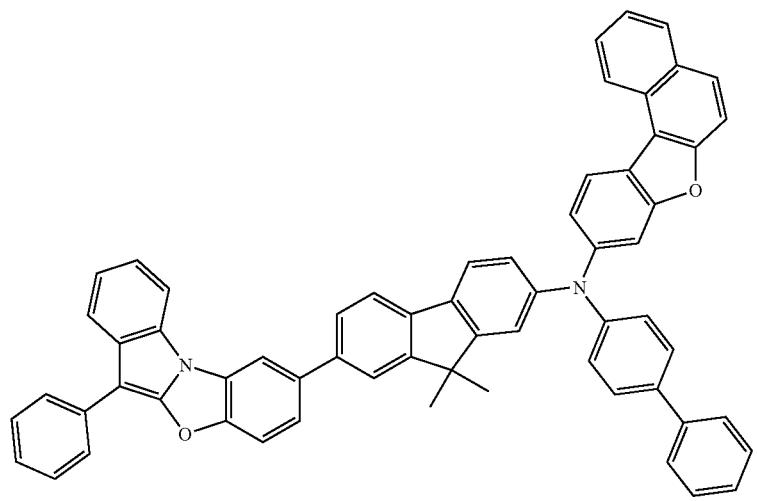
A69
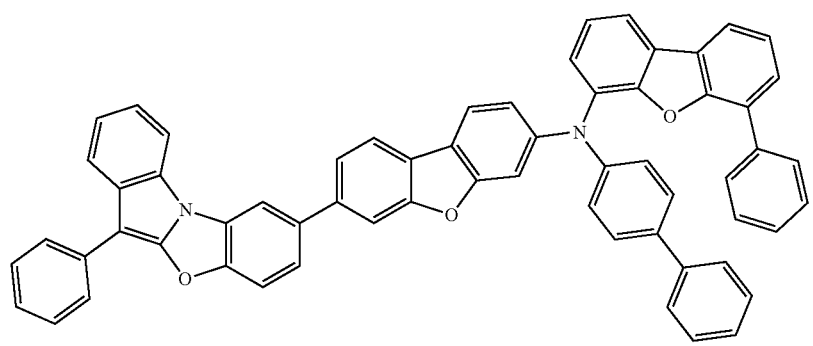
A70
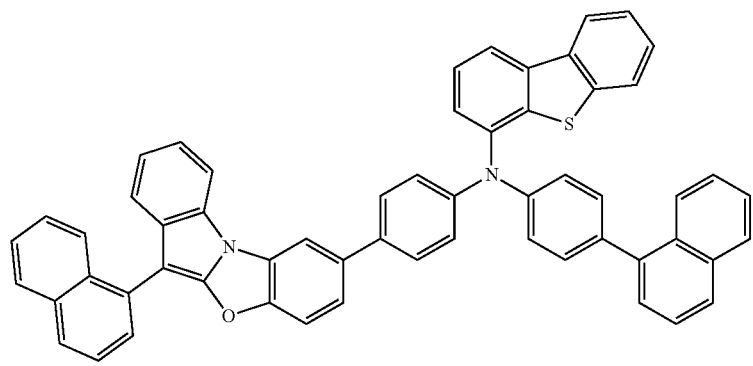
A71
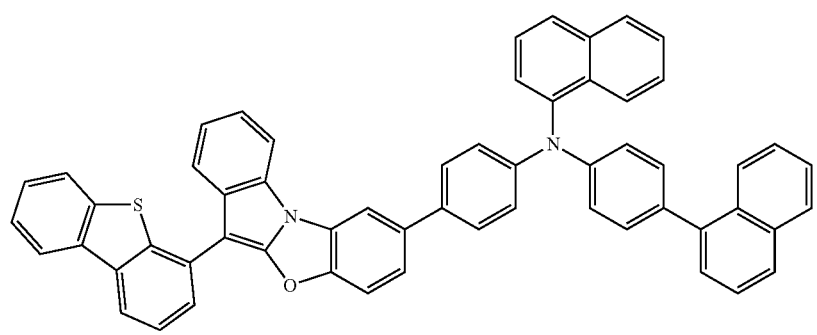

A72
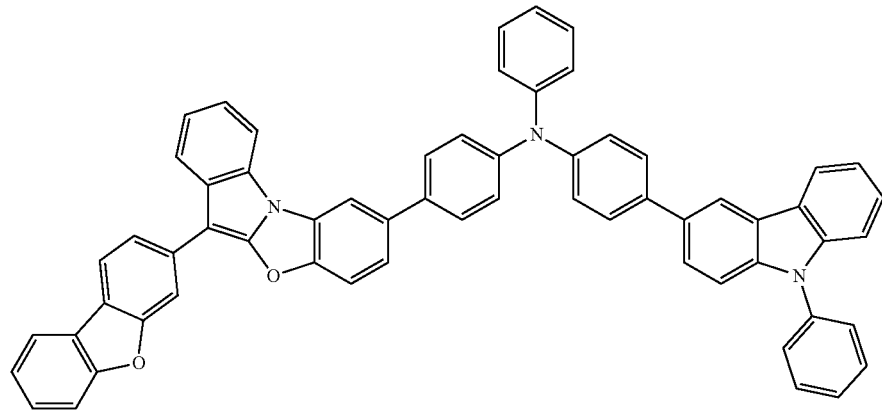
A73
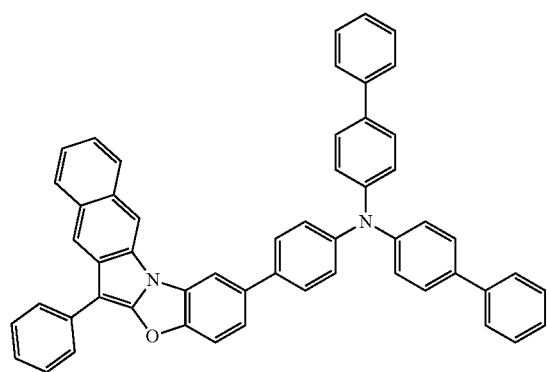
A74
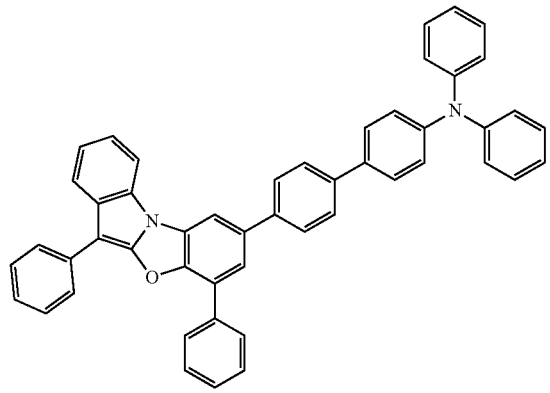
A75
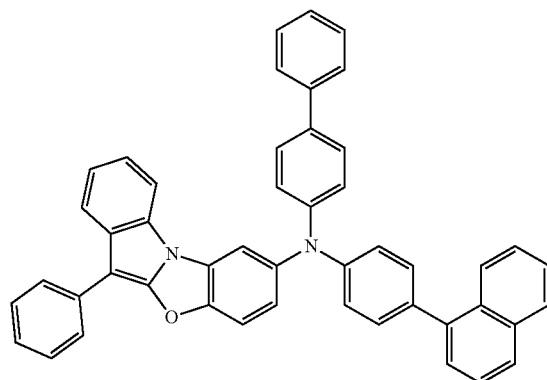
A76
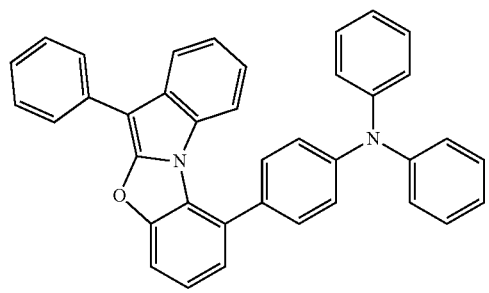
A77
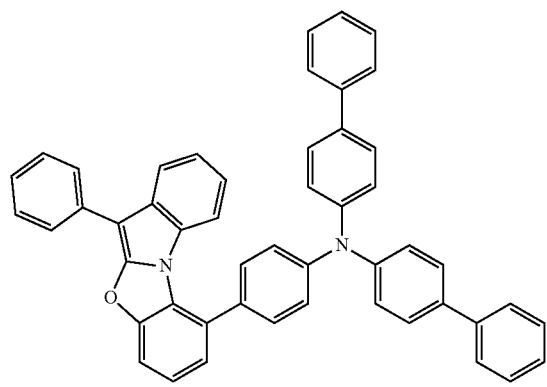
A78
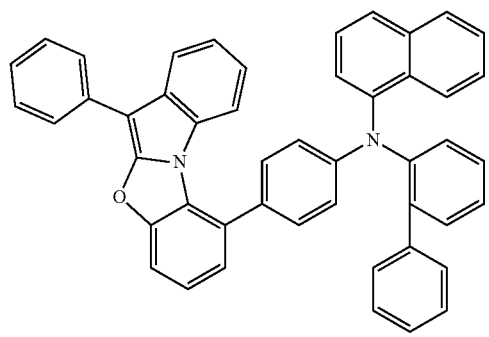

-continued
A79
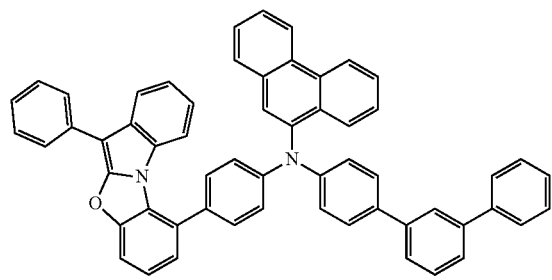
A80
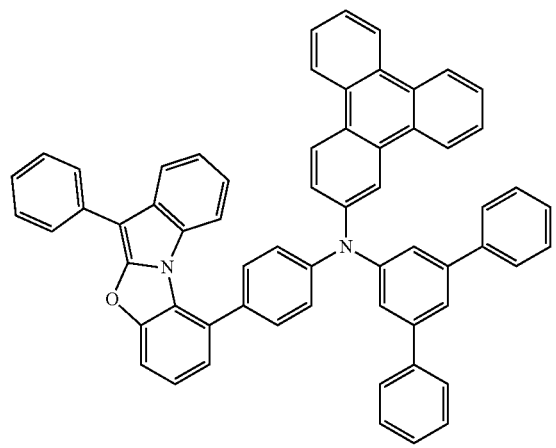
A81
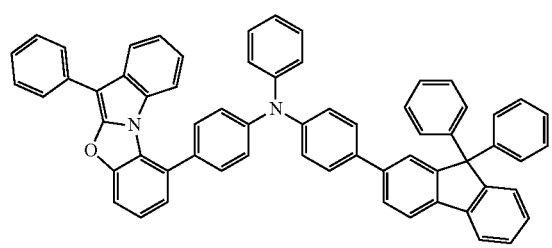
A82
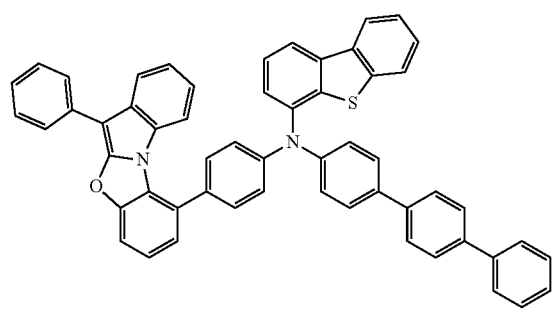
A83
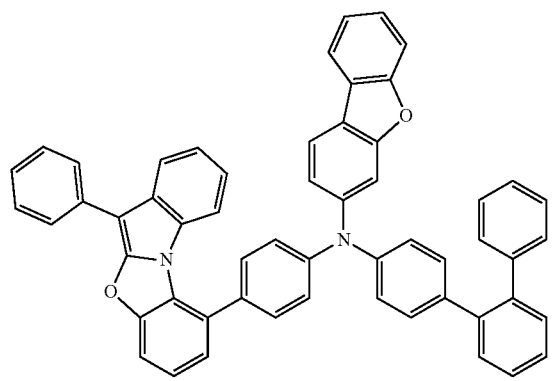
A84
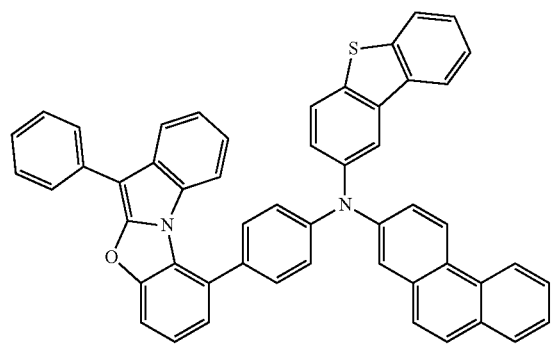
A85
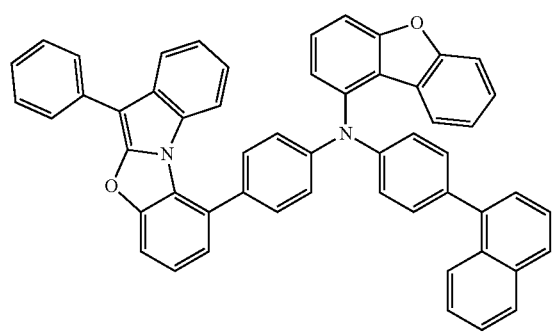
A86
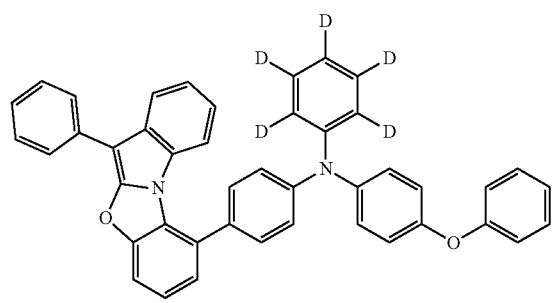

-continued
A87
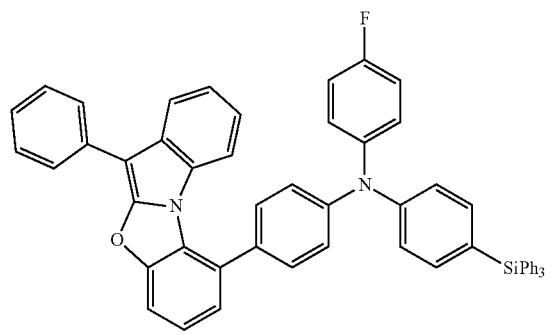
A88
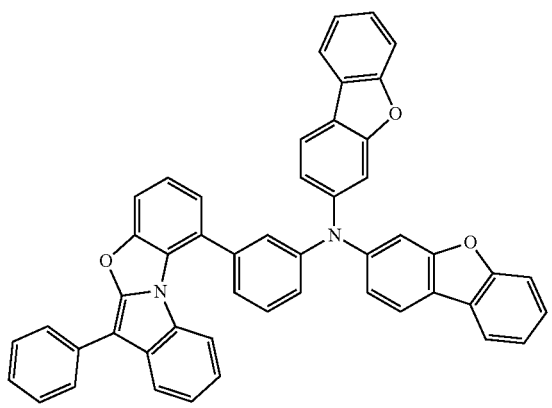
A89
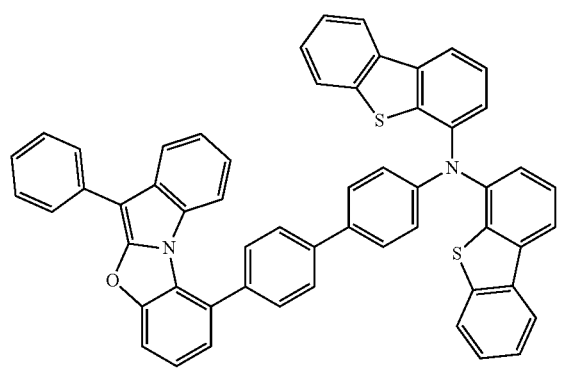
A90
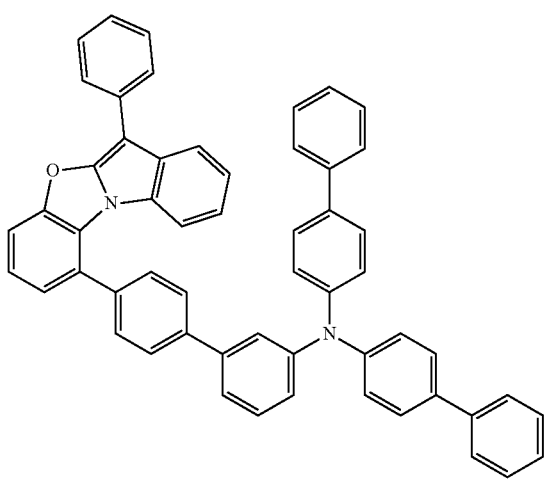
A91
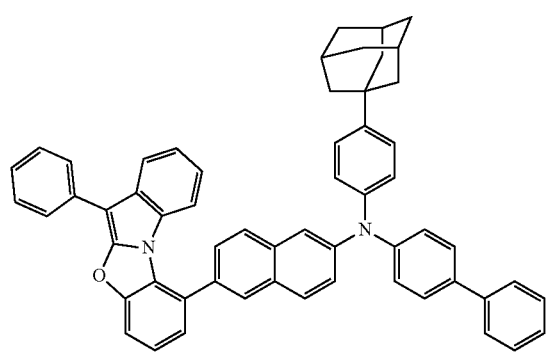
A92
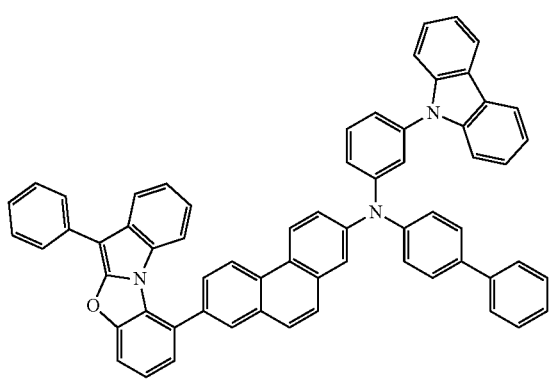

-continued
A93
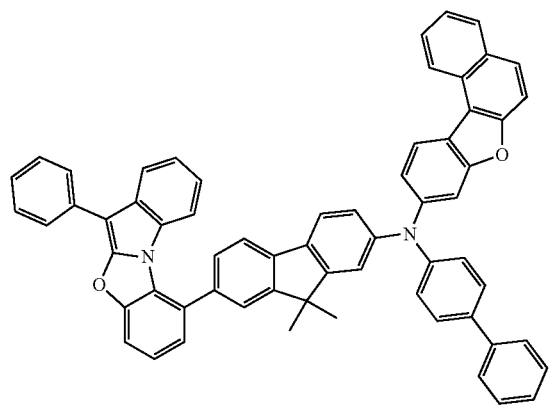
A94
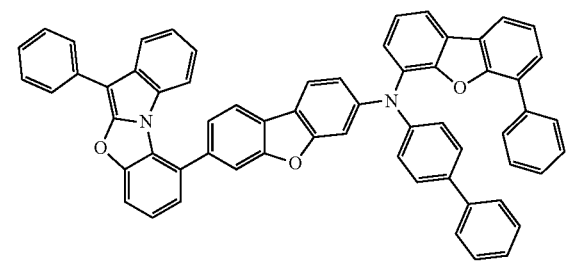
A95
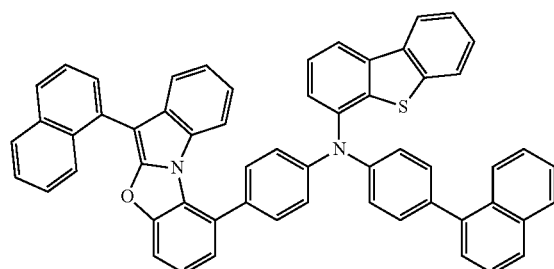
A96
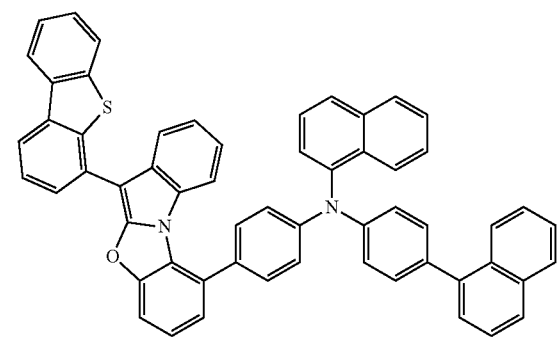
A97
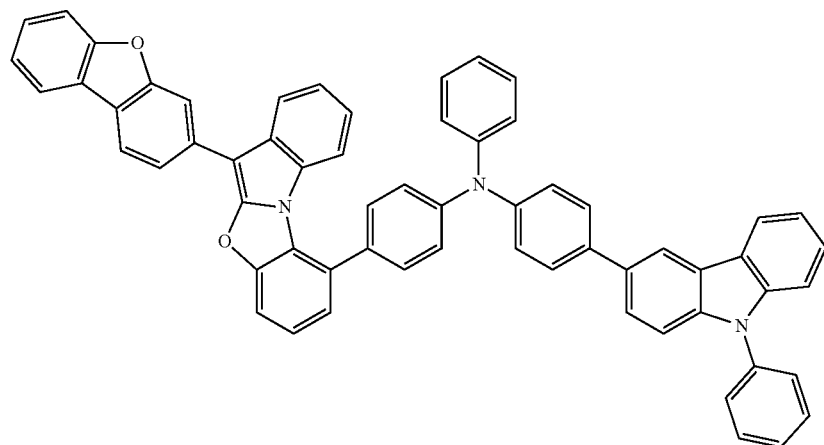
A98
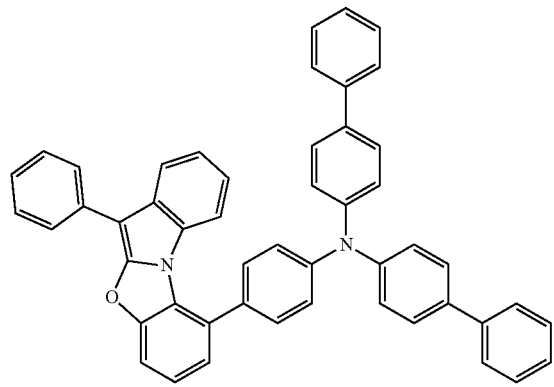
A99
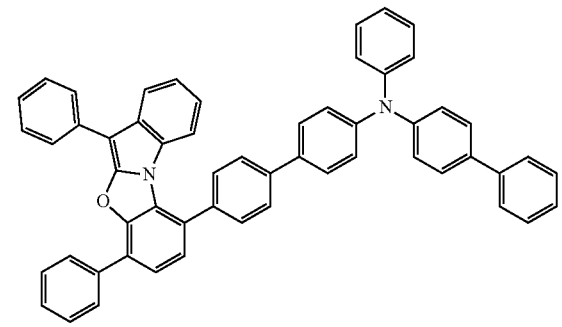

-continued
A100
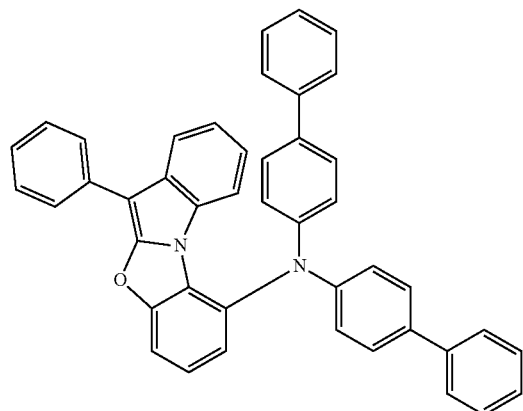
A101
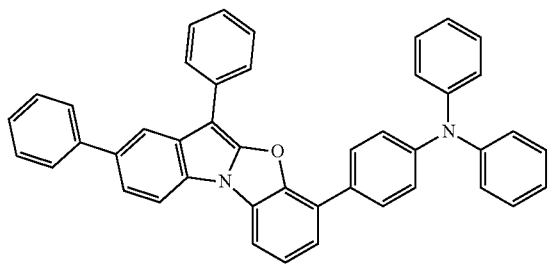
A102
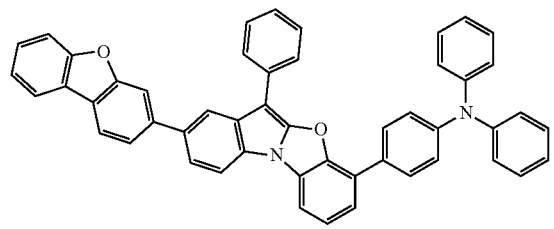
A103
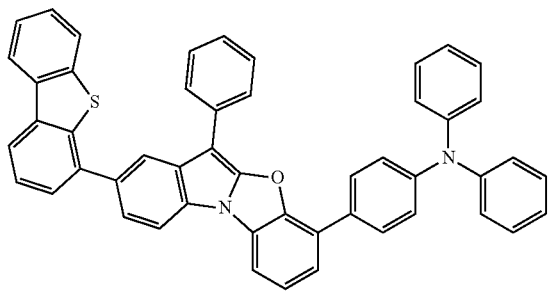
A104
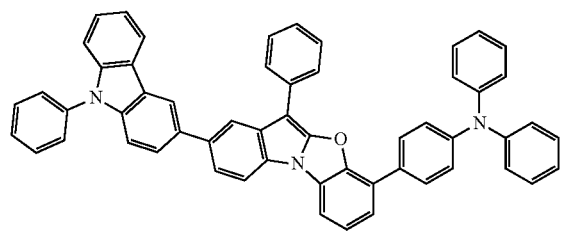
A105
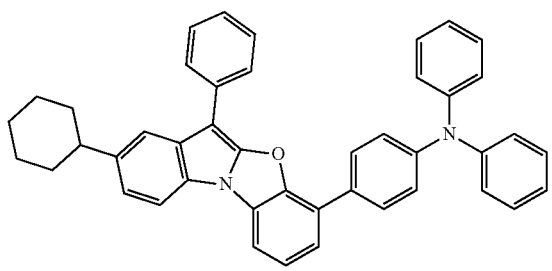
A106
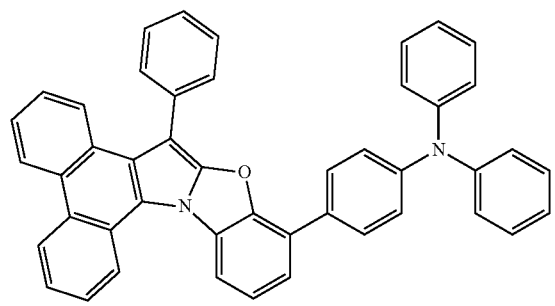
A107
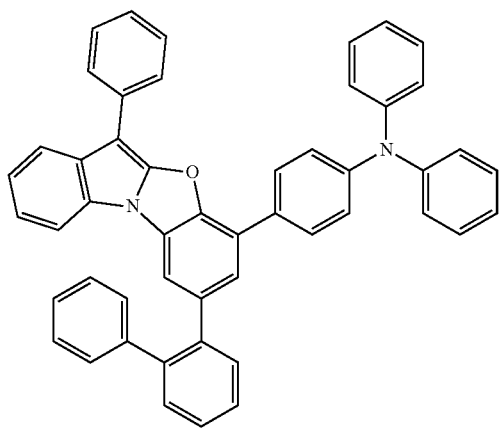

-continued
A108
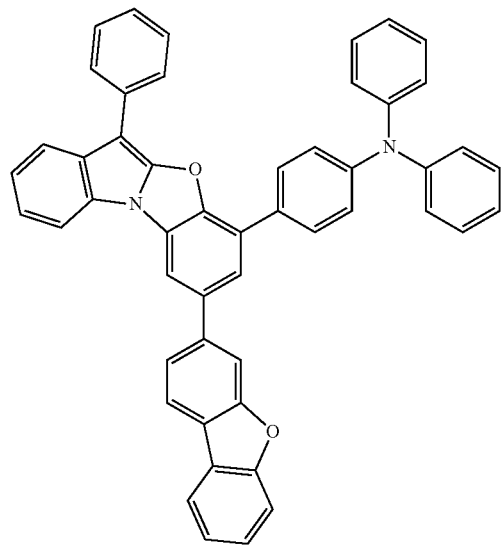
A109
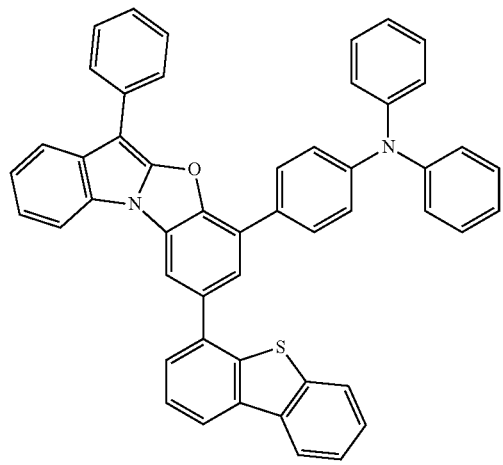
A110
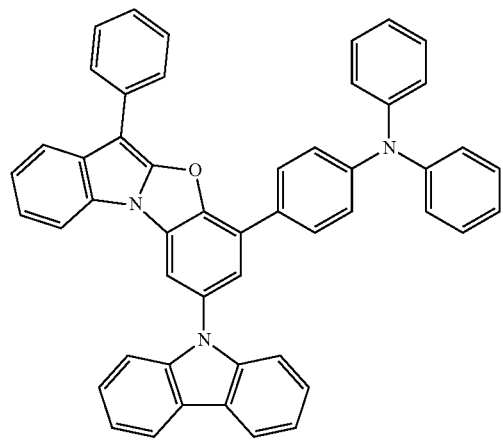
A111
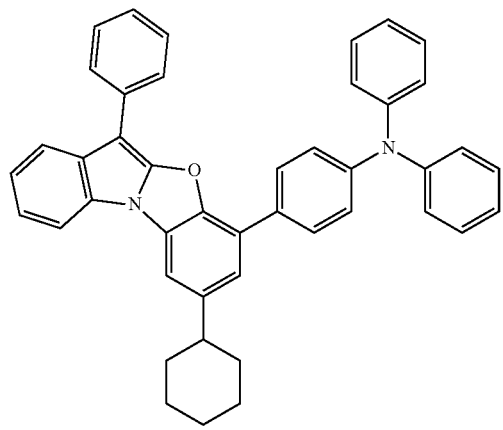
A112
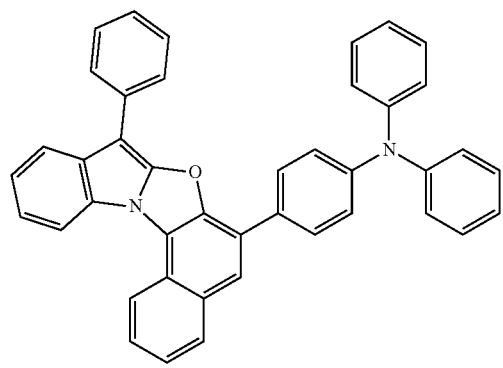

[Compound Group B]
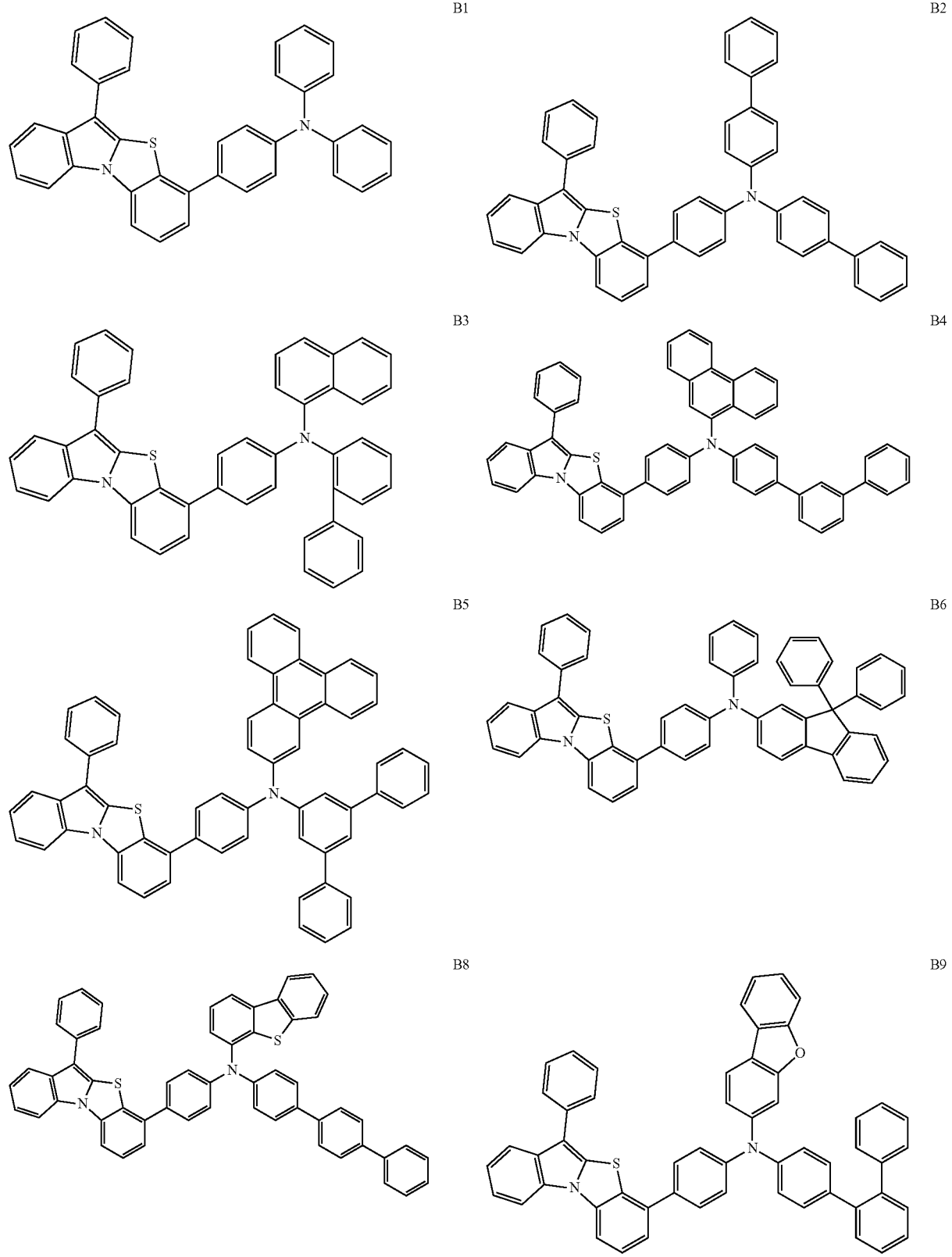

-continued
| B10 | B11 |
|---|---|
| 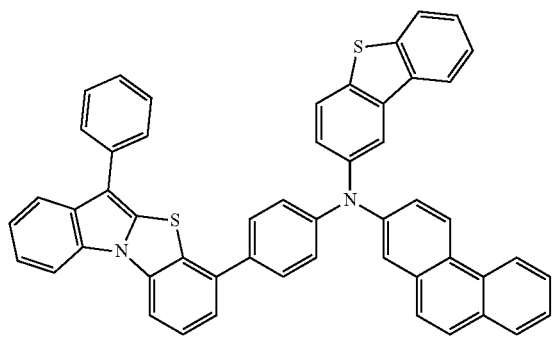 | 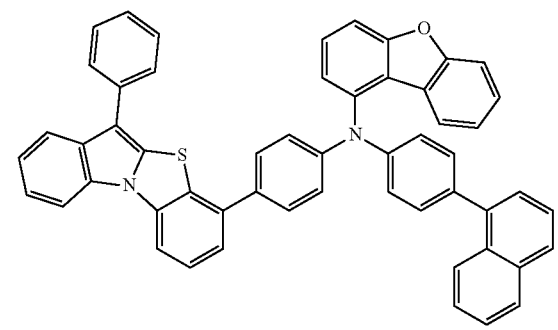 |
| B12 | B13 |
| 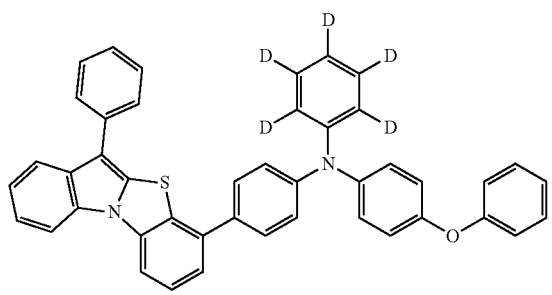 | 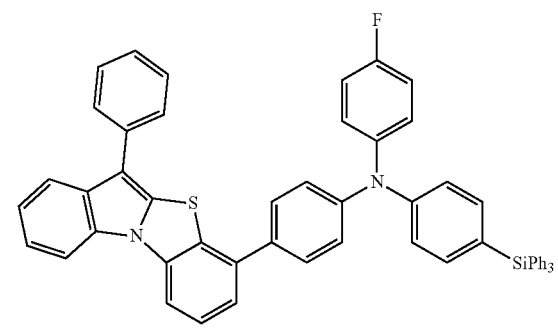 |
| B13 | B14 |
| 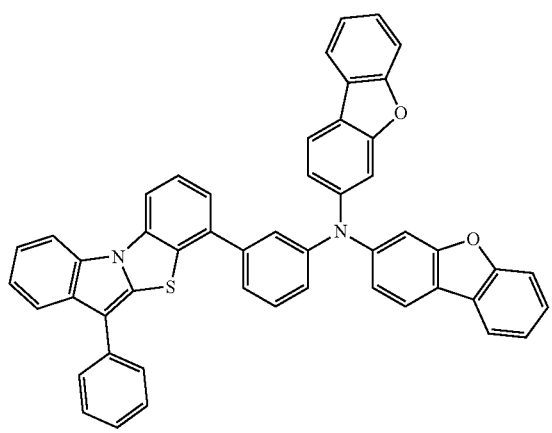 | 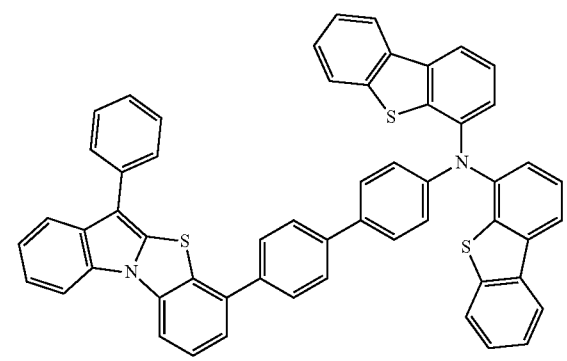 |
| B15 | B16 |
| 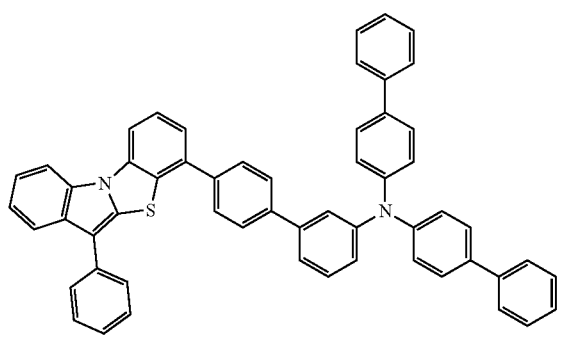 | 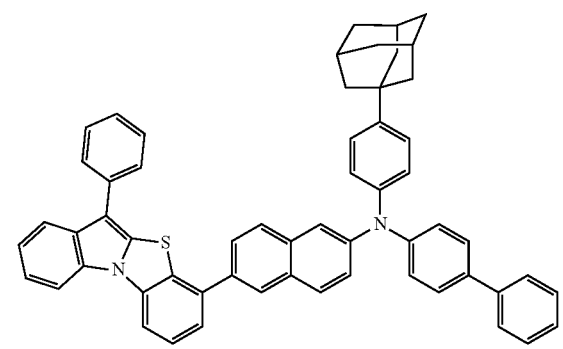 |

-continued
B17
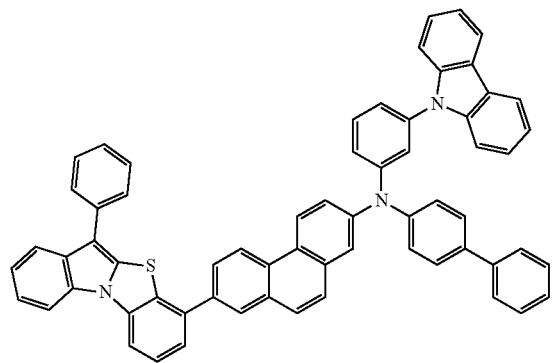
B18
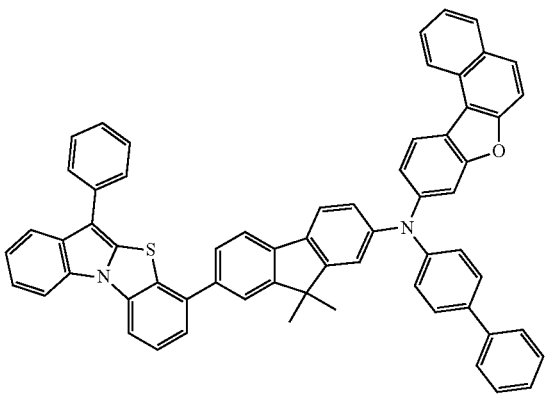
B19
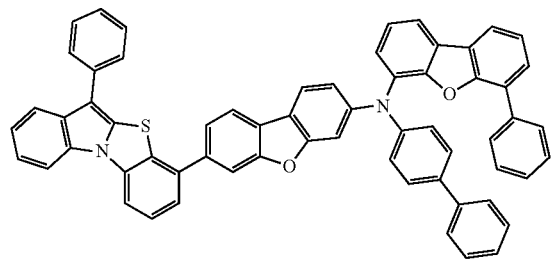
B20
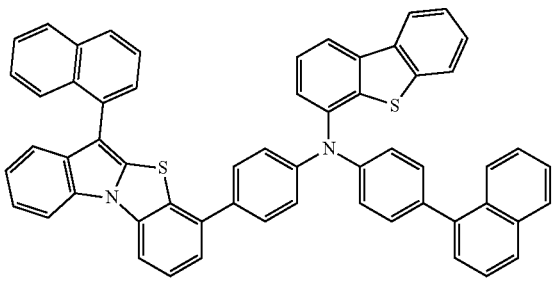
B21
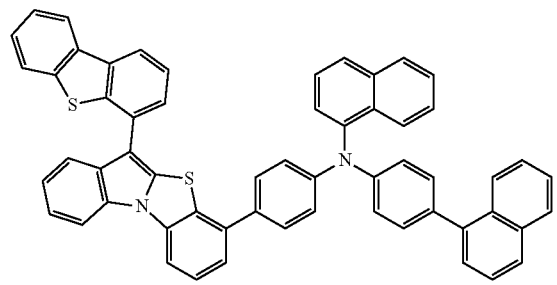
B22
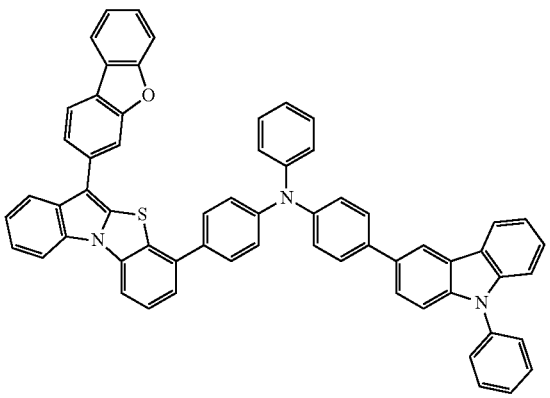
B23
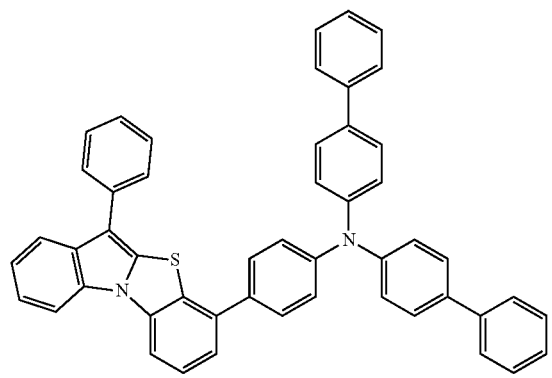
B24
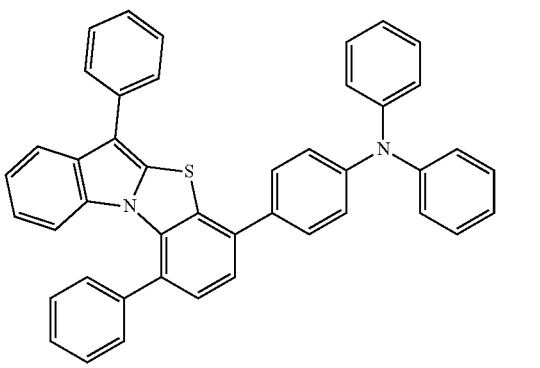

-continued
B25
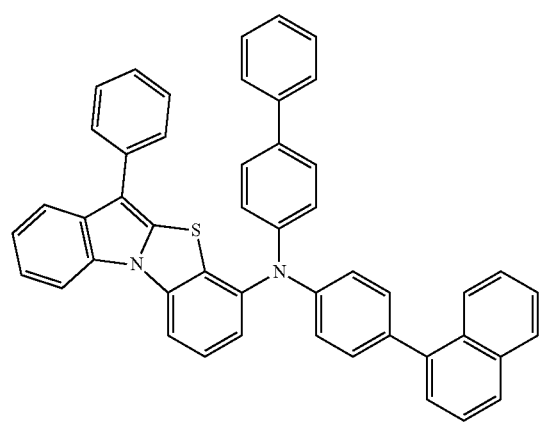
B26
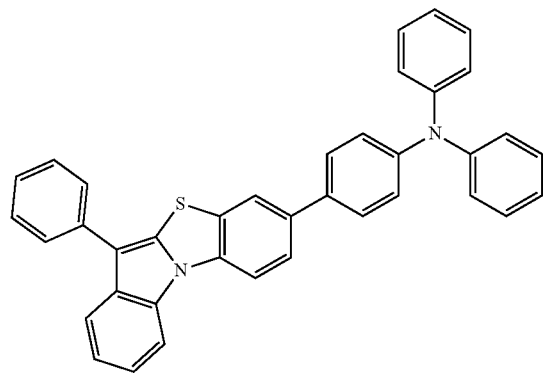
B27
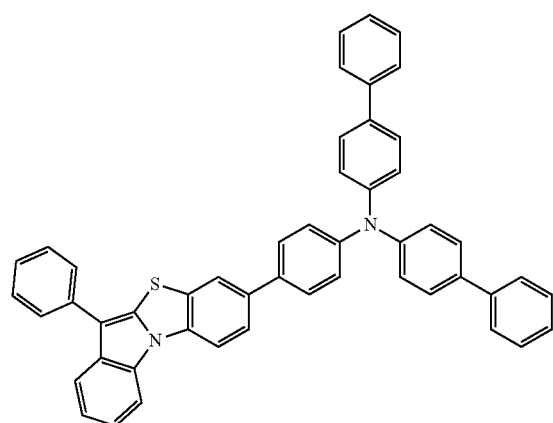
B28
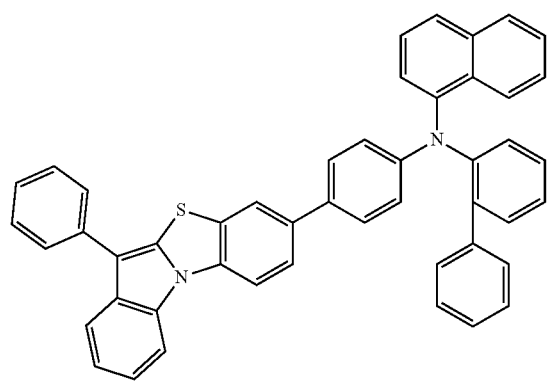
B29
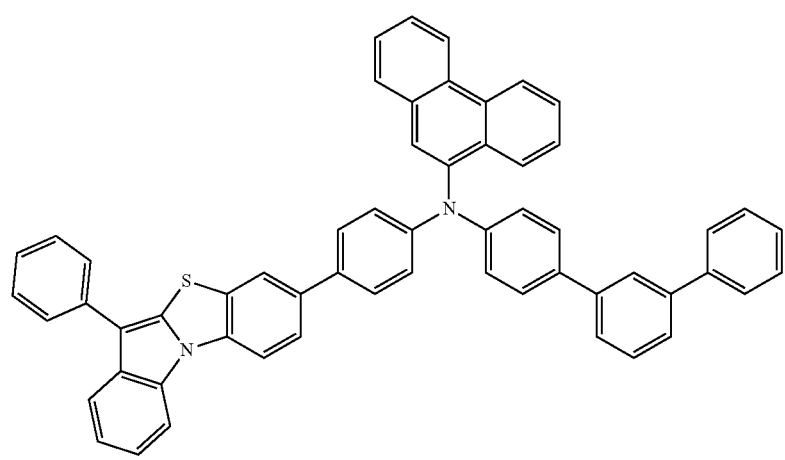

B30
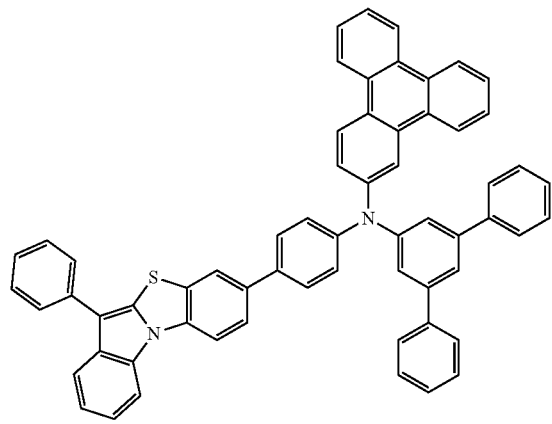
B31
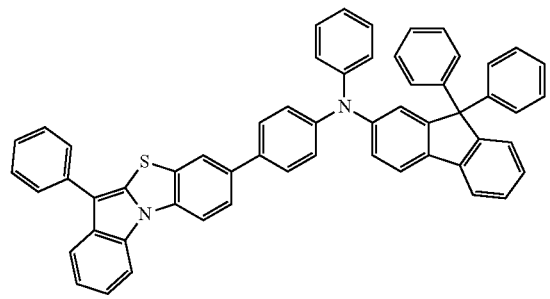
B32
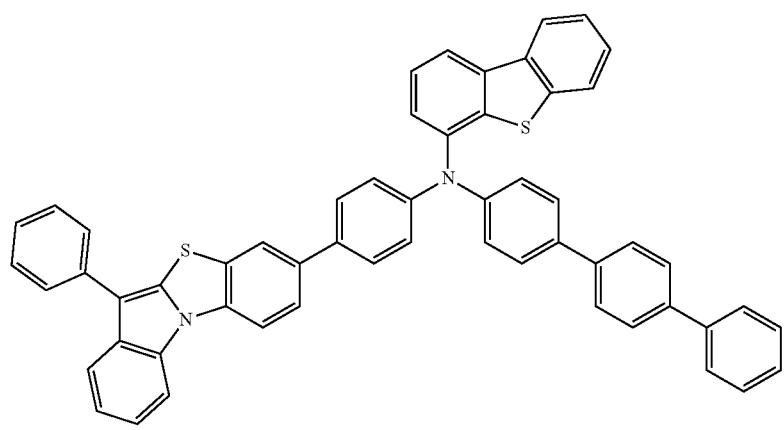
B33
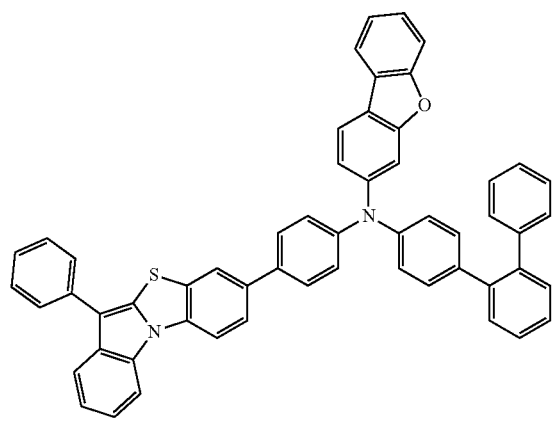
B34
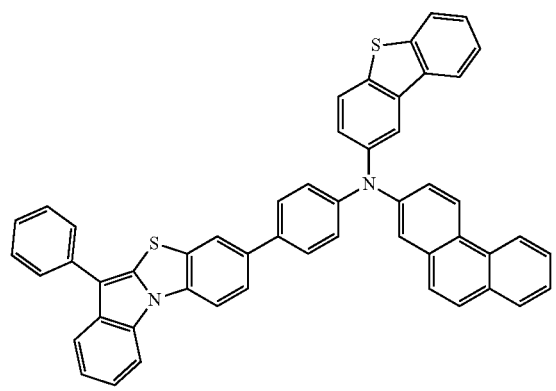

-continued
| B35 | B36 |
|---|---|
| 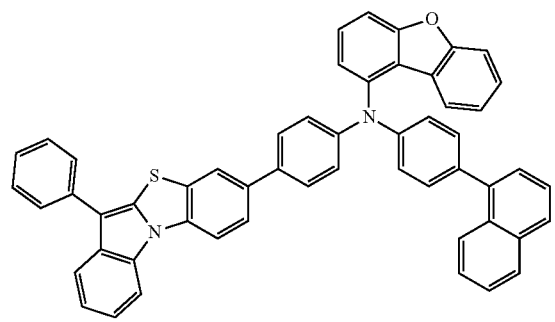 | 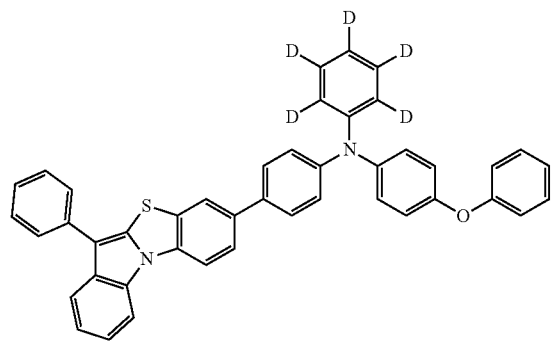 |
| B37 | B38 |
|---|---|
| 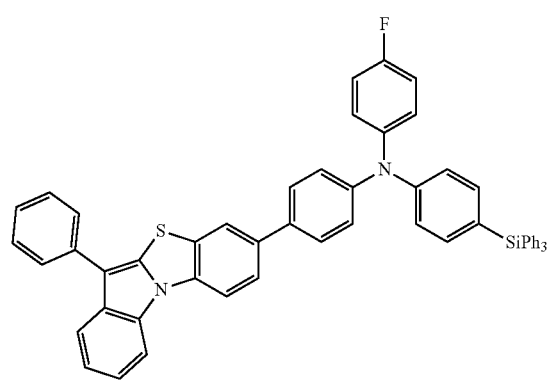 | 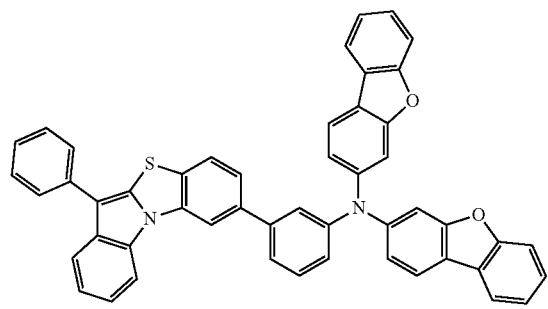 |
| B39 | B40 |
|---|---|
| 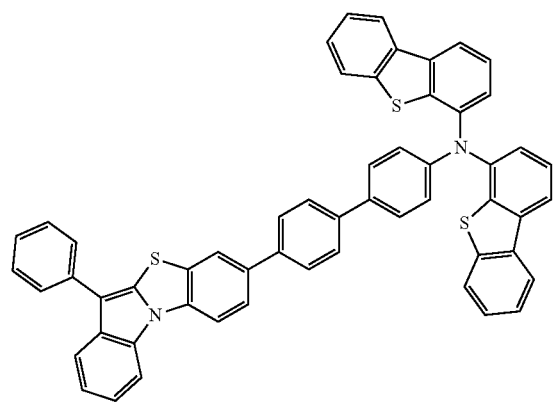 | 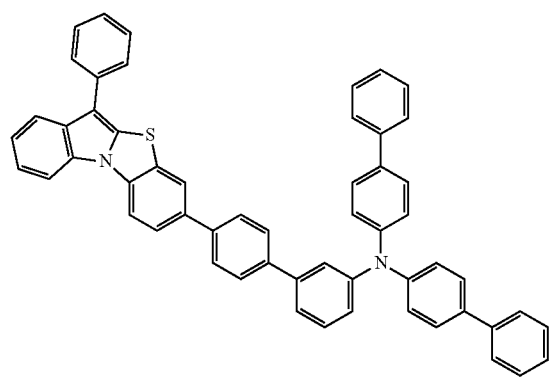 |

-continued
B41
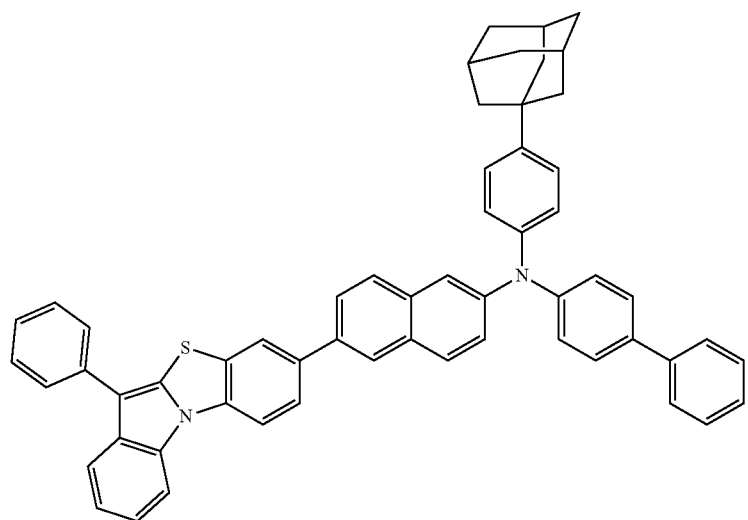
B42
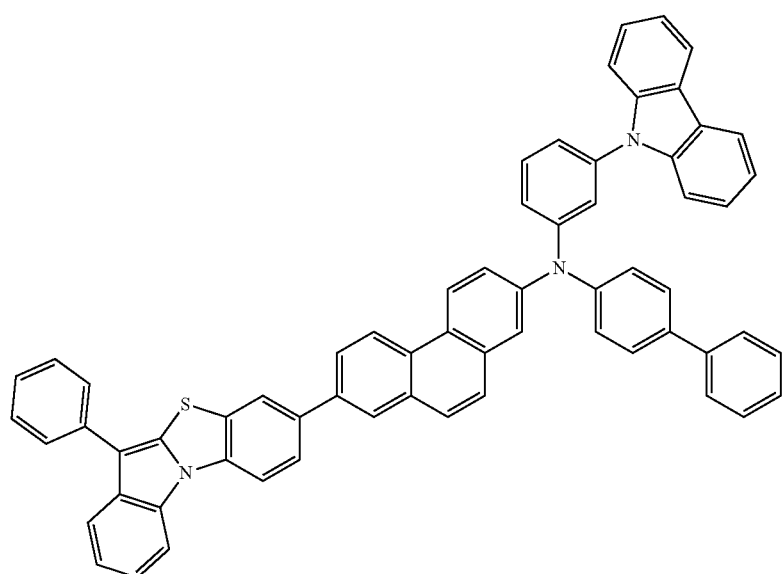
B43
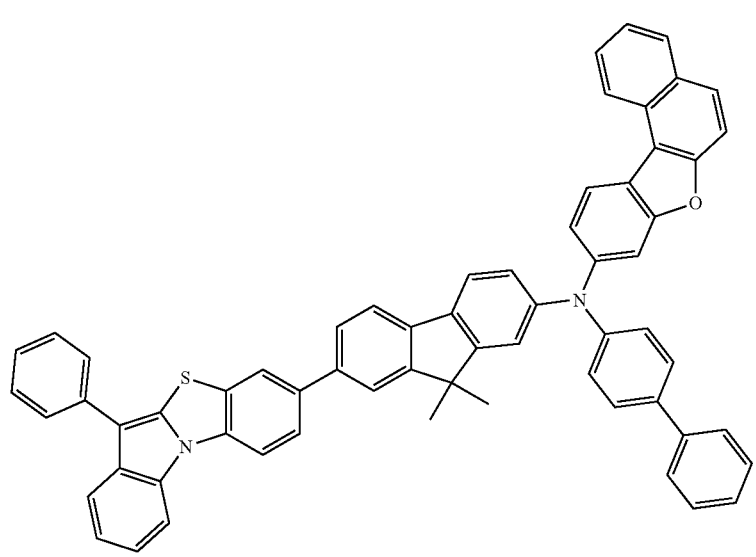

-continued
B44
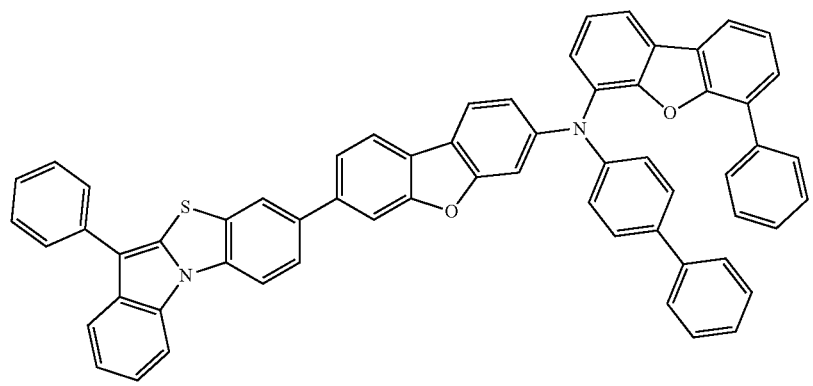
B45
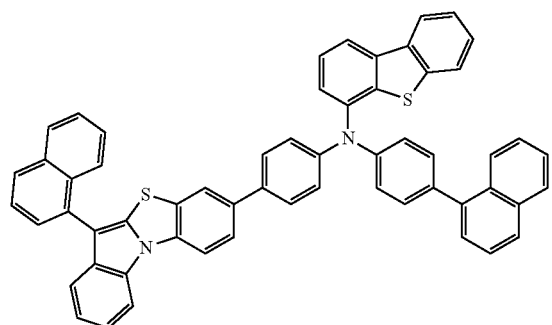
B46
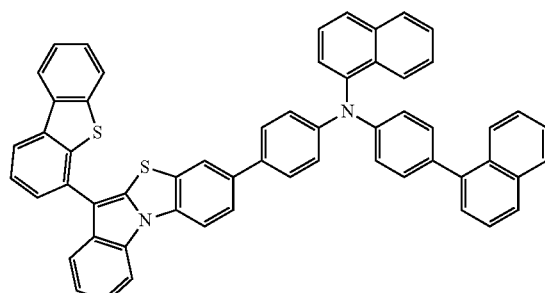
B47
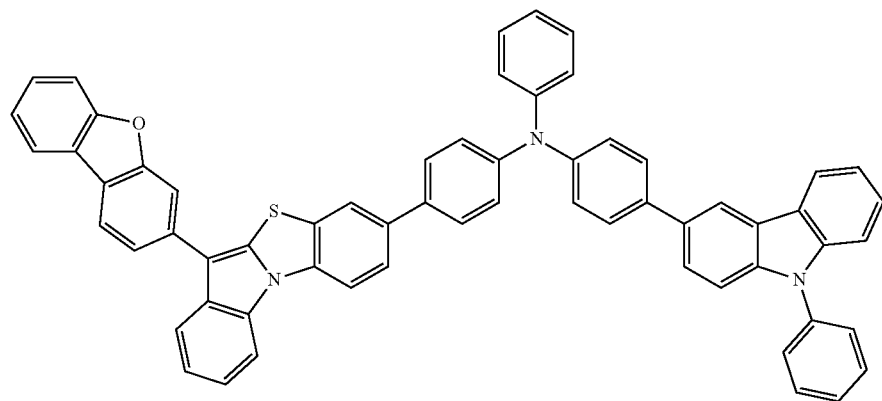
B48
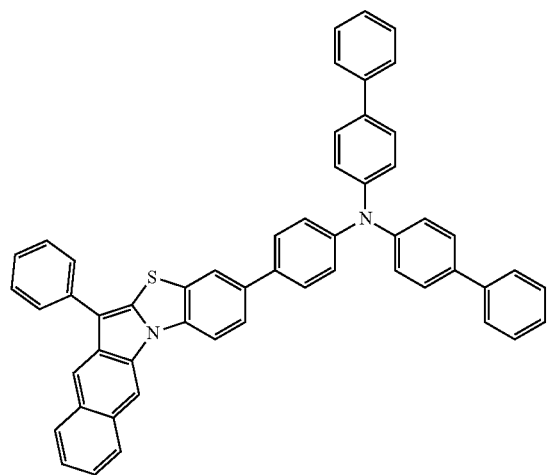
B49
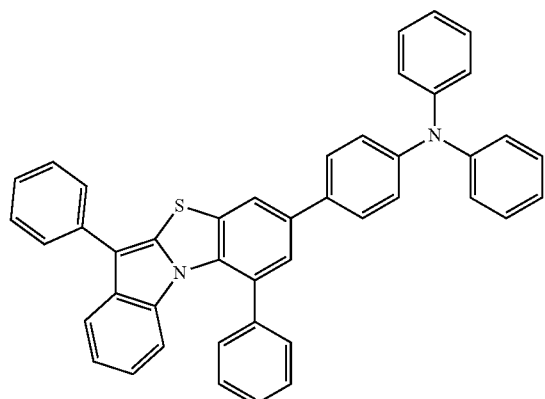

-continued
B50
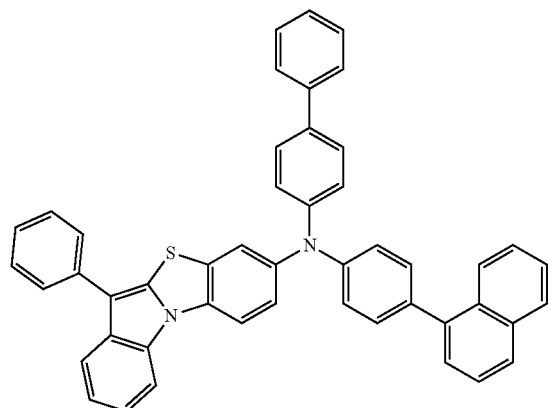
B51
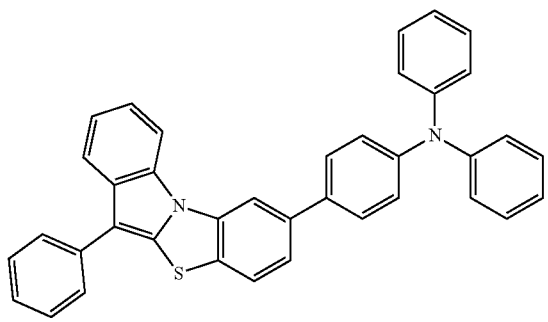
B52
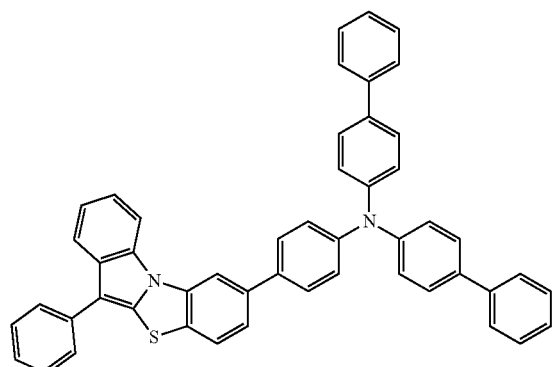
B53
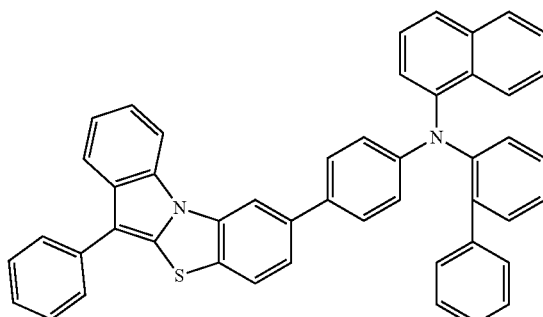
B54
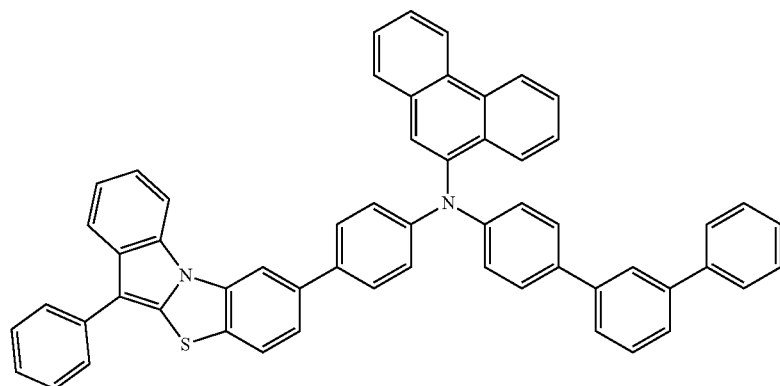
B55
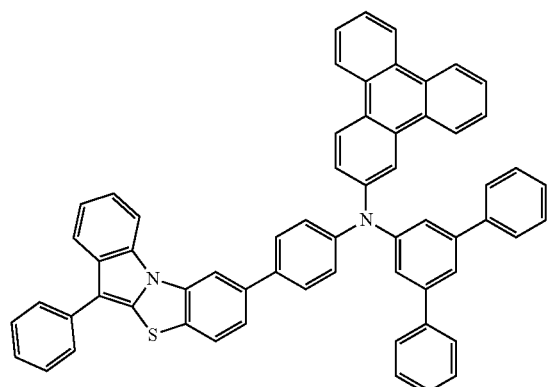
B56
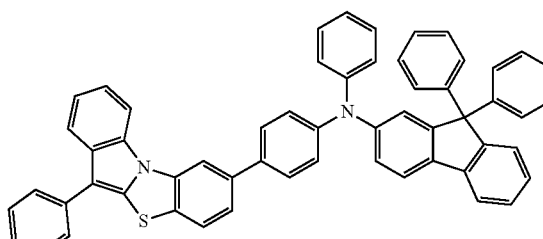

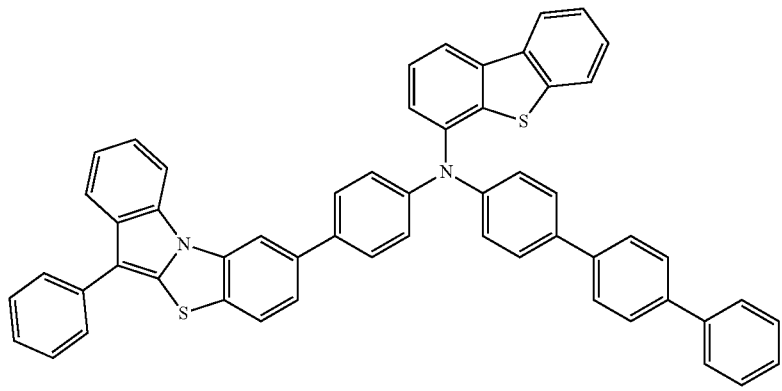
B57
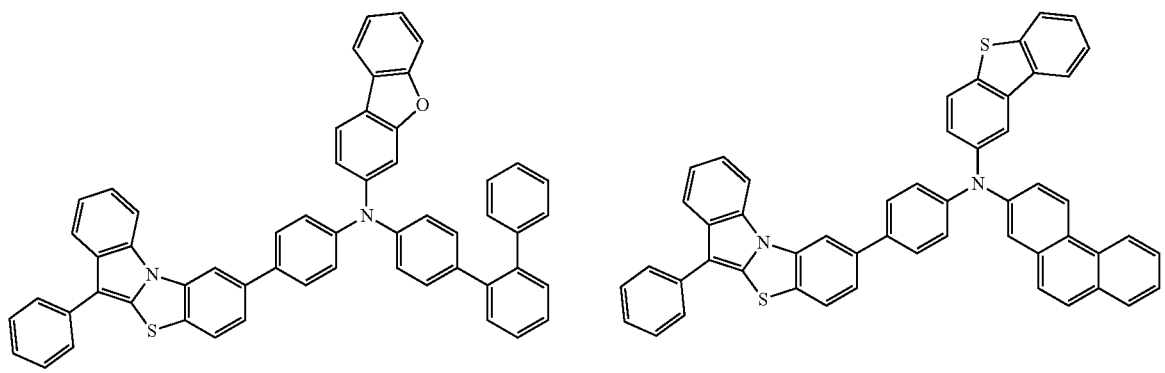
B58　　　　　　　　　　　　　　　　　　　　B59
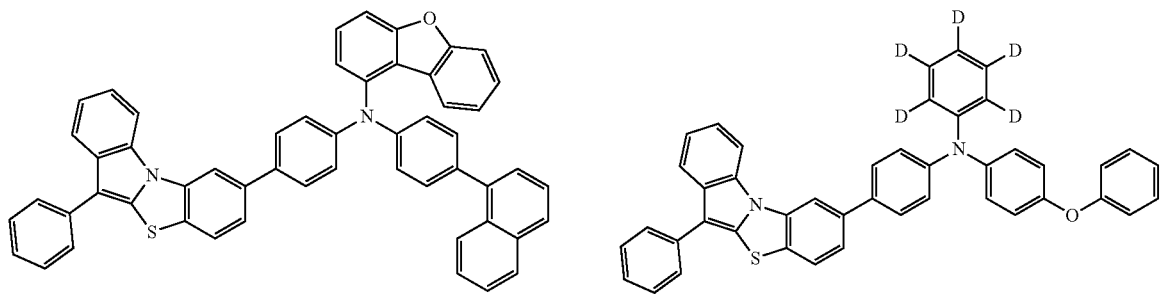
B60　　　　　　　　　　　　　　　　　　　　B61
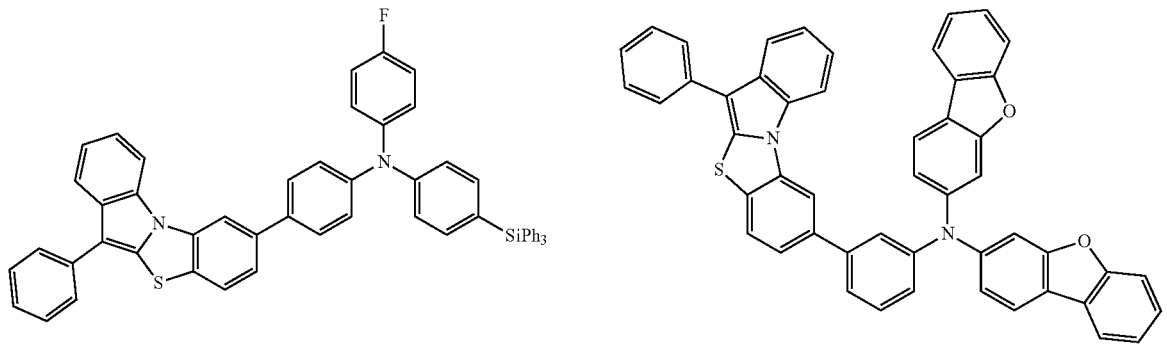
B62　　　　　　　　　　　　　　　　　　　　B63

-continued
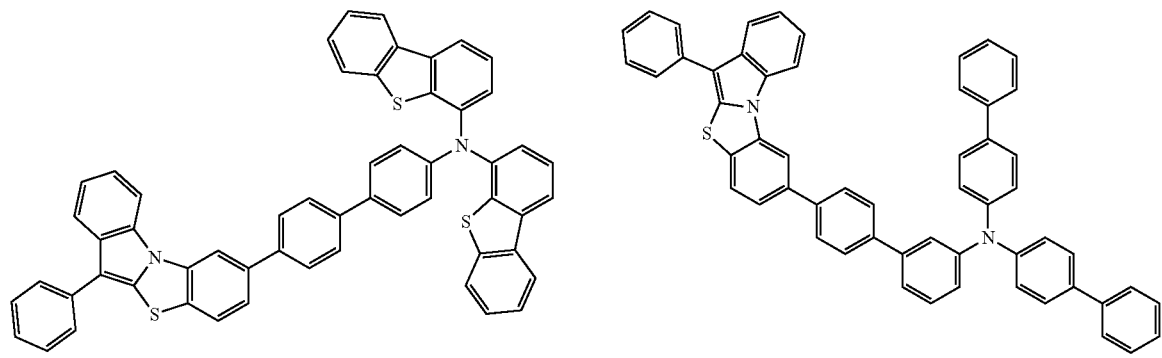
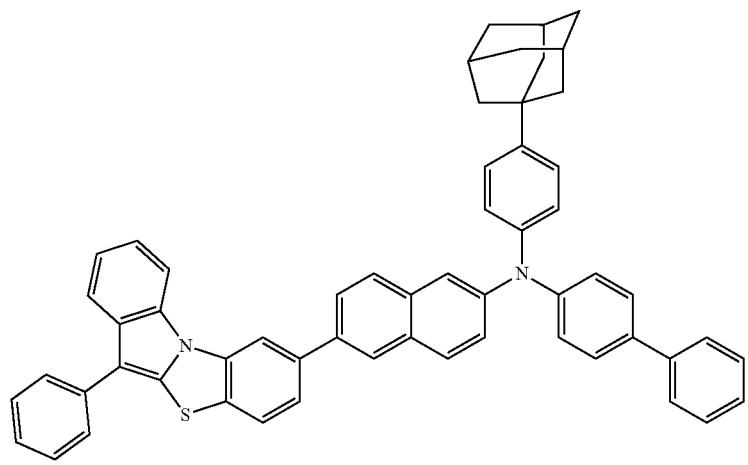
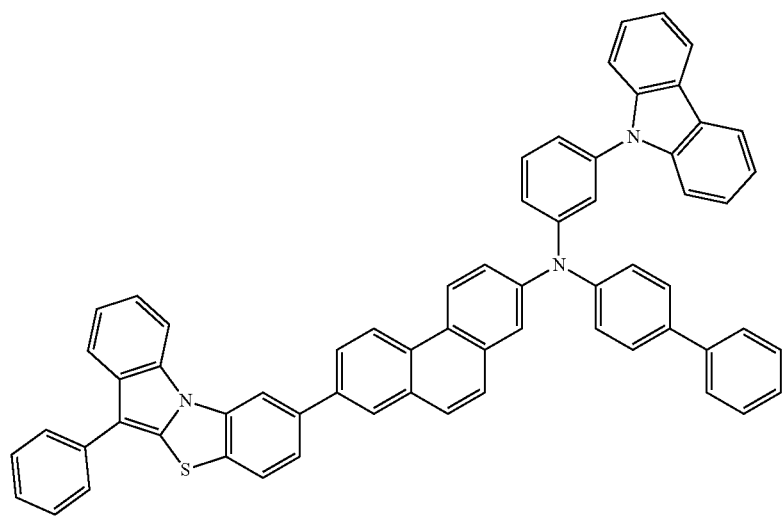

-continued
B68
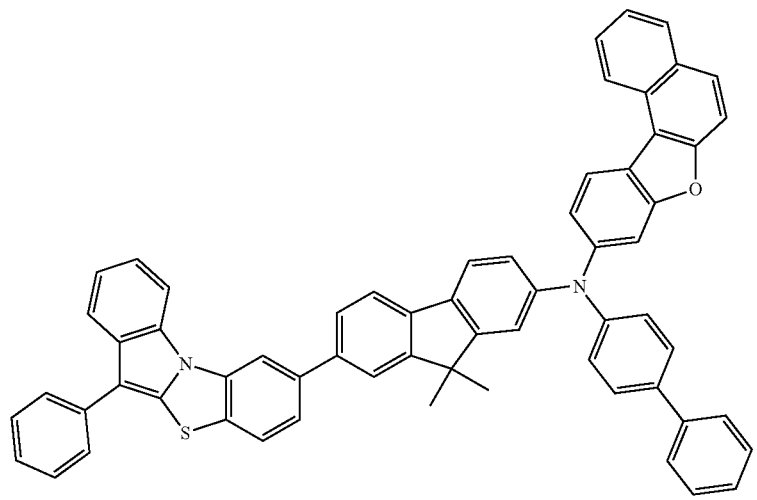
B69
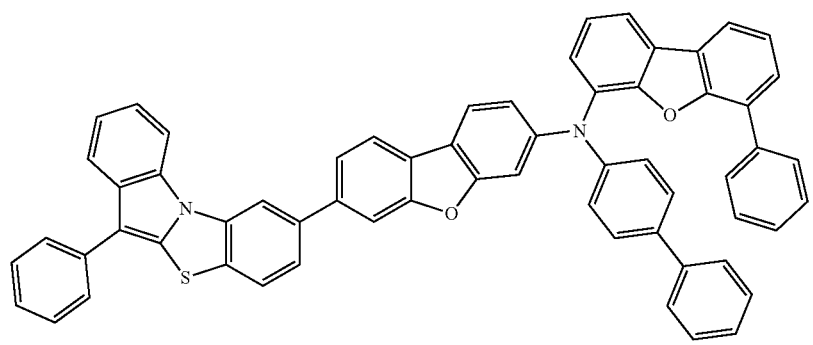
B70
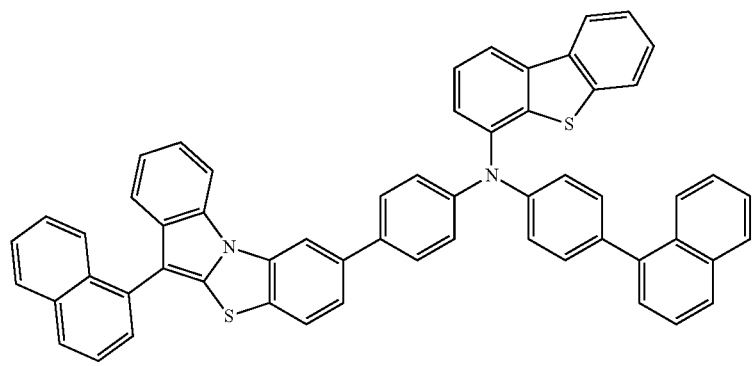
B71
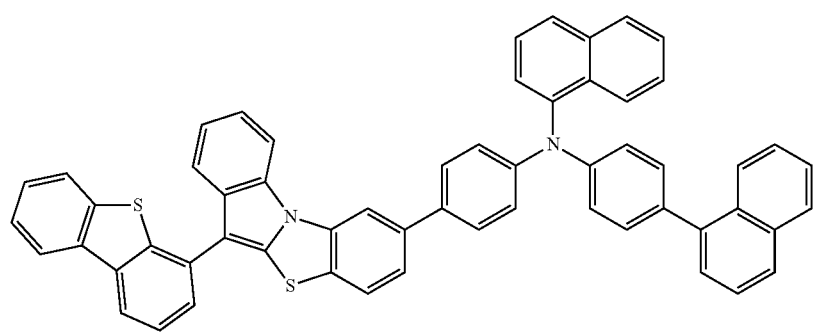

-continued
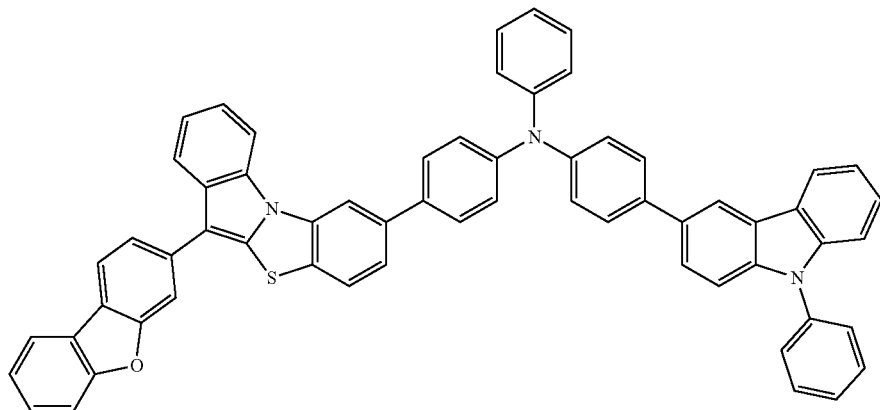
B72
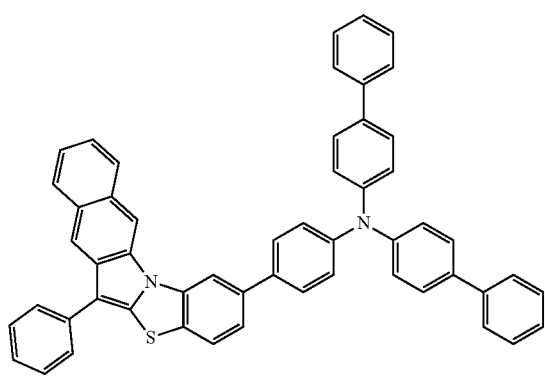
B73
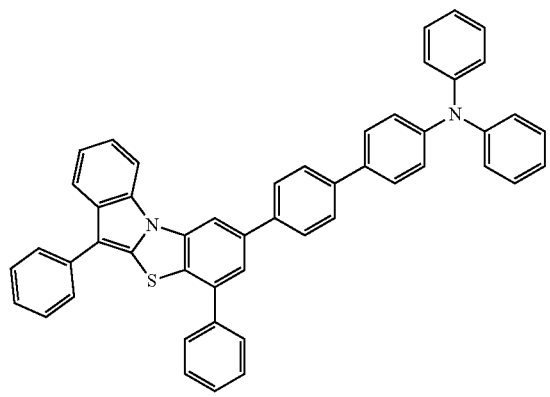
B74
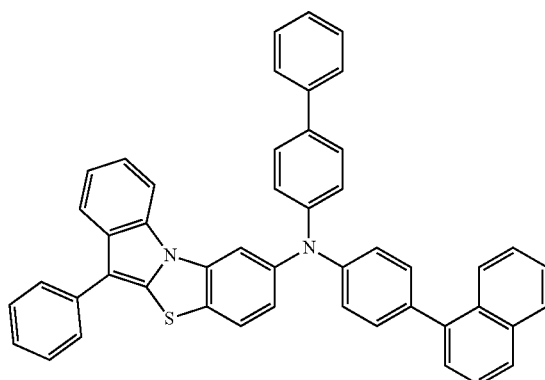
B75
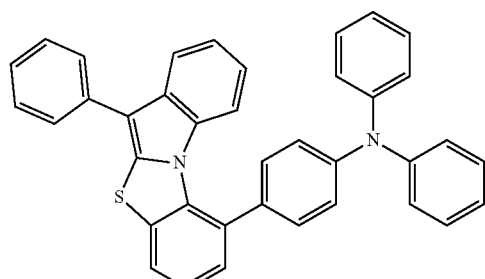
B76
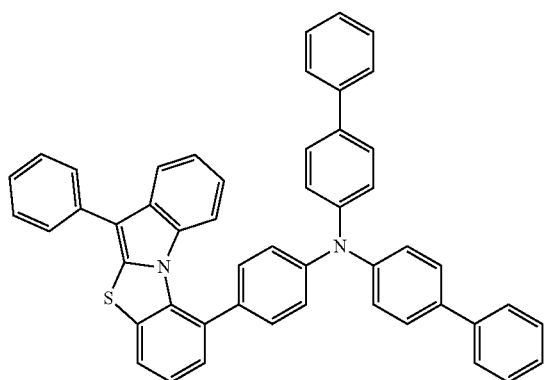
B77
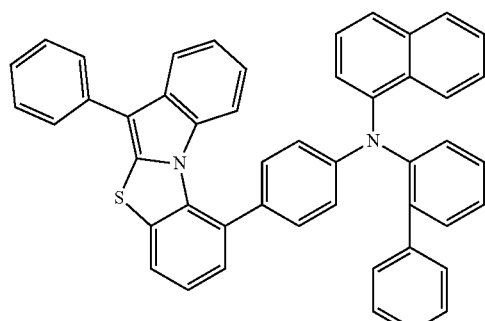
B78

-continued
B79
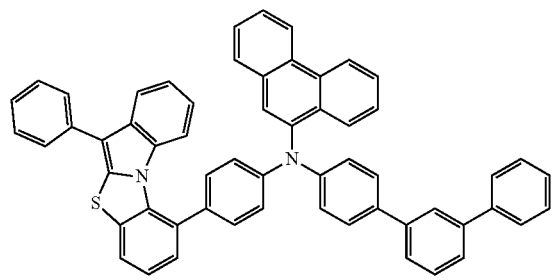
B80
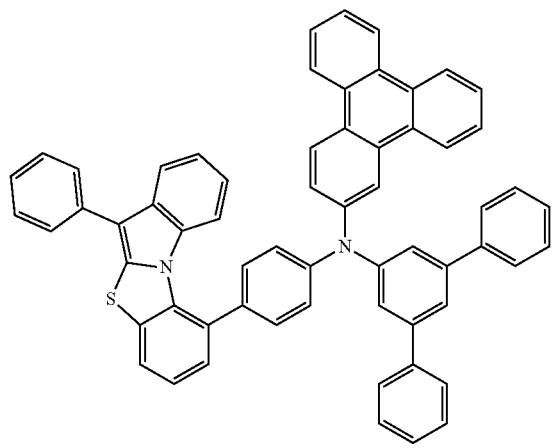
B81
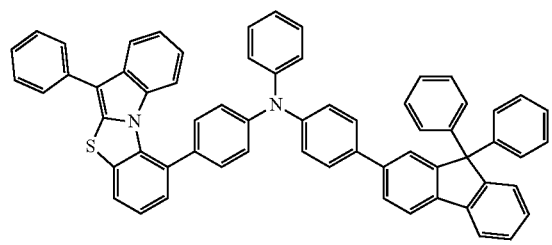
B82
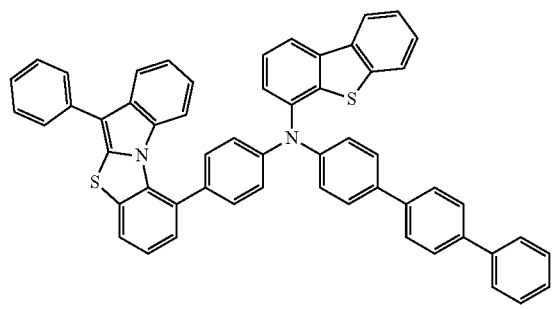
B83
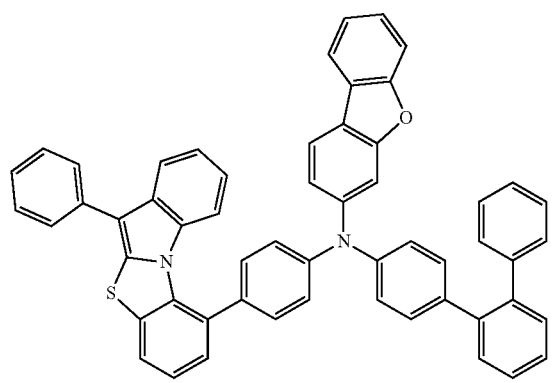
B84
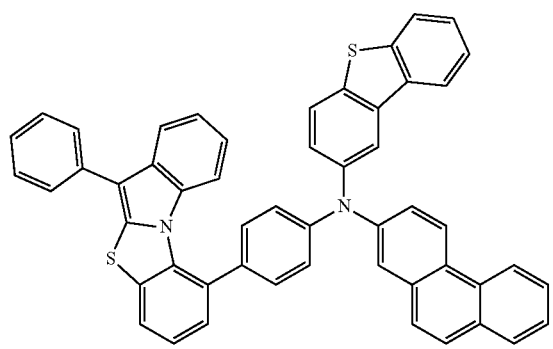
B85
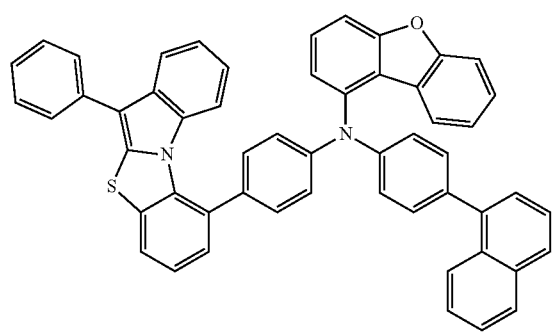
B86
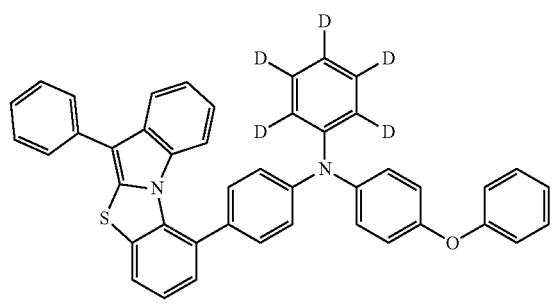

-continued
B87
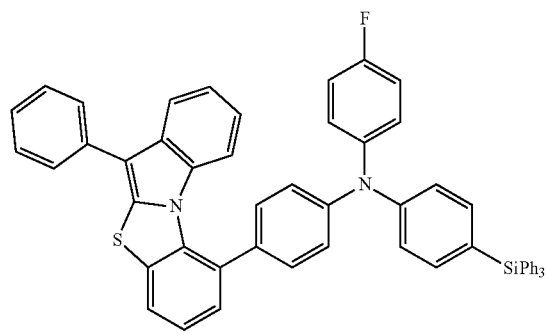
B88
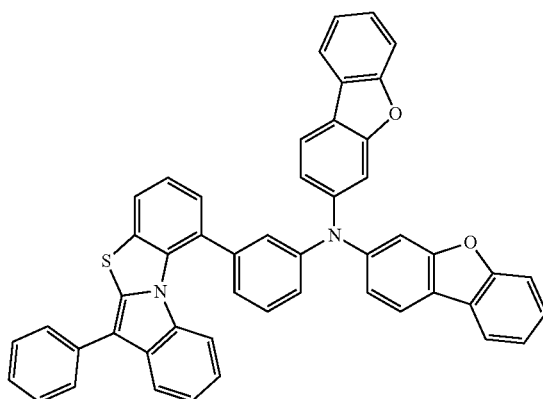
B89
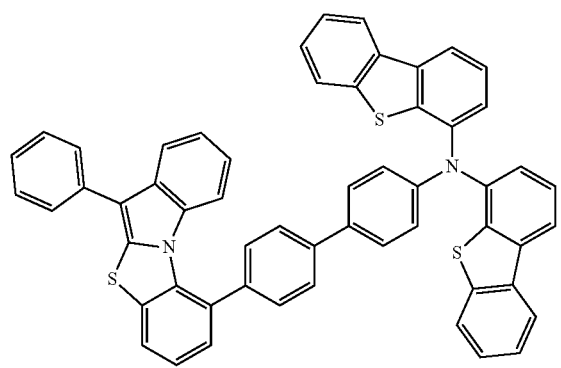
B90
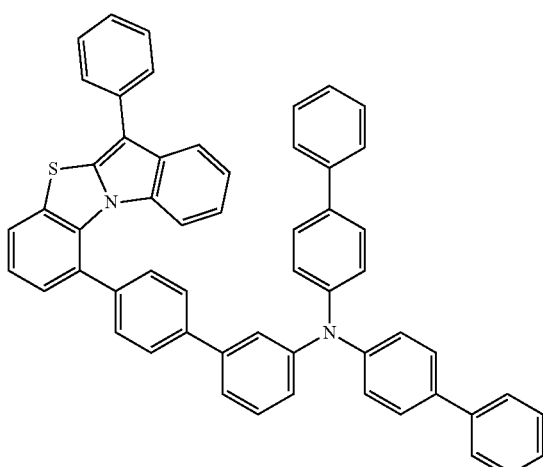
B91
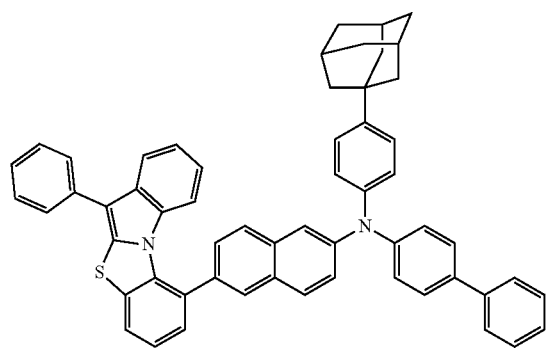
B92
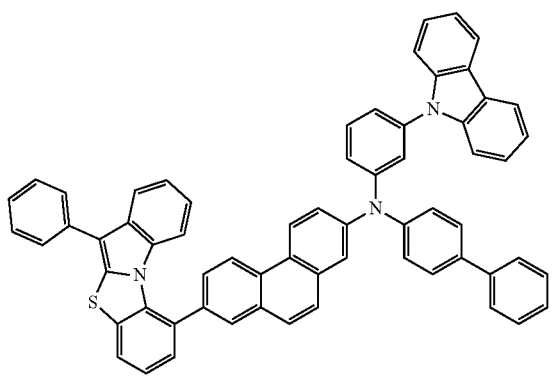

-continued
B93
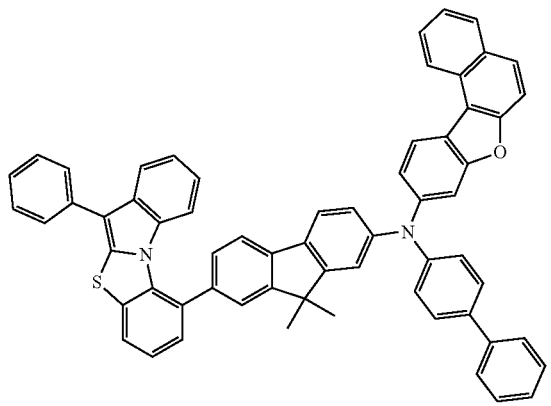
B94
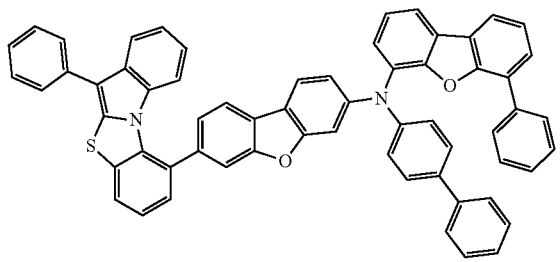
B95
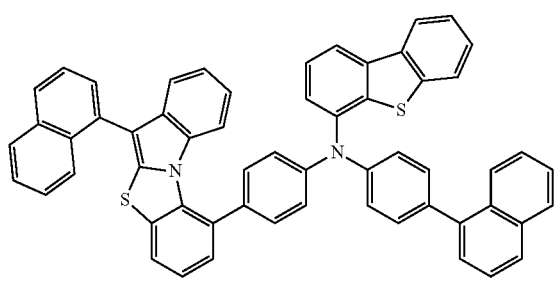
B96
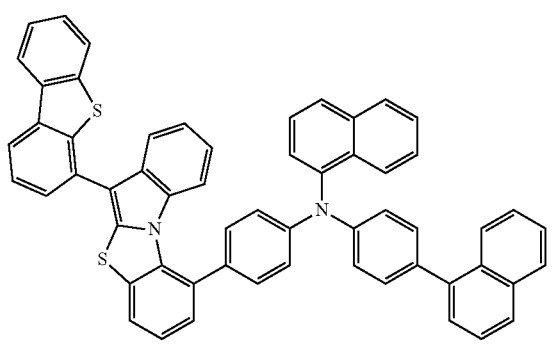
B97
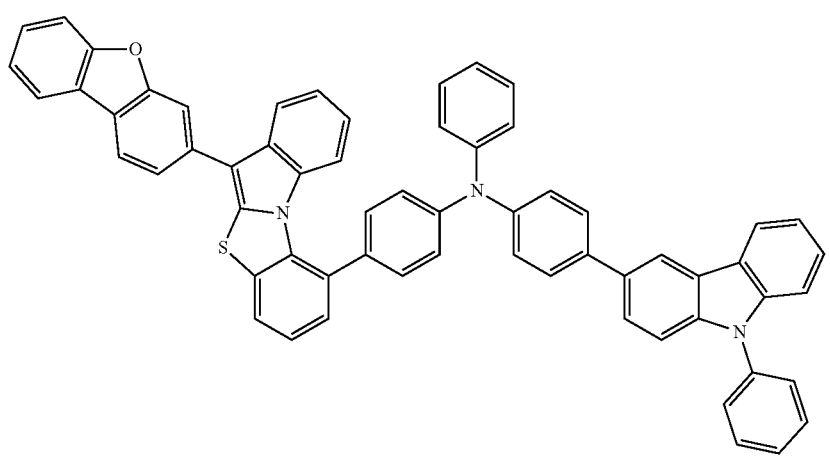
B98
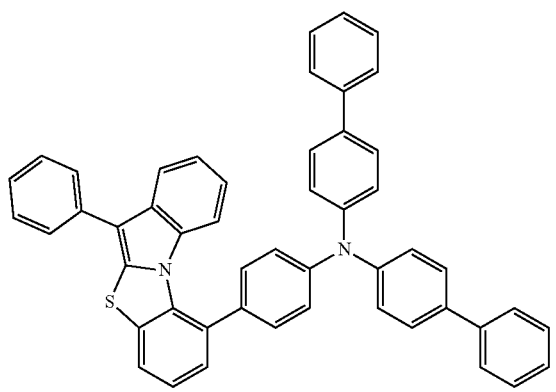
B99
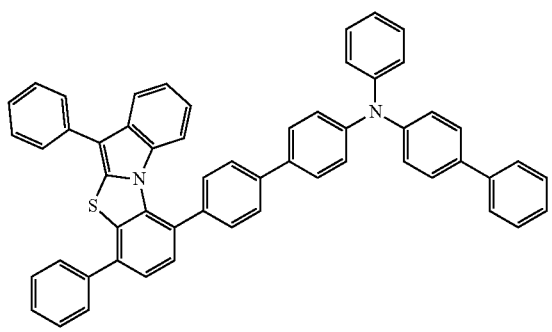

-continued
B100
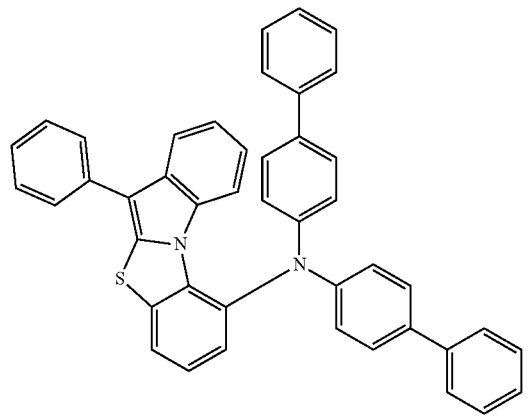
B101
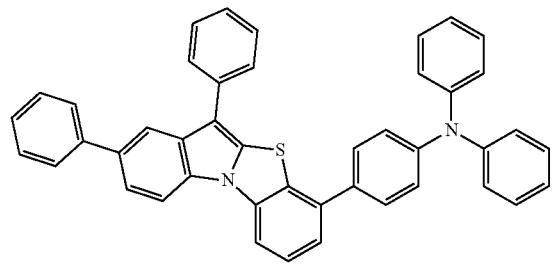
B102
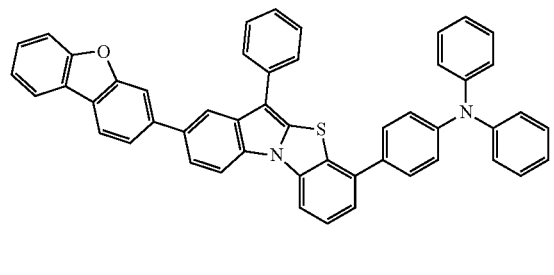
B103
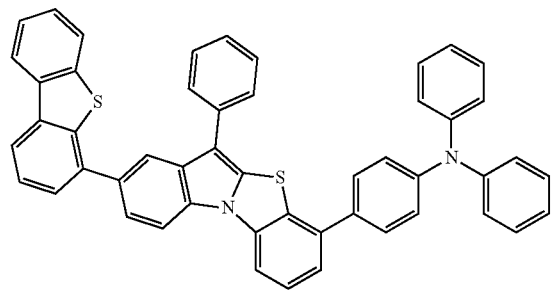
B104
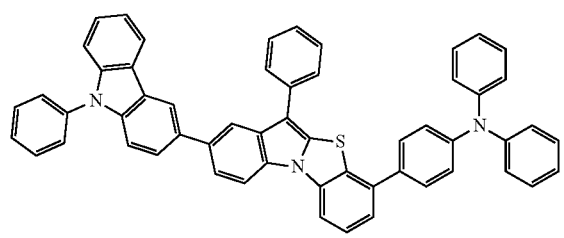
B105
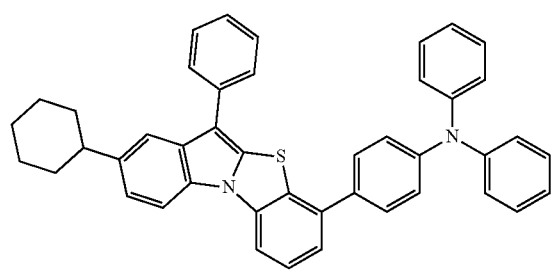
B106
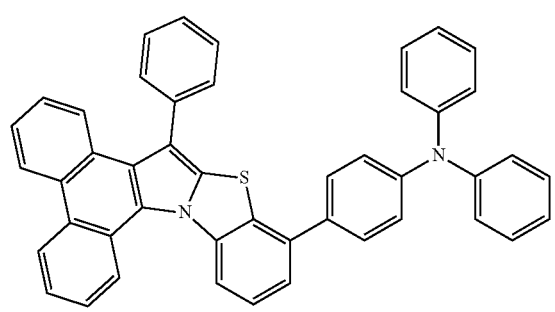
B107
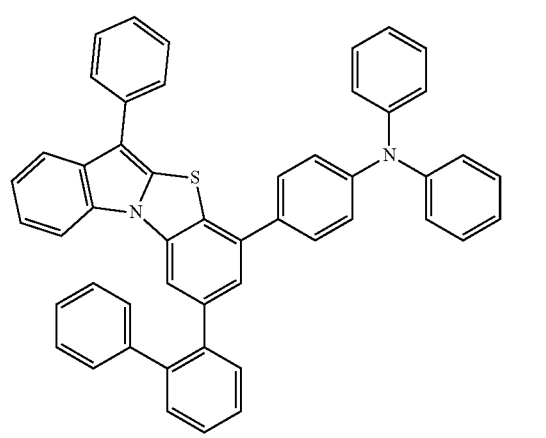

-continued
B108
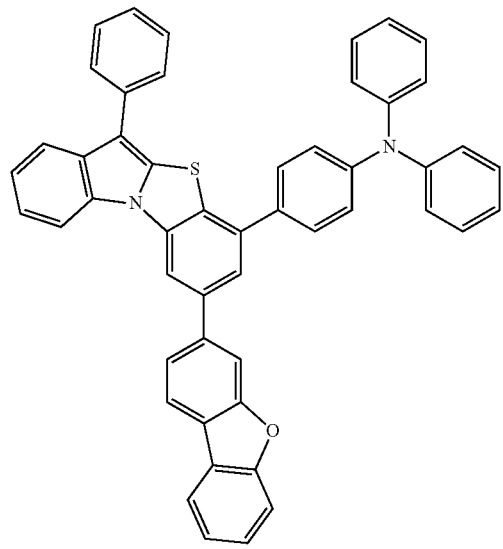
B109
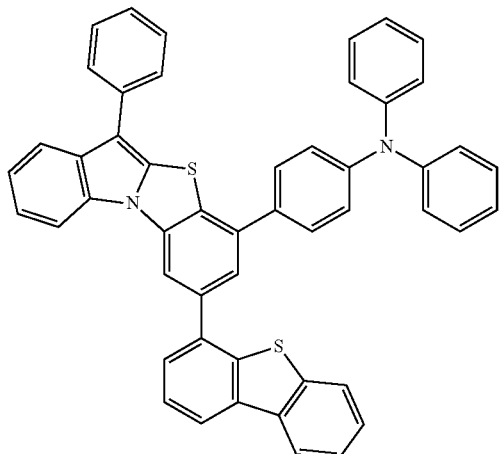
B110
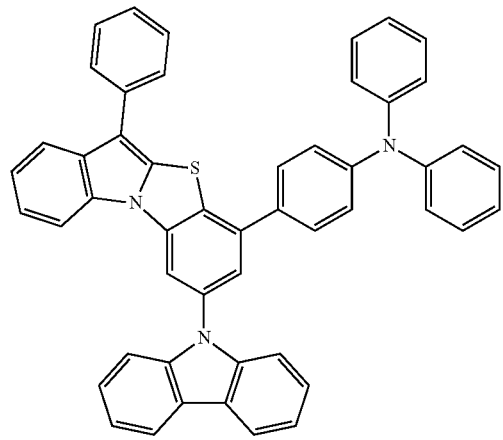
B111
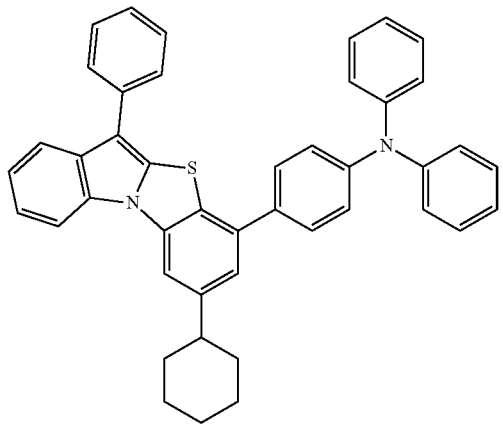
B112
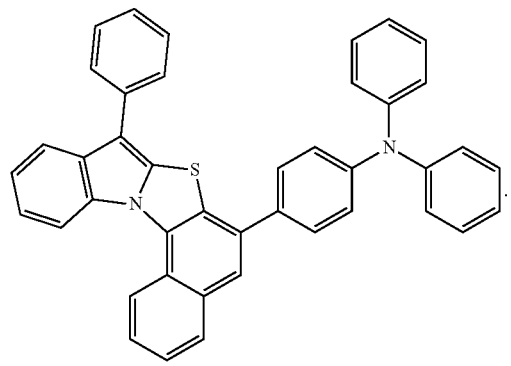
* * * * *

UNITED STATES PATENT AND TRADEMARK OFFICE
CERTIFICATE OF CORRECTION

PATENT NO. : 11,264,573 B2
APPLICATION NO. : 16/454465
DATED : March 1, 2022
INVENTOR(S) : Takuya Uno Page 1 of 11

It is certified that error appears in the above-identified patent and that said Letters Patent is hereby corrected as shown below:

In the Claims

Column 137, Line 15 (approx.), Claim 11,
Compound A23

Delete " 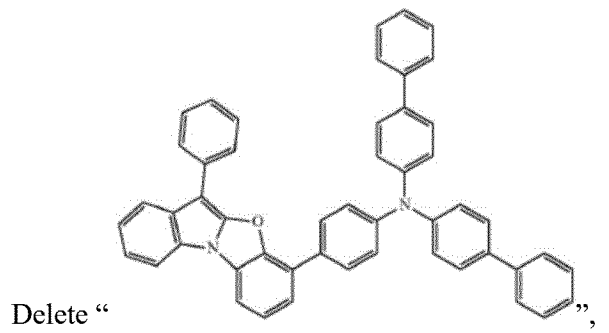 ",

Insert -- 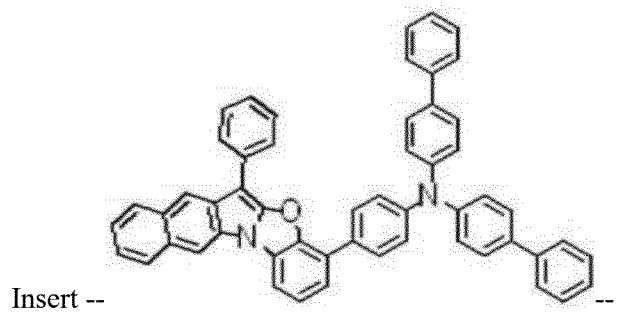 --

Column 151, Line 5, Claim 11    Delete "A61",
Insert -- A60 --

Column 152, Line 5, Claim 11    Delete "A60",
Insert -- A61 --

Signed and Sealed this
Twenty-seventh Day of June, 2023

*Katherine Kelly Vidal*
Katherine Kelly Vidal
*Director of the United States Patent and Trademark Office*

CERTIFICATE OF CORRECTION (continued)
U.S. Pat. No. 11,264,573 B2

Column 163, Line 15, Claim 11,
Compound A98

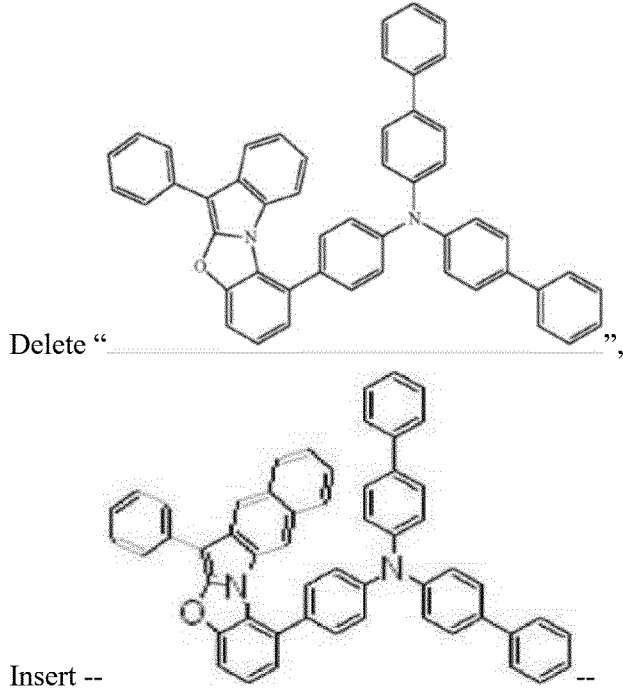

Delete " ",

Insert -- --

Column 163, Line 22, Claim 11,
Compound A100

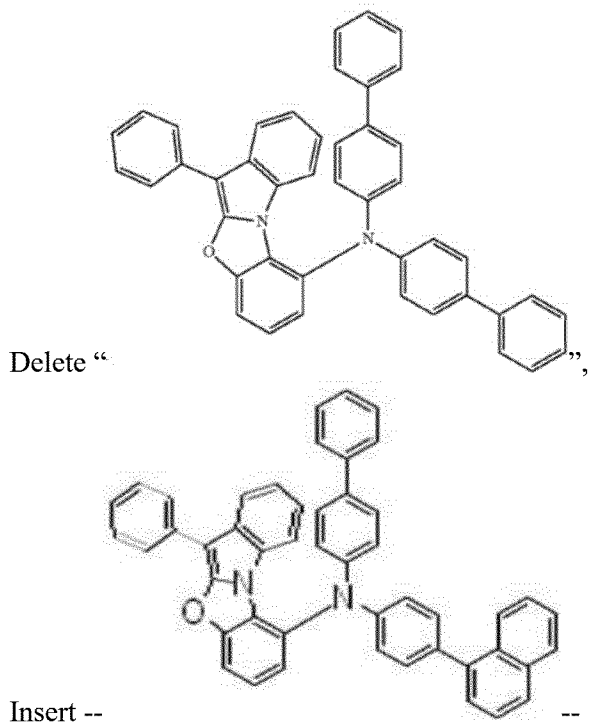

Delete " ",

Insert -- --

Column 164, Line 15, Claim 11,
Compound A99
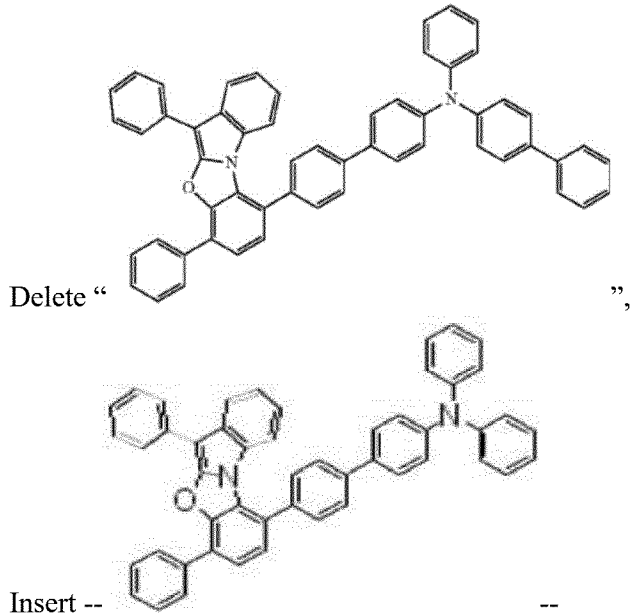
Delete " ",
Insert -- --
| | |
|---|---|
| Column 169, Line 6, Claim 11 | Delete "B8", Insert -- B7 -- |
| Column 169, Line 11, Claim 11 | Delete "B10", Insert -- B9 -- |
| Column 169, Line 16, Claim 11 | Delete "B12", Insert -- B11 -- |
| Column 170, Line 6, Claim 11 | Delete "B9", Insert -- B8 -- |
| Column 170, Line 11, Claim 11 | Delete "B11", Insert -- B10 -- |
| Column 170, Line 16, Claim 11 | Delete "B13", Insert -- B12 -- |

CERTIFICATE OF CORRECTION (continued)
U.S. Pat. No. 11,264,573 B2

Column 173, Line 10, Claim 11,
Compound B23

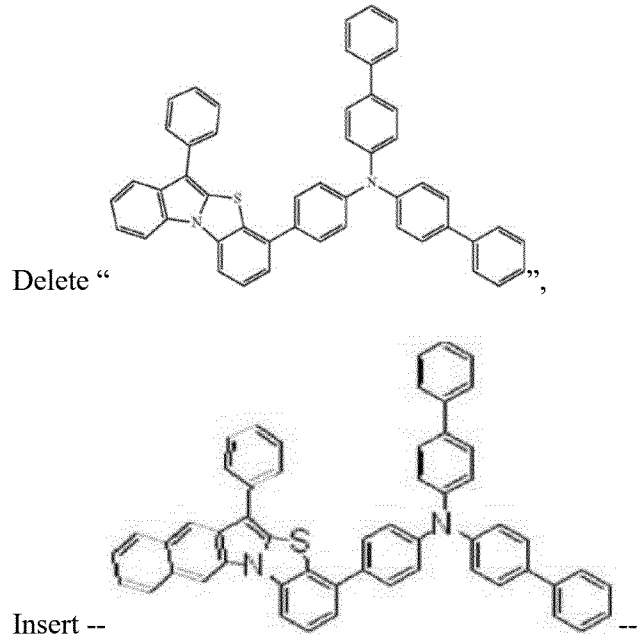

Delete " ",

Insert -- --

Columns 191-192, Line 9, Claim 11,
Compound B72

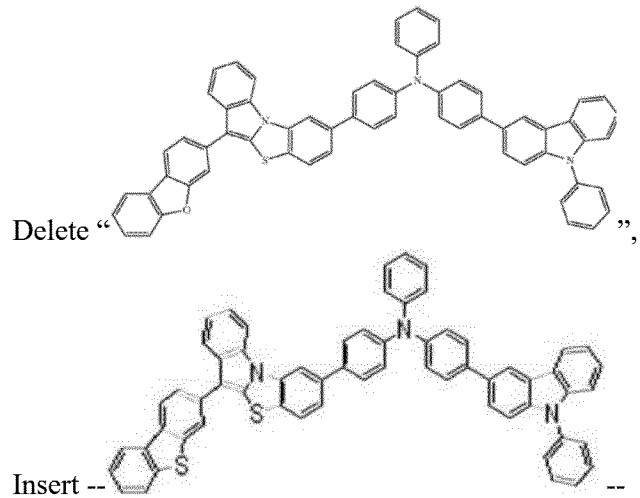

Delete " ",

Insert -- --

CERTIFICATE OF CORRECTION (continued)
U.S. Pat. No. 11,264,573 B2

Column 197, Line 25, Claim 11,
Compound B98

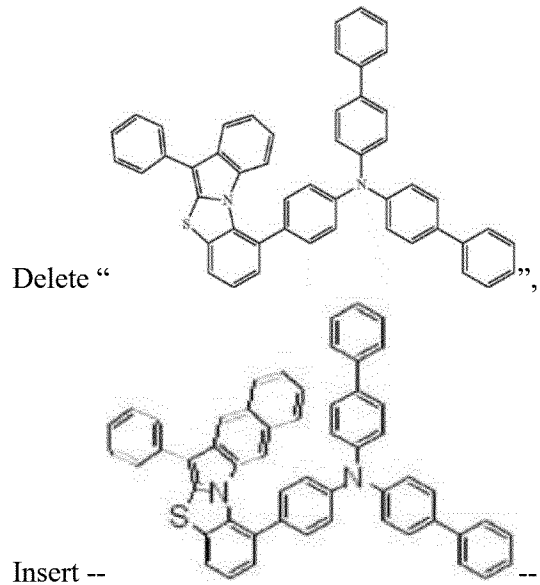

Delete " ",

Insert --  --

Column 198, Line 25, Claim 11,
Compound B99

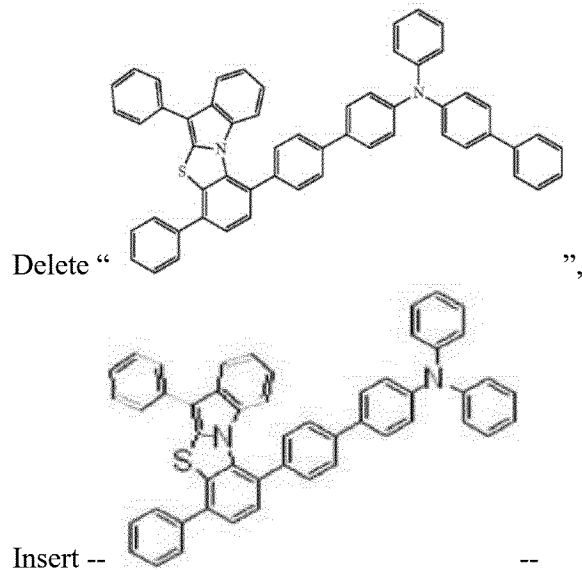

Delete " ",

Insert --  --

Column 199, Line 6, Claim 11,
Compound B100
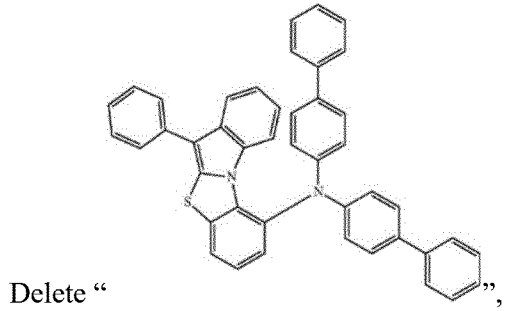
Delete " ",
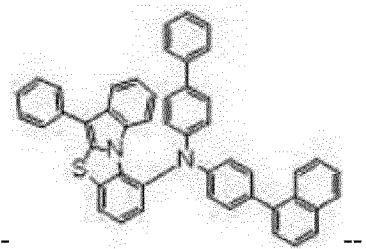
Insert -- --
Column 211, Line 4, Claim 20,
Compound A23
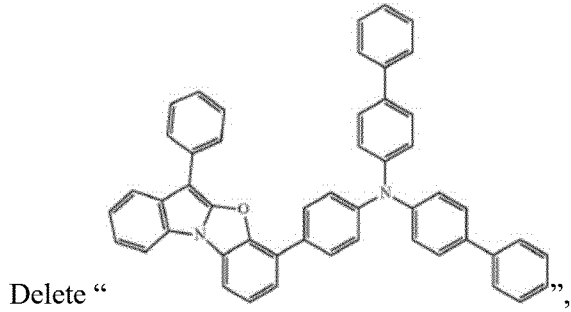
Delete " ",
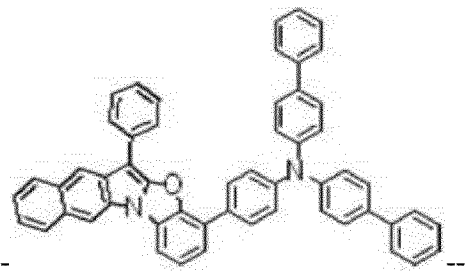
Insert -- --
Column 223, Line 16, Claim 20    Delete "A61",
Insert -- A60 --
Column 224, Line 16, Claim 20    Delete "A60",
Insert -- A61 --

CERTIFICATE OF CORRECTION (continued)
U.S. Pat. No. 11,264,573 B2

Column 235, Line 23, Claim 20,
Compound A98

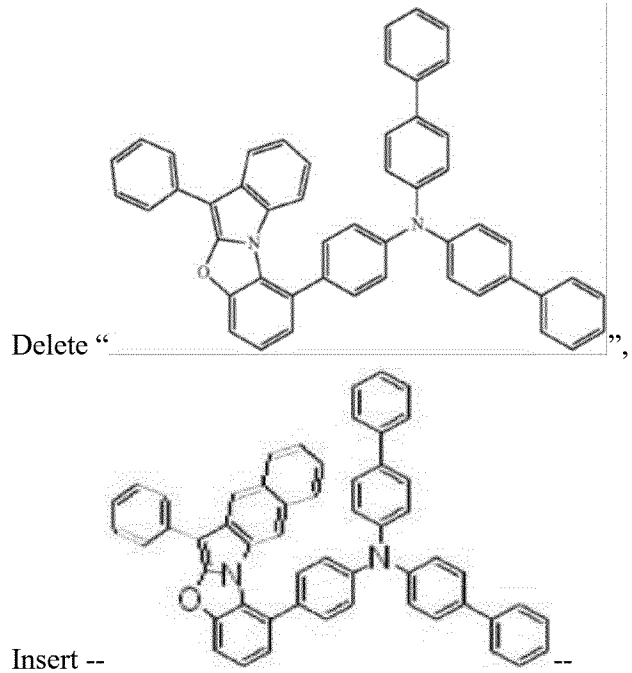

Delete " ",

Insert -- --

Column 236, Line 23, Claim 20,
Compound A99

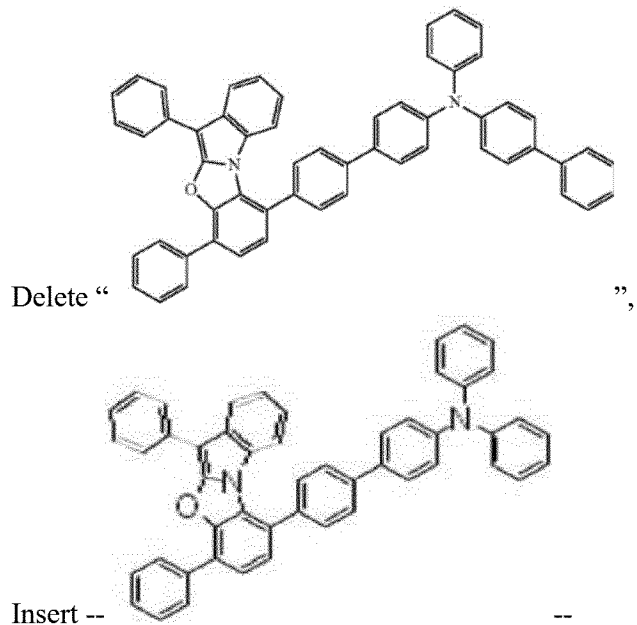

Delete " ",

Insert -- --

Column 237, Claim 20,
Compound A100
Delete " 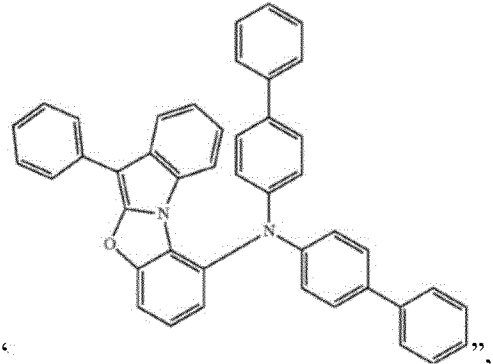 ",
Insert -- 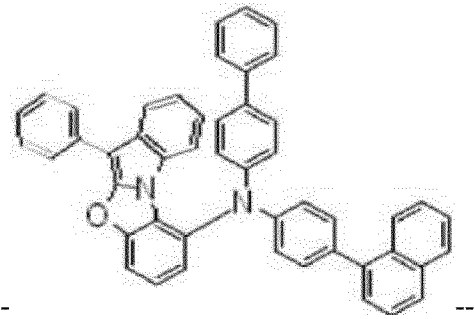 --
| | |
|---|---|
| Column 241, Line 15, Claim 20 | Delete "B8", Insert -- B7 -- |
| Column 242, Line 15, Claim 20 | Delete "B9", Insert -- B8 -- |
| Column 243, Line 2, Claim 20 | Delete "B10", Insert -- B9 -- |
| Column 243, Line 6, Claim 20 | Delete "B12", Insert -- B11 -- |
| Column 244, Line 2, Claim 20 | Delete "B11", Insert -- B10 -- |
| Column 244, Line 6, Claim 20 | Delete "B13", Insert -- B12 -- |

CERTIFICATE OF CORRECTION (continued)
U.S. Pat. No. 11,264,573 B2

Column 245, Line 23, Claim 20,
Compound B23

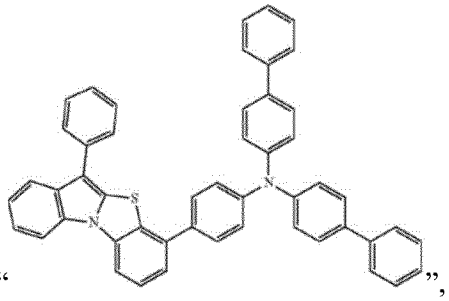

Delete " ",

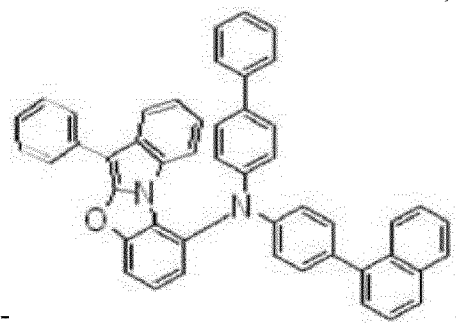

Insert -- --

Column 265-266, Line 6, Claim 20,
Compound B72

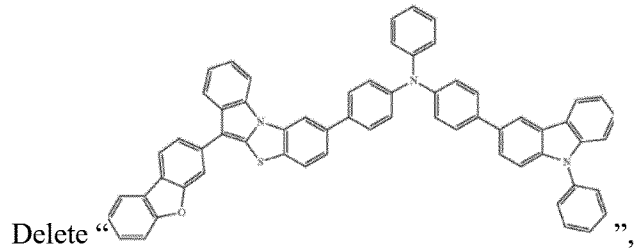

Delete " ",

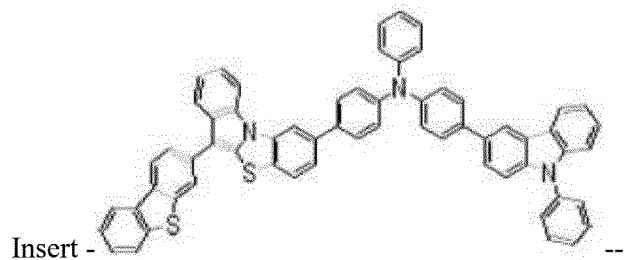

Insert - --

CERTIFICATE OF CORRECTION (continued)
U.S. Pat. No. 11,264,573 B2

Column 271, Line 20, Claim 20,
Compound B98

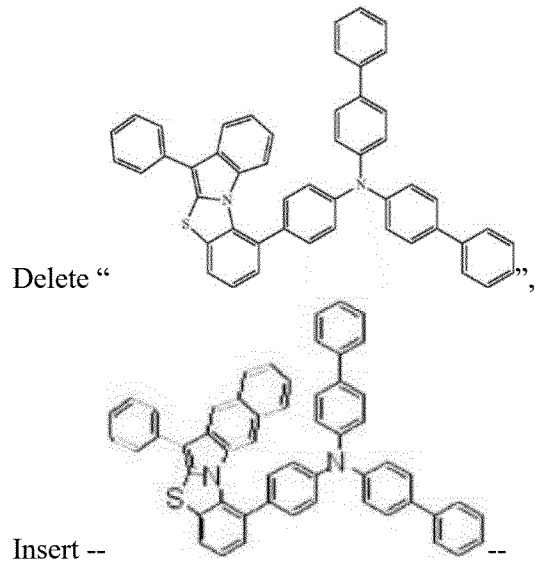

Delete " [structure] ",

Insert -- [structure] --

Column 272, Line 20, Claim 20,
Compound B99

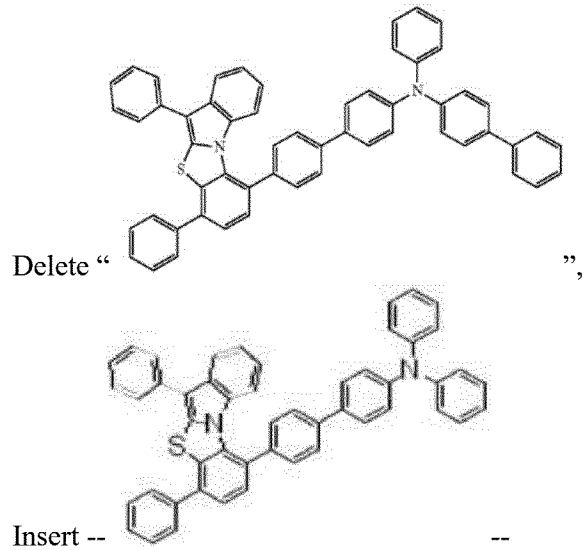

Delete " [structure] ",

Insert -- [structure] --

CERTIFICATE OF CORRECTION (continued)
U.S. Pat. No. 11,264,573 B2

Column 273, Line 5, Claim 20,
Compound B100

Delete " 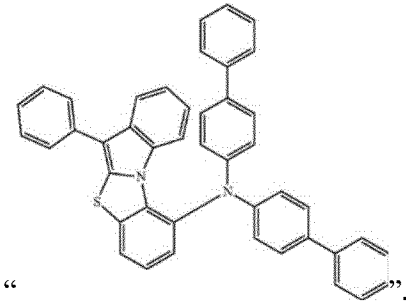 ",

Insert -- 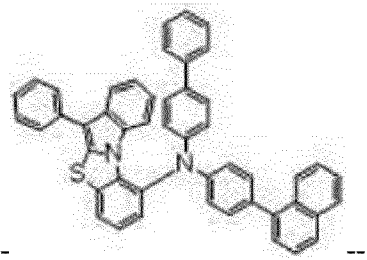 --